US007550651B2

(12) United States Patent
Damude

(10) Patent No.: US 7,550,651 B2
(45) Date of Patent: Jun. 23, 2009

(54) DELTA-8 DESATURASE AND ITS USE IN MAKING POLYUNSATURATED FATTY ACIDS

(75) Inventor: Howard G. Damude, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 271 days.

(21) Appl. No.: 11/166,003

(22) Filed: Jun. 24, 2005

(65) Prior Publication Data

US 2006/0195939 A1    Aug. 31, 2006

Related U.S. Application Data

(60) Provisional application No. 60/624,812, filed on Nov. 4, 2004, provisional application No. 60/583,041, filed on Jun. 25, 2004.

(51) Int. Cl.
*A01H 5/00* (2006.01)
*C12N 15/82* (2006.01)
(52) U.S. Cl. .................. 800/281; 800/298; 536/23.2; 435/410; 435/252.3
(58) Field of Classification Search .................. None
See application file for complete search history.

(56) References Cited

U.S. PATENT DOCUMENTS

| 5,057,419 | A | 10/1991 | Martin et al. |
|---|---|---|---|
| 5,443,974 | A | 8/1995 | Hitz et al. |
| 5,968,809 | A | 10/1999 | Knutzon et al. |
| 5,972,664 | A | 10/1999 | Knutzon et al. |
| 6,051,754 | A | 4/2000 | Knutzon |
| 6,075,183 | A | 6/2000 | Knutzon et al. |
| 6,136,574 | A | 10/2000 | Knutzon et al. |
| 6,410,288 | B1 | 6/2002 | Knutzon et al. |
| 6,459,018 | B1 | 10/2002 | Knutzon |
| 6,825,017 | B1 | 11/2004 | Browse et al. |
| 2002/0139974 | A1 | 10/2002 | Matsushita et al. |
| 2003/0019217 | A1 | 1/2003 | Sekiya et al. |

FOREIGN PATENT DOCUMENTS

| EP | 0 005 277 B1 | 11/1979 |
|---|---|---|
| WO | WO 91/13972 A1 | 9/1991 |
| WO | WO 93/11245 A1 | 6/1993 |
| WO | WO 94/11516 A1 | 5/1994 |
| WO | WO 98/46763 A1 | 10/1998 |
| WO | WO 98/46764 | 10/1998 |
| WO | WO 98/55625 A1 | 12/1998 |
| WO | WO 00/12720 A2 | 3/2000 |
| WO | WO 00/34439 A1 | 6/2000 |
| WO | WO 00/40705 | 7/2000 |
| WO | WO 02/08269 A2 | 1/2002 |
| WO | WO 02/26946 A2 | 4/2002 |
| WO | WO 02/31178 A | 4/2002 |
| WO | WO 02/077213 A2 | 10/2002 |
| WO | WO03/099216 A2 | 12/2003 |
| WO | WO 2004/057001 A | 7/2004 |
| WO | WO 2004/057001 A2 | 7/2004 |
| WO | WO 2004/071176 A2 | 8/2004 |
| WO | WO 2004/071467 A2 | 8/2004 |
| WO | WO 2004/101753 A2 | 11/2004 |
| WO | WO 2004/101757 A2 | 11/2004 |
| WO | WO 2004/104167 A2 | 12/2004 |
| WO | WO 2005/012316 A | 2/2005 |
| WO | WO 2005/047485 A | 5/2005 |
| WO | WO 2005/083093 A | 9/2005 |

OTHER PUBLICATIONS

U.S. Appl. No. 60/583,041, filed Jun. 25, 2004, Damude et al.
U.S. Appl. No. 60/624,812, filed Nov. 4, 2004, Damude et al.
Colin Ratledge, Microbial Oils and Fats: An Assessment of Their Commercial Potential, Progress in Industrial Microbiology, vol. 16:119-206, 1982.
National Center for Biotechnology Information General Identifier No. 5639724, Accession No. AAD45877, Jul. 29, 1999, J. G. Wallis et al., The Delta8-desaturase of Euglena gracilis: an alternate pathway for synthesis of 20-carbon polyunsaturated fatty acids.
James G. Wallis et al., The Delta8-Desaturase of Euglena gracilis: An Alternate Pathway for Synthesis of 20-Carbon Polyunsaturated Fatty Acids, Archives of Biochemistry and Biophysics, vol. 365(2):307-316, 1999.
Baoxiu Qi et al., Production of very long chain polyunsaturated omega-3 and omega-6 fatty acids in plants, Nature Biotechnology, vol. 22(6):739-745, 2004.
James P. Spychalla et al., Identification of an animal w-3 fatty acid desaturase by heterologous expression in Arabidopsis, PNAS, vol. 94:1142-1147, 1997.
Janice McColl, Health Benefits of Omega-3 Fatty Acids, Nutraceuticals, vol. 2(4):35-40, 2003.
National Center for Biotechnology Information General Identifier No. 22296825, Accession No. AY131238, Aug. 17, 2002, A. El Filali et al., Characterization and cloning of delta-6-desaturase in Argenia spinosa fruit.
National Center for Biotechnology Information General Identifier No. 17223796, Accession No. AY055118, Dec. 1, 2001, F. G. Maroto et al., Cloning and Molecular Characterization of the D6-Desaturase from Echium: Functional Expression in Yeast and Tobacco.
National Center for Biotechnology Information General Identifier No. 17223794, Accession No. AY055117, Dec. 1, 2001, F. G. Maroto et al., Cloning and Moleular Characterization of the D6-Desaturase from Echium: Functional Expression in Yeast and Tobacco.
National Center for Biotechnology Information General Identifier No. 11527282, Accession No. AF296076, Dec. 22, 2000, K. Laoteng et al., Delta(6)-desaturase of Mucor rouxii with high similarity to plant delta(6)-desaturase and its heterologous expression in *Saccharomyces cerevisiae*.
National Center for Biotechnology Information General Identifier No. 4102020, Accession No. AF007561, Jan. 5, 1999, A. N. Nunberg et al.

(Continued)

*Primary Examiner*—Elizabeth F McElwain

(57) ABSTRACT

Isolated nucleic acid fragments and recombinant constructs comprising such fragments encoding a delta-8 desaturase along with a method of making long chain polyunsaturated fatty acids (PUFAs) using this delta-8 desaturase in plants and oleaginous yeast.

14 Claims, 10 Drawing Sheets

OTHER PUBLICATIONS

National Center for Biotechnology Information General Identifier No. 349562, Accession No. L11421, Aug. 13, 1993, A. S. Reddy et al., Isolation of a delta 6-desaturase gene from the cyanobacterium Synechocystis sp. strain PCC 6803 by gain-of-function expression in Anabaena sp. strain PCC 7120.

National Center for Biotechnology Information General Identifier No. 52138608, Accession No. NM_031344, Jun. 14, 2005, C. Comte et al., Effects of streptozotocin and dietary fructose on delta-6 desaturation in spontaneously hypertensive rat liver.

National Center for Biotechnology Information General Identifier No. 18483178, Accession No. AF465283, Feb. 4, 2002, L. Liu et al., Cloning and sequence analysis of the delta 6 fatty acid desaturase gene from Mortiarella aplina ATCC16266 genomic and cDNA.

National Center for Biotechnology Information General Identifier No. 18483174, Accession No. AF465281, Feb. 4, 2002, L. Liu et al., Cloning and sequence analysis of the delta 6 fatty acid desaturase gene from Mortierella aplina ATCC16266 genomic and cDNA.

National Center for Biotechnology Information General Identifier No. 6448795, Accession No. AF110510, Nov. 18, 1999, Y. S. Huang et al., Cloning of delta12- and delta6-desaturases from Mortierella alpina and recombinant production of gamma-linolenic acid in *Saccharomyces cerevisiae*.

National Center for Biotechnology Information General Identifier No. 18483176, Accession No. AF465282, Feb. 4, 2002, L. Xing et al., Cloning and sequence analysis of the delta 6 fatty acid desaturase gene from Mortieralla isabellina M6-22 genomic and cDNA.

National Center for Biotechnology Information General Identifier No. 16033736, Accession No. AF419296, Oct. 11, 2001, H. Hong et al., A delta-6 fatty acid desaturase from Pythium irregulare.

National Center for Biotechnology Information General Identifier No. 15823619, Accession No. AB052086, Oct. 2, 2001, Y. Michinaka et al., Cloning and characterization of a delta-6 fatty acid desaturase from Mucor circinelloides.

National Center for Biotechnology Informaiton General Identifier No. 8670978, Accession No. AJ250735, Apr. 15, 2005, P. Sperling et al., A bifunctional delta-fatty acyl acetylenase/desaturase from the moss Ceratodon purpureus. A new member of the cyochrome b5 superfamily.

National Center for Biotechnology Information General Identifier No. 4406527, Accession No. AF126799, Jun. 21, 2000, H. P. Cho et al., Cloning, expression, and nutritional regulation of the mammalian Delta-6 desaturase.

National Center for Biotechnology Information General Identifier No. 4406525, Accession No. AF126798, Aug. 21, 2000, H. P. Cho et al., Cloning, expression, and nutritional regulation of the mammalian Delta-6 desaturase.

National Center for Biotechnology Information General Identifier No. 6842049, Accession No. AF199596, Jun. 21, 2003, H. P. Cho et al., Cloning, expression, and fatty acid regulation of the human delta-6 desaturase.

National Center for Biotechnology Information General Identifier No. 7861969, Accession No. AF226273, May 17, 2000, A. E. Leonard et al., cDNA cloning and characterization of human Delta5-desaturase involved in the biosynthesis of arachidonic acid.

National Center for Biotechnology Information General Identifier No. 11386008, Accession No. AF320509, Aug. 13, 2001, R. Zolfaghari et al., Fatty acid delta(5)-desaturase mRNA is regulatd by dietary vitamin A and exogenous retinoic acid in liver of adult rats.

National Center for Biotechnology Information General Identifier No. 16151828, Accession No. AB072976, Oct. 16, 2001, T. Matsuzaka et al., Dual gene regulation of mouse delta-5 and -6 desaturase by SREBP-1 and PPAR alpha.

National Center for Biotechnology Information General Identifier No. 20069122, Accession No. AF489588, Apr. 8, 2002, X. Qiu et al., Identification of a Delta 4 fatty acid desaturase from Thraustochytrium sp. involved in the biosynthesis of docosahexanoic acid by heterologous expression in *Saccharomyces cerevisiae* and *Brassica juncea*.

National Center for Biotechnology Information General Identifier No. 23894017, Accession No. AJ510244, Apr. 15, 2005, E. Hornung et al., Specific formation of arachidonic acid by a front-end delta5-desaturase from Phytophthora megasperma.

National Center for Biotechnology Information General Identifier No. 16033739, Accession No. AF419297, Mar. 24, 2005, H. Hong et al., Isolation and characterization of a delta5 FA desaturase from Pythlum irregulare by heterologous expression in *Saccharomyces cerevisiae* and oilseed crops.

National Center for Biotechnology Information General Identifier No. 4003522, Accession No. AF078796, Dec. 11, 1998, L. V. Michaelson et al., Functional identification of a fatty acid delta5 desaturase gene from *Caenorhabditis elegans*.

National Center for Bitoechnology Information General Identifier No. 3859487, Accession No. AF067654, Nov. 11, 1998, D. S. Knutzon et al., Identification of Delta5-desaturase from Mortierella alpina by heterologous expression in Bakers' yeast and canola.

National Center for Biotechnology Information General Identifier No. 4150955, Accession No. AB022097, Apr 17, 2003, T. Saito et al., A second functional delta5 fatty acid desaturase in the cellular slime mould Dictyostelium discoideum.

National Center for Biotechnology Information General Identifier No. 11527199, Accession No. AAG36933, Jul. 10, 2001, A. M. Calvo et al., Genetic connection between fatty acid metabolism and sporulation in *Aspergillus nidulans*.

National Center for Biotechnology Information General Identifier No. 6448793, Accession No. AF110509, Nov. 18, 1999, Y. S. Huang et al., Cloning of delta12- and delta6-desaturases from Mortierella alpina and recombinant production of gamma-linolenic acid in *Saccharomyces cerevisiae*.

National Center for Biotechnology Information General Identifier No. 5257238, Accession No. AB020033, Jun. 26, 1999, E. Sakuradani et al., Identification of Delta12-fatty acid desaturase from arachidonic acid-producing mortierella fungus by heterologous expression in the yeast *Saccharomyces cerevisiae* and the fungus *Aspergillus oryzae*.

National Center for Biotechnology Information General Identifier No. 16033618, Accession No. AAL13300, Oct. 11, 2001, L. Liu et al., Delta 12 fatty acid desaturase gene of *Mortierella alpina*.

National Center for Biotechnology Information General Identifier No. 16033617, Accession No. AF417244, Oct. 11, 2001, L. Liu et al., Delta 12 fatty acid desaturase gene of *Mortierella alpina*.

National Center for Biotechnology Information General Identifier No. 5917669, Accession No. AF161219, Oct. 12, 1999, S. Passorn et al., Heterologous expression of Mucor rouxii delta(12)-desaturase gene in *Saccharomyces cerevisiae*.

National Center for Biotechnology Information General Identifier No. 37683438, Accession No. AY332747, Nov. 7, 2003, T. Tonon et al., Identification of a very long chain polyunsaturated fatty acid delta4-desaturase from the microalga Pavlova lutheri.

National Center for Biotechnology Information General Identifier No. 805063, Accession No. X86736, May 9, 1995, N. Murata et al., Biosynthesis of gamma- linolenic acid in the cyanobacterium *Spirulina platensis*.

National Center for Biotechnology Information General Identifier No. 7546992, Accession No. AF240777, Apr. 13, 2000, M. M. Peyou-Ndi et al., Identification and characterization of an Animal Delta 12 Fatty Acid Desaturase Gene by Heterologous Expression in *Saccharomyces cerevisiae*.

National Center for Biotechnology Information General Identifier No. 2696716, Accession No. AB007640, Nov. 21, 2003, N. Sato et al., Cloning of a gene for chloroplast omega6 desaturase of a green alga, *Chlamydomonas reinhardtii*.

National Center for Biotechnology Information General Identifier No. 17402592, Accession No. AB075526, Sep. 17, 2005, K. Suga et al., Two low-temperature-inducible Chlorella genes for delta12 and omega-3 fatty acid desaturase (FAD): isolation of delta12 and omega-3 fad cDNA clones, expression of delta12 fad in *Saccharomyces cerevisiae*, and expression of omega-3 fad in Nicotiana tabacum.

National Center for Biotechnology Information General Identifier No. 9294104, Accession No. AP002063, Feb. 14, 2004, T. Kaneko et al., Structural analysis of *Arabidopsis thallana* chromosome 3. II. Sequence features of the 4,251,695 bp regions covered by 90 P1, TAC and BAC clones.

National Center for Biotechnology Information General Identifier No. 16330894, Accession No. NP_441622, Nov. 9, 2004, T. Kaneko et al., Sequence analysis of the genome of the unicellular cyanobacterium Synechocystis sp. strain PCC6803. II. Sequence determination of the entire genome and assignment of potential protein-coding regions.

National Center for Biotechnology Information General Identifier No. 1653388, Accession No. BAA18302, Dec. 9, 2004, T. Kaneko et al., Sequence analysis of the genome of the unicellular cyanobacterium Synechocystis sp. strain PCC6803. II. Sequence features in the 1 Mb region from map positions 64% to 92% of the genome.

National Center for Biotechnology Information General Identifier No. 600598, Accession No. BAA02924, Feb. 3, 1999, T. Sakamoto et al., Cloning of omega 3 desaturase from cyanobacteria and its use in altering the degree of membrane-lipid unsaturation.

National Center for Biotechnology Information General Identifier No. 17224294, Accession No. AAL36934, Feb. 2, 2001, K. -H. Kim et al., Cloning of Perilla delta-15 desaturase.

National Center for Biotechnology Information General Identifier No. 13430288, Accession No. AF338466, Nov. 15, 2002, M. H. Riddervold et al., Biochemical and molecular characterization of house cricket (*Acheta domesticus*, Orthoptera: Gryllidae) Delta9 desaturase.

National Center for Biotechnology Information General Identifier No. 20142324, Accession No. AF438199, Sep. 20, 2002, E. -F. Marillia et al., A desaturase-like protein from white spruce is a delta9 desaturase.

National Center for Biotechnology Information General Identifier No. 22025001, Accession No. E11368, Sep. 29, 1997, N. Murata, Recombinant Delta9 Unsaturated Enzyme and Gene Coding the Same.

National Center for Biotechnology Information General Identifier No. 22025000, Accession No. E11367, Sep. 29, 1997, N. Murata, Recombinant Delta9 Unsaturated Enzyme and Gene Coding the Same.

National Center for Biotechnology Information General Identifier No. 1871453, Accession No. D83185, Sep. 1, 2000, S. Anamnart et al., The P-OLE1 gene of Pichia anguste encodes a delta 9-fatty acid desaturase and complements of the ole1 mutation of *Saccharomyces cerevisiae*.

National Center for Biotechnology Information General Identifier No. 4099842, Accession No. U90417, Jul. 25, 2000, L. L. Kiseleva et al., Expression of the gene for the delta9 acyl-lipid desaturase in the thermophilic cyanobacterium.

National Center for Biotechnology Information General Identifier No. 6449429, Accession No. AF085500, Nov. 18, 1999, P. Wongwathanarat et al., Two fatty acid delta9-desaturase genes, ole1 and ole2, from Mortierella alpina complement the yeast ole1 mutation.

National Center for Biotechnology Information General Identifier No. 40737098, Accession No. AY504633, Mar. 30, 2004, R. A. Wilson et al., Two delta9-stearic acid desaturases are required for *Aspergillus nidulans* growth and development.

National Center for Biotechnology Information General Identifier No. 71994839, Accession No. NM_069854, Aug. 19, 2005.

National Center for Biotechnology Information General Identifier No. 13182880, Accession No. AF230693, May 7, 2003, M. Fourmann et al., From *Arabidopsis thaliana* to *Brassica napus*: development of amplified consensus genetic markers (ACGM) for construction of a gene map.

National Center for Biotechnology Information General Identifier No. 17226122, Accession No. AF390174, Feb. 13, 2001, B. Qi et al., Identification of a cDNA encoding a novel C18-Delta(9) polyunsaturated fatty acid-specific elongating activity from the docosahexaenoic acid (DNA)-producing microalga,*Isochrysls galbana*.

National Center for Biotechnology Information General Identifier No. 21899501, Accession No. AX464731, Jul. 16, 2002, P. Mukerji et al., Elongase genes and uses thereof.

National Center for Biotechnology Information General Identifier No. 30690063, Accession No. NM_119617, Feb. 23, 2005.

National Center for Biotechnology Information General Identifier No. 31981652, Accession No. NM_134255, Oct. 14, 2005, S. Katayama et al., Antisense transcription in the mammalian transcriptome.

National Center for Biotechnology Information General Identifier No. 25742685, Accession No. NM_134383, Apr. 23, 2005, K. Inagaki et al., Identification and expression of a rat fatty acid elongase involved in the biosynthesis of C18 fatty acids.

National Center for Biotechnology Information General Identifier No. 19705492, Accession No. NM_134382, Apr. 23, 2005, K. Inagaki et al., Identification and expression of a rat fatty acid elongase involved in the biosynthesis of C18 fatty acids.

National Center for Biotechnology Information General Identifier No. 71988477, Accession No. NM_068396, Aug. 19, 2005.

National Center for Biotechnology Information General Identifier No. 71988472, Accession No. NM_068392, Aug. 19, 2005.

National Center for Biotechnology Information General Identifier No. 71986287, Accession No. NM_070713, Aug. 19, 2005.

National Center for Biotechnology Information General Identifier No. 71985633, Accession No. NM_068746, Aug. 19, 2005.

National Center for Biotechnology Information General Identifier No. 17537430, Accession No. NM_064685, Aug. 19, 2005.

Database Uniport, May 1, 2000, Wallis, J.G. et al., The Delta8-desaturase of *Euglena gracilis*: an alternate pathway for RT synthesis of 20-carbon polyunsaturated fatty acids, Database Accession No. Q9SWQ9, XP002348565.

Database Biosis, Biosciences Information Service, Sep. 2002, Lin Tao et al, High-frequency codon analysis and its application in codon analysis of tobacco, Database Accession No. PREV200300003812, XP002348320.

Database EMBL, Feb. 23, 2005, Sequence 1 from Patent WO2005012316, EBI Accession No. EM_PRO:CS020047, XP002348321.

Database EMBL, Feb. 23, 2005, Sequence 2 from Patent WO2005012316, EBI Accession No. EPOP:CS020048, XP002348322.

Database EMBL, Jul. 29, 2004, Sequence 1 from Patent WO2004057001, EBI Accession No. EM_PRO:CQ831420, XP002348323.

Database EPO Proteins, Jul. 29, 2004, Sequence 2 from Patent WO2004057001, EBI Accession No. EPOP:CQ831421, XP002348324.

Database EMBL, Sep. 21, 2005, Sequence 1 from Patent WO2005083093, EBI Accession No. EM_PRO:CS160815, XP002348325.

National Center for Biotechnology Information General Identifier No. 390174, Accession No. T09146, Aug. 3, 1993, M. D. Adams et al., Rapid cDNA sequencing (expressed sequence tags) from a directionally cloned human infant brain cDNA library.

Figure 2

```
               ******* **      ****   ************************** *********
SEQ ID NO: 2   MKSKRQAL-PLTIDGTTYDVSAWVNFHPGGAEIIENYQGRDATDAFMVMHSQEAFDKLKR
SEQ ID NO: 4   MKSKRQAL-PLTIDGTTYDVSAWVNFHPGGAEIIENYQGRDATDAFMVMHSQEAFDKLKR
SEQ ID NO: 6   MKSKRQALSPLQLMEQTYDV---VNFHPGGAEIIENYQGRDATDAFMVMHFQEAFDKLKR
SEQ ID NO: 7   MKSKRQALSPLQLMEQTYDVSAWVNFHPGGAEIIENYQGRDATDAFMVMHFQEAFDKLKR

****** ************************************************
SEQ ID NO: 2   MPKINPSSELPPQAAVNEAQEDFRKLREELIATGMFDASPLWYSYKISTTLGLGVLGYFL
SEQ ID NO: 4   MPKINPSSELPPQAAVNEAQEDFRKLREELIATGMFDASPLWYSYKISTTLGLGVLGYFL
SEQ ID NO: 6   MPKINPSFELPPQAAVNEAQEDFRKLREELIATGMFDASPLWYSYKISTTLGLGVLGYFL
SEQ ID NO: 7   MPKINPSFELPPQAAVNEAQEDFRKLREELIATGMFDASPLWYSYKISTTLGLGVLGYFL

********************************************************* **
SEQ ID NO: 2   MVQYQMYFIGAVLLGMHYQQMGWLSHDICHHQTFKNRNWNNLVGLVFGNGLQGFSVTWWK
SEQ ID NO: 4   MVQYQMYFIGAVLLGMHYQQMGWLSHDICHHQTFKNRNWNNLVGLVFGNGLQGFSVTWWK
SEQ ID NO: 6   MVQYQMYFIGAVLLGMHYQQMGWLSHDICHHQTFKNRNWNNLVGLVFGNGLQGFSVTCWK
SEQ ID NO: 7   MVQYQMYFIGAVLLGMHYQQMGWLSHDICHHQTFKNRNWNNLVGLVFGNGLQGFSVTCWK

****************************  ******************************
SEQ ID NO: 2   DRHNAHHSATNVQGHDPDIDNLPLLAWSEDDVTRASPISRKLIQFQQYYFLVICILLRFI
SEQ ID NO: 4   DRHNAHHSATNVQGHDPDIDNLPLLAWSEDDVTRASPISRKLIQFQQYYFLVICILLRFI
SEQ ID NO: 6   DRHNAHHSATNVQGHDPDIDNLPPLAWSEDDVTRASPISRKLIQFQQYYFLVICILLRFI
SEQ ID NO: 7   DRHNAHHSATNVQGHDPDIDNLPPLAWSEDDVTRASPISRKLIQFQQYYFLVICILLRFI

******************** *********************************
SEQ ID NO: 2   WCFQSVLTVRSLKDRDNQFYRSQYKKEAIGLALHWTLKTLFHLFFMPSILTSLLVFFVSE
SEQ ID NO: 4   WCFQSVLTVRSLKDRDNQFYRSQYKKEAIGLALHWTLKALFHLFFMPSILTSLLVFFVSE
SEQ ID NO: 6   WCFQCVLTVRSLKDRDNQFYRSQYKKEAIGLALHWTLKALFHLFFMPSILTSLLVFFVSE
SEQ ID NO: 7   WCFQCVLTVRSLKDRDNQFYRSQYKKEAIGLALHWTLKALFHLFFMPSILTSLLVFFVSE

******************** ****************************************
SEQ ID NO: 2   LVGGFGIAIVVFMNHYPLEKIGDSVWDGHGFSVGQIHETMNIRRGIITDWFFGGLNYQIE
SEQ ID NO: 4   LVGGFGIAIVVFMNHYPLEKIGDSVWDGHGFSVGQIHETMNIRRGIITDWFFGGLNYQIE
SEQ ID NO: 6   LVGGFGIAIVVFMNHYPLEKIGDPVWDGHGFSVGQIHETMNIRRGIITDWFFGGLNYQIE
SEQ ID NO: 7   LVGGFGIAIVVFMNHYPLEKIGDPVWDGHGFSVGQIHETMNIRRGIITDWFFGGLNYQIE

************************************************************
SEQ ID NO: 2   HHLWPTLPRHNLTAVSYQVEQLCQKHNLPYRNPLPHEGLVILLRYLAVFARMAEKQPAGK
SEQ ID NO: 4   HHLWPTLPRHNLTAVSYQVEQLCQKHNLPYRNPLPHEGLVILLRYLAVFARMAEKQPAGK
SEQ ID NO: 6   HHLWPTLPRHNLTAVSYQVEQLCQKHNLPYRNPLPHEGLVILLRYLAVFARMAEKQPAGK
SEQ ID NO: 7   HHLWPTLPRHNLTAVSYQVEQLCQKHNLPYRNPLPHEGLVILLRYLAVFARMAEKQPAGK

*
SEQ ID NO: 2   AL.
SEQ ID NO: 4   AL.
SEQ ID NO: 6   A-L
SEQ ID NO: 7   A-L
```

DELTA-8 DESATURASE AND ITS USE IN MAKING POLYUNSATURATED FATTY ACIDS

This application claims the benefit of U.S. Provisional Application No. 60/583,041, filed Jun. 25, 2004, and U.S. Provisional Application No. 60/624,812, filed Nov. 4, 2004, the entire contents of which are herein incorporated by reference.

FIELD OF THE INVENTION

This invention pertains to a polynucleotide sequence encoding a delta-8 desaturase and the use of this desaturase in making long chain polyunsaturated fatty acids (PUFAs).

BACKGROUND OF THE INVENTION

Lipids/fatty acids are water-insoluble organic biomolecules that can be extracted from cells and tissues by nonpolar solvents such as chloroform, ether or benzene. Lipids have several important biological functions, serving as: (1) structural components of membranes; (2) storage and transport forms of metabolic fuels; (3) a protective coating on the surface of many organisms; and, (4) cell-surface components concerned in cell recognition, species specificity and tissue immunity. More specifically, polyunsaturated fatty acids (PUFAs) are important components of the plasma membrane of the cell, where they may be found in such forms as phospholipids and also can be found in triglycerides. PUFAs also serve as precursors to other molecules of importance in human beings and animals, including the prostacyclins, leukotrienes and prostaglandins. There are two main families of PUFAs (i.e., the omega-3 fatty acids and the omega-6 fatty acids).

The human body is capable of producing most of the PUFAs which it requires to function; however, eicosapentaenoic acid (EPA; 20:5, delta-5,8,11,14,17) and docosahexaenoic acid (DHA; 22:6, delta-4,7,10,13,16,19) cannot be synthesized efficiently by the human body and thus must be supplied through the diet. Since the human body cannot produce adequate quantities of these PUFAs, they are called essential fatty acids. Because of their important roles in human health and nutrition, EPA and DHA are the subject of much interest as discussed herein.

DHA is a fatty acid of the omega-3 series according to the location of the last double bond in the methyl end. It is synthesized via alternating steps of desaturation and elongation. Production of DHA is important because of its beneficial effect on human health; for example, increased intake of DHA has been shown to be beneficial or have a positive effect in inflammatory disorders (e.g., rheumatoid arthritis), Type II diabetes, hypertension, atherosclerosis, depression, myocardial infarction, thrombosis, some cancers and for prevention of the onset of degenerative disorders such as Alzheimer's disease. Currently the major sources of DHA are oils from fish and algae.

EPA and arachidonic acid (AA or ARA; 20:4, delta-5,8,11, 14) are both delta-5 essential fatty acids. EPA belongs to the omega-3 series with five double bonds in the acyl chain, is found in marine food, and is abundant in oily fish from the North Atlantic. Beneficial or positive effects of increased intake of EPA have been shown in patients with coronary heart disease, high blood pressure, inflammatory disorders, lung and kidney diseases, Type II diabetes, obesity, ulcerative colitis, Crohn's disease, anorexia nervosa, burns, osteoarthritis, osteoporosis, attention deficit/hyperactivity disorder and early stages of colorectal cancer (see, for example, the review of McColl, J., NutraCos 2(4):35-40 (2003)).

AA belongs to the omega-6 series with four double bonds. The lack of a double bond in the omega-3 position confers on AA different properties than those found in EPA. The eicosanoids produced from M have strong inflammatory and platelet aggregating properties, whereas those derived from EPA have anti-inflammatory and anti-platelet aggregating properties. AA is recognized as the principal ω-6 fatty acid found in the human brain and an important component of breast milk and many infant formulas, based on its role in early neurological and visual development. AA can be obtained from some foods such as meat, fish, and eggs, but the concentration is low.

Gamma-linolenic acid (GLA; 18:3, delta-6,9,12) is another essential fatty acid found in mammals. GLA is the metabolic intermediate for very long chain omega-6 fatty acids and for various active molecules. In mammals, formation of long chain PUFAs is rate-limited by delta-6 desaturation. Many physiological and pathological conditions such as aging, stress, diabetes, eczema, and some infections have been shown to depress the delta-6 desaturation step. In addition, GLA is readily catabolized from the oxidation and rapid cell division associated with certain disorders, e.g., cancer or inflammation.

As described above, research has shown that various omega fatty acids reduce the risk of heart disease, have a positive effect on children's development and on certain mental illnesses, autoimmune diseases and joint complaints. However, although there are many health benefits associated with a diet supplemented with these fatty acids, it is recognized that different PUFAs exert different physiological effects in the body (e.g., most notably, the opposing physiological effects of GLA and AA). Thus, production of oils using recombinant means is expected to have several advantages over production from natural sources. For example, recombinant organisms having preferred characteristics for oil production can be used, since the naturally occurring fatty acid profile of the host can be altered by the introduction of new biosynthetic pathways in the host and/or by the suppression of undesired pathways, thereby resulting in increased levels of production of desired PUFAs (or conjugated forms thereof) and decreased production of undesired PUFAs. Optionally, recombinant organisms can provide PUFAs in particular forms which may have specific uses; or, oil production can be manipulated such that the ratio of omega-3 to omega-6 fatty acids so produced is modified and/or a specific PUFA is produced without significant accumulation of other PUFA downstream or upstream products (e.g., production of oils comprising ARA and lacking GLA).

The mechanism of PUFA synthesis frequently occurs via the delta-6 desaturation pathway. For example, long chain PUFA synthesis in mammals proceeds predominantly by a delta-6 desaturation pathway, in which the first step is the delta-6 desaturation of LA and ALA to yield GLA and stearidonic acid (STA; 18:4, delta-6,9,12,15), respectively. Further fatty acid elongation and desaturation steps give rise to AA and EPA. Accordingly, genes encoding delta-6 desaturases, delta-6 elongase components (also identified as $C_{18/20}$ elongases) and delta-5 desaturases have been cloned from a variety of organisms including higher plants, algae, mosses, fungi, nematodes and humans. Humans can synthesize long chain PUFAs from the essential fatty acids, linoleic acid (LA;18:2, delta-9,12) and alpha-linolenic acid (ALA; 18:3, delta-9,12,15); LA and ALA must be obtained from the diet. However, biosynthesis of long chain PUFAs is somewhat limited and is regulated by dietary and hormonal changes.

WO 02/26946 (published Apr. 4, 2002) describes isolated nucleic acid molecules encoding FAD4, FAD5, FAD5-2 and FAD6 fatty acid desaturase family members which are expressed in long chain PUFA-producing organisms, e.g., *Thraustochytrium, Pythium irregulare, Schizichytrium* and *Crypthecodinium*. It is indicated that constructs containing the desaturase genes can be used in any expression system including plants, animals, and microorganisms for the production of cells capable of producing long chain PUFAs.

WO 98/55625 (published Dec. 19, 1998) describes the production of PUFAs by expression of polyketide-like synthesis genes in plants.

WO 98/46764 (published Oct. 22, 1998) describes compositions and methods for preparing long chain fatty acids in plants, plant parts and plant cells which utilize nucleic acid sequences and constructs encoding fatty acid desaturases, including delta-5 desaturases, delta-6 desaturases and delta-12 desaturases.

U.S. Pat. No. 6,075,183 (issued to Knutzon et al. on Jun. 13, 2000) describes methods and compositions for synthesis of long chain PUFAs in plants.

U.S. Pat. No. 6,459,018 (issued to Knutzon et al. on Oct. 1, 2002) describes a method for producing STA in plant seed utilizing a construct comprising a DNA sequence encoding a delta-6 desaturase.

Spychalla et al. (*Proc. Natl. Acad. Sci. USA,* 94:1142-1147 (1997)) describes the isolation and characterization of a cDNA from *C. elegans* that, when expressed in *Arabidopsis*, encodes a fatty acid desaturase which can catalyze the introduction of an omega-3 double bond into a range of 18- and 20-carbon fatty acids.

An alternate pathway for the biosynthesis of AA and EPA operates in some organisms (i.e., the delta-9 elongase/delta-8 desaturase pathway). Here LA and ALA are first elongated to eicosadienoic acid (EDA; 20:2, delta-11,14) and eicosatrienoic acid (EtrA; 20:3, delta-11,14,17), respectively, by a delta-9 elongase. Subsequent delta-8 and delta-5 desaturation of these products yields AA and EPA. The delta-8 pathway is present inter alia, in euglenoid species where it is the dominant pathway for formation of 20-carbon PUFAs.

WO 2000/34439 (published Jun. 15, 2000) discloses amino acid and nucleic acid sequences for delta-5 and delta-8 desaturase enzymes. Based on the information presented herein, it is apparent that the delta-8 nucleotide and amino acid sequences of WO 2000/34439 are not correct.

Wallis et al. (*Archives of Biochemistry and Biophysics,* 365(2):307-316 (May 15, 1999)) describes the cloning of a gene that appears to encode a delta-8 desaturase in *Euglena gracilis*. This appears to be the same sequence disclosed in WO 2000/34439.

Qi et al. (*Nature Biotechnology,* 22(6):739-45 (2004)) describes the production of long chain PUFAs using, among other things, a delta-8 desaturase from *E. gracilis*; however, the complete sequence of the delta-8 desaturase is not provided.

WO 2004/057001 (published Jul. 8, 2004) discloses amino acid and nucleic acid sequences for a delta-8 desaturase enzyme from *E. gracilis.*

An expansive study of PUFAs from natural sources and from chemical synthesis are not sufficient for commercial needs. Therefore, it is of interest to find alternative means to allow production of commercial quantities of PUFAs. Biotechnology offers an attractive route for producing long chain PUFAs in a safe, cost efficient manner in microorganisms and plants.

With respect to microorganisms, many algae, bacteria, molds and yeast can synthesize oils in the ordinary course of cellular metabolism. Thus, oil production involves cultivating the microorganism in a suitable culture medium to allow for oil synthesis, followed by separation of the microorganism from the fermentation medium and treatment for recovery of the intracellular oil. Attempts have been made to optimize production of fatty acids by fermentive means involving varying such parameters as microorganisms used, media and conditions that permit oil production. However, these efforts have proved largely unsuccessful in improving yield of oil or the ability to control the characteristics of the oil composition produced. One class of microorganisms that has not been previously examined as a production platform for PUFAs (prior to work by the Applicants' Assignee), however, are the oleaginous yeasts. These organisms can accumulate oil up to 80% of their dry cell weight. The technology for growing oleaginous yeast with high oil content is well developed (for example, see EP 0 005 277B1; Ratledge, C., *Prog. Ind. Microbiol.* 16:119-206 (1982)), and may offer a cost advantage compared to commercial micro-algae fermentation for production of omega-3 or omega-6 PUFAs. Whole yeast cells may also represent a convenient way of encapsulating omega-3 or omega-6 PUFA-enriched oils for use in functional foods and animal feed supplements.

WO 2004/101757 and WO 2004/101753 (published Nov. 25, 2004) concern the production of PUFAs in oleaginous yeasts and are Applicants' Assignee's copending applications.

WO 2004/071467 (published Aug. 26, 2004) concerns the production of PUFAs in plants, while WO 2004/071178 (published Aug. 26, 2004) concerns annexin promoters and their use in expression of transgenes in plants; both are Applicants' Assignee's copending applications.

SUMMARY OF THE INVENTION

This invention concerns an isolated polynucleotide comprising:

(a) a nucleotide sequence encoding a polypeptide having delta-8 desaturase activity, wherein the polypeptide has an amino acid sequence consisting essentially of SEQ ID NOs: 2 or 113; or, (b) a complement of the nucleotide sequence, wherein the complement and the nucleotide sequence consist of the same number of nucleotides and are 100% complementary.

In a second embodiment, this invention concerns a recombinant construct comprising SEQ ID NOs:1 or 112 operably linked to at least one regulatory sequence.

In a third embodiment, this invention concerns a cell comprising the recombinant construct of the invention.

In a fourth embodiment, this invention concerns a method for transforming cells, plants and yeast with the recombinant construct of the invention.

In a fifth embodiment, this invention concerns seeds obtained from such plants and oil obtained from such seeds.

In a sixth embodiment, this invention concerns a method for making polyunsaturated fatty acids in a cell.

In a seventh embodiment, this invention concerns an oilseed plant comprising a first recombinant DNA construct comprising an isolated polynucleotide encoding a delta-8 desaturase polypeptide, operably linked to at least one regulatory sequence; and at least one additional recombinant DNA construct comprising an isolated polynucleotide, operably linked to at least one regulatory sequence, encoding a polypeptide selected from the group consisting of a delta-4, a delta-5, delta-6, a delta-9, a delta-12, a delta-15, and a delta-17 desaturase, a delta-9 elongase, a C18 to C22 elongase and a C20 to C24 elongase.

In still another aspect, this invention concerns a method for producing at least one polyunsaturated fatty acid in a soybean cell comprising:

(a) transforming a soybean cell with a first recombinant DNA construct comprising an isolated polynucleotide encoding a delta-8 desaturase polypeptide, operably linked to at least one regulatory sequence and at least one additional recombinant DNA construct comprising an isolated polynucleotide, operably linked to at least one regulatory sequence, encoding a polypeptide selected from the group consisting of a delta-4, a delta-5, delta-6, a delta-9, a delta-12, a delta-15, and a delta-17 desaturase, a delta-9 elongase, a C18 to C22 elongase and a C20 to C24 elongase.

(b) regenerating a soybean plant from the transformed cell of step (a); and (c) selecting those seeds obtained from the plants of step (b) having an altered level of polyunsaturated fatty acids when compared to the level in seeds obtained from a non-transformed soybean plant.

In an eighth emodition this invention concerns an oilseed plant selected from the group consisting of soybean, *Brassica* species, sunflower, maize, cotton, flax, and safflower.

In a ninth embodiment this invention concerns oilseed plants wherein the polyunsaturated fatty acid is selected from the group consisting of AA, EDA, EPA, ETA, EtrA, DGLA, DPA, DHA, Further embodiments include seeds and oil obtained from the plants transformed with the isolated polynucleotides of the instant invention.

Additional embodiments concern food, feed and ingredients derived from the processing of the seeds obtained from the plants transformed with the isolated polynucleotides of the instant invention.

BIOLOGICAL DEPOSITS

The following plasmids have been deposited with the American Type Culture Collection (ATCC), 10801 University Boulevard, Manassas, Va. 20110-2209, and bear the following designations, accession numbers and dates of deposit.

| Plasmid | Accession Number | Date of Deposit |
|---|---|---|
| pKR681 | ATCC PTA-6046 | Jun. 4$^{th}$, 2004 |
| pKR685 | ATCC PTA-6047 | Jun. 4$^{th}$, 2004 |
| pY89-5 | ATCC PTA-6048 | Jun. 4$^{th}$, 2004 |
| pKR274 | ATCC PTA-4988 | Jan. 30$^{th}$, 2003 |
| PKR669 | ATCC PTA-6792 | Jun. 17, 2005 |
| PKR786 | ATCC PTA-6793 | Jun. 17, 2005 |

BRIEF DESCRIPTION OF THE DRAWINGS AND SEQUENCE LISTINGS

The invention can be more fully understood from the following detailed description and the accompanying drawings and Sequence Listing, which form a part of this application.

The sequence descriptions summarize the Sequences Listing attached hereto. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219(2):345-373 (1984).

FIG. 1 shows a chromatogram of the lipid profile of an *Euglena gracilis* cell extract as described in Example 10.

FIG. 2 shows an alignment of the claimed delta-8 desaturase polypeptide sequence from *Euglena gracilis* (SEQ ID NO:2), a version of a delta-8 desaturase with reduced activity (SEQ ID NO:4) and published non-functional versions of delta-8 desaturase sequences set forth in gi:5639724 (GenBank Accession No. AAD45877 and SEQ ID NO:6) and in WO 00/34439 or Wallis et al. (*Archives of Biochem. Biophys*, 365:307-316 (1999)) (SEQ ID NO:7). The method of alignment used corresponds to the "Clustal V method of alignment".

FIG. 3 provides plasmid maps for the following: (A) yeast expression vector pY89-5 as described in Example 5; and, (B) soybean expression vector pKR681 as described in Example 6.

FIG. 4 provides plasmid maps for the following: (A) soybean expression vector pKR685 as described in Example 8; and, (B) expression vector pKR274 as described in Example 9.

FIG. 5 provides plasmid maps for the following: (A) yeast expression vector pDMW240 as described in Example 1; (B) yeast expression vector pDMW255 as described in Example 1; (C) yeast expression vector pDMW261 as described in Example 1; and, (D) vector pKUNFmKF2 as described in Example 14.

FIG. 6 provides plasmid maps for the following: (A) yeast expression vector pDMW277 as described in Example 14; (B) vector pZF5T-PPC as described in Example 14; (C) yeast expression vector pDMW287 as described in Example 14; and, (D) yeast expression vector pDMW287F as described in Example 14.

FIG. 7 provides plasmid maps for the following: (A) vector pZUF17 as described in Example 15; (B) yeast expression vector pDMW237 as described in Example 15; (C) yeast expression vector pKUNT2 as described in Example 16; and, (D) yeast expression vector pDMW297 as described in Example 16.

FIG. 8 provides plasmid maps for the following: (A) soybean expression vector pKR682 as described in Example 17; (B) soybean expression vector pKR786 as described in Example 18; and, (C) soybean expression vector pKR669 as described in Example 19.

Figure 1:
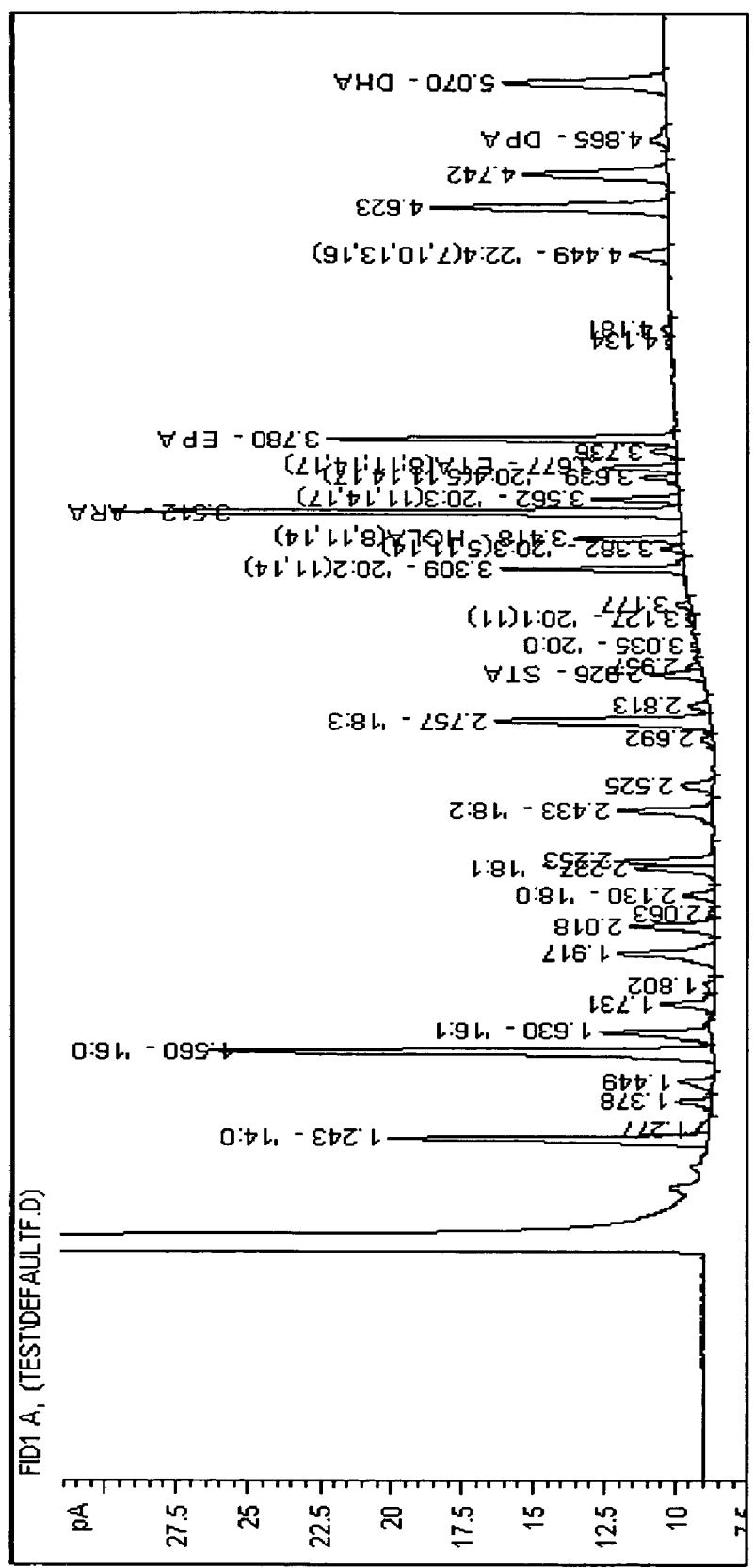

SEQ ID NO:1 represents the 1271 bp of the *Euglena gracilis* sequence containing the ORF (nucleotides 4-1269 (Stop)) of the delta-8 desaturase gene.

SEQ ID NO:2 is the amino acid sequence encoded by nucleotides 4-1269 of SEQ ID NO:1.

SEQ ID NO:3 represents the 1271 bp of the *Euglena gracilis* sequence containing the ORF (nucleotides 4-1269 (Stop)) of the delta-8 desaturase gene containing a guanine for adenine substitution at position 835, as compared to the sequence of SEQ ID NO:1.

SEQ ID NO:4 is the deduced amino acid sequence encoded by nucleotides 4-1269 of SEQ ID NO:3, which contains an alanine for threonine substitution at position 278, when compared to the polypeptide sequence of SEQ ID NO:2.

SEQ ID NO:5 represents 1275 bp of the *Euglena gracilis* sequence set forth in gi:5639724 (GenBank Accession No. AAD45877), containing the ORF (nucleotides 14-1273 (Stop)) of a non-functional version of the delta-8 desaturase gene.

SEQ ID NO:6 is the deduced amino acid sequence encoded by nucleotides of SEQ ID NO:5 and set forth in gi:5639724.

SEQ ID NO:7 is the amino acid sequence of a non-functional version of the delta-8 desaturase disclosed in Wallis et al. (*Archives of Biochem. Biophys.*, 365:307-316 (1999) and WO 00/34439).

SEQ ID NO:8 is the forward primer used for amplification of the delta-8 desaturase from *Euglena gracilis* in Example 3.

SEQ ID NO:9 is the reverse primer used for amplification of the delta-8 desaturase from *Euglena gracilis* in Example 3.

SEQ ID NO:10 is the forward primer used for sequencing a delta-8 desaturase clone as described in Example 3.

SEQ ID NO:11 is the reverse primer used for sequencing a delta-8 desaturase clone as described in Example 3.

SEQ ID NO:12 is the forward primer used for sequencing a delta-8 desaturase clone as described in Example 3.

SEQ ID NO:13 is the reverse primer used for sequencing a delta-8 desaturase clone as described in Example 3.

SEQ ID NO:14 is the multiple restriction enzyme site sequence introduced in front of the beta-conglycinin promoter as described in Example 6.

SEQ ID NO:15 is the forward primer used for amplification of the elongase.

SEQ ID NO:16 is the reverse primer used for amplification of the elongase.

SEQ ID NO:17 is the multiple restriction enzyme site sequence introduced upstream of the Kti promoter as described in Example 6.

SEQ ID NO:18 sets forth the sequence of the soy albumin transcription terminator with restriction enzyme sites as described in Example 6.

SEQ ID NO:19 is the primer oSalb-12 used for amplification of the albumin transcription terminator.

SEQ ID NO:20 is primer oSalb-13 used for amplification of the albumin transcription terminator.

SEQ ID NO:21 is primer GSP1 used for the amplification of the soybean annexin gene.

SEQ ID NO:22 is primer GSP2 used for the amplification of the soybean annexin gene.

SEQ ID NO:23 is primer GSP3 used for the amplification of soybean BD30.

SEQ ID NO:24 is primer GSP4 used for the amplification of soybean BD30.

SEQ ID NO:25 sets forth the soybean BD30 promoter sequence.

SEQ ID NO:26 sets forth the soybean Glycinin Gy1 promoter sequence.

SEQ ID NO:27 is the forward primer used for amplification of the soybean Glycinin Gy1 promoter sequence.

SEQ ID NO:28 is the reverse primer used for amplification of the soybean Glycinin Gy1 promoter sequence.

SEQ ID NO:29 sets forth the soybean annexin promoter sequence.

SEQ ID NO:30 is the forward primer used for amplification of the soybean annexin promoter sequence.

SEQ ID NO:31 is the reverse primer used for amplification of the soybean annexin promoter sequence.

SEQ ID NO:32 is the forward primer used for amplification of the soybean BD30 promoter sequence.

SEQ ID NO:33 is the reverse primer used for amplification of the soybean BD30 promoter sequence.

SEQ ID NO:34 is primer oKTi5 used for amplification of the Kti/NotI/Kti 3' cassette.

SEQ ID NO:35 is primer oKTi6 used for amplification of the Kti/NotI/Kti 3' cassette.

SEQ ID NO:36 is primer oSBD30-1 used for amplification of the soybean BD30 3' transcription terminator.

SEQ ID NO:37 is primer oSBD30-2 used for amplification of the soybean BD30 3' transcription terminator.

SEQ ID NO:38 is primer oCGR5-1 used for amplification of the *M. alpina* delta-6 desaturase.

SEQ ID NO:39 is primer oCGR5-2 used for amplification of the *M. alpina* delta-6 desaturase.

SEQ ID NO:40 is primer oSGly-1 used for amplification of the glycinin Gy1 promoter.

SEQ ID NO:41 is primer oSGly-2 used for amplification of the glycinin Gy1 promoter.

SEQ ID NO:42 is primer Leg Pro5' used for amplification of the legA2 promoter sequence.

SEQ ID NO:43 is primer LegPro3' used for amplification of the legA2 promoter sequence.

SEQ ID NO:44 is primer LegTerm5' used for amplification of the leg2A transcription terminator.

SEQ ID NO:45 is primer LegTerm3' used for amplification of the leg2A transcription terminator.

SEQ ID NO:46 is primer CGR4forward used for the amplification of the *M. alpina* desaturase.

SEQ ID NO:47 is primer CGR4reverse used for the amplification of the *M. alpina* desaturase.

SEQ ID NO:48 is the *Euglena gracilis* sequence, set forth in nucleotides 14-1275 of SEQ ID NO:5, optimized for codon usage in *Yarrowia lipolytica*.

SEQ ID NOs:49-74 correspond to primers D8-1A, D8-1A, D8-1B, D8-2A, D8-2B, D8-3A, D8-3B, D8-4A, D8-4B, D8-5A, D8-5B, D8-6A, D8-6B, D8-7A, D8-7B, D8-8A, D8-8B, D8-9A, D8-9B, D8-10A, D8-10B, D8-11A, D8-11B, D8-12A, D8-12B, D8-13A and D8-13B, respectively, used for amplification as described in Example 1.

SEQ ID NOs:75-82 correspond to primers D8-1F, D8-3R, D8-4F, D8-6R, D8-7F, D8-9R, D8-10F and D8-13R, respectively, used for amplification as described in Example 1.

SEQ ID NO:83 is the 309 bp Nco/BglII fragment described in Example 1.

SEQ ID NO:84 is the 321 bp BglII/XhoI fragment described in Example 1.

SEQ ID NO:85 is the 264 bp XhoI/SacI fragment described in Example 1.

SEQ ID NO:86 is the 369 bp SacI/NotI fragment described in Example 1.

SEQ ID NO:87 is primer ODMW390 used for amplification as described in Example 1.

SEQ ID NO:88 is primer ODMW391 used for amplification as described in Example 1.

SEQ ID NO:89 is the chimeric gene described in Example 1.

SEQ ID NO:90 is the chimeric gene described in Example 1.

SEQ ID NO:91 is primer ODMW392 used for amplification as described in Example 1.

SEQ ID NO:92 is primer ODMW393 used for amplification as described in Example 1.

SEQ ID NO:93 is the synthetic delta-8 desaturase described in Example 1.

SEQ ID NO:94 is primer ODMW404 used for amplification as described in Example 14.

SEQ ID NO:95 is the Kpn/NotI fragment described in Example 14.

SEQ ID NOs:96-111 correspond to primers YL521, YL522, YL525, YL526, YL527, YL528, YL529, YL530, YL531, YL532, YL533, YL534, YL535, YL536, YL537 and YL538, respectively, used for amplification as described in Example 14.

SEQ ID NO:112 is the nucleotide sequence for the synthetic delta-8 desaturase codon-optimized for expression in *Yarrowia lipolytica*.

SEQ ID NO:113 is the amino acid sequence encoded by nucleotides 2-1270 of SEQ ID NO:112.

SEQ ID NO:114 is the DNA sequence (995 bp) of the *Yarrowia lipolytica* fructose-bisphosphate aldolase promoter containing a *Yarrowia* intron (FBAIN).

SEQ ID NO:118 is the nucleotide sequence for the synthetic delta-9 elongase codon-optimized for expression in *Yarrowia lipolytica*.

SEQ ID NO:119 is the DNA sequence of the *Isochrysis galbana* delta-9 elongase (792 bp), while SEQ ID NO:120 is the amino acid sequence of the *Isochrysis galbana* delta-9 elongase (263 M).

SEQ ID NOs:121-136 correspond to primers IL3-1A, IL3-1B, IL3-2A, IL3-2B, IL3-3A, IL3-3B, IL3-4A, IL3-4B, IL3-5A, IL3-5B, IL3-6A, IL3-6B, IL3-7A, IL3-7B, IL3-8A and IL3-8B, respectively, used for amplification as described in Example 15.

SEQ ID NOs:137-140 correspond to primers IL3-1F, IL3-4R, IL3-5F and IL3-8R, respectively, used for amplification as described in Example 15.

SEQ ID NO:141 is the 417 bp NcoI/PstI fragment described in Example 15.

SEQ ID NO:142 is the 377 bp PstI/Not1 fragment described in Example 15.

SEQ ID NO:146 is the DNA sequence of the *Yaffowia lipolytica* delta-12 desaturase (1936 bp), while SEQ ID NO:147 is the amino acid sequence of the *Yarrowia lipolytica* delta-12 desaturase (419 AA).

SEQ ID NO:149 is primer oIGsel1-1 used for amplifying a delta-9 elongase as described in Example 17.

SEQ ID NO:150 is primer oIGsel1-2 used for amplifying a delta-9 elongase as described in Example 17.

SEQ ID NO:151 is the fragment described in Example 18.

SEQ ID NOs:115, 116, 117, 143, 144, 145 and 148 are plasmids as identified in Table 1.

TABLE 1

Summary of Plasmid SEQ ID Numbers

| Plasmid | SEQ ID NO | Length |
|---|---|---|
| pY54PC | 115 | 8,502 bp |
| pKUNFmkF2 | 116 | 7,145 bp |
| pZF5T-PPC | 117 | 5,553 bp |
| pZUF17 | 143 | 8,165 bp |
| pDMW237 | 144 | 7,879 |
| pKUNT2 | 145 | 6,457 bp |
| pDMW297 | 148 | 10,448 bp |

DETAILED DESCRIPTION OF THE INVENTION

All patents, patent applications, and publications cited herein are incorporated by reference in their entirety.

In the context of this disclosure, a number of terms shall be utilized.

Definitions

The term "fatty acids" refers to long chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in WO2004/101757.

Fatty acids are described herein by a simple notation system of "X:Y", wherein the number before the colon indicates the number of carbon atoms in the fatty acid and the number after the colon is the number of double bonds that are present. The number following the fatty acid designation indicates the position of the double bond from the carboxyl end of the fatty acid with the "c" affix for the cis-configuration of the double bond [e.g., palmitic acid (16:0), stearic acid (18:0), oleic acid (18:1, 9c), petroselinic acid (18:1, 6c), LA (18:2, 9c,12c), GLA (18:3, 6c,9c,12c) and ALA (18:3, 9c,12c,15c)]. Unless otherwise specified 18:1, 18:2 and 18:3 refer to oleic, LA and linolenic fatty acids. If not specifically written as otherwise, double bonds are assumed to be of the cis configuration. For instance, the double bonds in 18:2 (9,12) would be assumed to be in the cis configuration.

Figure 9:
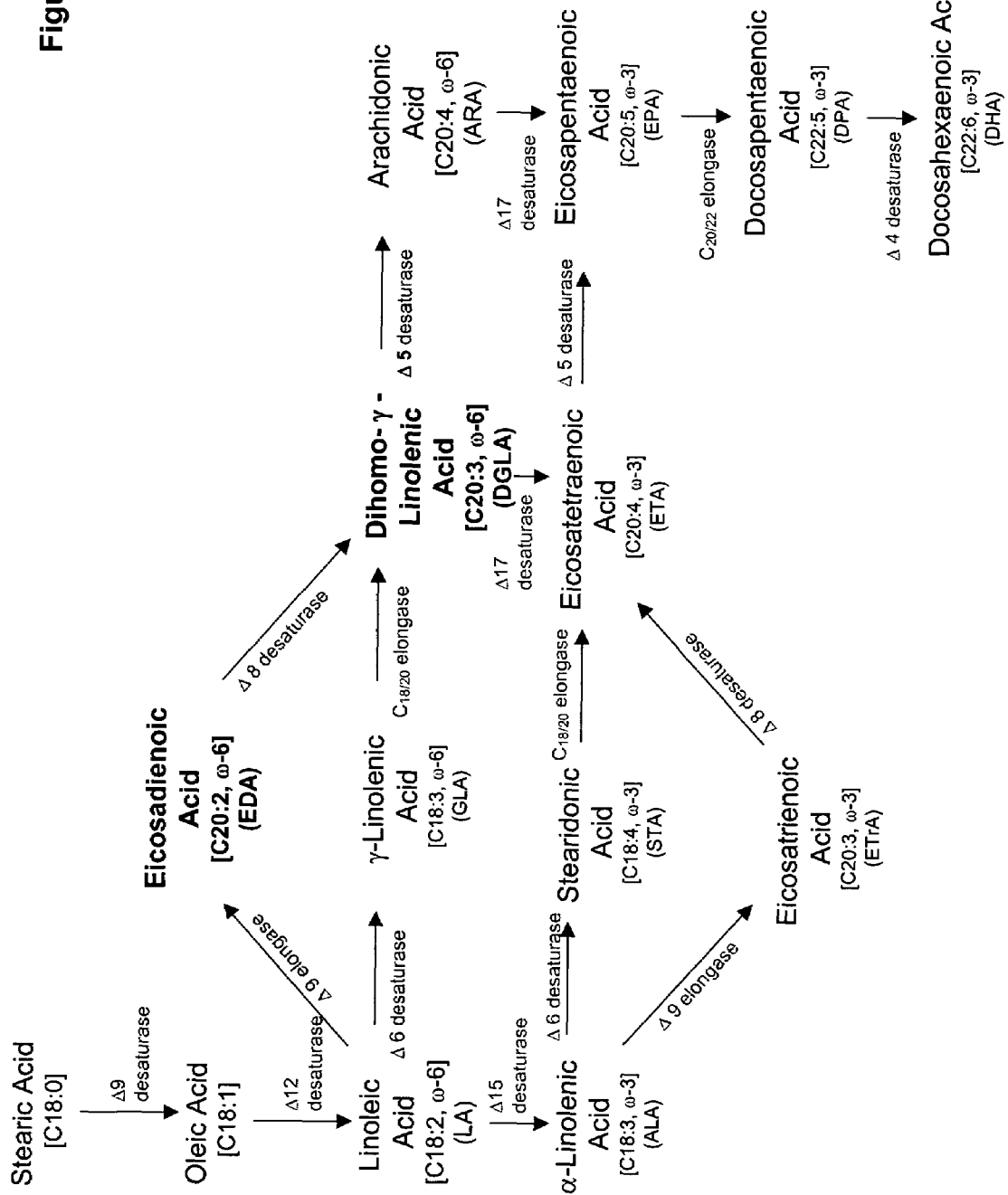
FIG. 9 is a representative PUFA biosynthetic pathway.

A representative pathway is illustrated in FIG. 9, providing for the conversion of stearic acid through various intermediates to DHA, which demonstrates how both ω-3 and ω-6 fatty acids may be produced from a common source.

Nomenclature used to describe PUFAs in the present disclosure is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of omega-3 and omega-6 fatty acids, the abbreviations that will be used throughout the remainder of the specification, and each compounds' chemical name.

TABLE 2

Nomenclature Of Polyunsaturated Fatty Acids

| Common Name | Abbreviation | Chemical Name | Shorthand Notation |
|---|---|---|---|
| Linoleic | LA | cis-9,12-octadecadienoic | 18:2 ω-6 |
| γ-Linoleic | GLA | cis-6,9,12-octadecatrienoic | 18:3 ω-6 |
| Eicosadienoic | EDA | cis-11,14-eicosadienoic | 20:2 ω-6 |
| Dihomo-γ-Linoleic | DGLA | cis-8,11,14-eicosatrienoic | 20:3 ω-6 |
| Arachidonic | AA or ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosatetraenoic | ETA | cis-8,11,14,17-eicosatetraenoic | 20:4 ω-3 |
| Eicosapentaenoic | EPA | cis-5,8,11,14,17-eicosapentaenoic | 20:5 ω-3 |
| Docosapentaenoic | DPA | cis-7,10,13,16,19-docosapentaenoic | 22:5 ω-3 |
| Docosahexaenoic | DHA | cis-4,7,10,13,16,19-docosahexaenoic | 22:6 ω-3 |

The term "essential fatty acid" refers to a particular PUFA that an organism must ingest in order to survive, being unable to synthesize the particular essential fatty acid de novo. For example, mammals can not synthesize the essential fatty acid LA. Other essential fatty acids include GLA, DGLA, ARA, EPA and DHA.

The term "fat" refers to a lipid substance that is solid at 25° C. and usually saturated.

The term "oil" refers to a lipid substance that is liquid at 25° C. and usually polyunsaturated. PUFAs are found in the oils of some algae, oleaginous yeasts and filamentous fungi. "Microbial oils" or "single cell oils" are those oils naturally produced by microorganisms during their lifespan. Such oils can contain long chain PUFAs.

The term "PUFA biosynthetic pathway" refers to a metabolic process that converts oleic acid to LA, EDA, GLA, DGLA, ARA, ALA, STA, ETrA, ETA, EPA, DPA and DHA. This process is well described in the literature (e.g., see WO2005/003322). Simplistically, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulim membrane. More specifically, "PUFA biosynthetic pathway enzymes" refer to any of the following enzymes (and genes which encode said enzymes) associated with the biosynthesis of a PUFA, including: a delta-4 desaturase, a delta-5 desaturase, a delta-6 desaturase, a delta-12 desaturase, a delta-15 desaturase, a delta-17 desaturase, a delta-9 desaturase, a delta-8 desaturase, a $C_{14/16}$ elongase, a $C_{16/18}$ elongase, a $C_{18/20}$ elongase and/or a $C_{20/22}$ elongase.

"Desaturase" is a polypeptide which can desaturate one or more fatty acids to produce a mono- or poly-unsaturated fatty acid or precursor which is of interest. Of particular interest herein are delta-8 desaturases that will desaturate a fatty acid between the $8^{th}$ and $9^{th}$ carbon atom numbered from the carboxyl-terminal end of the molecule and that can, for example, catalyze the conversion of EDA to DGLA and/or ETrA to ETA. Other useful fatty acid desaturases include, for example: 1.) delta-5 desaturases that catalyze the conversion of DGLA to ARA and/or ETA to EPA; 2.) delta-6 desaturases that catalyze the conversion of LA to GLA and/or ALA to STA; 3.) delta-4 desaturases that catalyze the conversion of DPA to DHA; 4.) delta-12 desaturases that catalyze the conversion of oleic acid to LA; 5.) delta-15 desaturases that catalyze the conversion of LA to ALA and/or GLA to STA; 6.) delta-17 desaturases that catalyze the conversion of ARA to EPA and/or DGLA to ETA; and 7.) delta-9 desaturases that catalyze the conversion of palmitate to palmitoleic acid (16:1) and/or stearate to oleic acid (18:1).

The term "elongase system" refers to a suite of four enzymes that are responsible for elongation of a fatty acid carbon chain to produce a fatty acid that is 2 carbons longer than the fatty acid substrate that the elongase system acts upon. More specifically, the process of elongation occurs in association with fatty acid synthase, whereby CoA is the acyl carrier (Lassner et al., *The Plant Cell* 8:281-292 (1996)). In the first step, which has been found to be both substrate-specific and also rate-limiting, malonyl-CoA is condensed with a long-chain acyl-CoA to yield $CO_2$ and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by elongase systems are the conversion of GLA to DGLA, STA to ETA and EPA to DPA.

For the purposes herein, an enzyme catalyzing the first condensation reaction (i.e., conversion of malonyl-CoA to β-ketoacyl-CoA) will be referred to generically as an "elongase". In general, the substrate selectivity of elongases is somewhat broad but segregated by both chain length and the degree of unsaturation. Accordingly, elongases can have different specificities. For example, a $C_{16/18}$ elongase will utilize a $C_{16}$ substrate (e.g., palmitate), a $C_{18/20}$ elongase will utilize a $C_{18}$ substrate (e.g., GLA, STA) and a $C_{20/22}$ elongase will utilize a $C_{20}$ substrate (e.g., EPA). In like manner, a delta-9 elongase is able to catalyze the conversion of LA and ALA to EDA and ETrA, respectively (see WO 2002/077213). It is important to note that some elongases have broad specificity and thus a single enzyme may be capable of catalyzing several elongase reactions (e.g., thereby acting as both a $C_{16/18}$ elongase and a $C_{18/20}$ elongase).

The term "delta-9 elongase/delta-8 desaturase pathway" refers to a biosynthetic pathway for production of long chain PUFAs, said pathway minimally comprising a delta-9 elongase and a delta-8 desaturase and thereby enabling biosynthesis of DGLA and/or ETA from LA and ALA, respectively. This pathway may be advantageous in some embodiments, as the biosynthesis of GLA and/or STA is excluded.

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions involves a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions involves the use of higher temperatures in which the washes are identical to those above except for the temperature of the final two 30 min washes in 0.2×SSC, 0.5% SDS was increased to 60° C. Another preferred set of highly stringent conditions involves the use of two final washes in 0.1×SSC, 0.1% SDS at 65° C.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. A "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same that plant is homozygous at that locus. If the alleles present at a given locus on a chromosome differ that plant is heterozygous at that locus.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B. *Biochemistry of Plants* 15:1-82 (1989).

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Mol. Biotechnol.* 3:225-236 (1995)).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. *Plant Cell* 1:671-680 (1989).

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F. and Maniatis, T.

Molecular Cloning: A Laboratory Manual; Cold Spring Harbor Laboratory: Cold Spring Harbor, N.Y. (1989). Transformation methods are well known to those skilled in the art and are described below.

"PCR" or "Polymerase Chain Reaction" is a technique for the synthesis of large quantities of specific DNA segments and consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a "cycle".

The term "recombinant" refers to an artificial combination of two otherwise separated segments of sequence, e.g., by chemical synthesis or by the manipulation of isolated segments of nucleic acids by genetic engineering techniques.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., a mRNA or a protein [either precursor or mature]).

The term "expression cassette" as used herein, refers to a discrete nucleic acid fragment into which a nucleic acid sequence or fragment can be moved.

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

"Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on overexpression of a nucleic acid sequence having homology to an endogenous mRNA, in the sense orientation, which results in the reduction of all RNA having homology to the overexpressed sequence (Vaucheret et al., Plant J. 16:651-659 (1998); Gura, Nature 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (WO 99/53050, published Oct. 21, 1999; WO 02/00904, published Jan. 3, 2002). This increases the frequency of co-suppression in the recovered transgenic plants. Another variation describes the use of plant viral sequences to direct the suppression, or "silencing", of proximal mRNA encoding sequences (WO 98/36083, published Aug. 20, 1998). Both of these co-suppressing phenomena have not been elucidated mechanistically, although genetic evidence has begun to unravel this complex situation (Elmayan et al., Plant Cell 10:1747-1757 (1998)).

The term "oleaginous" refers to those organisms that tend to store their energy source in the form of lipid (Weete, In: Fungal Lipid Biochemistry, $2^{nd}$ Ed., Plenum, 1980). Generally, the cellular oil content of these microorganisms follows a sigmoid curve, wherein the concentration of lipid increases until it reaches a maximum at the late logarithmic or early stationary growth phase and then gradually decreases during the late stationary and death phases (Yongmanitchai and Ward, Appl. Environ. Microbiol. 57:419-25 (1991)).

The term "oleaginous yeast" refers to those microorganisms classified as yeasts that make oil. It is not uncommon for oleaginous microorganisms to accumulate in excess of about 25% of their dry cell weight as oil. Examples of oleaginous yeast include, but are no means limited to, the following genera: Yarrowia, Candida, Rhodotorula, Rhodosporidium, Cryptococcus, Tnchosporon and Lipomyces.

The "Clustal V method of alignment" corresponds to the alignment method labeled Clustal V (described by Higgins and Sharp, CABIOS. 5:151-153 (1989)) and found in the Megalign program of the LASERGENE bioinformatics computing suite (DNASTAR Inc., Madison, Wis.). The "default parameters" are the parameters preset by the manufacturer of the program. For multiple alignments, they correspond to GAP PENALTY=10 and GAP LENGTH PENALTY=10; and, for pairwise alignments, they are KTUPLE 1, GAP PENALTY=3, WINDOW=5 and DIAGONALS SAVED=5. After alignment of the sequences using the Clustal V program, it is possible to obtain a "percent identity" by viewing the "sequence distances" table in the same program.

The present invention concerns an isolated polynucleotide comprising:
(a) a nucleotide sequence encoding a polypeptide having delta-8 desaturase activity, wherein the polypeptide has an amino acid sequnce consisting essentially of SEQ ID NOs:2 or 113; or,
(b) a complement of the nucleotide sequence, wherein the complement and the nucleotide sequence consist of the same number of nucleotides and are 100% complementary.

This delta-8 desaturase may be used alone or in combination with other desaturase and elongase components to produce various omega-6 and omega-3 PUFAs, including e.g., DGLA, ETA, ARA, EPA, DPA and/or DHA (FIG. 9). One skilled in the art will recognize the appropriate combinations of the delta-8 desaturase of the invention herein in conjunction with a delta-5 desaturase, a delta-6 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and/or a $C_{20/22}$ elongase, based on the particular host cell (and its native PUFA profile and/or desaturase and/or elongase profile), the availability of substrate, and the desired end product(s). In another embodiment, this invention concerns a recombinant construct comprising the polynucleotide of the invention operably linked to at least one regulatory sequence.

Plant Expression Systems, Cassettes and Vectors

As was noted above, a promoter is a DNA sequence that directs cellular machinery of a plant to produce RNA from the contiguous coding sequence downstream (3') of the promoter. The promoter region influences the rate, developmental stage, and cell type in which the RNA transcript of the gene is made. The RNA transcript is processed to produce mRNA which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cell to cause termination of the RNA transcript and the addition of polyadenylate nucleotides to the 3' end of the RNA.

The origin of the promoter chosen to drive expression of the coding sequence is not important as long as it has sufficient transcriptional activity to accomplish the invention by expressing translatable mRNA for the desired nucleic acid fragments in the desired host tissue at the right time. Either heterologous or non-heterologous (i.e., endogenous) promoters can be used to practice the invention. For example, suitable promoters include, but are not limited to: the alpha prime subunit of beta conglycinin promoter, Kunitz trypsin inhibitor 3 promoter, annexin promoter, Gly1 promoter, beta subunit of beta conglycinin promoter, P34/Gly Bd m 30K promoter, albumin promoter, Leg A1 promoter and Leg A2 promoter.

The annexin, or P34, promoter is described in WO 2004/071178 (published Aug. 26, 2004). The level of activity of the annexin promoter is comparable to that of many known strong promoters, such as: (1) the CaMV 35S promoter (Atanassova et al., *Plant Mol. Biol.* 37:275-285 (1998); Battraw and Hall, *Plant Mol. Biol.* 15:527-538 (1990); Holtorf et al., *Plant Mol. Biol.* 29:637-646 (1995); Jefferson et al., *EMBO J.* 6:3901-3907 (1987); Wilmink et al., *Plant Mol. Biol.* 28:949-955 (1995)); (2) the *Arabidopsis* oleosin promoters (Plant et al., *Plant Mol. Biol.* 25:193-205 (1994); Li, Texas A&M University Ph.D. dissertation, pp. 107-128 (1997)); (3) the *Arabidopsis* ubiquitin extension protein promoters (Callis et al., *J Biol Chem.* 265(21):12486-93 (1990)); (4) a tomato ubiquitin gene promoter (Rollfinke et al., *Gene.* 211(2):267-76 (1998)); (5) a soybean heat shock protein promoter (Schoffl et al., *Mol Gen Genet.* 217(2-3):246-53 (1989)); and, (6) a maize H3 histone gene promoter (Atanassova et al., *Plant Mol Biol.* 37(2):275-85 (1989)).

Another useful feature of the annexin promoter is its expression profile in developing seeds. The annexin promoter is most active in developing seeds at early stages (before 10 days after pollination) and is largely quiescent in later stages. The expression profile of the annexin promoter is different from that of many seed-specific promoters, e.g., seed storage protein promoters, which often provide highest activity in later stages of development (Chen et al., *Dev. Genet.* 10:112-122 (1989); Ellerstrom et al., *Plant Mol. Biol.* 32:1019-1027 (1996); Keddie et al., *Plant Mol. Biol.* 24:327-340 (1994); Plant et al., (supra); Li, (supra)). The annexin promoter has a more conventional expression profile but remains distinct from other known seed specific promoters. Thus, the annexin promoter will be a very attractive candidate when overexpression, or suppression, of a gene in embryos is desired at an early developing stage. For example, it may be desirable to overexpress a gene regulating early embryo development or a gene involved in the metabolism prior to seed maturation.

Following identification of an appropriate promoter suitable for expression of a specific coding sequence, the promoter is then operably linked in a sense orientation using conventional means well known to those skilled in the art.

Standard recombinant DNA and molecular cloning techniques used herein are well known in the art and are described by Sambrook, J., Fritsch, E. F. and Maniatis, T., *Molecular Cloning: A Laboratory Manual*, $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987).

Plant Transformation

Once the recombinant construct has been made, it may then be introduced into a plant cell of choice by methods well known to those of ordinary skill in the art (e.g., transfection, transformation and electroporation). Oilseed plant cells are the preferred plant cells. The transformed plant cell is then cultured and regenerated under suitable conditions permitting expression of the long chain PUFA which is then optionally recovered and purified.

The recombinant constructs of the invention may be introduced into one plant cell; or, alternatively, each construct may be introduced into separate plant cells.

Expression in a plant cell may be accomplished in a transient or stable fashion as is described above.

The desired long chain PUFAs can be expressed in seed. Also within the scope of this invention are seeds or plant parts obtained from such transformed plants.

Plant parts include differentiated and undifferentiated tissues including, but not limited to: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or group of tissues that constitute a morphologically and functionally distinct part of a plant. The term "genome" refers to the following: 1. The entire complement of genetic material (genes and non-coding sequences) is present in each cell of an organism, or virus or organelle. 2. A complete set of chromosomes inherited as a (haploid) unit from one parent.

Thus, this invention also concerns a method for transforming a cell, comprising transforming a cell with the recombinant construct of the invention and selecting those cells transformed with the recombinant construct of Claim 4.

Also of interest is a method for producing a transformed plant comprising transforming a plant cell with the polynucleotide of the instant invention and regenerating a plant from the transformed plant cell.

Methods for transforming dicots (primarily by use of *Agrobacterium tumefaciens*) and obtaining transgenic plants have been published, among others, for: cotton (U.S. Pat. No. 5,004,863; U.S. Pat. No. 5,159,135); soybean (U.S. Pat. No. 5,569,834; U.S. Pat. No. 5,416,011); *Brassica* (U.S. Pat. No. 5,463,174); peanut (Cheng et al. *Plant Cell Rep.* 15:653-657 (1996); McKently et al. *Plant Cell Rep.* 14:699-703 (1995)); papaya (Ling, K. et al. *Bio/technology* 9:752-758 (1991)); and pea (Grant et al. *Plant Cell Rep.* 15:254-258 (1995)). For a review of other commonly used methods of plant transformation see Newell, C. A. (*Mol. Biotechnol.* 16:53-65 (2000)). One of these methods of transformation uses *Agrobacterium rhizogenes* (Tepfler, M. and Casse-Delbart, F. *Microbiol. Sci.* 4:24-28 (1987)). Transformation of soybeans using direct delivery of DNA has been published using PEG fusion (WO 92/17598), electroporation (Chowrira, G. M. et al. *Mol. Biotechnol.* 3:17-23 (1995); Christou, P. et al. *Proc. Natl. Acad. Sci. U.S.A.* 84:3962-3966 (1987)), microinjection, or particle bombardment (McCabe, D. E. et. al. *Bio/Technology* 6:923 (1988); Christou et al. *Plant Physiol.* 87:671-674 (1988)).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, In: Methods for Plant Molecular Biology, (Eds.), Academic: San Diego, Calif. (1988)). This regeneration and growth process typically includes the steps of selection of transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones. See, for example: Sambrook et al., Molecular Cloning: A Laboratory Manual, Cold Spring Harbor: N.Y. (1989); Maliga et al., Methods in Plant Molecular Biology, Cold Spring Harbor: N.Y. (1995); Birren et al., Genome Analysis: Detecting Genes, Vol. 1, Cold Spring Harbor: N.Y. (1998); Birren et al., Genome Analysis: Analyzing DNA, Vol. 2, Cold Spring Harbor: N.Y. (1998); Plant Molecular Biology: A Laboratory Manual, eds. Clark, Springer: N.Y. (1997).

Examples of oilseed plants include, but are not limited to, soybean, *Brassica* species, sunflower, maize, cotton, flax, safflower.

Examples of polyunsaturated fatty acids having at least twenty carbon atoms and five or more carbon-carbon double bonds include, but are not limited to, omega-3 fatty acids such as EPA, DPA and DHA. Seeds obtained from such plants are also within the scope of this invention as well as oil obtained from such seeds.

In one embodiment this invention concerns an oilseed plant comprising: a) a first recombinant DNA construct comprising an isolated polynucleotide encoding a delta-8 desaturase polypeptide, operably linked to at least one regulatory sequence; and b) at least one additional recombinant DNA construct comprising an isolated polynucleotide, operably linked to at least one regulatory sequence, encoding a polypeptide selected from the group consisting of a delta-4, a delta-5, delta-6, a delta-9, a delta-12, a delta-15, and a delta-17 desaturase, a delta-9 elongase, a C18 to C22 elongase and a C20 to C24 elongase.

Such desaturases are discussed in U.S. Pat. Nos. 6,075,183, 5,968,809, 6,136,574, 5,972,664, 6,051,754, 6,410,288 and WO 98/46763, WO 98/46764, WO 00/12720, WO 00/40705.

The choice of combination of cassettes used depends in part on the PUFA profile and/or desaturase profile of the oilseed plant cells to be transformed and the LC-PUFA which is to be expressed.

In another aspect, this invention concerns a method for making long chain polyunsaturated fatty acids in a plant cell comprising:
   (a) transforming a cell with the recombinant construct of the invention; and
   (b) selecting those transformed cells that make long chain polyunsaturated fatty acids.

In still another aspect, this invention concerns a method for producing at least one polyunsaturated fatty acid in a soybean cell comprising:
   (a) transforming a soybean cell with a first recombinant DNA construct comprising an isolated polynucleotide encoding a delta-8 desaturase polypeptide, operably linked to at least one regulatory sequence and at least one additional recombinant DNA construct comprising an isolated polynucleotide, operably linked to at least one regulatory sequence, encoding a polypeptide selected from the group consisting of a delta-4, a delta-5, delta-6, a delta-9, a delta-12, a delta-15, and a delta-17 desaturase, a delta-9 elongase, a C18 to C22 elongase and a C20 to C24 elongase.
   (b) regenerating a soybean plant from the transformed cell of step (a); and
   (c) selecting those seeds obtained from the plants of step (b) having an altered level of polyunsaturated fatty acids when compared to the level in seeds obtained from a nontransformed soybean plant.

Plant Seed Oils: Isolation and Hydrogenation

Methods of isolating seed oils are well known in the art: (Young et al., Processing of Fats and Oils, In *The Lipid*

Handbook, Gunstone et al., eds., Chapter 5 pp 253-257; Chapman & Hall: London (1994)). For example, soybean oil is produced using a series of steps involving the extraction and purification of an edible oil product from the oil-bearing seed. Soybean oils and soybean byproducts are produced using the generalized steps shown in the Table below.

TABLE 3

Generalized Steps For Soybean Oil And Byproduct Production

| Process Step | Process | Impurities Removed And/Or By-Products Obtained |
|---|---|---|
| #1 | Soybean seed | |
| #2 | Oil extraction | Meal |
| #3 | Degumming | Lecithin |
| #4 | Alkali or physical refining | Gums, free fatty acids, pigments |
| #5 | Water washing | Soap |
| #6 | Bleaching | Color, soap, metal |
| #7 | (Hydrogenation) | |
| #8 | (Winterization) | Stearine |
| #9 | Deodorization | Free fatty acids, tocopherols, sterols, volatiles |
| #10 | Oil products | |

In general, soybean oil is produced using a series of steps involving the extraction and purification of an edible oil product from the oil bearing seed. Soybean oils and soybean byproducts are produced using the generalized steps shown in the diagram below.

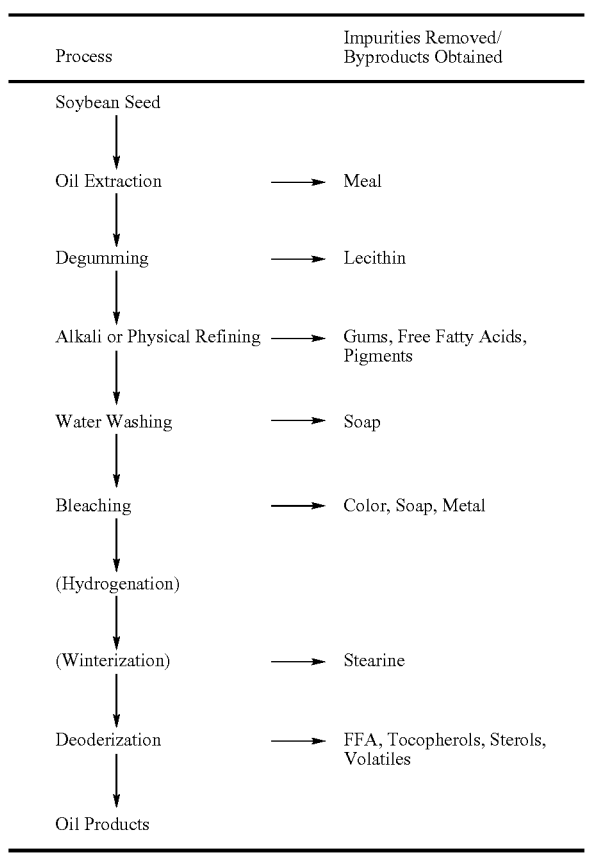

More specifically, soybean seeds are cleaned, tempered, dehulled and flaked, thereby increasing the efficiency of oil extraction. Oil extraction is usually accomplished by solvent (e.g., hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (i.e., antisticking) agents. Degummed oil may be further refined for the removal of impurities (primarily free fatty acids, pigments and residual gums). Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated, thereby resulting in fats with various melting properties and textures. Winterization (fractionation) may be used to remove stearine from the hydrogenated oil through crystallization under carefully controlled cooling conditions. Deodorization (principally via steam distillation under vacuum) is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production and byproduct utilization can be found in Erickson, Practical Handbook of Soybean Processing and Utilization, The American Oil Chemists' Society and United Soybean Board (1995).

Soybean oil is liquid at room temperature because it is relatively low in saturated fatty acids when compared with oils such as coconut, palm, palm kernel and cocoa butter. Many processed fats (including spreads, confectionary fats, hard butters, margarines, baking shortenings, etc.) require varying degrees of solidity at room temperature and can only be produced from soybean oil through alteration of its physical properties. This is most commonly achieved through catalytic hydrogenation.

Hydrogenation is a chemical reaction in which hydrogen is added to the unsaturated fatty acid double bonds with the aid of a catalyst such as nickel. High oleic soybean oil contains unsaturated oleic, LA and linolenic fatty acids and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction, which in turn alter the composition of the final product. Operating conditions including pressure, temperature, catalyst type and concentration, agitation and reactor design are among the more important parameters that can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings (used in the manufacture of baking products, solid fats and shortenings used for commercial frying and roasting operations) and base stocks for margarine manufacture are among the myriad of possible oil and fat products achieved through hydrogenation. A more detailed description of hydrogenation and hydrogenated products can be found in Patterson, H. B. W., Hydrogenation of Fats and Oils: Theory and Practice. The American Oil Chemists' Society (1994).

Hydrogenated oils have also become controversial due to the presence of trans-fatty acid isomers that result from the hydrogenation process. Ingestion of large amounts of trans-isomers has been linked with detrimental health effects including increased ratios of low density to high density lipoproteins in the blood plasma and increased risk of coronary heart disease.

Compared to other vegetable oils, the oils of the invention are believed to function similarly to other oils in food applications from a physical standpoint. Partially hydrogenated oils, such as soybean oil, are widely used as ingredients for soft spreads, margarine and shortenings for baking and frying.

Examples of food products or food analogs into which altered seed oils or altered seeds of the invention may be incorporated include a meat product such as a processed meat product, a cereal food product, a snack food product, a baked goods product, a fried food product, a health food product, an infant formula, a beverage, a nutritional supplement, a dairy product, a pet food product, animal feed or an aquaculture food product. Food analogs can be made use processes well known to those skilled in the art. U.S. Pat. Nos. 6,355,296 B1 and 6,187,367 B1 describe emulsified meat analogs and emulsified meat extenders. U.S. Pat. No. 5,206,050 B1 describes soy protein curd useful for cooked food analogs (also can be used as a process to form a curd useful to make food analogs). U.S. Pat. No. 4,284,656 to Hwa describes a soy protein curd useful for food analogs. U.S. Pat. No. 3,988,485 to Hibbert et al. describes a meat-like protein food formed from spun vegetable protein fibers. U.S. Pat. No. 3,950,564 to Puski et al. describes a process of making a soy based meat substitute and U.S. Pat. No. 3,925,566 to Reinhart et al. describes a simulated meat product. For example, soy protein that has been processed to impart a structure, chunk or fiber for use as a food ingredient is called "textured soy protein" (TSP). TSPs are frequently made to resemble meat, seafood, or poultry in structure and appearance when hydrated.

There can be mentioned meat analogs, cheese analogs, milk analogs and the like.

Meat analogs made from soybeans contain soy protein or tofu and other ingredients mixed together to simulate various kinds of meats. These meat alternatives are sold as frozen, canned or dried foods. Usually, they can be used the same way as the foods they replace. Meat alternatives made from soybeans are excellent sources of protein, iron and B vitamins. Examples of meat analogs include, but are not limited to, ham analogs, sausage analogs, bacon analogs, and the like.

Food analogs can be classified as imitation or substitutes depending on their functional and compositional characteristics. For example, an imitation cheese need only resemble the cheese it is designed to replace. However, a product can generally be called a substitute cheese only if it is nutritionally equivalent to the cheese it is replacing and meets the minimum compositional requirements for that cheese. Thus, substitute cheese will often have higher protein levels than imitation cheeses and be fortified with vitamins and minerals.

Milk analogs or nondairy food products include, but are not limited to, imitation milk, nondairy frozen desserts such as those made from soybeans and/or soy protein products.

Meat products encompass a broad variety of products. In the United States "meat" includes "red meats" produced from cattle, hogs and sheep. In addition to the red meats there are poultry items which include chickens, turkeys, geese, guineas, ducks and the fish and shellfish. There is a wide assortment of seasoned and processes meat products: fresh, cured and fried, and cured and cooked. Sausages and hot dogs are examples of processed meat products. Thus, the term "meat products" as used herein includes, but is not limited to, processed meat products.

A cereal food product is a food product derived from the processing of a cereal grain. A cereal grain includes any plant from the grass family that yields an edible grain (seed). The most popular grains are barley, corn, millet, oats, quinoa, rice, rye, sorghum, triticale, wheat and wild rice. Examples of a cereal food product include, but are not limited to, whole grain, crushed grain, grits, flour, bran, germ, breakfast cereals, extruded foods, pastas, and the like.

A baked goods product comprises any of the cereal food products mentioned above and has been baked or processed in a manner comparable to baking, i.e., to dry or harden by subjecting to heat. Examples of a baked good product include, but are not limited to bread, cakes, doughnuts, bread crumbs, baked snacks, mini-biscuits, mini-crackers, mini-cookies, and mini-pretzels. As was mentioned above, oils of the invention can be used as an ingredient.

A snack food product comprises any of the above or below described food products.

A fried food product comprises any of the above or below described food products that has been fried.

A health food product is any food product that imparts a health benefit. Many oilseed-derived food products may be considered as health foods.

The beverage can be in a liquid or in a dry powdered form.

For example, there can be mentioned non-carbonated drinks; fruit juices, fresh, frozen, canned or concentrate; flavored or plain milk drinks, etc. Adult and infant nutritional formulas are well known in the art and commercially available (e.g., Similac®, Ensure®, Jevity®, and Alimentum® from Ross Products Division, Abbott Laboratories).

Infant formulas are liquids or reconstituted powders fed to infants and young children. They serve as substitutes for human milk. Infant formulas have a special role to play in the diets of infants because they are often the only source of nutrients for infants. Although breast-feeding is still the best nourishment for infants, infant formula is a close enough second that babies not only survive but thrive. Infant formula is becoming more and more increasingly close to breast milk.

A dairy product is a product derived from milk. A milk analog or nondairy product is derived from a source other than milk, for example, soymilk as was discussed above. These products include, but are not limited to, whole milk, skim milk, fermented milk products such as yogurt or sour milk, cream, butter, condensed milk, dehydrated milk, coffee whitener, coffee creamer, ice cream, cheese, etc.

A pet food product is a product intended to be fed to a pet such as a dog, cat, bird, reptile, fish, rodent and the like. These products can include the cereal and health food products above, as well as meat and meat byproducts, soy protein products, grass and hay products, including but not limited to alfalfa, timothy, oat or brome grass, vegetables and the like.

Animal feed is a product intended to be fed to animals such as turkeys, chickens, cattle and swine and the like. As with the pet foods above, these products can include cereal and health food products, soy protein products, meat and meat byproducts, and grass and hay products as listed above.

Aqualculture feed is a product intended to be used in aquafarming which concerns the propagation, cultivation or farming of aquatic organisms, animals and/or plants in fresh or marine waters.

Microbial Biosynthesis of Fatty Acids

The process of de novo synthesis of palmitate (16:0) in oleaginous microorganisms is described in WO 2004/101757. This fatty acid is the precursor of longer-chain saturated and unsaturated fatty acid derivates, which are formed through the action of elongases and desaturases. For example, palmitate is converted to its unsaturated derivative [palmitoleic acid (16:1)] by the action of a delta-9 desaturase; similarly, palmitate is elongated to form stearic acid (18:0), which can be converted to its unsaturated derivative by a delta-9 desaturase to thereby yield oleic (18:1) acid.

Triacylglycerols (the primary storage unit for fatty acids) are formed by the esterification of two molecules of acyl-CoA to glycerol-3-phosphate to yield 1,2-diacylglycerol phosphate (commonly identified as phosphatidic acid). The phosphate is then removed, by phosphatidic acid phosphatase, to yield 1,2-diacylglycerol. Triacylglycerol is formed upon the addition of a third fatty acid by the action of a diacylglycerol-acyl transferase.

Genes Involved in Omega Fatty Acid Production

Many microorganisms, including algae, bacteria, molds and yeasts, can synthesize PUFAs and omega fatty acids in the ordinary course of cellular metabolism. Particularly well-studied are fungi including *Schizochytrium aggregatm*, species of the genus *Thraustochytrium* and *Morteriella alpina*. Additionally, many dinoflagellates (Dinophyceaae) naturally produce high concentrations of PUFAs. As such, a variety of genes involved in oil production have been identified through genetic means and the DNA sequences of some of these genes are publicly available. See, for example: AY131238, Y055118, AY055117, AF296076, AF007561, L11421, NM_031344, AF465283, AF465281, AF110510, AF465282, AF419296, AB052086, AJ250735, AF126799, AF126798 (delta-6 desaturases); AF199596, AF226273, AF320509, AB072976, AF489588, AJ510244, AF419297, AF07879, AF067654, AB022097 (delta-5 desaturases); AAG36933, AF110509, AB020033, AAL13300, AF417244, AF161219, AY332747, AAG36933, AF110509, AB020033, AAL13300, AF417244, AF161219, X86736, AF240777, AB007640, AB075526, AP002063 (delta-12 desaturases); NP_441622, BAA18302, BAA02924, AAL36934 (delta-15 desaturases); AF338466, AF438199, E11368, E11367, D83185, U90417, AF085500, AY504633, NM_069854, AF230693 (delta-9 desaturases); AF390174 (delta-9 elongase); and AX464731, NM_119617, NM_134255, NM_134383, NM_134382, NM_068396, NM_068392, NM_070713, NM_068746, NM_064685 (elongases).

Additionally, the patent literature provides many additional DNA sequences of genes (and/or details concerning several of the genes above and their methods of isolation) involved in PUFA production [e.g., U.S. Pat. No. 5,968,809 (delta-6 desaturases); U.S. Pat. Nos. 5,972,664 and 6,075,183 (delta-5 desaturases); WO 94/11516, U.S. Pat. No. 5,443,974 and WO 03/099216 (delta-12 desaturases); WO 93/11245 (delta-15 desaturases); WO 91/13972 and U.S. Pat. No. 5,057,419 (delta-9 desaturases); U.S. 2003/0196217 A1 (delta-17 desaturase); and, WO 00/12720, WO 2002/077213 and U.S. 2002/0139974A1 (elongases)].

As will be obvious to one skilled in the art, the particular functionalities required to be introduced into a microbial host organism for production of a particular PUFA final product will depend on the host cell (and its native PUFA profile and/or desaturase/elongase profile), the availability of substrate and the desired end product(s). LA, GLA, EDA, DGLA, ARA, ALA, STA, ETrA, ETA, EPA, DPA and DHA may all be produced in oleaginous yeasts, by introducing various combinations of the following PUFA enzyme functionalities: a delta-4 desaturase, a delta-5 desaturase, a delta-6 desaturase, a delta-8 desaturase, a delta-12 desaturase, a delta-15 desaturase, a delta-17 desaturase, a delta-9 desaturase, a $C_{14/16}$ elongase, a $C_{16/18}$ elongase, a $C_{18/20}$ elongase and/or a $C_{20/22}$ elongase. One skilled in the art will be able to identify various candidate genes encoding each of the above enzymes, according to publicly available literature (e.g., GenBank), the patent literature, and experimental analysis of microorganisms having the ability to produce PUFAs. The sequences may be derived from any source, e.g., isolated from a natural source (from bacteria, algae, fungi, plants, animals, etc.), produced via a semi-synthetic route or synthesized de novo. In some embodiments, manipulation of genes endogenous to the host is preferred; for other purposes, it is necessary to introduce heterologous genes.

Although the particular source of the desaturase and elongase genes introduced into the host is not critical to the invention, considerations for choosing a specific polypeptide having desaturase or elongase activity include: 1.) the substrate specificity of the polypeptide; 2.) whether the polypeptide or a component thereof is a rate-limiting enzyme; 3.) whether the desaturase or elongase is essential for synthesis of a desired PUFA; and/or 4.) co-factors required by the polypeptide. The expressed polypeptide preferably has parameters compatible with the biochemical environment of its location in the host cell. For example, the polypeptide may have to compete for substrate with other enzymes in the host cell. Analyses of the $K_M$ and specific activity of the polypeptide are therefore considered in determining the suitability of a given polypeptide for modifying PUFA production in a given host cell. The polypeptide used in a particular host cell is one that can function under the biochemical conditions present in the intended host cell but otherwise can be any polypeptide having desaturase or elongase activity capable of modifying the desired PUFA.

In some cases, the host organism in which it is desirable to produce PUFAs will possess endogenous genes encoding some PUFA biosynthetic pathway enzymes. For example, oleaginous yeast can typically produce 18:2 fatty acids (and some have the additional capability of synthesizing 18:3 fatty acids); thus, oleaginous yeast typically possess native delta-12 desaturase activity and may also have delta-15 desaturases. In some embodiments, therefore, expression of the native desaturase enzyme is preferred over a heterologous (or "foreign") enzyme since: 1.) the native enzyme is optimized for interaction with other enzymes and proteins within the cell; and 2.) heterologous genes are unlikely to share the same codon preference in the host organism. Additionally, advantages are incurred when the sequence of the native gene is known, as it permits facile disruption of the endogenous gene by targeted disruption.

In many instances, however, the appropriate desaturases and elongases are not present in the host organism of choice to enable production of the desired PUFA products. Thus, it is necessary to introduce heterologous genes. In one embodiment of the present invention, work was conducted toward the goal of the development of an oleaginous yeast that accumulates oils enriched in long-chain omega-3 and/or omega-6 fatty acids. In order to express genes encoding the delta-9 elongase/delta-8 desaturase pathway for the biosynthesis of ARA and EPA in these organisms, it was therefore necessary to: (1) identify a suitable desaturase that functioned relatively efficiently in oleaginous yeast based on substrate-feeding trials; and, (2) subject the desaturase gene to codon-optimization techniques (infra) to further enhance the expression of the heterologous enzyme in the alternate oleaginous yeast host, to thereby enable maximal production of omega-3 and/or omega-6 fatty acids.

Optimization of Omega Fatty Acid Genes for Expression in Particular Organisms

Although the particular source of a PUFA desaturase or elongase is not critical in the invention herein, it will be obvious to one of skill in the art that heterologous genes will be expressed with variable efficiencies in an alternate host. Thus, omega-3 and/or omega-6 PUFA production may be optimized by selection of a particular desaturase or elongase whose level of expression in a heterologous host is preferred relative to the expression of an alternate desaturase or elongase in the host organism of interest. Furthermore, it may be desirable to modify the expression of particular PUFA biosynthetic pathway enzymes to achieve optimal conversion efficiency of each, according to the specific PUFA product composition of interest. A variety of genetic engineering techniques are available to optimize expression of a particular enzyme. Two such techniques include codon optimization and gene mutation, as described below. Genes produced by e.g., either of these two methods, having desaturase and/or elongase activity(s) would be useful in the invention herein for synthesis of omega-3 and/or omega-6 PUFAs.

Codon Optimization: As will be appreciated by one skilled in the art, it is frequently useful to modify a portion of the codons encoding a particular polypeptide that is to be expressed in a foreign host, such that the modified polypeptide uses codons that are preferred by the alternate host. Use of host-preferred codons can substantially enhance the expression of the foreign gene encoding the polypeptide.

In general, host-preferred codons can be determined within a particular host species of interest by examining codon usage in proteins (preferably those expressed in the largest amount) and determining which codons are used with highest frequency. Then, the coding sequence for a polypeptide of interest having desaturase or elongase activity can be synthesized in whole or in part using the codons preferred in the host species. All (or portions) of the DNA also can be synthesized to remove any destabilizing sequences or regions of secondary structure that would be present in the transcribed mRNA. All (or portions) of the DNA also can be synthesized to alter the base composition to one more preferable in the desired host cell.

In the present invention, it was desirable to modify a portion of the codons encoding the polypeptide having delta-8 desaturase activity, to enhance the expression of the gene in the oleaginous yeast *Yarrowia lipolytica*. The nucleic acid sequence of the native gene (e.g., the *Euglena gracilis* delta-8 desaturase defined herein as Eg5) was modified to employ host-preferred codons. This wildtype desaturase has 421 amino acids (SEQ ID NO:2); in the codon-optimized gene created herein (SEQ ID NO:112), 207 bp of the 1263 bp coding region (corresponding to 192 codons) were codon-optimized and the translation initiation site was modified. The skilled artisan will appreciate that this optimization method will be equally applicable to other genes in the omega-3/omega-6 fatty acids biosynthetic pathway (see for example, WO 2004/101753, herein incorporated entirely by reference). Furthermore, modulation of the *E. gracilis* delta-8 desaturase is only exemplary; numerous other heterologous delta-8 desaturases from variable sources could be codon-optimized to improve their expression in an oleaginous yeast host. The present invention comprises the complete sequences of the synthetic codon-optimized gene as reported in the accompanying Sequence Listing, the complement of those complete sequences, and substantial portions of those sequences.

Gene Mutation: Methods for synthesizing sequences and bringing sequences together are well established in the literature. For example, in vitro mutagenesis and selection, site-directed mutagenesis, error prone PCR (Melnikov et al., *Nucleic Acids Research*, 27(4):1056-1062 (Feb. 15, 1999)), "gene shuffling" or other means can be employed to obtain mutations of naturally occurring desaturase or elongase genes (wherein such mutations may include deletions, insertions and point mutations, or combinations thereof). This would permit production of a polypeptide having desaturase or elongase activity, respectively, in vivo with more desirable physical and kinetic parameters for function in the host cell such as a longer half-life or a higher rate of production of a desired PUFA. Or, if desired, the regions of a polypeptide of interest (i.e., a desaturase or an elongase) important for enzymatic activity can be determined through routine mutagenesis, expression of the resulting mutant polypeptides and determination of their activities. An overview of these techniques are described in WO 2004/101757. All such mutant proteins and nucleotide sequences encoding them that are derived from the codon-optimized gene described herein are within the scope of the present invention.

Microbial Production of Omega-3 and/or Omega-6 Fatty Acids

Microbial production of omega-3 and/or omega-6 fatty acids has several advantages. For example: 1.) many microbes are known with greatly simplified oil compositions compared with those of higher organisms, making purification of desired components easier; 2.) microbial production is not subject to fluctuations caused by external variables, such as weather and food supply; 3.) microbially produced oil is substantially free of contamination by environmental pollutants; 4.) microbes can provide PUFAs in particular forms which may have specific uses; and 5.) microbial oil production can be manipulated by controlling culture conditions, notably by providing particular substrates for microbially expressed enzymes, or by addition of compounds/genetic engineering to suppress undesired biochemical pathways.

In addition to these advantages, production of omega-3 and/or omega-6 fatty acids from recombinant microbes provides the ability to alter the naturally occurring microbial fatty acid profile by providing new biosynthetic pathways in the host or by suppressing undesired pathways, thereby increasing levels of desired PUFAs, or conjugated forms thereof, and decreasing levels of undesired PUFAs. For example, it is possible to modify the ratio of omega-3 to omega-6 fatty acids so produced, produce either omega-3 or omega-6 fatty acids exclusively while eliminating production of the alternate omega fatty acid, or engineer production of a specific PUFA without significant accumulation of other PUFA downstream or upstream products (e.g., enable biosynthesis of ARA, EPA and/or DHA via the delta-9 elongase/delta-8 desaturase pathway, thereby avoiding synthesis of GLA and/or STA).

Microbial Expression Systems, Cassettes and Vectors

The genes and gene products described herein may be produced in heterologous microbial host cells, particularly in the cells of oleaginous yeasts (e.g., *Yaffowia lipolytica*). Expression in recombinant microbial hosts may be useful for the production of various PUFA pathway intermediates, or for the modulation of PUFA pathways already existing in the host for the synthesis of new products heretofore not possible using the host.

Microbial expression systems and expression vectors containing regulatory sequences that direct high level expression of foreign proteins are well known to those skilled in the art. Any of these could be used to construct chimeric genes for production of any of the gene products of the preferred desaturase and/or elongase sequences. These chimeric genes could then be introduced into appropriate microorganisms via transformation to provide high-level expression of the encoded enzymes.

Accordingly, it is expected that introduction of chimeric genes encoding a PUFA biosynthetic pathway, under the control of the appropriate promoters will result in increased production of omega-3 and/or omega-6 fatty acids. It is contemplated that it will be useful to express various combinations of these PUFA desaturase and elongase genes together in a host microorganism. It will be obvious to one skilled in the art that the particular genes included within a particular expression cassette(s) will depend on the host cell, its ability to synthesize PUFAs using native desaturases and elongases, the availability of substrate and the desired end product(s). For example, it may be desirable for an expression cassette to be constructed comprising genes encoding one or more of the following enzymatic activities: a delta-4 desaturase, a delta-5 desaturase, a delta-6 desaturase, a delta-8 desaturase, a delta-12 desaturase, a delta-15 desaturase, a delta-17 desaturase, a delta-9 desaturase, a $C_{14/16}$ elongase, a $C_{16/18}$ elongase, a $C_{18/20}$ elongase and/or a $C_{20/22}$ elongase. As such, the present invention encompasses a method of producing PUFAs comprising exposing a fatty acid substrate to the PUFA enzyme(s) described herein, such that the substrate is converted to the desired fatty acid product. Thus, each PUFA gene and corresponding enzyme product described herein (e.g., a wildtype, codon-optimized, synthetic and/or mutant enzyme having appropriate desaturase or elongase activity) can be used directly or indirectly for the production of PUFAs. Direct production of PUFAs occurs wherein the fatty acid substrate is converted directly into the desired fatty acid product without any intermediate steps or pathway intermediates. For example, production of ARA would occur in a host cell which produces or which is provided DGLA, by adding or introducing into said cell an expression cassette that provides delta-5 desaturase activity. Similarly, expression of the delta-8 desaturase of the invention permits the direct synthesis of DGLA and ETA (when provided EDA and ETrA, respectively, as substrate). Thus for example, the present invention is drawn to a method of producing either DGLA or ETA, respectively, comprising:
  a) providing an oleaginous yeast comprising: (i) a gene encoding a delta-8 desaturase polypeptide as set forth in SEQ ID NO:112; and
    (ii) a source of desaturase substrate consisting of either EDA or ETrA, respectively; and,
  b) growing the yeast of step (a) in the presence of a suitable fermentable carbon source wherein the gene encoding a delta-8 desaturase polypeptide is expressed and EDA is converted to DGLA or ETrA is converted to ETA, respectively; and,
  c) optionally recovering the DGLA or ETA, respectively, of step (b).

In contrast, multiple genes encoding the PUFA biosynthetic pathway may be used in combination, such that a series of reactions occur to produce a desired PUFA. For example, expression cassette(s) encoding elongase, delta-5 desaturase, delta-17 desaturase and delta-4 desaturase activity would enable a host cell that naturally produces GLA, to instead produce DHA (such that GLA is converted to DGLA by an elongase; DGLA may then be converted to ARA by a delta-5 desaturase; ARA is then converted to EPA by a delta-17 desaturase, which may in turn be converted to DPA by an elongase; and DPA would be converted to DHA by a delta-4 desaturase). In a related manner, expression of the delta-8 desaturase of the invention enables the indirection production of ARA, EPA, DPA and/or DHA as down-stream PUFAs, if subsequent desaturase and elongation reactions are catalyzed. In a preferred embodiment, wherein the host cell is an oleaginous yeast, expression cassettes encoding each of the enzymes necessary for PUFA biosynthesis will need to be introduced into the organism, since naturally produced PUFAs in these organisms are limited to 18:2 fatty acids (i.e., LA), and less commonly, 18:3 fatty acids (i.e., ALA). Alternatively, substrate feeding may be required.

Vectors or DNA cassettes useful for the transformation of suitable microbial host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation and a region 3' of the DNA fragment that controls transcriptional termination. It is most preferred when both control regions are derived from genes from the transformed host cell, although it is to be understood that such control regions need not be derived from the genes native to the specific species chosen as a production host.

Initiation control regions or promoters which are useful to drive expression of desaturase and/or elongase ORFs in the desired microbial host cell are numerous and familiar to those skilled in the art. Virtually any promoter capable of directing expression of these genes in the selected host cell is suitable for the present invention. Expression in a microbial host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species. The transcriptional initiation regulatory regions can be obtained, for example, from: 1.) genes in the glycolytic pathway, such as alcohol dehydrogenase, glyceraldehyde-3-phosphate-dehydrogenase (WO 2005/003310), phosphoglycerate mutase (WO 2005/003310), fructose-bisphosphate aldolase (WO 2005/049805), phosphoglucose-isomerase, phosphoglycerate kinase, glycerol-3-phosphate O-acyltransferase (see U.S. Patent Application No. 60/610060), etc.; or, 2.) regulatable genes such as acid phosphatase, lactase, metallothionein, glucoamylase, the translation elongation factor EF1-α (TEF) protein (U.S. Pat. No. 6,265,185), ribosomal protein S7 (U.S. Pat. No. 6,265,185), etc. Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, as demonstrated in the invention herein in *Yarrowia lipolytica*, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, the termination region is derived from a yeast gene, particularly *Saccharomyces, Schizosaccharomyces, Candida, Yarrowia* or *Kluyveromyces*. The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation in the host organism; 5.) the intrinsic stability of the cloned gene protein within the host cell; and 6.) the codon usage within the cloned gene, such that its frequency approaches the frequency of preferred codon usage of the host cell. Each of these types of modifications are encompassed in the present invention, as means to further optimize expression of the PUFA biosynthetic pathway enzymes.

Transformation of Microbial Hosts

Once the DNA encoding a desaturase or elongase polypeptide suitable for expression in an oleaginous yeast has been obtained, it is placed in a plasmid vector capable of autonomous replication in a host cell; or, it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

In the present invention, the preferred method of expressing genes in *Yarrowia lipolytica* is by integration of linear DNA into the genome of the host; and, integration into multiple locations within the genome can be particularly useful when high level expression of genes are desired. Toward this end, it is desirable to identify a sequence within the genome that is present in multiple copies.

Schmid-Berger et al. (*J. Bact.* 176(9):2477-2482 (1994)) discovered the first retrotransposon-like element Ylt1 in *Yarrowia lipolytica*. This retrotransposon is characterized by the presence of long terminal repeats (LTRs; each approximately 700 bp in length) called zeta regions. Ylt1 and solo zeta elements were present in a dispersed manner within the genome in at least 35 copies/genome and 50-60 copies/genome, respectively; both elements were determined to function as sites of homologous recombination. Further, work by Juretzek et al. (*Yeast* 18:97-113 (2001)) demonstrated that gene expression could be dramatically increased by targeting plasmids into the repetitive regions of the yeast genome (using linear DNA with LTR zeta regions at both ends), as compared to the expression obtained using low-copy plasmid transformants. Thus, zeta-directed integration can be ideal as a means to ensure multiple integration of plasmid DNA into *Y. lipolytica*, thereby permitting high-level gene expression. Unfortunately, however, not all strains of *Y. lipolytica* possess zeta regions (e.g., the strain identified as ATCC #20362). When the strain lacks such regions, it is also possible to integrate plasmid DNA comprising expression cassettes into alternate loci to reach the desired copy number for the expression cassette. For example, preferred alternate loci include: the Ura3 locus (GenBank Accession No. AJ306421), the Leu2 gene locus (GenBank Accession No. AF260230), the Lys5 gene (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the delta-12 desaturase gene locus (SEQ ID NO:23), the Lip1 gene locus (GenBank Accession No. Z50020) and/or the Lip2 gene locus (GenBank Accession No. AJ012632).

Advantageously, the Ura3 gene can be used repeatedly in combination with 5-fluoroorotic acid (5-fluorouracil-6-carboxylic acid monohydrate; "5-FOA") selection (infra), to readily permit genetic modifications to be integrated into the *Yarrowia* genome in a facile manner.

Where two or more genes are expressed from separate replicating vectors, it is desirable that each vector has a different means of selection and should lack homology to the other constructs to maintain stable expression and prevent reassortment of elements among constructs. Judicious choice of regulatory regions, selection means and method of propagation of the introduced construct can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [*Methods in Enzymology*, 194:186-187 (1991)]), protoplast fusion, bolistic impact, electroporation, microinjection, or any other method that introduces the gene of interest into the host cell. More specific teachings applicable for oleaginous yeasts (i.e., *Yarrowia lipolytica*) include U.S. Pat. No. 4,880,741 and U.S. Pat. No. 5,071,764 and Chen, D. C. et al. (*Appl Microbiol Biotechnol.* 48(2):232-235 (1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified or is present on an extrachromosomal element having multiple copy numbers.

The transformed host cell can be identified by various selection techniques, as described in WO2004/101757. Preferred selection methods for use herein are resistance to kanamycin, hygromycin and the amino glycoside G418, as well as ability to grow on media lacking uracil, leucine, lysine, tryptophan or histidine. In alternate embodiments, 5-FOA is used for selection of yeast Ura– mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of Ura⁻ mutant yeast strains (Bartel, P. L. and Fields, S., Yeast 2-Hybrid System, Oxford University: New York, v. 7, pp 109-147, 1997). More specifically, one can first knockout the native Ura3 gene to produce a strain having a Ura– phenotype, wherein selection occurs based on 5-FOA resistance. Then, a cluster of multiple chimeric genes and a new Ura3 gene could be integrated into a different locus of the *Yarrowia* genome to thereby produce a new strain having a Ura+ phenotype. Subsequent integration would produce a new Ura3– strain (again identified using 5-FOA selection), when the introduced Ura3 gene is knocked out. Thus, the Ura3 gene (in combination with 5-FOA selection) can be used as a selection marker in multiple rounds of transformation.

Following transformation, substrates suitable for the recombinantly expressed desaturases and/or elongases (and optionally other PUFA enzymes that are expressed within the host cell) may be produced by the host either naturally or transgenically, or they may be provided exogenously.

Metabolic Engineering of Omega-3 and/or Omega-6 Fatty Acid Biosynthesis in Microbes Methods for manipulating biochemical pathways are well known to those skilled in the art; and, it is expected that numerous manipulations will be possible to maximize omega-3 and/or omega-6 fatty acid biosynthesis in oleaginous yeasts, and particularly, in *Yarrowia lipolytica*. This may require metabolic engineering directly within the PUFA biosynthetic pathway or additional manipulation of pathways that contribute carbon to the PUFA biosynthetic pathway.

In the case of manipulations within the PUFA biosynthetic pathway, it may be desirable to increase the production of LA to enable increased production of omega-6 and/or omega-3 fatty acids. Introducing and/or amplifying genes encoding delta-9 and/or delta-12 desaturases may accomplish this.

To maximize production of omega-6 unsaturated fatty acids, it is well known to one skilled in the art that production is favored in a host microorganism that is substantially free of ALA. Thus, preferably, the host is selected or obtained by removing or inhibiting delta-15 or omega-3 type desaturase activity that permits conversion of LA to ALA. The endogenous desaturase activity can be reduced or eliminated by, for example: 1.) providing a cassette for transcription of antisense sequences to the delta-15 desaturase transcription product; 2.) disrupting the delta-15 desaturase gene through insertion, substitution and/or deletion of all or part of the target gene; or 3.) using a host cell which naturally has [or has been mutated to have] low or no delta-15 desaturase activity. Inhibition of undesired desaturase pathways can also be accomplished through the use of specific desaturase inhibitors such as those described in U.S. Pat. No. 4,778,630.

Alternatively, it may be desirable to maximize production of omega-3 fatty acids (and minimize synthesis of omega-6 fatty acids). Thus, one could utilize a host microorganism wherein the delta-12 desaturase activity that permits conversion of oleic acid to LA is removed or inhibited, using any of the means described above (see also e.g., WO 2004/104167, herein incorporated entirely by reference). Subsequently, appropriate expression cassettes would be introduced into the host, along with appropriate substrates (e.g., ALA) for conversion to omega-3 fatty acid derivatives of ALA (e.g., STA, ETrA, ETA, EPA, DPA, DHA).

Beyond the immediate PUFA biosynthetic pathway, it is expected that manipulation of several other enzymatic pathways leading to the biosynthesis of precursor fatty acids may contribute to the overall net biosynthesis of specific PUFAs. Identification and manipulation of these related pathways will be useful in the future.

Techniques to Up-Requlate Desirable Biosynthetic Pathways

Additional copies of desaturase and elongase genes may be introduced into the host to increase the output of omega-3 and/or omega-6 fatty acid biosynthetic pathways. Expression of the desaturase or elongase genes also can be increased at the transcriptional level through the use of a stronger promoter (either regulated or constitutive) to cause increased expression, by removing/deleting destabilizing sequences from either the mRNA or the encoded protein, or by adding stabilizing sequences to the mRNA (U.S. Pat. No. 4,910,141). Yet another approach to increase expression of the desaturase or elongase genes, as demonstrated in the instant invention, is to increase the translational efficiency of the encoded mRNAs by replacement of codons in the native gene with those for optimal gene expression in the selected host microorganism.

Techniques to Down-Regulate Undesirable Biosynthetic Pathways

Conversely, biochemical pathways competing with the omega-3 and/or omega-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA). For gene disruption, a foreign DNA fragment (typically a selectable marker gene) is inserted into the structural gene to be disrupted in order to interrupt its coding sequence and thereby functionally inactivate the gene. Transformation of the disruption cassette into the host cell results in replacement of the functional native gene by homologous recombination with the non-functional disrupted gene (see, for example: Hamilton et al. *J. Bacteriol.* 171:4617-4622 (1989); Balbas et al. *Gene* 136:211-213 (1993); Gueldener et al. *Nucleic Acids Res.* 24:2519-2524 (1996); and Smith et al. *Methods Mol. Cell. Biol.* 5:270-277 (1996)).

Antisense technology is another method of down-regulating genes when the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence-based (e.g., mutagenesis via UV radiation/chemical agents or use of transposable elements/transposons; see WO 2004/101757).

Within the context of the present invention, it may be useful to modulate the expression of the fatty acid biosynthetic pathway by any one of the methods described above. For example, the present invention provides methods whereby genes encoding key enzymes in the biosynthetic pathways are introduced into oleaginous yeasts for the production of omega-3 and/or omega-6 fatty acids. It will be particularly useful to express these genes in oleaginous yeasts that do not naturally possess omega-3 and/or omega-6 fatty acid biosynthetic pathways and coordinate the expression of these genes, to maximize production of preferred PUFA products using various means for metabolic engineering of the host organism.

Preferred Microbial Hosts for Recombinant Production of Omega-3 and/or Omega-6 Fatty Acids Microbial host cells for production of omega fatty acids may include microbial hosts that grow on a variety of feedstocks, including simple or complex carbohydrates, organic acids and alcohols, and/or hydrocarbons over a wide range of temperature and pH values.

Preferred microbial hosts, however, are oleaginous yeasts. These organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T cutaneum, Rhodotorula glutinus, R. graminis,* and *Yarrowia lipolytica* (formerly classified as *Candida lipolytica*).

Most preferred is the oleaginous yeast Yarrowia lipolytica; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.* 82(1):43-9 (2002)).

Historically, various strains of *Y. lipolytica* have been used for the manufacture and production of: isocitrate lyase (DD259637); lipases (SU1454852, WO2001083773, DD279267); polyhydroxyalkanoates (WO2001088144); citric acid (RU2096461, RU209061 1, DD285372, DD285370, DD275480, DD227448, PL160027); erythritol (EP770683); 2-oxoglutaric acid (DD267999); γ-decalactone (U.S. Pat. No. 6,451,565, FR2734843); γ-dodecalatone (EP578388); and pyruvic acid (JP09252790).

Microbial Fermentation Processes for PUFA Production

The transformed microbial host cell is grown under conditions that optimize desaturase and elongase activities and produce the greatest and the most economical yield of the preferred PUFAs. In general, media conditions that may be optimized include the type and amount of carbon source, the type and amount of nitrogen source, the carbon-to-nitrogen ratio, the oxygen level, growth temperature, pH, length of the biomass production phase, length of the oil accumulation phase and the time of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. Additionally, the carbon source may include one-carbon sources (e.g., carbon dioxide, methanol, formaldehyde, formate and carbon-containing amines) for which metabolic conversion into key biochemical intermediates has been demonstrated. Hence it is contemplated that the source of carbon utilized in the present invention may encompass a wide variety of carbon-containing sources and will only be limited by the choice of the host organism. Although all of the above mentioned carbon sources and mixtures thereof are expected to be suitable in the present invention, preferred carbon sources are sugars and/or fatty acids. Most preferred is glucose and/or fatty acids containing between 10-22 carbons.

Nitrogen may be supplied from an inorganic (e.g., $(NH_4)_2SO_4$) or organic source (e.g., urea or glutamate). In addition to appropriate carbon and nitrogen sources, the fermentation media must also contain suitable minerals, salts, cofactors, buffers, vitamins and other components known to those skilled in the art suitable for the growth of the microorganism and promotion of the enzymatic pathways necessary for PUFA production. Particular attention is given to several metal ions (e.g., $Mn^{+2}, Co^{+2}, Zn^{+2}, Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast. This approach is described in WO 2004/101757, as are various suitable fermentation process designs (i.e., batch, fed-batch and continuous) and considerations during growth.

Purification of Microbial PUFAs

The PUFAs may be found in the host microorganism as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Crtical Reviews in Biotechnology* 12(5/6):463-491 (1992)). A brief review of downstream processing is also available by A. Singh and O. Ward (*Adv. Appl. Microbiol.* 45:271-312 (1997)).

In general, means for the purification of PUFAs may include extraction with organic solvents, sonication, supercritical fluid extraction (e.g., using carbon dioxide), saponification and physical means such as presses, or combinations thereof. One is referred to the teachings of WO 2004/101757 for additional details.

DESCRIPTION OF PREFERRED EMBODIMENTS

The ultimate goal of the work described herein was the identification of a delta-8 desaturase suitable to enable expression of the delta-9 elongase/delta-8 desaturase pathway in plants and oleaginous yeast. Thus, initial work performed herein attempted to codon-optimize the delta-8 desaturase of *Euglena gracilis* (GenBank Accession No. AAD45877; WO 00/34439) for expression in *Yarrowia lipolytica*. Despite synthesis of three different codon-optimized genes (i.e., "D8S-1", "D8S-2" and "D8S-3"), none of the genes were capable of desaturating EDA to DGLA (Example 1). On the basis of these results, it was hypothesized that the previously published delta-8 desaturase sequences were incorrect.

Isolation of the delta-8 desaturase from *Euglena gracilis* directly, following mRNA isolation, cDNA synthesis and PCR (Examples 2 and 3) was attempted as described below. This resulted in two similar sequences, identified herein as Eg5 (SEQ ID NOs:1 and 2) and Eg12 (SEQ ID NOs:3 and 4), both of which possessed significant differences when compared to the previously published delta-8 desaturase sequences (Example 4). Eg5 and Eg12 were each cloned into a *Saccharomyces cerevisiae* yeast expression vector (Example 5) for functional analysis via substrate feeding trials (Example 11). This demonstrated that both Eg5 and Eg12 were able to desaturase EDA and ETrA to produce DGLA and ETA, respectively; Eg5 had significantly greater activity than Eg12.

Based on the confirmed delta-8 desaturase activity of Eg5 (SEQ ID NO:1 and 2), the sequence of Eg5 was codon-optimized for expression in *Yarrowia lipolytica* (Example 14), thereby resulting in the synthesis of a synthetic, functional codon-optimized delta-8 desaturase designated as "D8SF" (SEQ ID NOs:112 and 113). Co-expression of the codon-optimized delta-8 desaturase of the invention in conjunction with a codon-optimized delta-9 elongase (derived from Isochrysis galbana (GenBank Accession No. 390174)) in *Y. lipolytica* enabled synthesis of 6.4% DGLA, with no co-synthesis of GLA (Example 16).

A number of expression constructs were then created to enable synthesis of variousPUFAs in soybean, using the confirmed delta-8 desaturase sequence of Eg5, the *Yarrowia lipolytica* codon-optimized *Isochrysis galbana* delta-9 elongase or the *Mortierella alpina* elongase, the *Mortierella alpina* delta-5 desaturase, the *Fusarium* delta-15 desaturase, and the *Saprolegnia diclina* delta-17 desaturase and combinations thereof (Examples 17 through 22). Expression of these constructs resulted in production of up to about 29.9% DGLA and up to about 29.4% EPA (Examples 21 and 22 respectively).

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The meaning of abbreviations is as follows: "sec" means second(s), "min" means minute(s), "h" means hour(s), "d" means day(s), "μl" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Transformation and Cultivation of *Yarrowia lipolytica*

*Yarrowia lipolytica* strains ATCC #20362, #76982 and #90812 were purchased from the American Type Culture Collection (Rockville, Md.). *Y. lipolytica* strains were usually grown at 28° C. on YPD agar (1% yeast extract, 2% bactopeptone, 2% glucose, 2% agar).

Transformation of *Yarrowia lipolytica* was performed according to the method of Chen, D. C. et al. (*Appl. Microbiol Biotechnol.* 48(2):232-235 (1997)), unless otherwise noted. Briefly, *Yarrowia* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 μg sheared salmon sperm DNA. Then, approximately 500 ng of linearized plasmid DNA was incubated in 100 μl of resuspended cells, and maintained at 39° C. for 1 hr with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (DIFCO Laboratories, Detroit, Mich.) without ammonium sulfate or amino acids, 2% glucose, 0.1% proline, pH 6.1). Supplements of uracil were added as appropriate to a final concentration of 0.01% (thereby producing "MMU" selection media, prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (DIFCO Laboratories, Detroit, Mich.) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Fatty Acid Analysis of *Yarrowia lipolytica*

For fatty acid analysis, cells were collected by centrifugation and lipids were extracted as described in Bligh, E. G. & Dyer, W. J. (Can. *J. Biochem. Physiol.* 37:911-917 (1959)). Fatty acid methyl esters were prepared by transesterification of the lipid extract with sodium methoxide (Roughan, G., and Nishida I. *Arch Biochem Biophys.* 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 μl of 1%) was added to the sample, and then the sample was vortexed and rocked for 20 min. After adding 3 drops of 1 M NaCl and 400 μl hexane, the sample was vortexed and spun. The upper layer was removed and analyzed by GC as described above.

Example 1

Synthesis and Expression of a Codon-Optimized Delta-8 Desaturase Gene in *Yarrowia lipolytica*

In order to express the delta-8 desaturase gene of *Euglena gracilis* (SEQ ID NOs:5 and 6, GenBank Accession No. AAD45877) in *Yarrowia lipolytica*, the codon usage of the delta-8 desaturase gene was optimized for expression in *Y. lipolytica*. A codon-optimized delta-8 desaturase gene (designated "D8S-1", SEQ ID NO:48) was designed, based on the published sequence of *Euglena gracilis* (SEQ ID NO:5), according to the *Yarrowia* codon usage pattern (WO 2004/101753), the consensus sequence around the 'ATG' translation initiation codon, and the general rules of RNA stability (Guhaniyogi, G. and J. Brewer, *Gene* 265(1-2):11-23 (2001)). In addition to the modification of the translation initiation site, 200 bp of the 1260 bp coding region were modified (15.9%). None of the modifications in the codon-optimized gene changed the amino acid sequence of the encoded protein (SEQ ID NO:6) except the second amino acid from 'K' to 'E' to add the NcoI site around the translation initiation codon.

In Vitro Synthesis of a Codon-Optimized delta-8 Desaturase Gene for *Yarrowia*

The codon-optimized delta-8 desaturase gene was synthesized as follows. First, thirteen pairs of oligonucleotides were designed to extend the entire length of the codon-optimized coding region of the *E. gracilis* delta-8 desaturase gene (e.g., D8-1A, D8-1B, D8-2A, D8-2B, D8-3A, D8-3B, D8-4A, D8-4B, D8-5A, D8-5B, D8-6A, D8-6B, D8-7A, D8-7B, D8-8A, D8-8B, D8-9A, D8-9B, D8-10A, D8-10B, D8-11A, D8-11B, D8-12A, D8-12B, D8-13A and D8-13B, corresponding to SEQ ID NOs:49-74). Each pair of sense (A) and anti-sense (B) oligonucleotides were complementary, with the exception of a 4 bp overhang at each 5'-end. Additionally, primers D8-1A, D8-3B, D8-7A, D8-9B and D8-13B (SEQ ID NOs:49, 54, 60, 65 and 74) also introduced NcoI, BglII, XhoI, SacI and NotI restriction sites, respectively, for subsequent subcloning.

Each oligonucleotide (100 ng) was phosphorylated at 37° C. for 1 hr in a volume of 20 µl containing 50 mM Tris-HCl (pH 7.5), 10 mM MgCl$_2$, 10 mM DTT, 0.5 mM spermidine, 0.5 mM ATP and 10 U of T4 polynucleotide kinase. Each pair of sense and antisense oligonucleotides was mixed and annealed in a thermocycler using the following parameters: 95° C. (2 min), 85° C. (2 min), 65° C. (15 min), 37° C. (15 min), 24° C. (15 min), and 4° C. (15 min). Thus, D8-1A (SEQ ID NO:49) was annealed to D8-1B (SEQ ID NO:50) to produce the double-stranded product "D8-1AB". Similarly, D8-2A (SEQ ID NO:51) was annealed to D8-2B (SEQ ID NO:52) to produce the double-stranded product "D8-2AB", etc.

Four separate pools of annealed, double-stranded oligonucleotides were then ligated together, as shown below: (a) Pool 1: comprised D8-1AB, D8-2AB and D8-3AB; (b) Pool 2: comprised D8-4AB, D8-5AB and D8-6AB; (c) Pool 3: comprised D8-7AB, D8-8AB, and D8-9AB; and, (d) Pool 4; comprised D8-10AB, D8-11AB, D8-12AB and D8-13AB. Each pool of annealed oligonucleotides was mixed in a volume of 20 µl with 10 U of T4 DNA ligase and the ligation reaction was incubated overnight at 16° C.

The product of each ligation reaction was then used as template to amplify the designed DNA fragment by PCR. Specifically, using the ligated "Pool 1" mixture (i.e., D8-1AB, D8-2AB and D8-3AB) as template, and oligonucleotides D8-1F (SEQ ID NO:75) and D8-3R (SEQ ID NO:76) as primers, the first portion of the codon-optimized delta-8 desaturase gene was amplified by PCR. The PCR amplification was carried out in a 50 µl total volume, comprising PCR buffer containing 10 mM KCl, 10 mM (NH$_4$)$_2$SO$_4$, 20 mM Tris-HCl (pH 8.75), 2 mM MgSO$_4$, 0.1% Triton X-100, 100 µg/mL BSA (final concentration), 200 µM each deoxyribonucleotide triphosphate, 10 µmole of each primer and 1 µl of PfuTurbo DNA polymerase (Stratagene, San Diego, Calif.). Amplification was carried out as follows: initial denaturation at 95° C. for 3 min, followed by 35 cycles of the following: 95° C. for 1 min, 56° C. for 30 sec, 72° C. for 40 sec. A final extension cycle of 72° C. for 10 min was carried out, followed by reaction termination at 4° C. The 309 bp PCR fragment was subcloned into the PGEM-T easy vector (Promega) to generate pT8(1-3).

Using the ligated "Pool 2" mixture (i.e., D8-4AB, D8-5AB and D8-6AB) as the template, and oligonucleotides D8-4F (SEQ ID NO:77) and D8-6R (SEQ ID NO:78) as primers, the second portion of the codon-optimized delta-8 desaturase gene was amplified similarly by PCR and cloned into pGEM-T-easy vector to generate pT8(4-6). Using the ligated "Pool 3" mixture (i.e., D8-7AB, D8-8AB and D8-9AB) as the template and oligonucleotides D8-7F (SEQ ID NO: 79) and D8-9R (SEQ ID NO:80) as primers, the third portion of the codon-optimized delta-8 desaturase gene was amplified similarly by PCR and cloned into pGEM-T-easy vector to generate pT8(7-9). Finally, using the "Pool 4" ligation mixture (i.e., D8-10AB, D8-11AB, D8-12AB and D8-13AB) as template, and oligonucleotides D8-10F (SEQ ID NO: 81) and D8-13R (SEQ ID NO:82) as primers, the fourth portion of the codon-optimized delta-8 desaturase gene was amplified similarly by PCR and cloned into pGEM-T-easy vector to generate pT8 (10-13).

Figure 5:
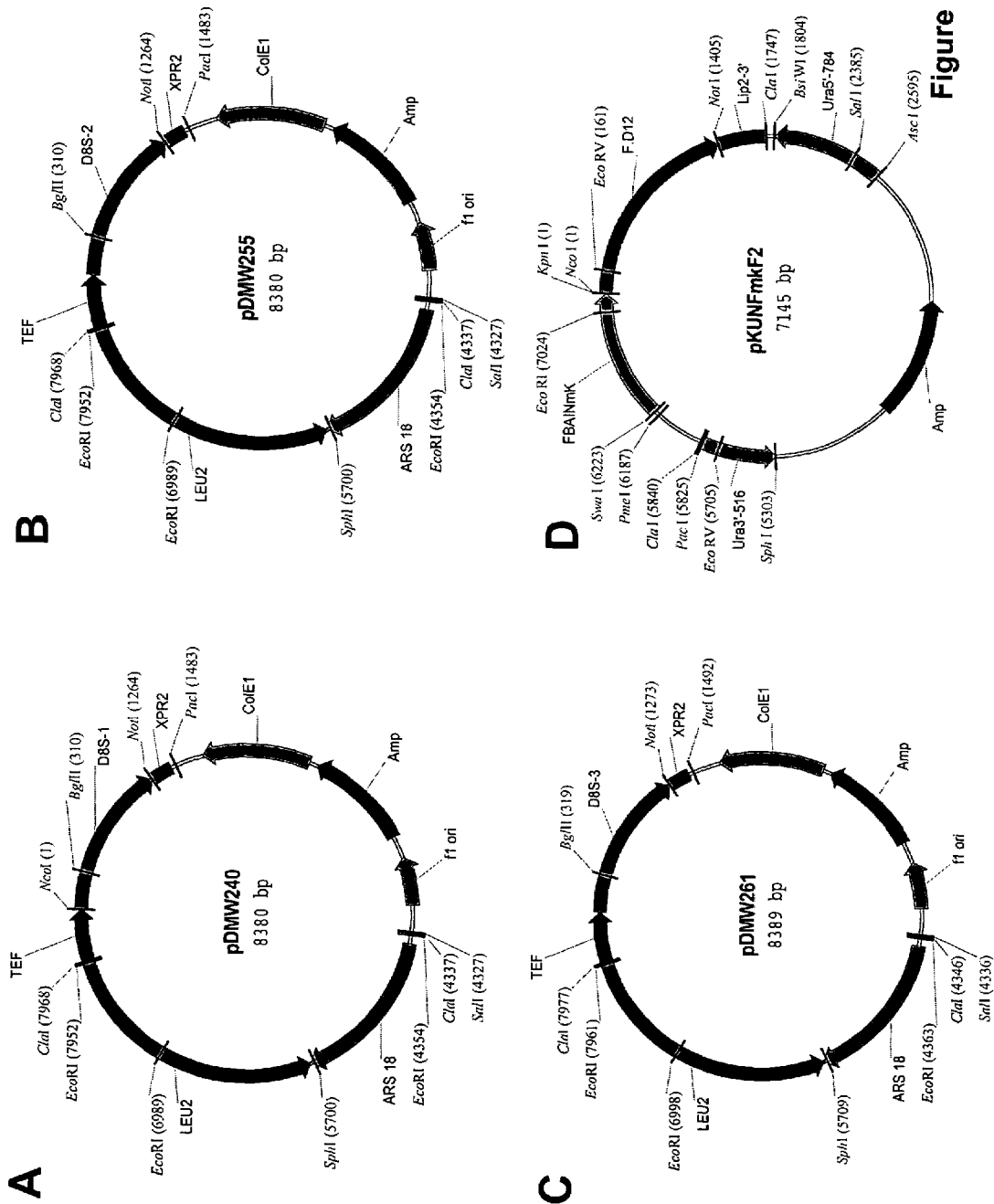

*E. coli* was transformed separately with pT8(1-3), pT8(4-6), pT8(7-9) and pT8(10-13) and the plasmid DNA was isolated from ampicillin-resistant transformants. Plasmid DNA was purified and digested with the appropriate restriction endonucleases to liberate the 309 bp NcoI/BglII fragment of pT8(1-3) (SEQ ID NO:83), the 321 bp BglII/XhoI fragment of pT8(4-6) (SEQ ID NO:84), the 264 bp XhoI/SacI fragment of pT8(7-9) (SEQ ID NO:85) and the 369 bp SacI/NotI fragment of pT8(10-13) (SEQ ID NO:86). These fragments were then combined and directionally ligated together with NcoI/NotI digested pY54PC (SEQ ID NO:115; WO2004/101757) to generate pDMW240 (FIG. 5A). This resulted in a synthetic delta-8 desaturase gene ("D8S-1", SEQ ID NO:48) in pDMW240.

Compared with the published delta-8 desaturase amino acid sequence (SEQ ID NO:6) of *E. gracilis*, the second amino acid of D8S-1 was changed from 'K' to 'E' in order to add the NcoI site around the translation initiation codon. Another version of the synthesized gene, with the exact amino acid sequence as the published *E. gracilis* delta-8 desaturase sequence SEQ ID NO:6), was constructed by in vitro mutagenesis (Stratagene, San Diego, Calif.) using pDMW240 as a template and oligonucleotides ODMW390 (SEQ ID NO:87) and ODMW391 (SEQ ID NO:88) as primers. The resulting plasmid was designated pDMW255 (FIG. 5B). The synthetic delta-8 desaturase gene in pDMW255 was designated as "D8S-2" and the amino acid sequence is exactly the same as the sequence depicted in SEQ ID NO:5.

*Yarrowia lipolytica* strain ATCC #76982(Leu−) was transformed with pDMW240 and pDMW255, respectively, as described in the General Methods. Yeast containing the recombinant constructs pDMW240 and pDMW255 (i.e., containing D8S-1 and D8S-2 respectively) were grown in MM supplemented with EDA, 20:2(11,14). Specifically, single colonies of transformant *Y. lipolytica* containing either pDMW240 or pDMW255 were grown in 3 mL MM at 30° C. to an $OD_{600}$~1.0. For substrate feeding, 100 µl of cells were then subcultured in 3 mL MM containing 10 µg of EDA substrate for about 24 hr at 30° C. The cells were collected by centrifugation, lipids were extracted, and fatty acid methyl esters were prepared by trans-esterification, and subsequently analyzed with a Hewlett-Packard 6890 GC.

Neither transformant produced DGLA from EDA and thus D8S-1 and D8S-2 were not functional and could not desaturate EDA. The chimeric D8S-1::XPR terminator and D8S-2::XPR terminator genes are shown in SEQ ID NOs:89 and 90, respectively.

A three amino acid difference between the protein sequence of the delta 8-desaturase deposited in GenBank (Accession No. AAD45877) and in WO 00/34439 or Wallis et al. (*Archives of Biochem. Biophys,* 365:307-316 (1999)) (SEQ ID NO:7 herein) was found. Specifically, three amino acids appeared to be missing in GenBank Accession No. AAD45877. Using pDMW255 as template and ODMW392 (SEQ ID NO:91) and ODMW393 (SEQ ID NO:92) as primers, 9 bp were added into the synthetic D8S-2 gene by in vitro mutagenesis (Stratagene, San Diego, Calif.), thus producing a protein that was identical to the sequence described in WO 00/34439 and Wallis et al. (supra) (SEQ ID NO:7). The resulting plasmid was called pDMW261 (FIG. 5C). The synthetic delta-8 desaturase gene in pDMW261 was designated as "D8S-3" (SEQ ID NO:93). Following transformation of the pDMW261 construct into *Yarrowia*, a similar feeding experiment using EDA was conducted, as described above. No desaturation of EDA to DGLA was observed with D8S-3.

Example 2

*Euglena gracilis* Growth Conditions, Lipid Profile and mRNA Isolation

*Euglena gracilis* was obtained from Dr. Richard Triemer's lab at Michigan State University (East Lansing, Mich.). From 10 mL of actively growing culture, a 1 mL aliquot was transferred into 250 mL of *Euglena gracilis* (Eg) Medium in a 500 mL glass bottle. Eg medium was made by combining: 1 g of sodium acetate, 1 g of beef extract (U126-01, Difco Laboratories, Detroit, Mich.), 2 g of Bacto®Tryptone (0123-17-3, Difco Laboratories) and 2 g of Bacto®Yeast Extract (0127-17-9, Difco Laboratories) in 970 mL of water. After filter sterilizing, 30 mL of Soil-Water Supernatant (Catalog #15-3790, Carolina Biological Supply Company, Burlington, N.C.) was aseptically added to produce the final Eg medium. *Euglena gracilis* cultures were grown at 23° C. with a 16 hr light, 8 hr dark cycle for 2 weeks with no agitation.

After 2 weeks, 10 mL of culture was removed for lipid analysis and centrifuged at 1,800×g for 5 min. The pellet was washed once with water and re-centrifuged. The resulting pellet was dried for 5 min under vacuum, resuspended in 100 µL of trimethylsulfonium hydroxide (TMSH) and incubated at room temperature for 15 min with shaking. After this, 0.5 mL of hexane was added and the vials were incubated for 15 min at room temperature with shaking. Fatty acid methyl esters (5 µL injected from hexane layer) were separated and quantified using a Hewlett-Packard 6890 Gas Chromatograph fitted with an Omegawax 320 fused silica capillary column (Catalog #24152, Supelco Inc.). The oven temperature was programmed to hold at 220° C. for 2.7 min, increase to 240° C. at 20° C./min and then hold for an additional 2.3 min. Carrier gas was supplied by a Whatman hydrogen generator. Retention times were compared to those for methyl esters of standards commercially available (Catalog #U-99-A, Nu-Chek Prep, Inc.) and the resulting chromatogram is shown in FIG. 1.

The remaining 2 week culture (240 mL) was pelleted by centrifugation at 1,800×g for 10 min, washed once with water and re-centrifuged. Total RNA was extracted from the resulting pellet using the RNA STAT-60™ reagent (TEL-TEST, Inc., Friendswood, Tex.) and following the manufacturer's protocol provided (use 5 mL of reagent, dissolved RNA in 0.5 mL of water). In this way, 1 mg of total RNA (2 mg/mL) was obtained from the pellet. The mRNA was isolated from 1 mg of total RNA using the mRNA Purification Kit (Amersham Biosciences, Piscataway, N.J.) following the manufacturer's protocol provided. In this way, 85 µg of mRNA was obtained.

Example 3 cDNA Synthesis and PCR of *Euglena gracilis* Delta-8 Desaturase cDNA was synthesized from 765 ng of mRNA (Example 2) using the SuperScript™ Choice System for cDNA synthesis (Invitrogen™ Life Technologies, Carlsbad, Calif.) with the provided oligo(dT) primer according to the manufacturer's protocol. The synthesized cDNA was dissolved in 20 µL of water.

The *Euglena gracilis* delta-8 desaturase was amplified from cDNA with oligonucleotide primers Eg5-1 (SEQ ID NO:8) and Eg3-3 (SEQ ID NO:9) using the conditions described below.

cDNA (1 µL) from the reaction described above was combined with 50 µmol of Eg5-1, 50 µmol of Eg5-1, 1 µL of PCR nucleotide mix (10 mM, Promega, Madison, Wis.), 5 µL of 10× PCR buffer (Invitrogen), 1.5 µL of $MgCl_2$ (50 mM, Invitrogen), 0.5 µL of Taq polymerase (Invitrogen) and water to 50 µL. The reaction conditions were 94° C. for 3 min followed by 35 cycles of 94° C. for 45 sec, 55° C. for 45 sec and 72° C. for 1 min. The PCR was finished at 72° C. for 7 min and then held at 4° C. The PCR reaction was analyzed by agarose gel electrophoresis on 5 µL and a DNA band with molecular weight around 1.3 kB was observed. The remaining 45 µL of product was separated by agarose gel electrophoresis and the DNA band was purified using the Zymoclean™ Gel DNA Recovery Kit (Zymo Research, Orange, Calif.) following the manufacturer's protocol. The resulting DNA was cloned into the pGEM®-T Easy Vector (Promega) following the manufacturer's protocol. Multiple clones were sequenced using T7 (SEQ ID NO:10), M13-28Rev (SEQ ID NO:11), Eg3-2 (SEQ ID NO:12) and Eg5-2 (SEQ ID NO:13).

Thus, two classes of DNA sequences were obtained, Eg5 (SEQ ID NO:1) and Eg12 (SEQ ID NO:3), that differed in only a few bp. Translation of Eg5 and Eg12 gave rise to protein sequences that differed in only one amino acid, SEQ ID NO:2 and 4, respectively. Thus, the DNA and protein sequences for Eg5 are set forth in SEQ ID NO:1 and SEQ ID NO:2, respectively; the DNA and protein sequences for Eg12 are set forth in SEQ ID NO:3 and SEQ ID NO:4, respectively.

Example 4

Comparison of the Polypeptide Sequences Set Forth in SEQ ID NOs:2 and 4 to Published *Euglena gracilis* Delta-8 Desaturase Sequences An alignment of the protein sequences set forth in SEQ ID NO:2 and SEQ ID NO:4 with the protein sequence from GenBank Accession No. AAD45877 (gi: 5639724) and with the published protein sequences of Wallis et al. (*Archives of Biochem. Biophys.*, 365:307-316 (1999); WO 00/34439) is shown in FIG. 2.

Amino acids conserved among all 4 sequences are indicated with an asterisk (*) Dashes are used by the program to maximize alignment of the sequences. The putative cytochrome $b_5$ domain is underlined. A putative His box is shown in bold.

Clearly, there are significant differences between the sequences of this invention and those described previously. Specifically, the N-terminus has multiple amino acid changes. As compared to SEQ ID NO:2, the published amino acid sequences have an extra serine between L9 and P10 and amino acids from position T12-T16 are completely different ('TIDGT' to 'QLMEQ'). These changes result from multiple insertions in the DNA sequence of the published sequence and this causes 3 shifts in frame in this region. These changes are only 10 amino acids away from the putative cytochrome $b_5$ domain ('HPGG').

In addition to this, there are seven other single amino acid changes (S50 to F, S67 to F, W177 to C, L203 to P, S244 to C, T278 to A, S323 to P) with the change at W177 being only 4 amino acids away from the second putative His box ('HNAHH'). Surprisingly, the published GenBank protein sequence is missing 3 amino acids (S20, A21, W22) as compared to that for either SEQ ID NO:2, SEQ ID NO:4 or WO 00/34439. The DNA sequence shown in WO 00/34439 codes for a protein that is identical to AAD45877. (i.e., missing these 3 amino acids) and not for the protein sequence described in WO 00/34439. Interestingly, the protein sequence set forth in SEQ ID NO:4 has a single amino acid change as compared to SEQ ID NO:2 (T278 to A). In Table 4 percent identities between the functional delta-8 desaturase protein sequence from *Euglena gracilis* claimed in this invention (SEQ ID NO:2) and the published sequences (SEQ ID NOs:6 and 7) are shown.

TABLE 4

Percent Identity Of The Amino Acid Sequences Of Delta-8 Desaturase From *Euglena gracilis* And Homologous Polypeptides From *Euglena gracilis*

|  | % Identity to SEQ ID NO: 6 | % Identity to SEQ ID NO: 7 |
|---|---|---|
| SEQ ID NO: 2 | 95.5 | 96.2 |

* "% Identity" is defined as the percentage of amino acids that are identical between the two proteins.

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp, *CABIOS*. 5:151-153 (1989)) with default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Example 5

Figure 3:
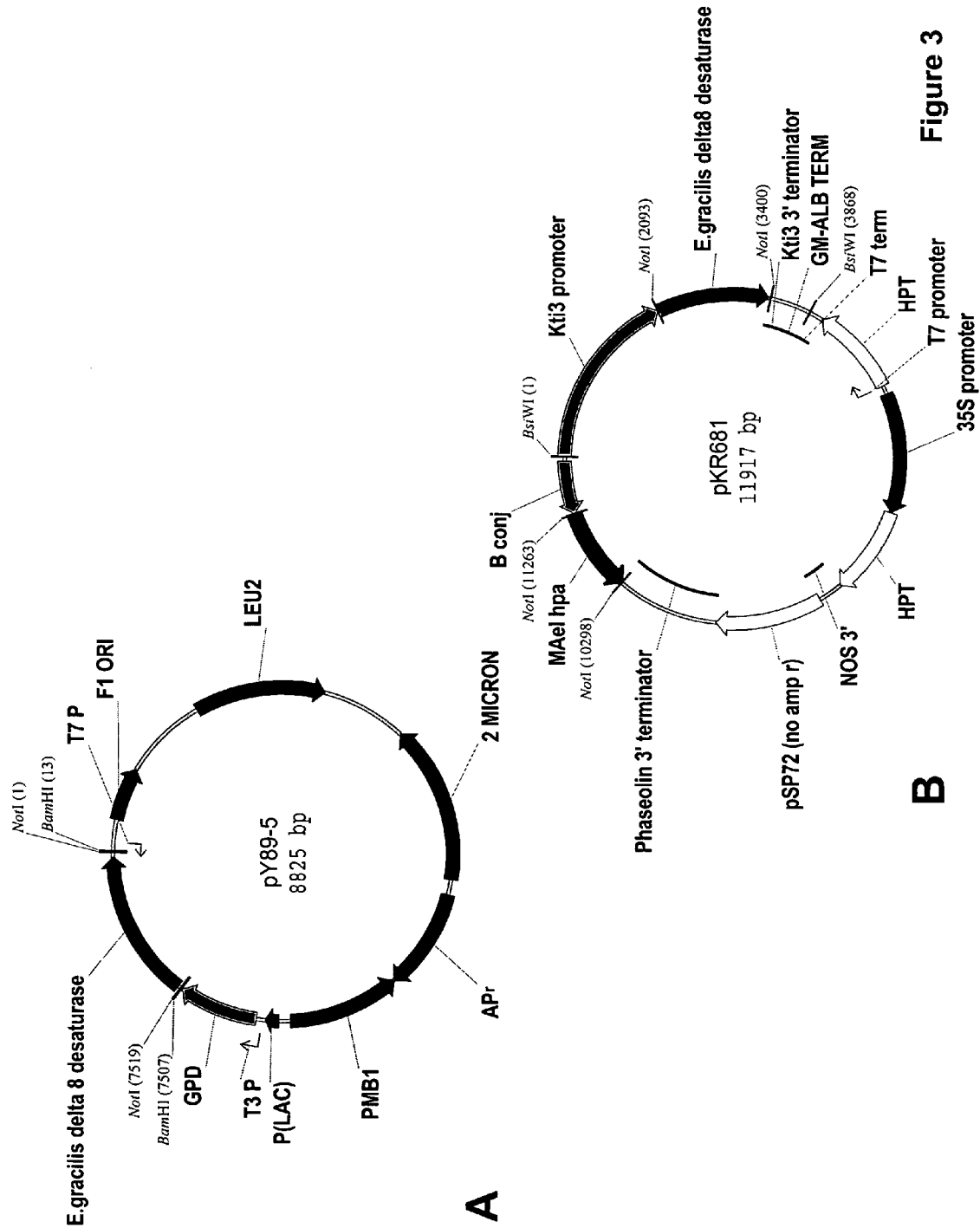

Cloning the *Euglena gracilis* Delta-8 Desaturase into a Yeast Expression Vector The yeast episomal plasmid (YEp)-type vector pRS425 (Christianson et al., *Gene*, 110:119-22 (1992)) contains sequences from the *Saccharomyces cerevisiae* 2 μl endogenous plasmid, a LEU2 selectable marker and sequences based on the backbone of a multifunctional phagemid, pBluescript II SK+. The *S. cerevisiae* strong, constitutive glyceraldehyde-3-phosphate dehydrogenase (GPD) promoter was cloned between the SacII and SpeI sites of pRS425 in the same way as described in Jia et al. (*Physiological Genomics*, 3:83-92 (2000)) to produce pGPD-425. A NotI site was introduced into the BamHI site of pGPD-425 thus producing a NotI site flanked by BamHI sites, thereby resulting in plasmid pY-75. Eg5 (SEQ ID NO:1) and Eg12 (SEQ ID NO:3) were released from the pGEM®-T Easy vectors described in Example 2 by digestion with NotI and cloned into the NotI site of pY-75 to produce pY89-5 and pY89-12, respectively. In this way, the delta-8 desaturases (i.e., Eg5 [SEQ ID NO:1] and Eg12 [SEQ ID NO:3]) were cloned behind a strong constitutive promoter for expression in *S. cerevisiae*. A map of pY89-5 is shown in FIG. 3A.

Example 6

Cloning the *Euglena gracilis* Delta-8 Desaturase into a Soybean Expression Vector and Co-Expression with a *Mortierella alpina* Elongase A starting plasmid pKS123 (WO 02/08269, the contents of which are hereby incorporated by reference) contains the hygromycin B phosphotransferase gene (HPT) [Gritz, L. and Davies, J. *Gene* 25:179-188 (1983)], flanked by the T7 promoter and transcription terminator (T7prom/hpt/T7term cassette), and a bacterial origin of replication (ori) for selection and replication in bacteria (e.g., *E. coli*). In addition, pKS123 also contains the hygromycin B phosphotransferase gene, flanked by the 35S promoter (Odell et al., *Nature* 313:810-812 (1985)) and NOS 3' transcription terminator (Depicker et al., *J. Mol. Appl. Genet.* 1:561:570 (1982)) (35S/hpt/NOS3' cassette) for selection in plants such as soybean. pKS123 also contains a NotI restriction site, flanked by the promoter for the 'α subunit of β-conglycinin (Beachy et al., *EMBO J*. 4:3047-3053 (1985)) and the 3' transcription termination region of the phaseolin gene (Doyle, J. J. et al. *J. Biol. Chem.* 261:9228-9238 (1986)) thus allowing for strong tissue-specific expression in the seeds of soybean of genes cloned into the NotI site.

Vector pKR72 is a derivative of pKS123, wherein the HindIII fragment containing the β-conglycinin/NotI/phaseolin cassette has been inverted and a sequence (SEQ ID NO:14) containing SbfI, FseI and BsiWI restriction enzyme sites was introduced between the HindIII and BamHI sites in front of the β-conglycinin promoter.

The gene for the *Mortierella alpina* elongase was amplified from pRPB2 (WO 00/12720) using primers RPB2forward (SEQ ID NO:15) and RPB2reverse (SEQ ID NO:16) which were designed to introduce NotI restriction enzyme sites at both ends of the elongase. The resulting PCR fragment was digested with NotI and cloned into the NotI site of pKR72 to produce pKR324.

Vector pKS121 (WO 02/00904) contains a NotI site flanked by the Kunitz soybean Trypsin Inhibitor (KTi) promoter (Jofuku et al., *Plant Cell* 1:1079-1093 (1989)) and the KTi 3' termination region, the isolation of which is described in U.S. Pat. No. 6,372,965 (KTi/NotI/KTi3' cassette). Vector pKR457 is a derivative of pKS121 where the restriction sites upstream and downstream of the Kti/NotI/Kti3' cassette have been altered through a number of subcloning steps. Vector pKR457 also contains the Soy albumin transcription terminator downstream of the Kti terminator to lengthen and strengthen termination of transcription. In pKR457, the BamHI site upstream of the Kti promoter in pKS121 was removed and a new sequence (SEQ ID NO:17) added containing a BsiWI, SalI, SbfI and HindIII site with the BsiWI site being closest the 5' end of the Kti promoter.

In addition, the SalI site downstream of the Kti terminator in pKS121 was removed and a new sequence (SEQ ID NO:18) was added containing a XbaI (closest to 3' end of Kti terminator), a BamHI site, the soy albumin transcription terminator sequence, a BsiWI site and another BamHI site.

The albumin transcription terminator was previously amplified from soy genomic DNA using primer oSalb-12 (SEQ ID NO:19; designed to introduce BamHI, XbaI and BsiWI sites at the 3' end of the terminator), and primer oSalb-13 (SEQ ID NO:20; designed to introduce BamHI sites at the 5' end of the terminator). After PCR, sites at ends were modified by sub-cloning through various intermediate vectors to finally produce the sequence shown in SEQ ID NO:5.

Eg5 (SEQ ID NO:1) was released from the pGEM®-T Easy by digestion with NotI and cloned into the NotI site of pKR457 to produce pKR680. Plasmid pKR680 was then digested with BsiWI and the fragment containing Eg5 (SEQ ID NO:1) was cloned into the BsiWI site of pKR324 (WO 2004/071467) to produce pKR681. Thus, the delta-8 desaturase (Eg5; SEQ ID NO:1) could be co-expressed with the *Mortierella alpina* elongase behind strong, seed-specific promoters. A map of pKR681 is shown in FIG. 3B.

Example 7

Isolation of Soybean Seed-Specific Promoters

The soybean annexin and BD30 promoters were isolated with the Universal GenomeWalker system (Clontech) according to its user manual (PT3042-1). To make soybean GenomeWalker libraries, samples of soybean genomic DNA were digested with DraI, EcoRV, PvuII and StuI separately for two hrs. After DNA purification, the digested genomic DNAs were ligated to the GenomeWalker adaptors AP1 and AP2.

Two gene specific primers (i.e., GSP1 [SEQ ID NO:21] and GSP2 [SEQ ID NO:22]) were designed for the soybean annexin gene based on the 5' annexin cDNA coding sequences available in an EST database (E.I. duPont de Nemours and Co., Inc., Wilmington, Del.).

The AP1 and the GSP1 primers were used in the $1^{st}$ round PCR using the conditions defined in the GenomeWalker system protocol. Cycle conditions were 94° C. for 4 min; 94° C. for 2 sec and 72° C. for 3 min, 7 cycles; 92° C. for 2 sec and 67° C. for 3 min, 32 cycles; 67° C. for 4 min. The products from the first run PCR were diluted 50-fold. One microliter of the diluted products were used as templates for the $2^{nd}$ PCR with primers AP2 and GSP2. Cycle conditions were 94° C. for 4 min; 94° C. for 2 sec and 72° C. for 3 min, 5 cycles; 94° C. for 2 sec and 67° C. for 3 min, 20 cycles; 67° C. for 3 min. A 2.1 kB genomic fragment was amplified and isolated from the EcoRV-digested GenomeWalker library. The genomic fragment was digested with BamHI and SalI and cloned into Bluescript KS+ vector for sequencing. The DNA sequence of this 2012 bp soybean annexin promoter fragment is set forth in SEQ ID NO:29. Based on this sequence, two oligonucleotides with either BamHI or NotI sites at the 5' ends were designed to re-amplify the promoter (i.e., SEQ ID NOs:30 and 31).

Two gene specific primers (GSP3 [SEQ ID NO:23] and GSP4 [SEQ ID NO:24]) were designed to amplify the soybean BD30 promoter based on the 5' BD30 cDNA coding sequences in GenBank (Accession No. J05560). The AP1 and the GSP3 primers were used in the $1^{st}$ round PCR using the same conditions defined in the GenomeWalker system protocol; however, the cycle conditions used for soybean annexin promoter did not work well for the soybean BD30 promoter. A modified touchdown PCR protocol was used, wherein cycle conditions were: 94° C. for 4 min; 94° C. for 2 sec and 74° C. for 3 min, 6 cycles in which annealing temperature drops 1° C. every cycle; 94° C. for 2 sec and 69° C. for 3 min, 32 cycles; 69° C. for 4 min. The products from the $1^{st}$ run PCR were diluted 50-fold. One microliter of the diluted products were used as templates for the $2^{nd}$ PCR with primers AP2 and GSP4. Cycle conditions were: 94° C. for 4 min; 94° C. for 2 sec and 74° C. for 3 min, 6 cycles in which annealing temperature drops 1° C. every cycle; 94° C. for 2 sec and 69° C. for 3 min, 20 cycles; 69° C. for 3 min. A 1.5 kB genomic fragment was amplified and isolated from the PvuII-digested GenomeWalker library. The genomic fragment was digested with BamHI and SalI and cloned into Bluescript KS+ vector for sequencing. DNA sequencing determined that this genomic fragment contained a 1408 bp soybean BD30 promoter sequence (SEQ ID NO:25). Based on the sequence of the cloned soybean BD30 promoter, two oligonucleotides with either BamHI or NotI sites at the 5' ends were designed to re-amplify the BD30 promoter (i.e., SEQ ID NOs:32 and 33).

The re-amplified annexin and BD30 promoter fragments (supra) were digested with BamHI and NotI, purified and cloned into the BamHI and NotI sites of plasmid pZBL115 to produce pJS88 and pJS89, respectively. The pZBL115 plasmid contains the origin of replication from pBR322, the bacterial HPT hygromycin resistance gene driven by a T7 promoter and T7 terminator, and a 35S promoter-HPT-Nos3' gene to serve as a hygromycin resistant plant selection marker. The *M. alpina* delta-6 desaturase gene was cloned into the NotI site of pJS88 and pJS89, in the sense orientation, to make plant expression cassettes pJS92 and pJS93, respectively.

Based on the sequences of the soybean Glycinin Gy1 promoter sequence in GenBank (Accession No. X15121), the oligonucleotides set forth in SEQ ID NOs:27 and 28 were designed to amplify the soybean Glycinin Gy1 promoter (SEQ ID NO:26), wherein the primers had either BamHI or NotI sites at the 5' ends. The amplified soybean glycinin Gy1 promoter fragment was digested with BamHI and NotI, purified and cloned into the BamHI and NotI sites of plasmid pZBL115 (supra) to produce pZBL117.

Example 8

Cloning the *Euglena gracilis* Delta-8 Desaturase into a Soybean Expression Vector and Co-Expression with EPA Biosynthetic Genes (Delta-8 Desaturase and Delta-17 Desaturase)

Plasmid pKR325 was generated from pKR72 (Example 5) by digestion with HindIII to remove the βcon/NotI/Phas3' cassette. Plasmid pKR680 (Example 5) was digested with BsiWI and the fragment containing Eg5 (SEQ ID NO:1) was cloned into the BsiWI site of pKR325 to produce pKR683.

The KTi/NotI/KTi3' cassette from pKS121 was PCR-amplified using primers oKTi5 (SEQ ID NO:34) and oKTi6 (SEQ ID NO:35), designed to introduce an XbaI and BsiWI site at both ends of the cassette. The resulting PCR fragment was subcloned into the XbaI site of the cloning vector pUC19 to produce plasmid pKR124, thus adding a PstI and SbfI site at the 3' end of the Kti transcription terminator.

The SalI fragment of pJS93 containing soy BD30 promoter (WO 01/68887) was combined with the SalI fragment of pUC19 to produce pKR227, thus adding a PstI and SbfI site at the 5' end of the BD30 promoter.

The BD30 3' transcription terminator was PCR-amplified from soy genomic DNA using primer oSBD30-1 (SEQ ID NO:36; designed to introduce an NotI site at the 5' end of the terminator) and primer oSBD30-2 (SEQ ID NO:37; designed to introduce a BsiWI site at the 3' end of the terminator). The resulting PCR fragment was subcloned into the intermediate cloning vector pCR-Script AMP SK(+) (Stratagene) according the manufacturer's protocol to produce plasmid pKR251r. The EcoRI/NotI fragment from pKR251r, containing the BD30 3' transcription terminator, was cloned into the EcoRI/NotI fragment of intermediate cloning vector pKR227 to produce pKR256.

The annexin promoter from pJS92 (Example 7) was released by BamHI digestion and the ends were filled. The resulting fragment was ligated into the filled BsiWI fragment from the vector backbone of pKR124 in a direction which added a PstI and SbfI site at the 5' end of the annexin promoter to produce pKR265. The annexin promoter was released from pKR265 by digestion with SbfI and NotI and was cloned into the SbfI/NotI fragment of pKR256 (containing the BD30 3'transcription terminator, an ampicillin resistance gene and a bacterial ori region) to produce pKR268.

The gene for the *Saprolegnia diclina* delta-17 desaturase was released from pKS203 (Pereira et al., *Biochem. J.* 378: 665-671 (2004)) by partial digestion with NotI, and was cloned into the NotI site of pKR268 to produce pKR271. In this way, the delta-17 desaturase was cloned as an expression cassette behind the annexin promoter with the BD30 transcription terminator.

Figure 4:
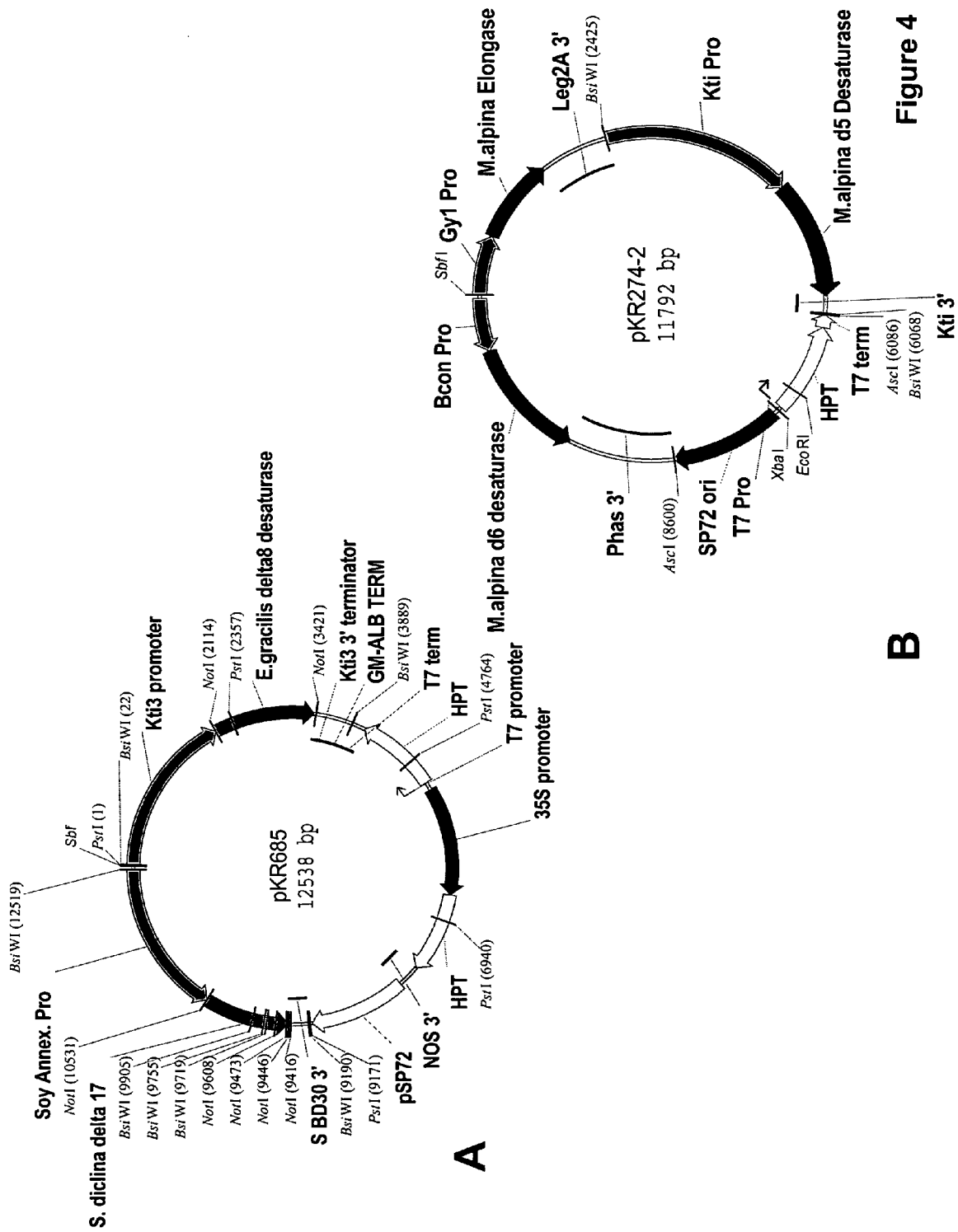

Plasmid pKR271 was then digested with PstI and the fragment containing the *Saprolegnia diclina* delta-17 desaturase was cloned into the SbfI site of pKR683 to produce pKR685. In this way, the delta-8 desaturase could be co-expressed with the *S. diclina* delta-17 desaturase behind strong, seed-specific promoters. A map of pKR685 is shown in FIG. 4A.

Example 9

Assembling EPA Biosynthetic Pathway Genes for Expression in Somatic Soybean Embryos And Soybean Seeds (Delta-6 Desaturase, Elongase And Delta-5 Desaturase)

The *M. alpina* delta-6 desaturase (U.S. Pat. No. 5,968, 809), *M. alpina* elongase (WO 00/12720) and *M. alpina* delta-5 desaturase (U.S. Pat. No. 6,075,183) were cloned into plasmid pKR274 (FIG. 4B) behind strong, seed-specific promoters allowing for high expression of these genes in somatic soybean embryos and soybean seeds. All of these promoters exhibit strong tissue specific expression in the seeds of soybean. Plasmid pKR274 also contains the hygromycin B phosphotransferase gene (Gritz, L. and Davies, J. *Gene* 25:179-188 (1983)) cloned behind the T7 RNA polymerase promoter and followed by the T7 terminator (T7prom/HPTMterm cassette) for selection of the plasmid on hygromycin B in certain strains of *E. coli* (e.g., NovaBlue(DE3) (Novagen, Madison, Wis.), a strain that is lysogenic for lambda DE3 and carries the T7 RNA polymerase gene under lacUV5 control). In addition, plasmid pKR274 contains a bacterial origin of replication (ori) functional in *E. coli* from the vector pSP72 (Stratagene).

More specifically, the delta-6 desaturase was cloned behind the promoter for the α' subunit of β-conglycinin (Beachy et al., *EMBO J.* 4:3047-3053 (1985)) followed by the 3' transcription termination region of the phaseolin gene (Doyle, J. J. et al. *J. Biol. Chem.* 261:9228-9238 (1986)) (βcon/Mad6/Phas3' cassette).

The delta-5 desaturase was cloned behind the Kunitz soybean Trypsin Inhibitor (KTi) promoter (Jofuku et al., Plant Cell 1:1079-1093 (1989)), followed by the KTi3' termination region, the isolation of which is described in U.S. Pat. No. 6,372,965 (KTi/Mad5/KTi3' cassette).

The elongase was cloned behind the glycinin Gy1 promoter followed by the pea leguminA2 3' termination region (Gy1/Maelo/legA2 cassette).

The gene for the *M. alpina* delta-6 desaturase was PCR-amplified from pCGR5 (U.S. Pat. No. 5,968,809) using primers oCGR5-1 (SEQ ID NO:38) and oCGR5-2 (SEQ ID NO:39), which were designed to introduce NotI restriction enzyme sites at both ends of the delta-6 desaturase and an NcoI site at the start codon of the reading frame for the enzyme. The resulting PCR fragment was subcloned into the intermediate cloning vector pCR-Script AMP SK(+) (Stratagene) according the manufacturer's protocol to produce plasmid pKR159. The NotI fragment of pKR159, containing the *M. alpina* delta-6 desaturase gene, was cloned into NotI site of pZBL17 (Example 7) in the sense orientation to produce plant expression cassette pZBL119.

Vector pKR197 was constructed by combining the AscI fragment from plasmid pKS102 (WO 02/00905), containing the T7prom/hpt/T7term cassette and bacterial ori, with the AscI fragment of plasmid pKR72 (Example 5), containing the βcon/NotI/Phas cassette. Plasmid pKR159 was digested with NotI to release the *M. alpina* delta-6 desaturase, which was, in turn, cloned into the NotI site of the soybean expression vector pKR197 to produce pKR269.

The glycinin Gy1 promoter was amplified from pZBL119 using primer oSGly-1 (SEQ ID NO:40; designed to introduce an SbfI/PstI site at the 5' end of the promoter) and primer oSGly-2 (SEQ ID NO:41; designed to introduce a NotI site at the 3' end of the promoter). The resulting PCR fragment was subcloned into the intermediate cloning vector pCR-Script AMP SK(+) (Stratagene) according to the manufacturer's protocol to produce plasmid pSGly12.

The legA2 promoter was amplified from pea genomic DNA using primer LegPro5' (SEQ ID NO:42; designed to introduce XbaI and BsiWI sites at the 5' end of the promoter) and primer LegPro3' (SEQ ID NO:43; designed to introduce a NotI site at the 3' end of the promoter). The legA2 transcription terminator was amplified from pea genomic DNA using primer LegTerm5' (SEQ ID NO:44; designed to introduce NotI site at the 5' end of the terminator) and primer LegTerm3' (SEQ ID NO:45; designed to introduce BsiWI and XbaI sites at the 3' end of the terminator). The resulting PCR fragments were then combined and re-amplified using primers LegPro5' and LegTerm3', thus forming a legA2/NotII/legA23' cassette. The legA2/NotI/legA23' cassette PCR fragment was subcloned into the intermediate cloning vector pCR-Script AMP SK(+) (Stratagene) according to the manufacturer's protocol to produce plasmid pKR140.

Plasmid pKR142 was constructed by cloning the BsiWI fragment of pKR140 (containing the legA2/NotI/legA23' cassette) into the BSIWI site of pKR124 (containing a bacterial ori and ampicillin resistance gene). The PstI/NotI fragment from plasmid pKR142 was then combined with the PstI/NofI fragment of plasmid pSGly12 (containing the glycininGy1 promoter) to produce pKR263. The gene for the *M. alpina* delta-5 desaturase was amplified from pCGR4 (U.S. Pat. No. 6,075,183) using primers CGR4foward (SEQ ID NO:46) and CGR4reverse (SEQ ID NO:47) which were designed to introduce NotI restriction enzyme sites at both ends of the desaturase. The resulting PCR fragment was digested with NotI and cloned into the NotI site of vector pKR124 (Example 6) to produce pKR136.

The NotI fragment containing the *M. alpina* elongase (Example 5) was cloned into the NotI site of vector pKR263 to produce pKR270. The Gy1/Maelo/legA2 cassette was released from plasmid pKR270 by digestion with BsiWI and SbfI and was cloned into the BsiWI/SbfI sites of plasmid pKR269 (containing the delta-6 desaturase, the T7prom/hpt/T7term cassette and the bacterial ori region). This was designated as plasmid pKR272. The KTi/Mad5/KTi3' cassette, released from pKR136 by digestion with BsIWI, was then cloned into the BsiWI site of pKR272 to produce pKR274 (FIG. 4B).

Example 10

Assembling EPA Biosynthetic Pathway Genes for Expression in Somatic Soybean Embryos and Soybean Seeds (Delta-17 Desaturase and Delta-5 Desaturase)

In a manner similar to that described in Example 9, the delta-17 desaturase from *S. diclina* could be cloned into a soy expression vector along with the delta-5 desaturase from *M. alpina*. The annexin/delta-17/BD30 cassette of pKR271 could be released by digestion with a suitable restriction enzyme such as PstI and cloned into a soy expression vector already carrying the *M. alpina* delta-5 desaturase behind a suitable promoter and a suitable selection marker such as hygromycin. The *M. alpina* delta-5 desaturase could be part of any suitable expression cassette described here. For instance, the NotI fragment containing the *M. alpina* delta-5 desaturase described above could be cloned into the NotI site of the Gy1/NotI/legA2 cassette of pKR263. This Gy1/delta5/legA2 cassette could then be cloned into a vector containing a suitable selectable marker for soy transformation. Such a vector could be co-transformed into soy with pKR681 (Example 6) and transformants expression genes from both plasmids selected. In this way, EPA could be produced using the delta-8 pathway independent of a delta-6 desaturase.

Example 11

Functional Analysis of the *Euglena gracilis* Delta-8 Desaturase in *Saccharomyces cerevisiae*

Plasmids pY89-5 (comprising the Eg5 sequence; see FIG. 3A and ATCC PTA-6048), pY89-12 (identical to pY89-5, with the exception that the Eg12 sequence was inserted instead of Eg5) and pY-75 (Example 5, negative control cloning vector [lacking Eg5 or Eg12]) were transformed into *Saccharomyces cerevisiae* BY4741 (ATCC #201388) using standard lithium acetate transformation procedures. Transformants were selected on DOBA media supplemented with CSM-leu (Qbiogene, Carlsbad, Calif.). Transformants from each plate were inoculated into 2 mL of DOB medium supplemented with CSM-leu (Qbiogene) and grown for 1 day at 30° C., after which 0.5 mL was transferred to the same medium supplemented with either EDA or EtrA to 1 mM. These were incubated overnight at 30° C., 250 rpm, pellets were obtained by centrifugation and dried under vacuum. Pellets were transesterified with 50 μL of TMSH and analyzed by GC as described in Example 1. Two clones for pY-75 (i.e., clones 75-1 and 75-2) and pY89-5 (i.e., clones 5-6-1 and 5-6-2) were analyzed, while two sets of clones for pY89-12 (i.e., clones 12-8-1, 12-8-2, 12-9-1 and 12-9-2) from two independent transformations were analyzed.

The lipid profile obtained by GC analysis of clones fed EDA are shown in Table 5; and the lipid profile obtained by GC analysis of clones fed EtrA are shown in Table 6.

TABLE 5

| Clone | 16:0 | 16:1 | 18:0 | 18:1 | 20:2 | 20:3 (8, 11, 14) | % 20:2 Converted |
|---|---|---|---|---|---|---|---|
| 75-1 | 14 | 32 | 5 | 38 | 10 | 0 | 0 |
| 75-2 | 14 | 31 | 5 | 41 | 9 | 0 | 0 |
| 5-6-1 | 14 | 32 | 6 | 40 | 6 | 2 | 24 |
| 5-6-2 | 14 | 30 | 6 | 41 | 7 | 2 | 19 |
| 12-8-1 | 14 | 30 | 6 | 41 | 9 | 1 | 7 |
| 12-8-2 | 14 | 32 | 5 | 41 | 8 | 1 | 8 |
| 12-9-1 | 14 | 31 | 5 | 40 | 9 | 1 | 8 |
| 12-9-2 | 14 | 32 | 5 | 41 | 8 | 1 | 7 |

TABLE 6

| Clone | 16:0 | 16:1 | 18:0 | 18:1 | 20:3 (11, 14, 17) | 20:4 (8, 11, 14, 17) | % 20:3 Converted |
|---|---|---|---|---|---|---|---|
| 75-1 | 12 | 25 | 5 | 33 | 24 | 0 | 0 |
| 75-2 | 12 | 24 | 5 | 36 | 22 | 1 | 5 |
| 5-6-1 | 13 | 25 | 6 | 34 | 15 | 7 | 32 |
| 5-6-2 | 13 | 24 | 6 | 34 | 17 | 6 | 27 |
| 12-8-1 | 12 | 24 | 5 | 34 | 22 | 2 | 8 |
| 12-8-2 | 12 | 25 | 5 | 35 | 20 | 2 | 9 |
| 12-9-1 | 12 | 24 | 5 | 34 | 22 | 2 | 9 |
| 12-9-2 | 12 | 25 | 6 | 35 | 20 | 2 | 9 |

The data in Tables 4 and 5 showed that the cloned *Euglena delta*-8 desaturase is able to desaturate EDA and EtrA. The sequence set forth in SEQ ID NO:4 has one amino acid change compared to the sequence set forth in SEQ ID NO:2 and has reduced delta-8 desaturase activity.

The small amount of 20:4(8,11,14,17) generated by clone 75-2 in Table 6 had a slightly different retention time than a standard for 20:4(8,11,14,17). This peak was more likely a small amount of a different fatty acid generated by the wild-type yeast in that experiment.

Example 12

Cloning Other Delta-8 Desaturases or Elongases into Soybean Expression Vectors

In addition to the delta-8 desaturase from *Euglena gracilis*, other delta-8 desaturases can be cloned into the soybean expression vectors such as those described in Example 6 and Example 8. For instance, a suitable delta-8 desaturase from an organism other than *Euglena gracilis* can be cloned using methods similar to, but not limited to, the methods described in Example 2 and Example 3. PCR primers designed to introduce NotI sites at the 5' and 3' ends of the delta-8 desaturase can be used to amplify the gene. The resulting PCR product can then be digested with NotI and cloned into a soybean expression vector such as pKR457. Further sub-cloning into other vectors as described in Example 6 or Example 8 would yield vectors suitable for expression and co-expression of the delta-8 desaturase in soybean.

Likewise, in addition to the elongase from *Mortierella alpina*, other elongases can be cloned into the soybean expression vectors such as those described in Example 6 and Example 8. Specifically, elongases with specificity for linoleic acid or alpha-linolenic acid such as that from *Isoch-*

*rysis galbana* (WO 2002/077213) can be used. For instance, a suitable elongase from an organism other than *Mortierella alpina* can be cloned using methods similar to, but limited not to, the methods described in Example 2 and Example 3. PCR primers designed to introduce NofI sites at the 5' and 3' ends of the elongase can be used to amplify the gene. The resulting PCR product can then be digested with NofI and cloned into soybean expression vectors such as pKR72 or pKR263. Further sub-cloning into other vectors as described in Example 6 or Example 8 would yield vectors suitable for expression and co-expression of the elongase in soybean.

Example 13

Transformation of Somatic Soybean Embryo Cultures

Culture Conditions: Soybean embryogenic suspension cultures (cv. Jack) can be maintained in 35 mL liquid medium SB196 (infra) on a rotary shaker, 150 rpm, 26° C. with cool white fluorescent lights on 16:8 hr day/night photoperiod at light intensity of 60-85 µE/m2/s. Cultures are subcultured every 7 days to two weeks by inoculating approximately 35 mg of tissue into 35 mL of fresh liquid SB196 (the preferred subculture interval is every 7 days).

Soybean embryogenic suspension cultures can be transformed with the plasmids and DNA fragments described earlier by the method of particle gun bombardment (Klein et al., *Nature*, 327:70 (1987)) using a DuPont Biolistic PDS1000/HE instrument (helium retrofit) for all transformations.

Soybean Embrvogenic Suspension Culture Initiation: Soybean cultures are initiated twice each month with 5-7 days between each initiation.

Pods with immature seeds from available soybean plants 45-55 days after planting are picked, removed from their shells and placed into a sterilized magenta box. The soybean seeds are sterilized by shaking them for 15 min in a 5% Clorox solution with 1 drop of ivory soap (i.e., 95 mL of autoclaved distilled water plus 5 mL Clorox and 1 drop of soap, mixed well). Seeds are rinsed using 2 1-liter bottles of sterile distilled water and those less than 4 mm were placed on individual microscope slides. The small end of the seed is cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.

Preparation of DNA for Bombardment: Either an intact plasmid or a DNA plasmid fragment containing the genes of interest and the selectable marker gene can be used for bombardment. Fragments from plasmids such pKR274 and pKR685 or pKR681 and/or other expression plasmids can be obtained by gel isolation of digested plasmids. In each case, 100 µg of plasmid DNA can be used in 0.5 mL of the specific enzyme mix described below. Plasmids could be digested with AscI (100 units) in NEBuffer 4 (20 mM Tris-acetate, 10 mM magnesium acetate, 50 mM potassium acetate, 1 mM dithiothreitol, pH 7.9), 100 µg/mL BSA, and 5 mM beta-mercaptoethanol at 37° C. for 1.5 hr. The resulting DNA fragments could be separated by gel electrophoresis on 1% SeaPlaque GTG agarose (BioWhitaker Molecular Applications) and the DNA fragments containing EPA biosynthetic genes could be cut from the agarose gel. DNA can be purified from the agarose using the GELase digesting enzyme following the manufacturer's protocol. Alternatively, whole plasmids or a combination of whole plasmid with fragment could be used.

A 50 µl aliquot of sterile distilled water containing 3 mg of gold particles can be added to 5 µl of a 1 µg/µl DNA solution (either intact plasmid or DNA fragment prepared as described above), 50 µl 2.5M $CaCl_2$ and 20 µl of 0.1 M spermidine. The mixture is shaken 3 min on level 3 of a vortex shaker and spun for 10 sec in a bench microfuge. After a wash with 400 µl 100% ethanol, the pellet is suspended by sonication in 40 µl of 100% ethanol. Five pl of DNA suspension is dispensed to each flying disk of the Biolistic PDS1000/HE instrument disk. Each 5 µl aliquot contained approximately 0.375 mg gold particles per bombardment (i.e., per disk).

Tissue Preparation and Bombardment with DNA: Approximately 150-200 mg of 7 day old embryonic suspension cultures are placed in an empty, sterile 60×15 mm petri dish and the dish is covered with plastic mesh. Tissue is bombarded 1 or 2 shots per plate with membrane rupture pressure set at 1100 PSI and the chamber is evacuated to a vacuum of 27-28 inches of mercury. Tissue is placed approximately 3.5 inches from the retaining/stopping screen.

Selection of Transformed Embryos: Transformed embryos are selected either using hygromycin (when the hygromycin phosphotransferase, HPT, gene was used as the selectable marker) or chlorsulfuron (when the acetolactate synthase, ALS, gene was used as the selectable marker). Specifically, following bombardment, the tissue is placed into fresh SB196 media and cultured as described above. Six days post-bombardment, the SB196 is exchanged with fresh SB196 containing either a selection agent of 30 mg/L hygromycin or a selection agent of 100 ng/mL chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Regeneration of Soybean Somatic Embryos into Plants: In order to obtain whole plants from embryogenic suspension cultures, the tissue must be regenerated.

Embryo Maturation: Embryos can be cultured for 4-6 weeks at 26° C. in SB196 under cool white fluorescent (Philips cool white Econowatt F40/CW/RS/EW) and Agro (Philips F40 Agro) bulbs (40 watt) on a 16:8 hr photoperiod with light intensity of 90-120 $\mu E/m^2s$. After this time embryo clusters are removed to a solid agar media, SB166, for 1-2 weeks. Clusters are then subcultured to medium SB103 for 3 weeks. During this period, individual embryos can be removed from the clusters and screened for alterations in their fatty acid compositions as described in Example 11. It should be noted that any detectable phenotype, resulting from the expression of the genes of interest, could be screened at this stage. This would include (but not be limited to) alterations in: fatty acid profile, protein profile and content, carbohydrate content, growth rate, viability, or the ability to develop normally into a soybean plant.

Embryo Desiccation and Germination: Matured individual embryos can be desiccated by placing them into an empty, small petri dish (35×10 mm) for approximately 4-7 days. The plates are sealed with fiber tape (creating a small humidity chamber). Desiccated embryos can be planted into SB714 medium where they are left to germinate under the same culture conditions described above. Germinated plantlets are removed from germination medium and rinsed thoroughly with water and then planted in Redi-Earth in 24-cell pack trays, covered with clear plastic domes. After 2 weeks the dome is removed and plants hardened off for a further week. If plantlets look hardy they are transplanted to 10" pots of Redi-Earth with up to 3 plantlets per pot. After 10 to 16 weeks, mature seeds can be harvested, chipped and analyzed for fatty acids as described above.

Media Recipes
SB 196 - FN Lite liquid proliferation medium (per liter)

| | |
|---|---|
| MS FeEDTA - 100x Stock 1 | 10 mL |
| MS Sulfate - 100x Stock 2 | 10 mL |
| FN Lite Halides - 100x Stock 3 | 10 mL |
| FN Lite P, B, Mo - 100x Stock 4 | 10 mL |
| B5 vitamins (1 mL/L) | 1.0 mL |
| 2,4-D (10 mg/L final concentration) | 1.0 mL |
| KNO$_3$ | 2.83 g |
| (NH$_4$)$_2$SO$_4$ | 0.463 g |
| Asparagine | 1.0 g |
| Sucrose (1%) | 10 g |
| pH 5.8 | |

FN Lite Stock Solutions

| Stock # | | 1000 mL | 500 mL |
|---|---|---|---|
| 1 | MS Fe EDTA 100x Stock | | |
| | Na$_2$ EDTA* | 3.724 g | 1.862 g |
| | FeSO$_4$—7H$_2$O | 2.784 g | 1.392 g |

*Add first, dissolve in dark bottle while stirring

| | | | |
|---|---|---|---|
| 2 | MS Sulfate 100x stock | | |
| | MgSO$_4$—7H$_2$O | 37.0 g | 18.5 g |
| | MnSO$_4$—H$_2$O | 1.69 g | 0.845 g |
| | ZnSO$_4$—7H$_2$O | 0.86 g | 0.43 g |
| | CuSO$_4$—5H$_2$O | 0.0025 g | 0.00125 g |
| 3 | FN Lite Halides 100x Stock | | |
| | CaCl$_2$—2H$_2$O | 30.0 g | 15.0 g |
| | KI | 0.083 g | 0.0715 g |
| | CoCl$_2$—6H$_2$O | 0.0025 g | 0.00125 g |
| 4 | FN Lite P, B, Mo 100x Stock | | |
| | KH$_2$PO$_4$ | 18.5 g | 9.25 g |
| | H$_3$BO$_3$ | 0.62 g | 0.31 g |
| | Na$_2$MoO$_4$—2H$_2$O | 0.025 g | 0.0125 g |

SB1 solid medium (per liter)

1 pkg. MS salts (Catalog #11117-066, Gibco/BRL)
1 mL B5 vitamins 1000X stock
31.5 g sucrose
2 mL 2,4-D (20 mg/L final concentration)
pH 5.7
8 g TC agar

SB 166 solid medium (per liter)

1 pkg. MS salts (Catalog #11117-066, Gibco/BRL)
1 mL B5 vitamins 1000X stock
60 g maltose
750 mg MgCl$_2$ hexahydrate
5 g activated charcoal
pH 5.7
2 g gelrite

SB 103 solid medium (per liter)

1 pkg. MS salts (Catalog #11117-066, Gibco/BRL)
1 mL B5 vitamins 1000X stock
60 g maltose
750 mg MgCl$_2$ hexahydrate
pH 5.7
2 g gelrite

SB 71-4 solid medium (per liter)

1 bottle Gamborg's B5 salts with sucrose
(Catalog #21153-036, Gibco/BRL)
pH 5.7
5 g TC agar
2,4-D stock: obtained premade from Phytotech, Catalog #D 295;

concentration is 1 mg/mL
B5 Vitamins Stock (per 100 mL; store aliquots at −20° C.)

10 g myo-inositol
100 mg nicotinic acid 100 mg pyridoxine HCl
1 g thiamine

* If the solution does not dissolve quickly enough, apply a low level of heat via the hot stir plate.

Chlorsulfuron Stock 1 mg/mL in 0.01 N ammonium hydroxide

To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos, which produce secondary embryos, are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. *Nature* (London) 327:70-73 (1987); U.S. Pat. No. 4,945,050). A DuPont Biolistic PDS1000/HE instrument (helium retrofit) can be used for these transformations.

A selectable marker gene which can be used to facilitate soybean transformation is a recombinant DNA construct composed of the 35S promoter from Cauliflower Mosaic Virus (Odell et al. *Nature* 313:810-812 (1985)), the hygromycin phosphotransferase gene from plasmid pJR225 (from *E. coli*; Gritz et al. *Gene* 25:179-188 (1983)) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL CaCl$_2$ (2.5 M). The particle preparation is then agitated for three min, spun in a microfuge for 10 sec and the supernatant removed. The DNA-coated particles are then washed once in 400 μL 70% ethanol and resuspended in 40 μL of anhydrous ethanol. The DNA/particle suspension can be sonicated three times for one sec each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 14

Further Modification of the Delta-8 Desaturase Gene Codon-Optimized for *Yarrowia lipolytica*

Figure 6:
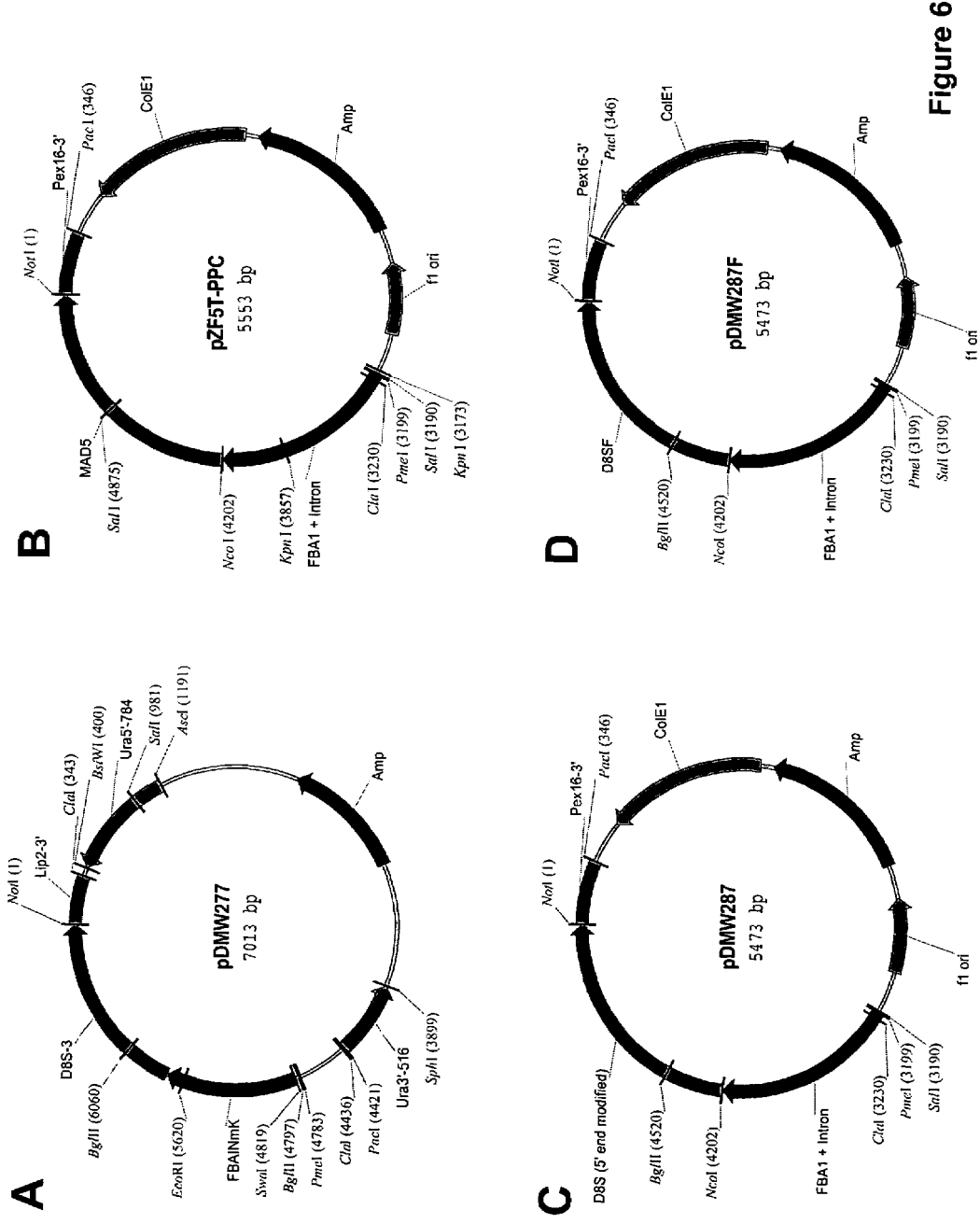

The amino acid sequence of the synthetic codon-optimized D8S-3 gene in pDMW261 (Example 1) was corrected according to the amino acid sequence of the functional *Euglena delta*-8 desaturase (SEQ ID NOs:1 and 2). Using pDMW261 as a template and oligonucleotides ODMW404 (SEQ ID NO:94) and D8-13R (SEQ ID NO:36), the DNA fragment encoding the synthetic D8S-3 desaturase gene was amplified. The resulting PCR fragment was purified with Bio101's Geneclean kit and subsequently digested with KpnI and NotI (primer ODMW404 introduced a KpnI site while primer D8-13R introduced a NotI site). The KpnI/NotI fragment (SEQ ID NO:95) was cloned into KpnI/NotI digested pKUNFmKF2 (FIG. 5D; SEQ ID NO:116) to produce pDMW277 (FIG. 6A).

Oligonucleotides YL521 (SEQ ID NO:96) and YL522 (SEQ ID NO:97), which were designed to amplify and correct the 5' end of the D8S-3 gene, were used as primers in another PCR reaction where pDMW277 was used as the template. The primers introduced into the PCR fragment a NcoI site and BglII site at its 5' and 3'ends, respectively. The 318 bp PCR product was purified with Bio101's GeneClean kit and subsequently digested with NcoI and BglII. The digested fragment, along with the 954 bp BglII/NotI fragment from pDMW277, was used to exchange the NcoI/NotI fragment of pZF5T-PPC (FIG. 6B; SEQ ID NO:117) to form pDMW287 (FIG. 6C). In addition to correcting the 5' end of the synthetic D8S-3 gene, this cloning reaction also placed the synthetic delta-8 desaturase gene under control of the *Yarrowia lipolytica* fructose-bisphosphate aldolase promoter containing a *Yarrowia* intron (FBAIN; SEQ ID NO:114; see WO 2005/049805).

The first reaction in a final series of site-directed mutagenesis reactions was then performed on pDMW287. The first set of primers, YL525 (SEQ ID NO:98) and YL526 (SEQ ID NO:99), was designed to correct amino acid from F to S (position #50) of the synthetic D8S-3 gene in pDMW287. The plasmid resulting from this mutagenesis reaction then became the template for the next site-directed mutagenesis reaction with YL527 (SEQ ID NO:100) and YL528 (SEQ ID NO:101) as primers. These primers were designed to correct the amino acid from F to S (position #67) of the D8S-3 gene and resulted in creation of plasmid pDMW287/YL527.

To complete the sequence corrections within the second quarter of the gene, the following reactions were carried out concurrently with the mutations on the first quarter of the gene. Using pDMW287 as template and oligonucleotides YL529 (SEQ ID NO:102) and YL530 (SEQ ID NO:103) as primers, an in vitro mutagenesis reaction was carried out to correct the amino acid from C to W (position #177) of the synthetic D8S-3 gene. The product (i.e., pDMW287/Y529) of this mutagenesis reaction was used as the template in the following reaction using primers YL531 (SEQ ID NO:104) and YL532 (SEQ ID NO:105) to correct the amino acid from P to L (position #213). The product of this reaction was called pDMW287/YL529-31.

Concurrently with the mutations on the first and second quarter of the gene, reactions were similarly carried out on the 3' end of the gene. Each subsequent mutagenesis reaction used the plasmid product from the preceding reaction. Primers YL533 (SEQ ID NO:106) and YL534 (SEQ ID NO:107) were used on pDMW287 to correct the amino acid from C to S (position #244) to create pDMW287/YL533. Primers YL535 (SEQ ID NO:108) and YL536 (SEQ ID NO:109) were used to correct the amino acid A to T (position #280) in the synthetic D8S-3 gene of pDMW287/YL533 to form pDMW287/YL533-5. Finally, the amino acid P at position of #333 was corrected to S in the synthetic D8S-3 gene using pDMW287/YL533-5 as the template and YL537 (SEQ ID NO:110) and YL538 (SEQ ID NO:111) as primers. The resulting plasmid was named pDMW287/YL533-5-7.

The BglII/XhoI fragment of pDMW287/YL529-31, and the XhoI/NotI fragment of pDMW287/YL533-5-7 was used to change the BglII/NotI fragment of pDMW287/YL257 to produce pDMW287F (FIG. 6D) containing the completely corrected synthetic delta-8 desaturase gene, designated "D8SF" and set forth in SEQ ID NO:112. SEQ ID NO:113 sets forth the amino acid sequence encoded by nucleotides 2-1270 of SEQ ID NO:112, which is essentially the same as the sequence set forth in SEQ ID NO:2, except for an additional valine following the start methionine.

Example 15

Synthesis and Functional Expression of a Codon-Optimized Delta-9 Elongase Gene in *Yarrowia lipolytica*

In order to express the delta-9 elongase/delta-8 desaturase pathway in *Yarrowia lipolytica*, it was necessary to obtain an appropriate delta-9 elongase that could be co-expressed with the synthetic codon-optimized delta-8 desaturase from Example 14. Thus, the codon usage of the delta-9 elongase gene of *Isochrysis galbana* (GenBank Accession No. AF390174) was optimized for expression in *Y. lipolytica*. According to the *Yarrowia* codon usage pattern, the consensus sequence around the ATG translation initiation codon, and the general rules of RNA stability (Guhaniyogi, G. and J. Brewer, *Gene* 265(1-2):11-23 (2001)), a codon-optimized delta-9 elongase gene was designed (SEQ ID NO:118), based on the DNA sequence of *Isochrysis galbana*; SEQ ID NO:119. In addition to modification of the translation initiation site, 126 bp of the 792 bp coding region were modified, and 123 codons were optimized. None of the modifications in the codon-optimized gene changed the amino acid sequence of the encoded protein (GenBank Accession No. AF390174; SEQ ID NO:120).

In Vitro Synthesis of a Codon-Optimized Delta-9 Elongase Gene for *Yarrowia*

The method used to synthesize the codon-optimized delta-9 elongase gene was the same as that used for synthesis of the delta-8 desaturase gene (Example 1). First, eight pairs of oligonucleotides were designed to extend the entire length of the codon-optimized coding region of the *I. galbana* delta-9 elongase gene (e.g., IL3-1A, IL3-1B, IL3-2A, IL3-2B, IL3-3A, IL3-3B, IL3-4A, IL3-5A, IL3-5B, IL3-6A, IL3-6B, IL3-7A, IL3-7B, IL3-8A, IL3-8B, corresponding to SEQ ID NOs:121-136). Each pair of sense (A) and anti-sense (B)

oligonucleotides were complementary, with the exception of a 4 bp overhang at each 5'-end. Additionally, primers IL3-1F, IL3-4R, IL3-5F and IL3-8R (SEQ ID NOs:137-140) also introduced NcoI, PstI, PstI and Not1 restriction sites, respectively, for subsequent subcloning.

Each oligonucleotide (100 ng) was phosphorylated at 37° C. for 1 hr in a volume of 20 µl containing 50 mM Tris-HCl (pH 7.5), 10 mM MgCl$_2$, 10 mM DTT, 0.5 mM spermidine, 0.5 mM ATP and 10 U of T4 polynucleotide kinase. Each pair of sense and antisense oligonucleotides was mixed and annealed in a thermocycler using the following parameters: 95° C. (2 min), 85° C. (2 min), 65° C (15 min), 37° C. (15 min), 24° C. (15 min) and 4° C. (15 min). Thus, IL3-1A (SEQ ID NO:121) was annealed to IL3-1B (SEQ ID NO:122) to produce the double-stranded product "IL3-1AB". Similarly, IL3-2A (SEQ ID NO:123) was annealed to IL3-2B (SEQ ID NO:124) to produce the double-stranded product "IL3-2AB", etc.

Two separate pools of annealed, double-stranded oligonucleotides were then ligated together, as shown below: Pool 1 (comprising IL3-l1AB, IL3-2AB, IL3-3AB and IL3-4AB); and, Pool 2 (comprising IL3-5AB, IL3-6AB, IL3-7AB and IL3-8AB). Each pool of annealed oligonucleotides was mixed in a volume of 20 µl with 10 U of T4 DNA ligase and the ligation reaction was incubated overnight at 16° C.

The product of each ligation reaction was then used as template to amplify the designed DNA fragment by PCR. Specifically, using the ligated "Pool 1" mixture (i.e., IL3-1AB, IL3-2AB, IL3-3AB and IL3-4AB) as template, and oligonucleotides IL3-1F and IL3-4R (SEQ ID NOs:137 and 138) as primers, the first portion of the codon-optimized delta-9 elongase gene was amplified by PCR (as described in Example 1). The 417 bp PCR fragment was subcloned into the PGEM-T easy vector (Promega) to generate pT9(1-4).

Using the ligated "Pool 2" mixture (i.e. IL3-5AB, IL3-6AB, IL3-7AB and IL3-8AB) as the template, and oligonucleotides IL3-5F and IL3-8R (SEQ ID NOs:139 and 140) as primers, the second portion of the codon-optimized delta-9 elongase gene was amplified similarly by PCR and cloned into the pGEM-T-easy vector to generate pT9(5-8).

Figure 7:
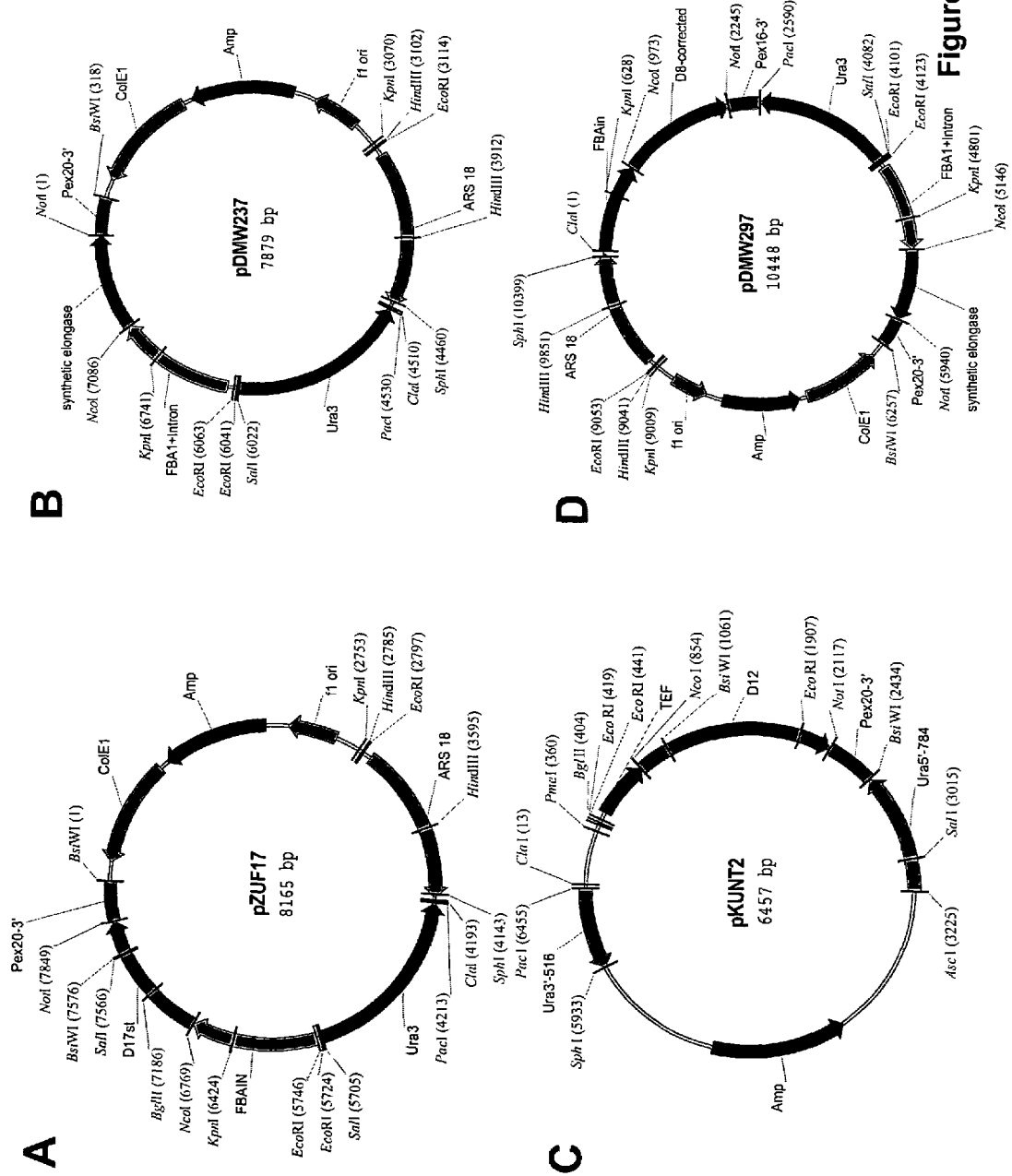

E. coli was transformed separately with pT9(1-4) and pT9(5-8) and the plasmid DNA was isolated from ampicillin-resistant transformants. Plasmid DNA was purified and digested with the appropriate restriction endonucleases to liberate the 417 bp NcoI/PstI fragment of pT9(1-4) (SEQ ID NO:141) and the 377 bp PstI/NotI fragment of pT9(5-8) (SEQ ID NO:142). These two fragments were then combined and directionally ligated together with NcoI/NotI digested pZUF17 (SEQ ID NO:143; FIG. 7A) to generate pDMW237 (FIG. 7B; SEQ ID NO:144). The DNA sequence of the resulting synthetic delta-9 elongase gene ("IgD9e") in pDMW237 was exactly the same as the originally designed codon-optimized gene (i.e., SEQ ID NO:118) for *Yarrowia*.

Generation of *Y. lipolytica* Strain Y2031 (A Ura-Derivative of ATCC #20362)

Strain Y2031 was generated by integration of the TEF::Y.Δ12::Pex20 chimeric gene of plasmid pKUNT2 (FIG. 7C) into the Ura3 gene locus of *Yarrowia lipolytica* ATCC #20362, to thereby generate the Ura-genotype of strain Y2031.

Specifically, plasmid pKUNT2 contained the following components:

TABLE 7

Description of Plasmid pKUNT2 (SEQ ID NO: 145)

| RE Sites And Nucleotides Within SEQ ID NO: 145 | Description Of Fragment And Chimeric Gene Components |
|---|---|
| AscI/BsiWI (3225-3015) | 784 bp 5' part of *Yarrowia* Ura3 gene (GenBank Accession No. AJ306421) |
| SphI/PacI (5933-13) | 516 bp 3' part of *Yarrowia* Ura3 gene (GenBank Accession No. AJ306421) |
| EcoRI/ BsiWI (6380-8629) | TEF::Y.Δ12::Pex20, comprising: TEF: TEF promoter (GenBank Accession No. AF054508) Y.Δ12: *Yarrowia* delta-12 desaturase gene (SEQ ID NO: 146; see also WO 2004/104167) Pex20: Pex20 terminator sequence from *Yarrowia* Pex20 gene (GenBank Accession No. AF054613) |

The pKUNT2 plasmid was digested with AscI/SphI, and then used for transformation of wild type *Y. lipolytica* ATCC #20362 according to the General Methods. The transformant cells were plated onto 5-fluoroorotic acid ("FOA"; also 5-fluorouracil-6-carboxylic acid monohydrate) selection media plates and maintained at 30° C. for 2 to 3 days. Specifically, FOA selection media comprised: 0.17% yeast nitrogen base (DIFCO Laboratories, Detroit, Mich.) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar. The FOA resistant colonies were picked and streaked onto MM and MMU selection plates. The colonies that could grow on MMU plates but not on MM plates were selected as Ura-strains. Single colonies (5) of Ura-strains were then inoculated into liquid MMU at 30° C. and shaken at 250 rpm/min for 2 days.

The cells were collected by centrifugation, lipids were extracted, and fatty acid methyl esters were prepared by trans-esterification, and subsequently analyzed with a Hewlett-Packard 6890 GC. GC analyses showed that there were about 45% LA in two Ura-strains (strains #2 and #3), compared to about 20% LA in the wild type ATCC #20362. Transformant strain #2 was designated as strain "Y2031".

Expression of the Codon-Optimized Delta-9 Elongase Gene in *Y. lipolytica*

Construct pDMW237 (comprising the chimeric FBAIN::IgD9e::Pex20 gene) was transformed into *Yarrowia lipolytica* strain Y2031, as described in the General Methods. Three transformants of Y2031 with pDMW237 were grown individually in MM media for two days. The cells were collected by centrifugation, lipids were extracted, and fatty acid methyl esters were prepared by trans-esterification, and subsequently analyzed with a Hewlett-Packard 6890 GC.

The GC results showed that there were about 7.1%, 7.3% and 7.4% EDA produced in these transformants with pDMW237. These data demonstrated that the synthetic IgD9e could convert the C18:2 to EDA. The "percent (%) substrate conversion" or "conversion efficiency" of the codon-optimized gene was determined to be about 13%, wherein the conversion efficiency was calculated according to the following formula: ([product]/[substrate+product])*100, where 'product' includes the immediate product and all products in the pathway derived from it. This term refers to the efficiency by which the particular enzyme can convert substrate to product.

Example 16

Delta-9 Elongase/ Delta-8 Desaturase Pathway Expression to Produce DGLA in *Yarrowia lipolytica*

The present Example describes DGLA biosynthesis and accumulation in *Yarrowia lipolytica* that was transformed to express the delta-9 elongase/delta-8 desaturase pathway. Thus, this required co-synthesis of the synthetic codon-optimized delta-9 elongase (SEQ ID NO:118; Example 15) and the synthetic codon-optimized delta-8 desaturase (SEQ ID NO:112; Example 14).

Specifically, the ClaI/PacI fragment comprising the chimeric FBAIN::D8SF::Pex16 gene of construct pDMW287F (FIG. 6D) was inserted into the ClaI/PacI sites of pDMW237 (FIG. 7B) to generate the construct pDMW297 (FIG. 7D). Thus, plasmid pDMW297 contained the following components:

TABLE 8

Description of Plasmid pDMW297 (SEQ ID NO: 148)

| RE Sites And Nucleotides Within SEQ ID NO: 148 | Description Of Fragment And Chimeric Gene Components |
|---|---|
| EcoRI/ClaI (9053-10448) | ARS18 sequence (GenBank Accession No. A17608) |
| ClaI/PacI (1-2590) | FBAIN::Δ8S::Pex16, comprising:<br>FBAIN: FBAIN promoter (SEQ ID NO: 114)<br>Δ8S: codon-optimized delta-8 desaturase gene (SEQ ID NO: 112), derived from *Euglena gracilis* (GenBank Accession No. AF139720)<br>Pex16: Pex16 terminator sequence of *Yarrowia* Pex16 gene (GenBank Accession No. U75433) |
| PacI/SalI (2590-4082) | *Yarrowia* Ura3 gene (GenBank Accession No. AJ306421) |
| SalI/BsiWI (4082-6257) | FBAIN::Δ9ES::Pex120, comprising:<br>FBAIN: FBAIN promoter (SEQ ID NO: 114)<br>Δ9ES: codon-optimized delta-9 elongase gene (SEQ ID NO: 118), derived from *Isochrysis galbana* (GenBank Accession No. 390174)<br>Pex20: Pex20 terminator sequence of *Yarrowia* Pex20 gene (GenBank Accession No. AF054613) |

The pDMW297 plasmid was then used for transformation of strain Y2031 (Example 15) according to the General Methods. The transformant cells were plated onto MM selection media plates and maintained at 30° C. for 2 to 3 days. A total of 8 transformants grown on the MM plates were picked and re-streaked onto fresh MM plates. Once grown, these strains were individually inoculated into liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that DGLA was produced in all of the transformants analyzed. One strain produced about 3.2%, 4 strains produced 4.34.5%, two strains produced 5.5-5.8% and one strain produced 6.4% DGLA (designated herein as strain "Y0489"). The "percent (%) substrate conversion" of the codon-optimized D8SF gene in strain Y0489 was determined to be 75% (using the formula of Example 15).

It will be obvious to one of skill in the art that other chimeric genes could be co-expressed with the D8SF and IgD9e genes in engineered Yarrowia to enable production of various other PUFAs. For example, in addition to the codon-optimized delta-9 elongase and delta-8 desaturase genes, one could readily express: (1) a delta-15 desaturase to enable production of ETA; (2) a delta-5 desaturase to enable production of ARA; (3) a delta-17 desaturase to enable production of ETA; (4) a delta-5 desaturase and a delta-17 desaturase to enable production of EPA; (6) a delta-5 desaturase, a delta-17 desaturase and a $C_{20/22}$ elongase to enable production of DPA; or (7) a delta-5 desaturase, a delta-17 desaturase, a $C_{20/22}$ elongase and a delta-4 desaturase to enable production of DHA (FIG. 9).

Example 17

Cloning the *Euglena gracilis* Delta-8 Desaturase into a Soybean Expression Vector and Co-Expression with an *Isochrysis galbana* Elongase The gene for the Isochrysis galbana elongase was amplified from pDMW237 (FIG. 7B; SEQ ID NO:144) using primers oIGsel1-1 (SEQ ID NO:149) and oIGsel1-2 (SEQ ID NO:150) which were designed to introduce NotI restriction enzyme sites at both ends of the elongase. The resulting PCR fragment was digested with NotI and cloned into the NotI site of pKR72 to give pKR607.

Figure 8:
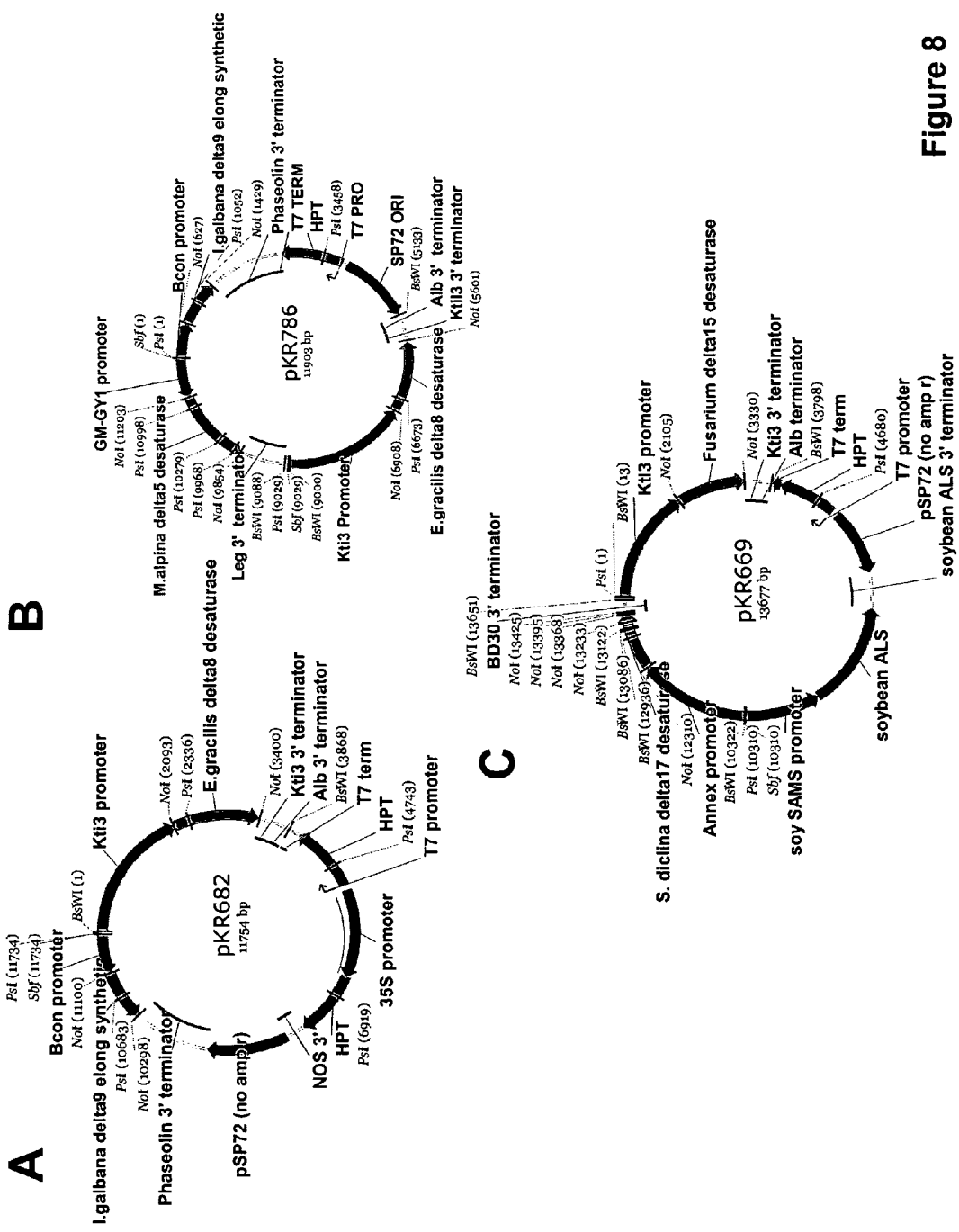

Plasmid pKR680 was digested with BsiWI and the fragment containing Eg5 (SEQ ID NO:1) was cloned into the BsiWI site of pKR607 to give pKR682. Thus, the delta-8 desaturase (Eg5; SEQ ID NO:1) could be co-expressed with the *Isochrysis galbana* elongase behind strong, seed-specific promoters. A map of pKR682 is shown in FIG. 8A.

Example 18

Assembling EPA Biosynthetic Pathway Genes with the *Euglena gracilis* Delta-8 Desaturase and *Isochrysis galbana* Elongase for Expression in Somatic Soybean Embryos and Soybean Seeds An soybean expression vector (pKR786) containing the *Euglena gracilis* delta-8 desaturase, the Isochrysis galbana delta-9 elongase and the *Mortierella alpina* delta-5 desaturase (all under control of strong seed specific promoters) was constructed in the following way.

Through a number of sub-cloning steps, a sequence of DNA (SEQ ID NO:151) was effectively added into the SmaI site of vector pKR287 (WO 2004/071467 A2) to produce pKR767. In this way, a SbfI restriction site was added to the 3' end of the leg1A transcription terminator of the Gy1/Mad5/legA2 cassette.

The AscI fragment of pKR682 was cloned into the AscI site of pKR277 (WO 2004/071467 A2) to produce pKR769.

The Gy1/Mad5/legA2 cassette was released from pKR767 by digestion with SbfI and the resulting fragment was cloned into the SbfI site of pKR769 to produce pKR786. A map of pKR786 is shown in FIG. 8B.

Example 19

Cloning the Fusarium Delta-15 Desaturase into a Soybean Expression Vector and Co-Expression with EPA Biosynthetic Genes (Delta-15 Desaturase, Delta-17 Desaturase)

The Kti3 promoter:Fm Δ15 desaturase ORF:Kti3 terminator cassette was released from plasmid pKR578 (WO 2005/

047479) by digestion with BsiWI and was cloned into the BsiWI site of plasmid pKR226 (WO 2004/071467 A2), containing the ALS gene for selection, the T7prom/hpt/T7term cassette and the bacterial ori region, to produce pKR667.

Plasmid pKR271 was digested with PstI and the fragment containing the *Saprolegnia diclina* delta-17 desaturase was cloned into the SbfI site of pKR667 to produce pKR669. In this way, the delta-15 desaturase could be co-expressed with the *Saprolegnia diclina* delta-17 desaturase behind strong, seed-specific promoters. A map of pKR669 is shown in FIG. 8C.

Example 20

Analysis of Somatic Soy Embryos Containing the *Euglena gracilis* Delta-8 Desaturase and *Mortierella alpina* Elongase Genes (pKR681)

Mature somatic soybean embryos are a good model for zygotic embryos. While in the globular embryo state in liquid culture, somatic soybean embryos contain very low amounts of triacylglycerol or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, α'-subunit of β-conglycinin, kunitz trypsin inhibitor 3, and seed lectin are essentially absent. Upon transfer to hormone-free media to allow differentiation to the maturing somatic embryo state, triacylglycerol becomes the most abundant lipid class. As well, mRNAs for α'-subunit of β-conglycinin, kunitz trypsin inhibitor 3 and seed lectin become very abundant messages in the total mRNA population. On this basis, the somatic soybean embryo system behaves very similarly to maturing zygotic soybean embryos in vivo, and is thus a good and rapid model system for analyzing the phenotypic effects of modifying the expression of genes in the fatty acid biosynthesis pathway (Example 3 in WO 02/00904). Most importantly, the model system is also predictive of the fatty acid composition of seeds from plants derived from transgenic embryos.

Transgenic somatic soybean embryos containing the constructs described above were analyzed in a similar way. For this, fatty acid methyl esters were prepared from single, matured, somatic soy embryos by transesterification. Embryos were placed in a vial containing 50 μL of trimethylsulfonium hydroxide (TMSH) and 0.5 mL of hexane and incubated for 30 min at room temperature while shaking. Fatty acid methyl esters (5 μL injected from hexane layer) are separated and quantified using a Hewlett-Packard 6890 Gas Chromatograph fitted with an Omegawax 320 fused silica capillary column (Catalog #24152, Supelco Inc.). The oven temperature was programmed to hold at 220° C. for 2.7 min, increase to 240° C. at 20° C./min and then hold for an additional 2.3 min. Carrier gas was supplied by a Whatman hydrogen generator. Retention times were compared to those for methyl esters of standards commercially available (Catalog #U-99-A, Nu-Chek Prep, Inc.). Routinely, 6-10 embryos per event were analyzed by GC, using the methodology described above.

More specifically, embryo fatty acid profiles for ~6 lines containing pKR681 are shown in Table 9. The best line (i.e., 1618-1-1-1) had embryos with an average DGLA content of 8.9% and an average ETA content of 3.1%. For lines 1618-1-8-1, 1618-3-6-1 and 16184-1-1, only the elongase appeared to be functioning. The best elongase line (i.e., 1618-4-1-1) had embryos with an average EDA content of 10.6% and an average EtrA content of 6.5%. Calculated % elongation, % desaturation and elongation and desaturation ratios are shown in Table 10. In line 1618-1-1-1, the delta-8 desaturase converts an average of 76.3% of the elongated C20 fatty acids to product with the best embryo converting 82.1% to product. The delta-8 desaturase appears to utilize EDA and EtrA equally well as the ratio of their respective % desaturations is around 1.0. In line 16184-1-1, the *Mortiella alpina* elongase converts an average of 23% of the C18 fatty axcids to product with the best embryo converting 30.2% to product. The elongase appears to have a slight preference for ALA as the ratio of their respective % elongations is around 0.6. Expression of only the elongase in these lines likely resulted from fragmentation of the construct during the transformation procedure or due to positional insertion effects differentially affecting expression of the delta-8.

TABLE 9

Accumulation Of Long Chain PUFAs In Lines Transformed With pKR681

| Line | 16:0 | 18:0 | 18:1 | LA | GLA | ALA | EDA | DGLA | EtrA | ETA |
|---|---|---|---|---|---|---|---|---|---|---|
| 1618-1-1-1 | 13.9 | 6.8 | 7.1 | 40.2 | 0.0 | 14.4 | 3.0 | 10.2 | 1.1 | 3.3 |
| -2 | 14.5 | 10.0 | 6.2 | 38.9 | 0.0 | 11.0 | 4.1 | 10.5 | 1.2 | 3.0 |
| -3 | 14.1 | 4.9 | 4.7 | 42.2 | 0.0 | 21.5 | 2.0 | 7.2 | 1.0 | 2.5 |
| -4 | 14.1 | 7.1 | 6.2 | 42.7 | 0.0 | 13.3 | 3.3 | 9.1 | 1.1 | 2.8 |
| -5 | 12.0 | 5.0 | 5.8 | 46.3 | 0.0 | 16.0 | 2.2 | 8.1 | 1.0 | 3.2 |
| -6 | 12.1 | 4.7 | 5.7 | 42.0 | 0.0 | 20.9 | 1.7 | 8.5 | 0.9 | 3.5 |
| Ave | 13.5 | 6.4 | 6.0 | 42.1 | 0.0 | 16.2 | 2.7 | 8.9 | 1.0 | 3.1 |
| 1618-1-2-1 | 11.7 | 4.3 | 4.6 | 46.8 | 0.0 | 17.4 | 3.9 | 5.7 | 2.4 | 3.1 |
| -2 | 12.2 | 6.0 | 4.7 | 45.5 | 0.0 | 14.9 | 5.1 | 5.8 | 2.9 | 2.9 |
| -3 | 12.7 | 5.0 | 7.1 | 44.7 | 0.0 | 17.5 | 4.2 | 4.1 | 2.4 | 2.3 |
| -4 | 12.4 | 6.3 | 6.8 | 43.0 | 0.0 | 13.9 | 6.6 | 4.9 | 3.9 | 2.3 |
| -5 | 13.4 | 8.7 | 5.2 | 39.6 | 0.0 | 13.2 | 6.3 | 7.2 | 3.2 | 3.1 |
| -6 | 12.8 | 5.5 | 6.2 | 45.7 | 0.0 | 15.6 | 4.3 | 5.2 | 2.2 | 2.5 |
| Ave | 12.5 | 6.0 | 5.8 | 44.2 | 0.0 | 15.4 | 5.1 | 5.5 | 2.8 | 2.7 |
| 1618-1-8-1 | 8.7 | 3.5 | 6.7 | 53.3 | 0.0 | 17.2 | 6.9 | 0.0 | 3.6 | 0.0 |
| -2 | 9.2 | 2.9 | 12.0 | 49.0 | 0.0 | 18.9 | 4.7 | 0.0 | 3.3 | 0.0 |
| -3 | 11.2 | 2.8 | 7.7 | 48.6 | 0.0 | 22.4 | 4.1 | 0.0 | 3.2 | 0.0 |
| -4 | 12.0 | 3.6 | 13.6 | 46.7 | 0.0 | 16.0 | 4.8 | 0.0 | 3.2 | 0.0 |
| -5 | 9.1 | 3.6 | 5.0 | 52.6 | 0.0 | 16.5 | 8.5 | 0.0 | 4.8 | 0.0 |
| -6 | 9.3 | 2.8 | 12.7 | 47.2 | 0.0 | 20.0 | 4.6 | 0.0 | 3.4 | 0.0 |
| Ave | 9.9 | 3.2 | 9.6 | 49.6 | 0.0 | 18.5 | 5.6 | 0.0 | 3.6 | 0.0 |

TABLE 9-continued

Accumulation Of Long Chain PUFAs In Lines Transformed With pKR681

| Line | 16:0 | 18:0 | 18:1 | LA | GLA | ALA | EDA | DGLA | EtrA | ETA |
|---|---|---|---|---|---|---|---|---|---|---|
| 1618-3-6-1 | 11.8 | 2.4 | 8.3 | 42.1 | 0.0 | 28.2 | 3.3 | 0.0 | 3.9 | 0.0 |
| -2 | 10.6 | 4.2 | 12.8 | 43.7 | 0.0 | 17.6 | 6.7 | 0.0 | 4.3 | 0.0 |
| -3 | 10.3 | 4.9 | 5.6 | 45.7 | 0.0 | 18.4 | 8.7 | 0.0 | 6.3 | 0.0 |
| -4 | 11.8 | 5.2 | 21.2 | 39.5 | 0.0 | 15.2 | 4.4 | 0.0 | 2.8 | 0.0 |
| -5 | 10.3 | 3.0 | 9.2 | 47.8 | 0.0 | 21.5 | 4.7 | 0.0 | 3.5 | 0.0 |
| -6 | 9.4 | 2.5 | 9.4 | 47.9 | 0.0 | 23.2 | 4.0 | 0.0 | 3.7 | 0.0 |
| Ave | 10.7 | 3.7 | 11.1 | 44.4 | 0.0 | 20.7 | 5.3 | 0.0 | 4.1 | 0.0 |
| 1618-4-1-1 | 15.4 | 9.2 | 6.5 | 38.1 | 0.0 | 9.9 | 13.8 | 0.0 | 7.0 | 0.0 |
| -2 | 11.1 | 5.6 | 5.7 | 43.3 | 0.0 | 16.8 | 10.2 | 0.0 | 7.4 | 0.0 |
| -3 | 10.5 | 5.0 | 6.6 | 45.4 | 0.0 | 15.4 | 10.1 | 0.0 | 6.9 | 0.0 |
| -4 | 10.2 | 5.8 | 6.5 | 45.1 | 0.0 | 12.9 | 12.3 | 0.0 | 7.2 | 0.0 |
| -5 | 11.4 | 4.4 | 10.1 | 45.3 | 0.0 | 16.1 | 7.4 | 0.0 | 5.2 | 0.0 |
| -6 | 10.7 | 5.2 | 13.6 | 42.9 | 0.0 | 12.6 | 9.6 | 0.0 | 5.3 | 0.0 |
| Ave | 11.5 | 5.9 | 8.2 | 43.4 | 0.0 | 14.0 | 10.6 | 0.0 | 6.5 | 0.0 |

Fatty acid compositions listed in Table 9 are expressed as wt. %. 16:0=Palmitic acid, 18:0=Stearic acid, 18:1=Oleic acid, LA=Linoleic acid, GLA=γ-Linoleic acid, ALA=alpha-Linolenic acid, EDA=Eicosadienoic acid, DGLA=Dihomo-γ-Linoleic, EtrA=Eicosatrienoic acid, ETA=Eicosa-tetraenoic acid.

The C18% Elongation (C18% Elong) in Table 10 was calculated by dividing the sum of the wt. % for EDA, DGLA, EtrA and ETA (Table 9) by the sum of the wt. % for LA, ALA, EDA, DGLA, EtrA and ETA (Table 9) and multiplying by 100 to express as a %. The C20% Δ8 desaturation (C20% Δ8 desat. Table 10) was calculated by dividing the sum of the wt.

TABLE 10

Comparison Of % Desaturation And % Elongation In Lines Transformed With pKR681

| Line | C18 % Elong | C20 % delta-8 desat | LA % Elong | ALA % Elong | Ratio (LA/ALA) Elong | EDA % delta-8 desat | EtrA % delta-8 desat | Ratio (EDA/EtrA) de;ta-8 seat |
|---|---|---|---|---|---|---|---|---|
| 1618-1-1-1 | 24.4 | 76.6 | 24.7 | 23.5 | 1.1 | 77.1 | 75.0 | 1.0 |
| -2 | 27.3 | 71.9 | 27.2 | 27.7 | 1.0 | 72.1 | 71.1 | 1.0 |
| -3 | 16.6 | 76.4 | 17.9 | 14.0 | 1.3 | 78.1 | 72.0 | 1.1 |
| -4 | 22.5 | 73.3 | 22.4 | 22.7 | 1.0 | 73.5 | 72.6 | 1.0 |
| -5 | 18.9 | 77.7 | 18.3 | 20.7 | 0.9 | 78.4 | 76.0 | 1.0 |
| -6 | 18.8 | 82.1 | 19.6 | 17.4 | 1.1 | 83.1 | 79.9 | 1.0 |
| Ave | 21.4 | 76.3 | 21.7 | 21.0 | 1.1 | 77.0 | 74.4 | 1.0 |
| 1618-1-2-1 | 19.1 | 58.1 | 17.0 | 24.0 | 0.7 | 59.0 | 56.6 | 1.0 |
| -2 | 21.7 | 52.2 | 19.3 | 28.0 | 0.7 | 53.2 | 50.4 | 1.1 |
| -3 | 17.3 | 49.2 | 15.8 | 21.0 | 0.8 | 49.5 | 48.5 | 1.0 |
| -4 | 23.7 | 40.6 | 21.0 | 30.8 | 0.7 | 42.6 | 36.9 | 1.2 |
| -5 | 27.3 | 51.8 | 25.5 | 32.2 | 0.8 | 53.3 | 48.6 | 1.1 |
| -6 | 18.9 | 54.1 | 17.3 | 23.1 | 0.7 | 54.6 | 53.1 | 1.0 |
| Ave | 21.3 | 51.0 | 19.3 | 26.5 | 0.7 | 52.0 | 49.0 | 1.1 |
| 1618-1-8-1 | 13.0 | | 11.5 | 17.5 | 0.7 | | | |
| -2 | 10.6 | | 8.8 | 14.8 | 0.6 | | | |
| -3 | 9.4 | | 7.9 | 12.5 | 0.6 | | | |
| -4 | 11.4 | | 9.3 | 16.8 | 0.6 | | | |
| -5 | 16.2 | | 13.9 | 22.7 | 0.6 | | | |
| -6 | 10.7 | | 9.0 | 14.6 | 0.6 | | | |
| Ave | 11.9 | | 10.1 | 16.5 | 0.6 | | | |
| 1618-3-6-1 | 9.3 | | 7.4 | 12.0 | 0.6 | | | |
| -2 | 15.2 | | 13.3 | 19.5 | 0.7 | | | |
| -3 | 19.0 | | 15.9 | 25.6 | 0.6 | | | |
| -4 | 11.6 | | 10.0 | 15.6 | 0.6 | | | |
| -5 | 10.6 | | 9.0 | 14.0 | 0.6 | | | |
| -6 | 9.8 | | 7.7 | 13.9 | 0.6 | | | |
| Ave | 12.6 | | 10.5 | 16.8 | 0.6 | | | |
| 1618-4-1-1 | 30.2 | | 26.6 | 41.4 | 0.6 | | | |
| -2 | 22.6 | | 19.0 | 30.5 | 0.6 | | | |
| -3 | 21.9 | | 18.2 | 31.0 | 0.6 | | | |
| -4 | 25.2 | | 21.5 | 35.8 | 0.6 | | | |
| -5 | 17.1 | | 14.1 | 24.4 | 0.6 | | | |
| -6 | 21.1 | | 18.3 | 29.6 | 0.6 | | | |
| Ave | 23.0 | | 19.6 | 32.1 | 0.6 | | | |

% for DGLA and ETA (Table 9) by the sum of the wt. % for EDA, DGLA, EtrA and ETA (Table 9) and multiplying by 100 to express as a %. The individual elongations (LA % Elong or ALA % Elong) or Δ8 desaturations (EDA % Δ8 desat or EtrA % Δ8 desat) shown in Table 10 were calculated in a similar way but only using either the ω-6 substrates/products or the ω-3 substrates/products for each. The Ratio elongation for LA and ALA was obtained by dividing the LA % Elongation by the ALA % elongation. Similarly, the Ratio delta-8 desaturation was obtained by dividing the EDA % delta-8 desaturation by the EtrA % delta-8 desaturation.

Example 21

Analysis of Somatic Soy Embryos Containing the *Euglena gracilis* Delta-8 Desaturase and *Isochrysis galbana* Elongase Genes (pKR682)

Embryo fatty acid profiles for 9 lines containing pKR682 are shown in Table 11. Calculated % elongation, % desaturation and elongation and desaturation ratios are shown in Table 12. The best line (1619-6-7) had embryos with an average DGLA content of 21.8% and an average ETA content of 4.1%. As can be seen from Table 12, in this line, the delta-8 desaturase converts an average of 91.6% of the elongated C20 fatty acids to product and, in the best embryo (1619-6-7-1), 95.1% of the elongated fatty acids are converted to product. As for pKR681, the delta-8 desaturase appears to utilize EDA and EtrA equally well with the ratio of their respective % desaturations being around 1.0 (Table 12). In these lines, the average % conversion of C18 fatty acids to C20 fatty acids ranges from 40.0% to 49.5%. As seen with pKR681, there are lines (1619-64, 1619-84) where only the elongase is functioning (Table 11). Again, this is likely due to positional effects or fragmentation of DNA. In lines where the delta-8 desaturase is not functioning, the best elongase line (1619-64) had embryos with an average EDA content of 24.1% and an average ETrA content of 8.7%. The best embryo analyzed had 27.4% EDA and 10.3% ETrA. Average elongation in this line is 49.5% with the best embryo (1619-64-6) having 58.9% elongation (Table 12). In these lines, the elongase appears to have no preference for LA or ALA as the ratio of their respective % elongations is around 1.0. Interestingly, in lines that also express the delta-8 desaturase, there seems to be a slight preference of the elongase for LA and the average elongation ratio is as high as 2.3 in line 1617-16-2-7. In many of the lines, a small amount of a fatty acid that runs with retention time identical to GLA is present when the delta-8 desaturase is functioning well.

TABLE 11

Accumulation Of Long Chain PUFAs In Lines Transformed With pKR682

|  | 16:0 | 18:0 | 18:1 | LA | GLA | ALA | EDA | DGLA | EtrA | ETA |
|---|---|---|---|---|---|---|---|---|---|---|
| 1617-16-2-7 | 20.1 | 2.7 | 5.9 | 18.0 | 2.0 | 12.8 | 5.1 | 26.5 | 2.4 | 4.4 |
| -8 | 19.3 | 1.3 | 5.0 | 22.7 | 1.7 | 23.4 | 3.7 | 16.8 | 1.6 | 4.5 |
| -9 | 20.4 | 2.4 | 4.7 | 13.7 | 2.3 | 15.3 | 5.2 | 26.2 | 3.5 | 6.3 |
| -10 | 17.0 | 1.7 | 6.2 | 19.9 | 1.7 | 27.0 | 2.5 | 17.4 | 1.1 | 5.5 |
| -11 | 16.4 | 1.3 | 5.1 | 21.5 | 3.3 | 28.2 | 2.8 | 15.2 | 2.1 | 4.1 |
| -12 | 26.7 | 2.4 | 6.1 | 0.0 | 4.1 | 20.2 | 6.5 | 26.9 | 2.2 | 5.0 |
| -13 | 17.5 | 1.5 | 5.8 | 21.6 | 2.6 | 20.3 | 3.9 | 19.9 | 1.8 | 5.1 |
| -14 | 20.2 | 2.4 | 8.9 | 24.6 | 1.6 | 17.9 | 4.3 | 14.7 | 1.4 | 4.2 |
| Ave | 19.7 | 2.0 | 6.0 | 17.7 | 2.4 | 20.6 | 4.2 | 20.4 | 2.0 | 4.9 |
| 1619-6-4-1 | 18.5 | 1.7 | 9.4 | 25.0 | 0.0 | 8.2 | 27.4 | 0.0 | 9.7 | 0.0 |
| -2 | 14.5 | 2.0 | 15.9 | 26.8 | 0.0 | 7.8 | 24.5 | 0.0 | 8.5 | 0.0 |
| -3 | 23.6 | 3.8 | 12.2 | 19.3 | 0.0 | 8.7 | 23.8 | 0.0 | 8.8 | 0.0 |
| -4 | 15.5 | 1.2 | 12.6 | 34.5 | 0.0 | 14.7 | 15.4 | 0.0 | 6.0 | 0.0 |
| -5 | 15.2 | 1.6 | 15.7 | 25.5 | 0.0 | 6.7 | 26.4 | 0.0 | 8.9 | 0.0 |
| -6 | 15.8 | 2.2 | 18.0 | 19.1 | 0.0 | 7.2 | 27.4 | 0.0 | 10.3 | 0.0 |
| Ave | 17.2 | 2.1 | 14.0 | 25.0 | 0.0 | 8.9 | 24.1 | 0.0 | 8.7 | 0.0 |
| 1619-6-5-1 | 22.1 | 2.1 | 6.2 | 23.9 | 3.9 | 10.5 | 4.2 | 21.1 | 1.3 | 4.8 |
| -2 | 17.4 | 1.6 | 9.5 | 32.3 | 1.5 | 11.0 | 3.0 | 18.0 | 0.7 | 4.6 |
| -3 | 17.5 | 2.6 | 9.9 | 32.9 | 0.5 | 11.3 | 5.8 | 15.3 | 0.6 | 3.3 |
| -4 | 17.2 | 2.0 | 12.1 | 29.5 | 0.6 | 10.6 | 6.0 | 13.9 | 2.8 | 4.7 |
| -5 | 24.2 | 3.1 | 7.1 | 25.4 | 2.0 | 10.7 | 5.2 | 16.8 | 1.9 | 3.4 |
| -6 | 17.9 | 1.6 | 5.9 | 30.8 | 2.4 | 12.3 | 5.7 | 18.2 | 1.6 | 3.7 |
| Ave | 19.4 | 2.2 | 8.5 | 29.2 | 1.8 | 11.1 | 5.0 | 17.2 | 1.5 | 4.1 |
| 1619-6-7-1 | 19.1 | 1.7 | 4.8 | 32.0 | 1.1 | 21.7 | 1.0 | 16.3 | 0.0 | 2.3 |
| -2 | 19.0 | 1.3 | 5.0 | 40.1 | 1.2 | 17.9 | 1.4 | 11.9 | 0.2 | 2.0 |
| -3 | 17.8 | 1.2 | 6.2 | 26.6 | 2.0 | 13.1 | 2.1 | 24.6 | 0.4 | 5.9 |
| -4 | 19.4 | 1.3 | 8.1 | 29.4 | 1.2 | 12.6 | 3.0 | 20.5 | 0.5 | 4.1 |
| -5 | 19.9 | 1.4 | 9.2 | 19.6 | 3.1 | 8.8 | 2.1 | 29.9 | 0.5 | 5.4 |
| -6 | 20.1 | 1.6 | 6.9 | 25.0 | 2.9 | 8.4 | 2.5 | 27.6 | 0.4 | 4.6 |
| Ave | 19.2 | 1.4 | 6.7 | 28.8 | 1.9 | 13.7 | 2.0 | 21.8 | 0.3 | 4.1 |
| 1619-7-3-1 | 15.4 | 1.9 | 9.4 | 34.7 | 0.6 | 12.1 | 11.9 | 6.7 | 4.3 | 3.0 |
| -2 | 15.2 | 1.5 | 9.6 | 37.4 | 0.0 | 17.0 | 9.9 | 3.7 | 3.6 | 1.9 |
| -3 | 17.0 | 3.0 | 14.5 | 26.6 | 0.5 | 9.9 | 11.0 | 10.5 | 3.1 | 3.9 |
| -4 | 18.5 | 3.4 | 8.6 | 17.7 | 1.3 | 4.2 | 21.7 | 16.9 | 4.0 | 3.7 |
| -5 | 16.5 | 2.4 | 10.2 | 25.8 | 0.8 | 7.0 | 15.1 | 12.6 | 4.7 | 5.0 |
| -6 | 16.9 | 2.2 | 10.3 | 24.4 | 0.4 | 6.8 | 22.7 | 6.3 | 7.3 | 2.6 |
| Ave | 16.6 | 2.4 | 10.4 | 27.8 | 0.6 | 9.5 | 15.4 | 9.5 | 4.5 | 3.4 |
| 1619-7-7-1 | 21.2 | 1.5 | 12.8 | 17.6 | 1.3 | 8.8 | 6.8 | 23.1 | 2.1 | 4.8 |
| -2 | 15.1 | 1.2 | 19.9 | 27.7 | 0.7 | 11.2 | 7.4 | 12.1 | 1.7 | 3.0 |
| -3 | 17.4 | 2.1 | 16.4 | 23.8 | 0.6 | 9.1 | 10.4 | 15.2 | 1.9 | 3.2 |
| -4 | 17.2 | 1.5 | 18.3 | 21.4 | 0.9 | 9.2 | 9.3 | 16.6 | 1.8 | 3.9 |
| -5 | 16.4 | 1.0 | 13.4 | 24.2 | 1.2 | 15.9 | 6.5 | 16.2 | 2.1 | 3.3 |
| -6 | 20.3 | 2.3 | 7.5 | 19.5 | 1.3 | 9.5 | 8.9 | 22.9 | 2.4 | 5.1 |
| Ave | 17.9 | 1.6 | 14.7 | 22.4 | 1.0 | 10.60 | 8.2 | 17.7 | 2.0 | 3.9 |

TABLE 11-continued

Accumulation Of Long Chain PUFAs In Lines Transformed With pKR682

|  | 16:0 | 18:0 | 18:1 | LA | GLA | ALA | EDA | DGLA | EtrA | ETA |
|---|---|---|---|---|---|---|---|---|---|---|
| 1619-7-8-1 | 19.2 | 1.8 | 5.7 | 21.7 | 2.1 | 11.1 | 12.1 | 17.5 | 4.0 | 4.9 |
| -2 | 15.0 | 1.1 | 10.6 | 28.5 | 1.0 | 16.2 | 10.3 | 10.8 | 3.5 | 3.1 |
| -3 | 17.0 | 1.6 | 11.3 | 20.6 | 1.2 | 8.6 | 12.4 | 17.8 | 4.3 | 5.2 |
| -4 | 16.5 | 1.5 | 10.3 | 25.4 | 1.0 | 13.6 | 11.1 | 13.4 | 3.3 | 3.8 |
| -5 | 16.0 | 1.3 | 10.0 | 29.0 | 0.8 | 12.6 | 4.7 | 19.0 | 1.2 | 5.5 |
| -6 | 15.6 | 1.6 | 12.2 | 28.7 | 1.0 | 9.9 | 9.4 | 15.6 | 1.7 | 4.6 |
| Ave | 16.6 | 1.5 | 10.0 | 25.6 | 1.2 | 12.0 | 1.0.0 | 15.7 | 3.0 | 4.5 |
| 1619-8-1-1 | 20.4 | 1.7 | 5.8 | 24.4 | 2.7 | 15.0 | 4.3 | 20.3 | 1.5 | 3.9 |
| -2 | 17.2 | 1.9 | 14.5 | 24.2 | 0.0 | 9.3 | 5.0 | 20.9 | 1.1 | 5.9 |
| -3 | 16.4 | 1.8 | 13.0 | 23.5 | 1.4 | 11.6 | 6.9 | 19.9 | 1.3 | 4.1 |
| -4 | 17.2 | 1.5 | 15.3 | 22.2 | 1.1 | 7.2 | 7.7 | 21.5 | 1.2 | 4.9 |
| -5 | 19.4 | 1.3 | 9.9 | 21.7 | 2.8 | 13.8 | 5.1 | 20.2 | 1.7 | 4.1 |
| -6 | 17.9 | 1.3 | 10.5 | 23.4 | 1.5 | 9.9 | 6.5 | 22.8 | 1.4 | 4.8 |
| Ave | 18.1 | 1.6 | 11.5 | 23.3 | 1.6 | 11.1 | 5.9 | 20.9 | 1.4 | 4.6 |
| 1619-8-4-1 | 15.7 | 1.1 | 6.7 | 50.5 | 0.0 | 18.1 | 6.2 | 0.0 | 1.8 | 0.0 |
| -2 | 15.0 | 1.8 | 8.2 | 38.6 | 0.0 | 28.4 | 5.8 | 0.0 | 2.2 | 0.0 |
| -3 | 18.1 | 2.9 | 7.2 | 35.6 | 0.0 | 32.2 | 2.7 | 0.0 | 1.3 | 0.0 |
| -4 | 18.0 | 2.7 | 9.7 | 40.7 | 0.0 | 18.2 | 8.7 | 0.0 | 1.9 | 0.0 |
| -5 | 16.0 | 1.5 | 6.9 | 50.4 | 0.0 | 20.8 | 3.0 | 0.0 | 1.4 | 0.0 |
| -6 | 15.3 | 0.9 | 7.7 | 50.8 | 0.0 | 20.6 | 3.6 | 0.0 | 1.2 | 0.0 |
| Ave | 16.4 | 1.8 | 7.7 | 44.4 | 0.0 | 23.00 | 5.0 | 0.0 | 1.6 | 0.0 |

Fatty acid compositions listed in Table 11 are expressed as wt. %. 16:0=Palmitic acid, 18:0=Stearic acid, 18:1=Oleic acid, LA=Linoleic acid, GLA=γ-Linoleic acid, ALA=alpha-Linolenic acid, EDA=Eicosadienoic acid, DGLA=Dihomo-γ-Linoleic, EtrA=Eicosatrienoic acid, ETA=Eicosatetraenoic acid.

TABLE 12

Comparison Of % Desaturation And % Elongation In Lines Transformed With pKR682

| Line | C18 % Elong | C20 % delta-8 desat | LA % Elong | ALA % Elong | Ratio (LA/ALA) Elong | EDA % delta-8 desat | EtrA % delta-8 desat | Ratio (EDA/EtrA) de;ta-8 seat |
|---|---|---|---|---|---|---|---|---|
| 1617-16-2-7 | 55.5 | 80.5 | 63.8 | 34.7 | 1.8 | 83.9 | 65.0 | 1.3 |
| -8 | 36.6 | 80.2 | 47.4 | 20.8 | 2.3 | 82.1 | 73.6 | 1.1 |
| -9 | 58.8 | 78.8 | 69.6 | 39.3 | 1.8 | 83.4 | 64.1 | 1.3 |
| -10 | 36.0 | 86.6 | 49.9 | 19.5 | 2.6 | 87.5 | 83.9 | 1.0 |
| -11 | 32.8 | 79.6 | 45.6 | 18.1 | 2.5 | 84.3 | 66.1 | 1.3 |
| -12 | 66.7 | 78.6 | 100.0 | 26.1 | 3.8 | 80.6 | 69.5 | 1.2 |
| -13 | 42.3 | 81.3 | 52.4 | 25.4 | 2.1 | 83.5 | 74.0 | 1.1 |
| -14 | 36.6 | 76.7 | 43.5 | 23.8 | 1.8 | 77.4 | 74.4 | 1.0 |
| Ave | 45.7 | 80.3 | 59.0 | 26.0 | 2.3 | 82.8 | 71.3 | 1.2 |
| 1619-6-4-1 | 52.8 |  | 52.3 | 54.2 | 1.0 |  |  |  |
| -2 | 48.8 |  | 47.7 | 52.1 | 0.9 |  |  |  |
| -3 | 53.8 |  | 55.2 | 50.3 | 1.1 |  |  |  |
| -4 | 30.3 |  | 30.8 | 29.1 | 1.1 |  |  |  |
| -5 | 52.3 |  | 50.9 | 57.0 | 0.9 |  |  |  |
| -6 | 58.9 |  | 58.9 | 58.9 | 1.0 |  |  |  |
| Ave | 49.5 |  | 49.3 | 50.3 | 1.0 |  |  |  |
| 1619-6-5-1 | 47.6 | 82.5 | 51.3 | 36.7 | 1.4 | 83.4 | 78.5 | 1.1 |
| -2 | 37.8 | 85.8 | 39.4 | 32.3 | 1.2 | 85.5 | 86.9 | 1.0 |
| -3 | 36.0 | 74.5 | 39.0 | 25.5 | 1.5 | 72.6 | 84.7 | 0.9 |
| -4 | 40.6 | 67.7 | 40.2 | 41.7 | 1.0 | 69.6 | 62.5 | 1.1 |
| -5 | 43.1 | 74.0 | 46.4 | 33.2 | 1.4 | 76.3 | 64.6 | 1.2 |
| -6 | 40.4 | 74.9 | 43.7 | 30.1 | 1.5 | 76.0 | 70.1 | 1.1 |
| Ave | 40.9 | 76.6 | 43.3 | 33.2 | 1.3 | 77.3 | 74.6 | 1.0 |
| 1619-6-7-1 | 26.8 | 95.1 | 35.1 | 9.6 | 3.6 | 94.4 | 100.0 | 0.9 |
| -2 | 21.2 | 89.5 | 25.0 | 11.1 | 2.3 | 89.4 | 90.1 | 1.0 |
| -3 | 45.4 | 92.4 | 50.1 | 32.4 | 1.5 | 92.0 | 94.1 | 1.0 |
| -4 | 40.1 | 87.6 | 44.4 | 26.5 | 1.7 | 87.2 | 89.9 | 1.0 |
| -5 | 57.2 | 93.2 | 62.0 | 40.1 | 1.5 | 93.4 | 92.3 | 1.0 |
| -6 | 51.2 | 91.9 | 54.6 | 37.4 | 1.5 | 91.8 | 92.9 | 1.0 |
| Ave | 40.3 | 91.6 | 45.2 | 26.2 | 2.0 | 91.4 | 93.2 | 1.0 |
| 1619-7-3-1 | 35.6 | 37.6 | 34.9 | 37.6 | 0.9 | 36.0 | 41.5 | 0.9 |
| -2 | 26.1 | 29.4 | 26.8 | 24.5 | 1.1 | 27.3 | 34.6 | 0.8 |
| -3 | 43.9 | 50.4 | 44.7 | 41.4 | 1.1 | 48.8 | 55.2 | 0.9 |

TABLE 12-continued

Comparison Of % Desaturation And % Elongation In Lines Transformed With pKR682

| Line | C18 % Elong | C20 % delta-8 desat | LA % Elong | ALA % Elong | Ratio (LA/ALA) Elong | EDA % delta-8 desat | EtrA % delta-8 desat | Ratio (EDA/EtrA) de;ta-8 seat |
|---|---|---|---|---|---|---|---|---|
| -4 | 67.8 | 44.5 | 68.5 | 64.6 | 1.1 | 43.8 | 48.1 | 0.9 |
| -5 | 53.3 | 47.0 | 51.8 | 58.0 | 0.9 | 45.4 | 51.6 | 0.9 |
| -6 | 55.5 | 23.0 | 54.3 | 59.2 | 0.9 | 21.8 | 26.5 | 0.8 |
| Ave | 47.0 | 38.7 | 46.8 | 47.6 | 1.0 | 37.2 | 42.9 | 0.9 |
| 1619-7-7-1 | 58.3 | 75.7 | 63.0 | 44.0 | 1.4 | 77.1 | | |
| -2 | 38.4 | 62.4 | 41.3 | 29.8 | 1.4 | 61.9 | 86.9 | 1.0 |
| -3 | 48.3 | 60.0 | 51.8 | 36.0 | 1.4 | 59.3 | 84.7 | 0.9 |
| -4 | 50.7 | 64.9 | 54.6 | 38.2 | 1.4 | 64.2 | 62.5 | 1.1 |
| -5 | 41.1 | 69.5 | 48.3 | 25.4 | 1.9 | 76.3 | 64.6 | 1.2 |
| -6 | 57.5 | 71.1 | 62.0 | 44.0 | 1.4 | 76.0 | 70.1 | 1.1 |
| Ave | 49.0 | 67.2 | 53.5 | 36.2 | 1.5 | 77.3 | 74.6 | 1.0 |
| 1619-7-8-1 | 54.0 | 58.2 | 57.7 | 44.4 | 1.3 | 59.2 | 54.9 | 1.1 |
| -2 | 38.2 | 50.1 | 42.6 | 28.8 | 1.5 | 51.2 | 46.6 | 1.1 |
| -3 | 57.6 | 57.9 | 59.4 | 52.2 | 1.1 | 58.9 | 54.6 | 1.1 |
| -4 | 44.8 | 54.5 | 49.1 | 34.5 | 1.4 | 54.8 | 53.5 | 1.0 |
| -5 | 42.2 | 80.7 | 45.0 | 34.7 | 1.3 | 80.3 | 82.1 | 1.0 |
| -6 | 44.7 | 64.6 | 46.5 | 38.8 | 1.2 | 62.4 | 73.0 | 0.9 |
| Ave | 46.9 | 61.0 | 50.1 | 38.9 | 1.3 | 61.1 | 60.8 | 1.0 |
| 1619-8-1-1 | 43.2 | 80.7 | 50.2 | 26.4 | 1.9 | 82.6 | 72.1 | 1.1 |
| -2 | 49.5 | 81.5 | 51.7 | 42.7 | 1.2 | 80.7 | 84.7 | 1.0 |
| -3 | 47.9 | 74.5 | 53.3 | 31.8 | 1.7 | 74.2 | 76.0 | 1.0 |
| -4 | 54.6 | 74.1 | 56.8 | 45.8 | 1.2 | 73.7 | 79.6 | 0.9 |
| -5 | 46.6 | 78.3 | 53.8 | 29.4 | 1.8 | 80.0 | 70.9 | 1.1 |
| -6 | 51.5 | 77.8 | 55.6 | 38.3 | 1.5 | 77.8 | 77.9 | 1.0 |
| Ave | 48.9 | 77.9 | 53.6 | 35.7 | 1.6 | 78.2 | 76.9 | 1.0 |
| 1619-8-4-1 | 10.5 | | 11.0 | 9.1 | 1.2 | | | |
| -2 | 10.7 | | 13.1 | 7.1 | 1.8 | | | |
| -3 | 5.6 | | 7.1 | 3.8 | 1.9 | | | |
| -4 | 15.3 | | 17.7 | 9.5 | 1.8 | | | |
| -5 | 5.8 | | 5.7 | 6.1 | 0.9 | | | |
| -6 | 6.3 | | 6.6 | 5.4 | 1.2 | | | |
| Ave | 9.0 | | 10.2 | 6.8 | 1.5 | | | |

The C18% Elongation (C18% Elong) in Table 12 was calculated by dividing the sum of the wt. % for EDA, DGLA, EtrA and ETA (Table 11) by the sum of the wt. % for LA, ALA, EDA, DGLA, EtrA and ETA (Table 11) and multiplying by 100 to express as a %. The C20% Δ8 desaturation (C20% Δ8 desat. Table 12) was calculated by dividing the sum of the wt. % for DGLA and ETA (Table 11) by the sum of the wt. % for EDA, DGLA, EtrA and ETA (Table 11) and multiplying by 100 to express as a %. The individual elongations (LA % Elong or ALA % Elong) or Δ8 desaturations (EDA % Δ8 desat or EtrA % Δ8 desat) shown in Table 12 were calculated in a similar way but only using either the ω-6 substrates/products or the ω-3 substrates/products for each. The Ratio elongation for LA and ALA was obtained by dividing the LA % Elongation by the ALA % elongation. Similarly, the Ratio delta-8 desaturation was obtained by dividing the EDA % delta-8 desaturation by the EtrA % delta-8 desaturation.

Example 22

Analysis of Somatic Soy Embryos Containing the *Euglena gracilis* Delta-8 Desaturase, *Isochrysis galbana* Elongase and Other EPA Biosynthetic Genes (pKR786, pKR669)

Plasmid pKR786 and pKR669 were digested with AscI and the DNA fragments containing ALS selection and EPA biosynthetic genes were transformed into soy as described previously. Fatty acids from ten embryos for each line obtained containg pKR786 and pKR669 were analyzed by GC as described.

Figure 10:
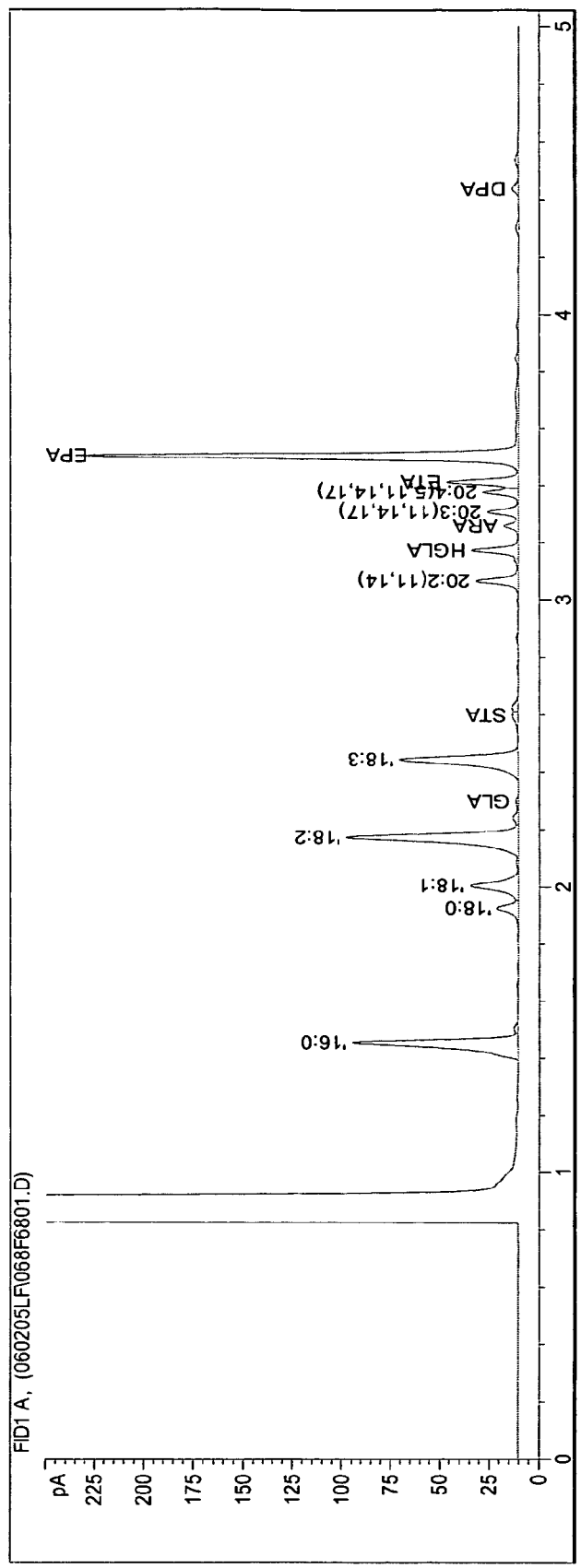
FIG. 10 shows a chromatogram of the lipid profile of a soybean embryo extract as described in Example 22.

Ten embryos were analyzed for each individual transformation event. Fatty acids were identified by comparison of retention times to those for authentic standards. In this way, 169 events were analyzed. From the 169 lines analyzed, 25 were identified that produced EPA (average of 10 individual embryos) at a relative abundance greater than 10% of the total fatty acids. The ten best EPA-producing events are shown in Table 13 and Table 14. The results for 10 embryos from the best event are shown in Tables 15 and 16. The best line analyzed averaged 21.2% EPA with the best embryo of this line having 29.4% EPA (Table 16). A chromatogram for the embryo is shown in FIG. 10.

Fatty acids in Table 13 and Table 14 are defined as X:Y where X is the fatty acid chain length and Y is the number of double bonds. In addition, fatty acids from Table 13 and Table 14 are further defined as follows where the number in parentheses corresponds to the position of the double bonds from the carboxyl end of the fatty acid: 18:1=18:1(9), 18:2=18:2 (9,12), GLA=18:3(6,9,12), 18:3=18:3(9,12,15), STA=18:4 (6,9,12,15), DGLA=20:3(8,11,14), ARA=20:4(5,8,11,14), ETA=20:4(8,11,14,17), EPA=20:5(5,8,11,14,17) and DPA=22:5(7,10,13,16,19). Fatty acids listed as "others" include: 18:2(6,9), 20:0, 20:1(11), 20:2(8,11) and 20:3 (5,11, 14). Each of these fatty acids is present at a relative abundance of less than 2% of the total fatty acids. In all of the top lines, GLA is not present or is present at levels less than 0.2%.

Fatty acid compositions listed in Table 13 are expressed as wt. %. 16:0=Palmitic acid, 18:0=Stearic acid, 18:1 =Oleic acid, LA=Linoleic acid, GLA=γ-Linoleic acid, ALA=alpha-Linolenic acid, STA=Stearidonic acid, EDA=Eicosadienoic acid, DGLA=Dihomo-γ-Linoleic, ARA=Arachidonic acid.

TABLE 13

Accumulation Of Long Chain PUFAs In Lines Transformed With pKR786 And pKR669 (Averages of 10 embryos per line)

| Line | 16:0 | 18:0 | 18:1 | LA | GLA | ALA | STA | EDA | DGLA | ARA |
|---|---|---|---|---|---|---|---|---|---|---|
| AFS 4314-2-1 | 17.0 | 2.6 | 15.6 | 16.8 | 0.1 | 20.4 | 0.3 | 2.7 | 1.2 | 0.1 |
| AFS 4310-1-2 | 16.7 | 2.4 | 14.9 | 15.5 | 0.1 | 17.0 | 0.9 | 4.4 | 1.4 | 0.4 |
| AFS 4310-5-6 | 15.7 | 3.0 | 15.7 | 17.6 | 0.0 | 10.1 | 0.7 | 7.4 | 1.7 | 0.2 |
| AFS 4310-1-8 | 15.2 | 2.7 | 16.4 | 15.2 | 0.1 | 17.2 | 0.8 | 4.7 | 1.6 | 0.5 |
| AFS 4314-6-1 | 14.0 | 3.1 | 12.3 | 17.0 | 0.1 | 8.5 | 0.7 | 11.2 | 2.4 | 0.4 |
| AFS 4314-5-6 | 15.6 | 2.7 | 12.9 | 4.6 | 0.0 | 28.0 | 1.2 | 1.7 | 1.0 | 0.7 |
| AFS 4310-7-5 | 17.3 | 1.9 | 9.6 | 16.0 | 0.0 | 22.9 | 0.8 | 2.4 | 2.1 | 1.9 |
| AFS 4310-1-9 | 14.8 | 2.8 | 13.8 | 12.8 | 0.0 | 17.2 | 0.7 | 4.8 | 1.2 | 0.2 |
| AFS 4314-3-4 | 16.1 | 2.5 | 12.6 | 14.9 | 0.1 | 18.6 | 0.3 | 3.4 | 1.4 | 0.2 |
| AFS 4310-5-2 | 15.8 | 2.5 | 8.5 | 15.8 | 0.1 | 17.5 | 0.6 | 4.2 | 2.4 | 0.8 |

Fatty acid compositions listed in Table 13 are expressed as wt. %. 16:0=Palmitic acid, 18:0=Stearic acid, 18:1=Oleic acid, LA=Linoleic acid, GLA=γ-Linoleic acid, ALA=alpha-Linolenic acid, STA=Stearidonic acid, EDA=Eicosadienoic acid, DGLA=Dihomo-γ-Linoleic, ARA=Arachidonic acid.

TABLE 14

Accumulation Of Long Chain PUFAs In Lines Transformed With pKR786 And pKR669 (Averages of 10 embryos per line)

| Line | EtrA | 20:4 (5, 11, 14, 17) | ETA | EPA | DPA | Other |
|---|---|---|---|---|---|---|
| AFS 4314-2-1 | 2.4 | 2.1 | 4.0 | 13.6 | 0.1 | 1.0 |
| AFS 4310-1-2 | 3.6 | 3.6 | 3.1 | 14.1 | 0.4 | 1.6 |
| AFS 4310-5-6 | 3.8 | 2.8 | 4.2 | 15.1 | 0.4 | 1.4 |
| AFS 4310-1-8 | 2.9 | 2.7 | 3.1 | 15.3 | 0.2 | 1.6 |
| AFS 4314-6-1 | 4.8 | 3.0 | 4.8 | 15.6 | 0.2 | 1.9 |
| AFS 4314-5-6 | 5.3 | 3.1 | 5.1 | 16.2 | 0.3 | 1.5 |
| AFS 4310-7-5 | 2.4 | 1.6 | 4.0 | 16.6 | 0.1 | 0.5 |
| AFS 4310-1-9 | 4.5 | 4.8 | 3.6 | 16.8 | 0.3 | 1.8 |
| AFS 4314-3-4 | 3.3 | 3.2 | 4.6 | 16.9 | 0.4 | 1.6 |
| AFS 4310-5-2 | 3.0 | 2.1 | 4.6 | 21.2 | 0.2 | 0.7 |

Fatty acid compositions listed in Table 14 are expressed as wt. %. EtrA=Eicosatrienoic acid, ETA=Eicosa-tetraenoic acid, EPA=Eicosa-pentaenoic acid, DPA=Docosa-pentaenoic acid

TABLE 15

Accumulation Of Long Chain PUFAs In Line AFS 4310-5-2 Transformed With pKR786 And pKR669

| Embryo # | 16:0 | 18:0 | 18:1 | LA | GLA | ALA | STA | EDA | DGLA | ARA |
|---|---|---|---|---|---|---|---|---|---|---|
| 1 | 16.9 | 2.1 | 8.4 | 20.4 | 0.0 | 18.1 | 0.0 | 2.0 | 1.9 | 0.5 |
| 2 | 16.3 | 1.8 | 5.3 | 15.6 | 0.1 | 22.3 | 0.4 | 2.2 | 1.9 | 0.9 |
| 3 | 17.4 | 3.6 | 10.9 | 14.4 | 0.1 | 21.4 | 0.4 | 5.3 | 2.1 | 0.2 |
| 4 | 18.3 | 2.6 | 7.9 | 11.5 | 0.2 | 20.4 | 0.9 | 6.9 | 2.9 | 2.0 |
| 5 | 13.8 | 3.8 | 11.1 | 14.5 | 0.1 | 15.0 | 0.7 | 7.7 | 3.0 | 1.0 |
| 6 | 15.3 | 3.0 | 11.8 | 15.5 | 0.0 | 18.6 | 0.9 | 4.9 | 1.6 | 0.5 |
| 7 | 14.3 | 2.0 | 7.6 | 16.4 | 0.2 | 15.9 | 0.6 | 3.2 | 2.1 | 0.3 |
| 8 | 15.7 | 2.0 | 5.0 | 17.4 | 0.2 | 12.5 | 0.6 | 3.0 | 3.1 | 1.0 |
| 9 | 15.1 | 2.2 | 8.1 | 16.3 | 0.2 | 17.0 | 1.1 | 2.6 | 2.8 | 1.3 |
| 10 | 15.1 | 1.5 | 8.5 | 15.8 | 0.2 | 13.7 | 0.8 | 4.3 | 2.3 | 0.5 |
| Ave | 15.8 | 2.5 | 8.5 | 15.8 | 0.1 | 17.5 | 0.6 | 4.2 | 2.4 | 0.8 |

TABLE 16

Accumulation Of Long Chain PUFAs In Line AFS 4310-5-2 Transformed With pKR786 And pKR669

| Embryo # | EtrA | 20:4 (5, 11, 14, 17) | ETA | EPA | DPA | Other |
|---|---|---|---|---|---|---|
| 1 | 1.9 | 2.1 | 4.5 | 21.1 | 0.0 | 0.0 |
| 2 | 2.5 | 2.0 | 5.1 | 22.8 | 0.3 | 0.6 |
| 3 | 2.9 | 1.0 | 4.7 | 14.7 | 0.0 | 0.6 |
| 4 | 5.6 | 1.9 | 4.1 | 13.6 | 0.1 | 1.0 |
| 5 | 3.7 | 2.4 | 3.3 | 18.5 | 0.1 | 1.2 |
| 6 | 4.1 | 2.5 | 3.6 | 16.4 | 0.1 | 1.1 |
| 7 | 2.7 | 2.6 | 5.6 | 25.7 | 0.3 | 0.6 |
| 8 | 2.0 | 2.3 | 4.6 | 29.4 | 0.6 | 0.7 |
| 9 | 1.8 | 2.0 | 4.2 | 24.0 | 0.3 | 0.9 |
| 10 | 2.9 | 2.2 | 5.9 | 25.6 | 0.2 | 0.6 |
| Ave | 3.0 | 2.1 | 4.6 | 21.2 | 0.2 | 0.7 |

Fatty acid compositions listed in Table 14 are expressed as wt. %. EtrA=Eicosatrienoic acid, ETA=Eicosa-tetraenoic acid, EPA=Eicosa-pentaenoic acid, DPA=Docosa-pentaenoic acid

What is claimed is:

1. An isolated polynucleotide comprising:
   (a) a nucleotide sequence encoding a polypeptide having delta 8 desaturase activity, wherein the polypeptide has an amino acid sequence comprising SEQ ID NO:2; or,
   (b) a complement of the nucleotide sequence, wherein the complement and the nucleotide sequence consist of the same number of nucleotides and are 100% complementary.

2. The polynucleotide of claim 1 wherein the nucleotide sequence comprises SEQ ID NO:1.

3. A recombinant construct comprising the polynucleotide of claim 1 operably linked to at least one regulatory sequence.

4. A cell comprising the recombinant construct of claim 3.

5. The cell of claim 4 wherein said cell is a plant cell.

6. A method for transforming a cell, comprising transforming a cell with the recombinant construct of claim 3 and selecting those cells transformed with the recombinant construct of claim 3.

7. A method for producing a transformed plant comprising transforming a plant cell with the polynucleotide of claim 1 and regenerating a plant from the transformed plant cell.

8. The method of claim 7 wherein the plant is a soybean plant.

9. A seed comprising the recombinant construct of claim 3.

10. A seed obtained from the plant made by the method of claim 7 or 8.

11. A method for making long chain polyunsaturated fatty acids in a cell comprising:
    (a) transforming a cell with the recombinant construct of claim 3;
    (b) selecting those transformed cells that make long chain polyunsaturated fatty acids.

12. A method for making long chain polyunsaturated fatty acids in a plant cell comprising:
    (a) transforming a cell with the recombinant construct of claim 3;
    (b) selecting those transformed cells that make long chain polyunsaturated fatty acids.

13. A method for producing at least one polyunsaturated fatty acid in a soybean cell comprising:
    (a) transforming a soybean cell with a first recombinant DNA construct comprising SEQ ID NO:2, operably linked to at least one regulatory sequence and at least one additional recombinant DNA construct comprising an isolated polynucleotide, operably linked to at least one regulatory sequence, encoding a polypeptide selected from the group consisting of a delta-4, a delta-5, delta-6, a delta-9, a delta-12, a delta-15, and a delta-17 desaturase, a delta-9 elongase, a C18 to C22 elongase and a C20 to C24 elongase;
    (b) regenerating a soybean plant from the transformed cell of step (a); and
    (c) selecting those seeds obtained from the plants of step (b) having an altered level of polyunsaturated fatty acids when compared to the level in seeds obtained from a nontransformed soybean plant.

14. An oilseed plant comprising the recombinant construct of claim 3.

* * * * *

SEQUENCE LISTING

<160> NUMBER OF SEQ ID NOS: 151

<210> SEQ ID NO 1
<211> LENGTH: 1271
<212> TYPE: DNA
<213> ORGANISM: Euglena gracilis
<220> FEATURE:
<221> NAME/KEY: misc_feature
<222> LOCATION: (4)..(1269)
<223> OTHER INFORMATION: Eg5: delta-8 desaturase

<400> SEQUENCE: 1

```
gaaatgaagt caaagcgcca agcgcttccc cttacaattg atggaacaac atatgatgtg     60
tctgcctggg tcaatttcca ccctggtggt gcggaaatta tagagaatta ccaaggaagg    120
gatgccactg atgccttcat ggttatgcac tctcaagaag ccttcgacaa gctcaagcgc    180
atgcccaaaa tcaatcccag ttctgagttg ccaccccagg ctgcagtgaa tgaagctcaa    240
gaggatttcc ggaagctccg agaagagttg atcgcaactg gcatgtttga tgcctccccc    300
ctctggtact catacaaaat cagcaccaca ctgggccttg gagtgctggg ttatttcctg    360
atggttcagt atcagatgta tttcattggg gcagtgttgc ttgggatgca ctatcaacag    420
atgggctggc tttctcatga catttgccac caccagactt tcaagaaccg aactggaac     480
aacctcgtgg gactggtatt tggcaatggt ctgcaaggtt tttccgtgac atggtggaag    540
gacagacaca atgcacatca ttcggcaacc aatgttcaag gcacgaccc tgatattgac     600
aacctccccc tcttagcctg gtctgaggat gacgtcacac gggcgtcacc gatttcccgc    660
aagctcattc agttccagca gtactatttc ttggtcatct gtatcttgtt gcggttcatt    720
tggtgtttcc agagcgtgtt gaccgtgcgc agtttgaagg acagagataa ccaattctat    780
cgctctcagt ataagaagga ggccattggc ctcgccctgc actggacctt gaagaccctg    840
ttccacttat tctttatgcc cagcatcctc acatcgctgt tggtgttttt cgtttcggag    900
ctggttggcg gcttcggcat tgcgatcgtg gtgttcatga accactaccc actggagaag    960
atcggggact cagtctggga tggccatgga ttctcggttg gccagatcca tgagaccatg   1020
aacattcggc gagggattat cacagattgg tttttcggag gcttgaatta ccagattgag   1080
caccatttgt ggccgaccct ccctcgccac aacctgacag cggttagcta ccaggtggaa   1140
cagctgtgcc agaagcacaa cctgccgtat cggaacccgc tgccccatga agggttggtc   1200
atcctgctgc gctatctggc ggtgttcgcc cggatggcgg agaagcaacc cgcggggaag   1260
gctctataag g                                                        1271
```

<210> SEQ ID NO 2
<211> LENGTH: 421
<212> TYPE: PRT
<213> ORGANISM: Euglena gracilis

<400> SEQUENCE: 2

```
Met Lys Ser Lys Arg Gln Ala Leu Pro Leu Thr Ile Asp Gly Thr Thr
1               5                   10                  15

Tyr Asp Val Ser Ala Trp Val Asn Phe His Pro Gly Gly Ala Glu Ile
            20                  25                  30

Ile Glu Asn Tyr Gln Gly Arg Asp Ala Thr Asp Ala Phe Met Val Met
        35                  40                  45

His Ser Gln Glu Ala Phe Asp Lys Leu Lys Arg Met Pro Lys Ile Asn
    50                  55                  60
```

```
Pro Ser Ser Glu Leu Pro Pro Gln Ala Ala Val Asn Glu Ala Gln Glu
 65                  70                  75                  80

Asp Phe Arg Lys Leu Arg Glu Glu Leu Ile Ala Thr Gly Met Phe Asp
                 85                  90                  95

Ala Ser Pro Leu Trp Tyr Ser Tyr Lys Ile Ser Thr Thr Leu Gly Leu
            100                 105                 110

Gly Val Leu Gly Tyr Phe Leu Met Val Gln Tyr Gln Met Tyr Phe Ile
        115                 120                 125

Gly Ala Val Leu Leu Gly Met His Tyr Gln Gln Met Gly Trp Leu Ser
130                 135                 140

His Asp Ile Cys His His Gln Thr Phe Lys Asn Arg Asn Trp Asn Asn
145                 150                 155                 160

Leu Val Gly Leu Val Phe Gly Asn Gly Leu Gln Gly Phe Ser Val Thr
                165                 170                 175

Trp Trp Lys Asp Arg His Asn Ala His His Ser Ala Thr Asn Val Gln
            180                 185                 190

Gly His Asp Pro Asp Ile Asp Asn Leu Pro Leu Leu Ala Trp Ser Glu
        195                 200                 205

Asp Asp Val Thr Arg Ala Ser Pro Ile Ser Arg Lys Leu Ile Gln Phe
210                 215                 220

Gln Gln Tyr Tyr Phe Leu Val Ile Cys Ile Leu Leu Arg Phe Ile Trp
225                 230                 235                 240

Cys Phe Gln Ser Val Leu Thr Val Arg Ser Leu Lys Asp Arg Asp Asn
                245                 250                 255

Gln Phe Tyr Arg Ser Gln Tyr Lys Lys Glu Ala Ile Gly Leu Ala Leu
            260                 265                 270

His Trp Thr Leu Lys Thr Leu Phe His Leu Phe Phe Met Pro Ser Ile
        275                 280                 285

Leu Thr Ser Leu Val Phe Phe Val Ser Glu Leu Val Gly Gly Phe
290                 295                 300

Gly Ile Ala Ile Val Val Phe Met Asn His Tyr Pro Leu Glu Lys Ile
305                 310                 315                 320

Gly Asp Ser Val Trp Asp Gly His Gly Phe Ser Val Gly Gln Ile His
                325                 330                 335

Glu Thr Met Asn Ile Arg Arg Gly Ile Ile Thr Asp Trp Phe Phe Gly
            340                 345                 350

Gly Leu Asn Tyr Gln Ile Glu His His Leu Trp Pro Thr Leu Pro Arg
        355                 360                 365

His Asn Leu Thr Ala Val Ser Tyr Gln Val Glu Gln Leu Cys Gln Lys
370                 375                 380

His Asn Leu Pro Tyr Arg Asn Pro Leu Pro His Glu Gly Leu Val Ile
385                 390                 395                 400

Leu Leu Arg Tyr Leu Ala Val Phe Ala Arg Met Ala Glu Lys Gln Pro
                405                 410                 415

Ala Gly Lys Ala Leu
            420

<210> SEQ ID NO 3
<211> LENGTH: 1271
<212> TYPE: DNA
<213> ORGANISM: Euglena gracilis
<220> FEATURE:
<221> NAME/KEY: misc_feature
<222> LOCATION: (4)..(1269)
<223> OTHER INFORMATION: Egl2: delta-8 desaturase
```

<400> SEQUENCE: 3

```
gaaatgaagt caaagcgcca agcgcttccc cttacaattg atggaacaac atatgatgtg      60
tctgcctggg tcaatttcca ccctggtggt gcggaaatta tagagaatta ccaaggaagg     120
gatgccactg atgccttcat ggttatgcac tctcaagaag ccttcgacaa gctcaagcgc     180
atgcccaaaa tcaatcccag ttctgagttg ccaccccagg ctgcagtgaa tgaagctcaa     240
gaggatttcc ggaagctccg agaagagttg atcgcaactg gcatgtttga tgcctccccc     300
ctctggtact catacaaaat cagcaccaca ctgggccttg gagtgctggg ttatttcctg     360
atggttcagt atcagatgta tttcattggg gcagtgttgc ttgggatgca ctatcaacag     420
atgggctggc tttctcatga catttgccac caccagactt tcaagaaccg gaactggaac     480
aacctcgtgg gactggtatt tggcaatggt ctgcaaggtt tttccgtgac atggtggaag     540
gacagacaca atgcacatca ttcggcaacc aatgttcaag ggcacgaccc tgatattgac     600
aacctccccc tcttagcctg gtctgaggat gacgtcacac gggcgtcacc gatttcccgc     660
aagctcattc agttccagca gtactatttc ttggtcatct gtatcttgtt gcggttcatt     720
tggtgtttcc agagcgtgtt gaccgtgcgc agtttgaagg acagagataa ccaattctat     780
cgctctcagt ataagaagga ggccattggc ctcgccctgc actggacctt gaaggccctg     840
ttccacttat tctttatgcc cagcatcctc acatcgctgt tggtgttttt cgtttcggag     900
ctggttggcg gcttcggcat tgcgatcgtg gtgttcatga accactaccc actggagaag     960
atcgggggact cagtctggga tggccatgga ttctcggttg gccagatcca tgagaccatg    1020
aacattcggc gagggattat cacagattgg ttttcggag gcttgaatta ccagattgag    1080
caccattgt ggccgaccct ccctcgccac aacctgacag cggttagcta ccaggtggaa    1140
cagctgtgcc agaagcacaa cctgccgtat cggaacccgc tgcccatga agggttggtc    1200
atcctgctgc gctatctggc ggtgttcgcc cggatggcgg agaagcaacc cgcggggaag    1260
gctctataag g                                                         1271
```

<210> SEQ ID NO 4
<211> LENGTH: 421
<212> TYPE: PRT
<213> ORGANISM: Euglena gracilis

<400> SEQUENCE: 4

```
Met Lys Ser Lys Arg Gln Ala Leu Pro Leu Thr Ile Asp Gly Thr Thr
  1               5                  10                  15

Tyr Asp Val Ser Ala Trp Val Asn Phe His Pro Gly Gly Ala Glu Ile
             20                  25                  30

Ile Glu Asn Tyr Gln Gly Arg Asp Ala Thr Asp Ala Phe Met Val Met
         35                  40                  45

His Ser Gln Glu Ala Phe Asp Lys Leu Lys Arg Met Pro Lys Ile Asn
     50                  55                  60

Pro Ser Ser Glu Leu Pro Pro Gln Ala Ala Val Asn Glu Ala Gln Glu
 65                  70                  75                  80

Asp Phe Arg Lys Leu Arg Glu Glu Leu Ile Ala Thr Gly Met Phe Asp
                 85                  90                  95

Ala Ser Pro Leu Trp Tyr Ser Tyr Lys Ile Ser Thr Thr Leu Gly Leu
            100                 105                 110

Gly Val Leu Gly Tyr Phe Leu Met Val Gln Tyr Gln Met Tyr Phe Ile
        115                 120                 125
```

Gly Ala Val Leu Leu Gly Met His Tyr Gln Gln Met Gly Trp Leu Ser
            130                 135                 140

His Asp Ile Cys His His Gln Thr Phe Lys Asn Arg Asn Trp Asn Asn
145                 150                 155                 160

Leu Val Gly Leu Val Phe Gly Asn Gly Leu Gln Gly Phe Ser Val Thr
                165                 170                 175

Trp Trp Lys Asp Arg His Asn Ala His His Ser Ala Thr Asn Val Gln
            180                 185                 190

Gly His Asp Pro Asp Ile Asp Asn Leu Pro Leu Leu Ala Trp Ser Glu
        195                 200                 205

Asp Val Thr Arg Ala Ser Pro Ile Ser Arg Lys Leu Ile Gln Phe
210                 215                 220

Gln Gln Tyr Tyr Phe Leu Val Ile Cys Ile Leu Leu Arg Phe Ile Trp
225                 230                 235                 240

Cys Phe Gln Ser Val Leu Thr Val Arg Ser Leu Lys Asp Arg Asp Asn
                245                 250                 255

Gln Phe Tyr Arg Ser Gln Tyr Lys Lys Glu Ala Ile Gly Leu Ala Leu
            260                 265                 270

His Trp Thr Leu Lys Ala Leu Phe His Leu Phe Phe Met Pro Ser Ile
        275                 280                 285

Leu Thr Ser Leu Leu Val Phe Phe Val Ser Glu Leu Val Gly Gly Phe
290                 295                 300

Gly Ile Ala Ile Val Val Phe Met Asn His Tyr Pro Leu Glu Lys Ile
305                 310                 315                 320

Gly Asp Ser Val Trp Asp Gly His Gly Phe Ser Val Gly Gln Ile His
                325                 330                 335

Glu Thr Met Asn Ile Arg Arg Gly Ile Ile Thr Asp Trp Phe Phe Gly
            340                 345                 350

Gly Leu Asn Tyr Gln Ile Glu His His Leu Trp Pro Thr Leu Pro Arg
        355                 360                 365

His Asn Leu Thr Ala Val Ser Tyr Gln Val Glu Gln Leu Cys Gln Lys
370                 375                 380

His Asn Leu Pro Tyr Arg Asn Pro Leu Pro His Glu Gly Leu Val Ile
385                 390                 395                 400

Leu Leu Arg Tyr Leu Ala Val Phe Ala Arg Met Ala Glu Lys Gln Pro
                405                 410                 415

Ala Gly Lys Ala Leu
            420

<210> SEQ ID NO 5
<211> LENGTH: 1275
<212> TYPE: DNA
<213> ORGANISM: Euglena gracilis (GenBank Accession Nos. AF139720 and
      AAD45877)
<220> FEATURE:
<221> NAME/KEY: misc_feature
<222> LOCATION: (14)..(1273)
<223> OTHER INFORMATION: non-functional delta-8 desaturase

<400> SEQUENCE: 5
attttttttc gaaatgaagt caaagcgcca agcgctatcc cccttacaat tgatggaaca      60
aacatatgat gtggtcaatt tccaccctgg tggtgcggaa attatagaga attaccaagg     120
aagggatgcc actgatgcct tcatggttat gcactttcaa gaagccttcg acaagctcaa     180
gcgcatgccc aaaatcaatc ccagttttga gttgccaccc caggctgcag tgaatgaagc     240
tcaagaggat ttccggaagc tccgagaaga gttgatcgca actggcatgt tgatgcctc      300

```
cccctctgg tactcataca aaatcagcac cacactgggc cttggagtgc tgggttattt      360
cctgatggtt cagtatcaga tgtatttcat tggggcagtg ttgcttggga tgcactatca      420
acagatgggc tggctttctc atgacatttg ccaccaccag actttcaaga accggaactg      480
gaacaacctc gtgggactgg tatttggcaa tggtctgcaa ggttttccg tgacatgttg       540 gaaggacaga cacaatgcac atcattcggc aaccaatgtt caagggcacg accctgatat      600
tgacaacctc ccccccttag cctggtctga ggatgacgtc acacgggcgt caccgatttc      660
ccgcaagctc attcagttcc agcagtacta tttcttggtc atctgtatct tgttgcggtt      720
catttggtgt ttccagtgcg tgttgaccgt gcgcagtttg aaggacagag ataaccaatt      780
ctatcgctct cagtataaga aggaggccat tggcctcgcc ctgcactgga ccttgaaggc      840
cctgttccac ttattcttta tgcccagcat cctcacatcg ctgttggtgt ttttcgtttc      900
ggagctggtt ggcggcttcg gcattgcgat cgtggtgttc atgaaccact acccactgga      960
gaagatcggg gacccagtct gggatggcca tggattctcg gttggccaga tccatgagac      1020
catgaacatt cggcgaggga ttatcacaga ttggtttttc ggaggcttga attaccagat      1080
tgagcaccat ttgtggccga ccctccctcg ccacaacctg acagcggtta gctaccaggt      1140
ggaacagctg tgccagaagc acaacctgcc gtatcggaac ccgctgcccc atgaagggtt      1200
ggtcatcctg ctgcgctatc tggcggtgtt cgcccggatg gcggagaagc aacccgcggg      1260
gaaggctcta taagg                                                       1275
```

<210> SEQ ID NO 6
<211> LENGTH: 419
<212> TYPE: PRT
<213> ORGANISM: Euglena gracilis (GenBank Accession No. AF139720 and AAD45877)

<400> SEQUENCE: 6

```
Met Lys Ser Lys Arg Gln Ala Leu Ser Pro Leu Gln Leu Met Glu Gln
1               5                   10                  15

Thr Tyr Asp Val Val Asn Phe His Pro Gly Gly Ala Glu Ile Ile Glu
            20                  25                  30

Asn Tyr Gln Gly Arg Asp Ala Thr Asp Ala Phe Met Val Met His Phe
        35                  40                  45

Gln Glu Ala Phe Asp Lys Leu Lys Arg Met Pro Lys Ile Asn Pro Ser
    50                  55                  60

Phe Glu Leu Pro Pro Gln Ala Ala Val Asn Glu Ala Gln Glu Asp Phe
65                  70                  75                  80

Arg Lys Leu Arg Glu Glu Leu Ile Ala Thr Gly Met Phe Asp Ala Ser
                85                  90                  95

Pro Leu Trp Tyr Ser Tyr Lys Ile Ser Thr Thr Leu Gly Leu Gly Val
            100                 105                 110

Leu Gly Tyr Phe Leu Met Val Gln Tyr Gln Met Tyr Phe Ile Gly Ala
        115                 120                 125

Val Leu Leu Gly Met His Tyr Gln Gln Met Gly Trp Leu Ser His Asp
    130                 135                 140

Ile Cys His His Gln Thr Phe Lys Asn Arg Asn Trp Asn Asn Leu Val
145                 150                 155                 160

Gly Leu Val Phe Gly Asn Gly Leu Gln Gly Phe Ser Val Thr Cys Trp
                165                 170                 175

Lys Asp Arg His Asn Ala His His Ser Ala Thr Asn Val Gln Gly His
            180                 185                 190
```

```
Asp Pro Asp Ile Asp Asn Leu Pro Pro Leu Ala Trp Ser Glu Asp Asp
            195                 200                 205

Val Thr Arg Ala Ser Pro Ile Ser Arg Lys Leu Ile Gln Phe Gln Gln
    210                 215                 220

Tyr Tyr Phe Leu Val Ile Cys Ile Leu Leu Arg Phe Ile Trp Cys Phe
225                 230                 235                 240

Gln Cys Val Leu Thr Val Arg Ser Leu Lys Asp Arg Asp Asn Gln Phe
                245                 250                 255

Tyr Arg Ser Gln Tyr Lys Lys Glu Ala Ile Gly Leu Ala Leu His Trp
                260                 265                 270

Thr Leu Lys Ala Leu Phe His Leu Phe Phe Met Pro Ser Ile Leu Thr
            275                 280                 285

Ser Leu Leu Val Phe Phe Val Ser Glu Leu Val Gly Gly Phe Gly Ile
            290                 295                 300

Ala Ile Val Val Phe Met Asn His Tyr Pro Leu Glu Lys Ile Gly Asp
305                 310                 315                 320

Pro Val Trp Asp Gly His Gly Phe Ser Val Gly Gln Ile His Glu Thr
                325                 330                 335

Met Asn Ile Arg Arg Gly Ile Ile Thr Asp Trp Phe Phe Gly Gly Leu
                340                 345                 350

Asn Tyr Gln Ile Glu His His Leu Trp Pro Thr Leu Pro Arg His Asn
                355                 360                 365

Leu Thr Ala Val Ser Tyr Gln Val Glu Gln Leu Cys Gln Lys His Asn
    370                 375                 380

Leu Pro Tyr Arg Asn Pro Leu Pro His Glu Gly Leu Val Ile Leu Leu
385                 390                 395                 400

Arg Tyr Leu Ala Val Phe Ala Arg Met Ala Glu Lys Gln Pro Ala Gly
                405                 410                 415

Lys Ala Leu

<210> SEQ ID NO 7
<211> LENGTH: 422
<212> TYPE: PRT
<213> ORGANISM: Euglena gracilis

<400> SEQUENCE: 7

Met Lys Ser Lys Arg Gln Ala Leu Ser Pro Leu Gln Leu Met Glu Gln
1               5                   10                  15

Thr Tyr Asp Val Ser Ala Trp Val Asn Phe His Pro Gly Gly Ala Glu
            20                  25                  30

Ile Ile Glu Asn Tyr Gln Gly Arg Asp Ala Thr Asp Ala Phe Met Val
            35                  40                  45

Met His Phe Gln Glu Ala Phe Asp Lys Leu Lys Arg Met Pro Lys Ile
    50                  55                  60

Asn Pro Ser Phe Glu Leu Pro Pro Gln Ala Ala Val Asn Glu Ala Gln
65              70                  75                  80

Glu Asp Phe Arg Lys Leu Arg Glu Glu Leu Ile Ala Thr Gly Met Phe
                85                  90                  95

Asp Ala Ser Pro Leu Trp Tyr Ser Tyr Lys Ile Ser Thr Thr Leu Gly
            100                 105                 110

Leu Gly Val Leu Gly Tyr Phe Leu Met Val Gln Tyr Gln Met Tyr Phe
        115                 120                 125

Ile Gly Ala Val Leu Leu Gly Met His Tyr Gln Gln Met Gly Trp Leu
    130                 135                 140
```

```
Ser His Asp Ile Cys His His Gln Thr Phe Lys Asn Arg Asn Trp Asn
145                 150                 155                 160

Asn Leu Val Gly Leu Val Phe Gly Asn Gly Leu Gln Gly Phe Ser Val
            165                 170                 175

Thr Cys Trp Lys Asp Arg His Asn Ala His His Ser Ala Thr Asn Val
            180                 185                 190

Gln Gly His Asp Pro Asp Ile Asp Asn Leu Pro Pro Leu Ala Trp Ser
        195                 200                 205

Glu Asp Asp Val Thr Arg Ala Ser Pro Ile Ser Arg Lys Leu Ile Gln
210                 215                 220

Phe Gln Gln Tyr Tyr Phe Leu Val Ile Cys Ile Leu Leu Arg Phe Ile
225                 230                 235                 240

Trp Cys Phe Gln Cys Val Leu Thr Val Arg Ser Leu Lys Asp Arg Asp
            245                 250                 255

Asn Gln Phe Tyr Arg Ser Gln Tyr Lys Lys Glu Ala Ile Gly Leu Ala
            260                 265                 270

Leu His Trp Thr Leu Lys Ala Leu Phe His Leu Phe Phe Met Pro Ser
        275                 280                 285

Ile Leu Thr Ser Leu Leu Val Phe Phe Val Ser Glu Leu Val Gly Gly
290                 295                 300

Phe Gly Ile Ala Ile Val Val Phe Met Asn His Tyr Pro Leu Glu Lys
305                 310                 315                 320

Ile Gly Asp Pro Val Trp Asp Gly His Gly Phe Ser Val Gly Gln Ile
            325                 330                 335

His Glu Thr Met Asn Ile Arg Arg Gly Ile Ile Thr Asp Trp Phe Phe
            340                 345                 350

Gly Gly Leu Asn Tyr Gln Ile Glu His His Leu Trp Pro Thr Leu Pro
        355                 360                 365

Arg His Asn Leu Thr Ala Val Ser Tyr Gln Val Glu Gln Leu Cys Gln
370                 375                 380

Lys His Asn Leu Pro Tyr Arg Asn Pro Leu Pro His Glu Gly Leu Val
385                 390                 395                 400

Ile Leu Leu Arg Tyr Leu Ala Val Phe Ala Arg Met Ala Glu Lys Gln
            405                 410                 415

Pro Ala Gly Lys Ala Leu
            420

<210> SEQ ID NO 8
<211> LENGTH: 19
<212> TYPE: DNA
<213> ORGANISM: Artificial Sequence
<220> FEATURE:
<223> OTHER INFORMATION: Primer Eg5-1

<400> SEQUENCE: 8
gaaatgaagt caaagcgcc                                              19

<210> SEQ ID NO 9
<211> LENGTH: 19
<212> TYPE: DNA
<213> ORGANISM: Artificial Sequence
<220> FEATURE:
<223> OTHER INFORMATION: Primer Eg3-3

<400> SEQUENCE: 9
ccttatagag ccttccccg                                              19
```

```
<210> SEQ ID NO 10
<211> LENGTH: 22
<212> TYPE: DNA
<213> ORGANISM: Artificial Sequence
<220> FEATURE:
<223> OTHER INFORMATION: Primer T7

<400> SEQUENCE: 10
gtaatacgac tcactatagg gc                                              22

<210> SEQ ID NO 11
<211> LENGTH: 19
<212> TYPE: DNA
<213> ORGANISM: Artificial Sequence
<220> FEATURE:
<223> OTHER INFORMATION: Primer M13-28Rev

<400> SEQUENCE: 11
ggaaacagct atgaccatg                                                  19

<210> SEQ ID NO 12
<211> LENGTH: 19
<212> TYPE: DNA
<213> ORGANISM: Artificial Sequence
<220> FEATURE:
<223> OTHER INFORMATION: Primer Eg3-2

<400> SEQUENCE: 12
ttggcaatgg tctgcaagg                                                  19

<210> SEQ ID NO 13
<211> LENGTH: 19
<212> TYPE: DNA
<213> ORGANISM: Artificial Sequence
<220> FEATURE:
<223> OTHER INFORMATION: Primer Eg5-2

<400> SEQUENCE: 13
aatgttcatg gtctcatgg                                                  19

<210> SEQ ID NO 14
<211> LENGTH: 37
<212> TYPE: DNA
<213> ORGANISM: Artificial Sequence
<220> FEATURE:
<223> OTHER INFORMATION: Primer

<400> SEQUENCE: 14
ggatctcctg caggatctgg ccggccggat ctcgtac                              37

<210> SEQ ID NO 15
<211> LENGTH: 24
<212> TYPE: DNA
<213> ORGANISM: Artificial Sequence
<220> FEATURE:
<223> OTHER INFORMATION: Primer RPB2forward

<400> SEQUENCE: 15
gcggccgcat ggagtcgatt gcgc                                            24

<210> SEQ ID NO 16
<211> LENGTH: 24
<212> TYPE: DNA
<213> ORGANISM: Artificial Sequence
<220> FEATURE:
<223> OTHER INFORMATION: Primer RPB2reverse
```

<400> SEQUENCE: 16
gcggccgctt actgcaactt cctt                                          24

<210> SEQ ID NO 17
<211> LENGTH: 34
<212> TYPE: DNA
<213> ORGANISM: Artificial Sequence
<220> FEATURE:
<223> OTHER INFORMATION: Primer

<400> SEQUENCE: 17
aagcttgcat gcctgcaggt cgactcgacg tacg                               34

<210> SEQ ID NO 18
<211> LENGTH: 280
<212> TYPE: DNA
<213> ORGANISM: soybean albumin transcription terminator

<400> SEQUENCE: 18
tctagaggat ccaaggccgc gaagttaaaa gcaatgttgt cacttgtcgt actaacacat    60
gatgtgatag tttatgctag ctagctataa cataagctgt ctctgagtgt gttgtatatt   120
aataaagatc atcactggtg aatggtgatc gtgtacgtac cctacttagt aggcaatgga   180
agcacttaga gtgtgctttg tgcatggcct tgcctctgtt ttgagacttt tgtaatgttt   240
tcgagtttaa atctttgcct ttgcgtacgt gggcggatcc                        280

<210> SEQ ID NO 19
<211> LENGTH: 32
<212> TYPE: DNA
<213> ORGANISM: Artificial Sequence
<220> FEATURE:
<223> OTHER INFORMATION: Primer oSalb-12

<400> SEQUENCE: 19
tttggatcct ctagacgtac gcaaaggcaa ag                                 32

<210> SEQ ID NO 20
<211> LENGTH: 36
<212> TYPE: DNA
<213> ORGANISM: Artificial Sequence
<220> FEATURE:
<223> OTHER INFORMATION: Primer oSalb-13

<400> SEQUENCE: 20
aaaggatcca aggccgcgaa gttaaaagca atgttg                             36

<210> SEQ ID NO 21
<211> LENGTH: 24
<212> TYPE: DNA
<213> ORGANISM: Artificial Sequence
<220> FEATURE:
<223> OTHER INFORMATION: Primer GSP1

<400> SEQUENCE: 21 gcccccatc ctttgaaagc ctgt                                           24

<210> SEQ ID NO 22
<211> LENGTH: 34
<212> TYPE: DNA
<213> ORGANISM: Artificial Sequence
<220> FEATURE:
<223> OTHER INFORMATION: Primer GSP2

```
<400> SEQUENCE: 22
cgcggatccg agagcctcag catcttgagc agaa                              34

<210> SEQ ID NO 23
<211> LENGTH: 27
<212> TYPE: DNA
<213> ORGANISM: Artificial Sequence
<220> FEATURE:
<223> OTHER INFORMATION: Primer GSP3

<400> SEQUENCE: 23
ggtccaatat ggaacgatga gttgata                                      27

<210> SEQ ID NO 24
<211> LENGTH: 35
<212> TYPE: DNA
<213> ORGANISM: Artificial Sequence
<220> FEATURE:
<223> OTHER INFORMATION: Primer GSP4

<400> SEQUENCE: 24
cgcggatccg ctggaactag aagagagacc taaga                             35

<210> SEQ ID NO 25
<211> LENGTH: 1408
<212> TYPE: DNA
<213> ORGANISM: Glycine max
<220> FEATURE:
<221> NAME/KEY: misc_feature
<223> OTHER INFORMATION: BD30 promoter

<400> SEQUENCE: 25
aactaaaaaa agctctcaaa ttacattttg agttgtttca ggttccattg ccttattgct      60
aaaactccaa ctaaaataac aaatagcaca tgcaggtgca acaacacgt tactctgatg      120 aaggtgatgt gcctctagca gtctagctta tgaggctcgc tgcttatcaa cgattcatca     180
ttccccaaga cgtgtacgca gattaaacaa tggacaaaac ttcaatcgat tatagaataa     240 taatttaac agtgccgact tttttctgta aacaaaggc cagaatcata tcgcacatca       300
tcttgaatgc agtgtcgagt ttggaccatt tgagtacaaa gccaatattg aatgattttt     360
cgattttaca tgtgtgaatc agacaaaagt gcatgcaatc acttgcaagt aaattaagga    420
tactaatcta ttcctttcat tttatatgct ccacttttat ataaaaaaat atacattatt    480
atatatgcat tattaattat tgcagtatta tgctattggt tttatggccc tgctaaataa    540
cctaaatgag tctaactatt gcatatgaat caaatgaagg aagaatcatg atctaaacct    600
gagtacccaa tgcaataaaa tgcgtcctat tacctaaact tcaaacacac attgccatcg    660
gacgtataaa ttaatgcata taggttattt tgagaaaaga aaacatcaaa agctctaaaa    720
cttcttttaa ctttgaaata agctgataaa aatacgcttt aaatcaactg tgtgctgtat    780
ataagctgca atttcacatt ttaccaaacc gaaacaagaa tggtaacagt gaggcaaaaa    840
tttgaaaaat gtcctacttc acattccat caaattaatt acaactaaat aaataaacat     900
cgtgattcaa gcagtaatga aagtcgaaat cagatagaat atacacgttt aacatcaatt    960 gaatttttt ttaatggat atatacaagt ttactatttt atatataatg aaaattcatt     1020
ttgtgttagc acaaaactta cagaaagaga taaatttaa ataagagaa ttatatccaa     1080 ttttataatc caaataatc aaattaaga atattggcta gatagaccgg cttttcact       1140 gcccctgctg gataatgaaa attcatatca aaacaataca gaagttctag tttaataata    1200
```

```
aaaaagttgg caaactgtca ttccctgttg gtttttaagc caaatcacaa ttcaattacg    1260
tatcagaaat taatttaaac caaatatata gctacgaggg aacttcttca gtcattacta    1320
gctagctcac taatcactat atatacgaca tgctacaagt gaagtgacca tatcttaatt    1380
tcaaatcata aaattcttcc accaagtt                                       1408

<210> SEQ ID NO 26
<211> LENGTH: 690
<212> TYPE: DNA
<213> ORGANISM: Glycine max
<220> FEATURE:
<221> NAME/KEY: misc_feature
<223> OTHER INFORMATION: Glycinin Gy1 promoter

<400> SEQUENCE: 26
tagcctaagt acgtactcaa aatgccaaca ataaaaaaa aagttgcttt aataatgcca      60
aaacaaatta ataaaacact acaacaccg gatttttttt aattaaaatg tgccatttag    120
gataaatagt taatattttt aataattatt taaaaagccg tatctactaa aatgattttt    180
atttggttga aaatattaat atgtttaaat caacacaatc tatcaaaatt aaactaaaaa    240
aaaaataagt gtacgtggtt aacattagta cagtaatata agaggaaaat gagaaattaa    300
gaaattgaaa gcgagtctaa ttttttaaatt atgaacctgc atatataaaa ggaaagaaag    360
aatccaggaa gaaagaaat gaaccatgc atggtcccct cgtcatcacg agtttctgcc      420
atttgcaata gaaacactga aacacctttc tctttgtcac ttaattgaga tgccgaagcc    480
acctcacacc atgaacttca tgaggtgtag cacccaaggc ttccatagcc atgcatactg    540
aagaatgtct caagctcagc accctacttc tgtgacgttg tccctcattc accttcctct    600
cttccctata aataaccacg cctcaggttc tccgcttcac aactcaaaca ttctcctcca    660
ttggtcctta aacactcatc agtcatcacc                                     690

<210> SEQ ID NO 27
<211> LENGTH: 36
<212> TYPE: DNA
<213> ORGANISM: Artificial Sequence
<220> FEATURE:
<223> OTHER INFORMATION: Primer

<400> SEQUENCE: 27
cgcggatcct agcctaagta cgtactcaaa atgcca                              36

<210> SEQ ID NO 28
<211> LENGTH: 41
<212> TYPE: DNA
<213> ORGANISM: Artificial Sequence
<220> FEATURE:
<223> OTHER INFORMATION: Primer

<400> SEQUENCE: 28
gaattcgcgg ccgcggtgat gactgatgag tgtttaagga c                        41

<210> SEQ ID NO 29
<211> LENGTH: 2012
<212> TYPE: DNA
<213> ORGANISM: Glycine max
<220> FEATURE:
<221> NAME/KEY: misc_feature
<223> OTHER INFORMATION: annexin promoter

<400> SEQUENCE: 29
atcttaggcc cttgattata tggtgtttag atggattcac atgcaagttt ttatttcaat     60
```

```
cccttttcct ttgaataact gaccaagaac aacaagaaaa aaaaaaaaag aaaaggatca    120
ttttgaaagg atattttccg ctcctattca aatactgtat ttttaccaaa aaaactgtat    180
ttttcctaca ctctcaagct tgttttttcg cttcgactct catgatttcc ttcatatgcc    240
aatcactcta tttataaatg cataaggta gtgtgaacaa ttgcaaagct tgtcatcaaa     300
agcttgcaat gtacaaatta atgttttttca tgcctttcaa aattatctgc acccctagc   360 tattaatcta acatctaagt aaggctagtg aattttttcg aatagtcatg cagtgcatta   420
atttccccgt gactattttg gctttgactc caacactggc cccgtacatc cgtccctcat   480
tacatgaaaa gaaatattgt ttatattctt aattaaaaat attgtccctt ctaaattttc   540
atatagttaa ttattatatt actttttttct ctattctatt agttctatttt tcaaattatt  600 atttatgcat atgtaaagta cattatattt ttgctatata cttaaatatt tctaaattat   660 taaaaaaga ctgatgaa aaatttattc tttttaaagc tatatcattt tatatatact     720
ttttcttttc ttttctttca ttttctattc aatttaataa gaaataaatt ttgtaaattt   780
ttatttatca atttataaaa atatttact ttatatgttt tttcacattt ttgttaaaca    840
aatcatatca ttatgattga aagagaggaa attgacagtg agtaataagt gatgagaaaa   900
aaatgtgtta tttcctaaaa aaaacctaaa caaacatgta tctactctct atttcatcta   960
tctctcattt catttttctc tttatctctt tctttatttt tttatcatat catttcacat  1020
taattatttt tactctcttt attttttctc tctatccctc tcttatttcc actcatatat   1080
acactccaaa attggggcat gcctttatca ctactctatc tcctccacta aatcatttaa  1140
atgaaactga aaagcattgg caagtctcct cccctcctca agtgatttcc aactcagcat  1200
tggcatctga ttgattcagt atatctattg catgtgtaaa agtcttttcca caatacataa  1260 ctattaatta atcttaaata aataaggat aaaatatttt ttttttcttca taaaattaaa   1320 atatgttatt ttttgtttag atgtatattc gaataaatct aaatatatga taatgatttt   1380
ttatattgat taaacatata atcaatatta aatatgatat ttttttatat aggttgtaca   1440 cataattta taaggataaa aaatatgata aaaataaatt ttaaatattt ttatatttac    1500
gagaaaaaaa aatatttag ccataaataa atgaccagca tattttacaa ccttagtaat    1560 tcataaaattc ctatatgtat atttgaaatt aaaaacagat aatcgttaag ggaaggaatc  1620
ctacgtcatc tcttgccatt tgttttttcat gcaaacagaa agggacgaaa aaccacctca   1680
ccatgaatca ctcttcacac cattttttact agcaaacaag tctcaacaac tgaagccagc 1740
tctctttccg tttcttttta caacacttct tttgaaatag tagtattttt ttttcacatg   1800
atttattaac gtgccaaaag atgcttattg aatagagtgc acatttgtaa tgtactacta   1860
attagaacat gaaaaagcat tgttctaaca cgataatcct gtgaaggcgt taactccaaa    1920
gatccaattt cactatataa aattgtgacga aagcaaaatg aattcacata gctgagagag   1980
aaaggaaagg ttaactaaga agcaatactt ca                                  2012

<210> SEQ ID NO 30
<211> LENGTH: 37
<212> TYPE: DNA
<213> ORGANISM: Artificial Sequence
<220> FEATURE:
<223> OTHER INFORMATION: Primer

<400> SEQUENCE: 30
cgcggatcca tcttaggccc ttgattatat ggtgttt                              37
```

<210> SEQ ID NO 31
<211> LENGTH: 43
<212> TYPE: DNA
<213> ORGANISM: Artificial Sequence
<220> FEATURE:
<223> OTHER INFORMATION: Primer

<400> SEQUENCE: 31
gaattcgcgg ccgctgaagt attgcttctt agttaacctt tcc                43

<210> SEQ ID NO 32
<211> LENGTH: 41
<212> TYPE: DNA
<213> ORGANISM: Artificial Sequence
<220> FEATURE:
<223> OTHER INFORMATION: Primer

<400> SEQUENCE: 32
cgcggatcca actaaaaaaa gctctcaaat tacattttga g                  41

<210> SEQ ID NO 33
<211> LENGTH: 44
<212> TYPE: DNA
<213> ORGANISM: Artificial Sequence
<220> FEATURE:
<223> OTHER INFORMATION: Primer

<400> SEQUENCE: 33
gaattcgcgg ccgcaacttg gtggaagaat tttatgattt gaaa               44

<210> SEQ ID NO 34
<211> LENGTH: 29
<212> TYPE: DNA
<213> ORGANISM: Artificial Sequence
<220> FEATURE:
<223> OTHER INFORMATION: Primer oKTi5

<400> SEQUENCE: 34
atctagacgt acgtcctcga agagaaggg                                29

<210> SEQ ID NO 35
<211> LENGTH: 22
<212> TYPE: DNA
<213> ORGANISM: Artificial Sequence
<220> FEATURE:
<223> OTHER INFORMATION: Primer oKTi6

<400> SEQUENCE: 35
ttctagacgt acggatataa tg                                       22

<210> SEQ ID NO 36
<211> LENGTH: 17
<212> TYPE: DNA
<213> ORGANISM: Artificial Sequence
<220> FEATURE:
<223> OTHER INFORMATION: Primer oSBD30-1

<400> SEQUENCE: 36
tgcggccgca tgagccg                                             17

<210> SEQ ID NO 37
<211> LENGTH: 32
<212> TYPE: DNA
<213> ORGANISM: Artificial Sequence
<220> FEATURE:
<223> OTHER INFORMATION: Primer oSBD30-2

<400> SEQUENCE: 37
acgtacggta ccatctgcta atattttaaa tc					32

<210> SEQ ID NO 38
<211> LENGTH: 32
<212> TYPE: DNA
<213> ORGANISM: Artificial Sequence
<220> FEATURE:
<223> OTHER INFORMATION: Primer oCGR5-1

<400> SEQUENCE: 38
ttgcggccgc aaaccatggc tgctgctccc ag					32

<210> SEQ ID NO 39
<211> LENGTH: 24
<212> TYPE: DNA
<213> ORGANISM: Artificial Sequence
<220> FEATURE:
<223> OTHER INFORMATION: Primer oCGR5-2

<400> SEQUENCE: 39
aagcggccgc ttactgcgcc ttac					24

<210> SEQ ID NO 40
<211> LENGTH: 29
<212> TYPE: DNA
<213> ORGANISM: Artificial Sequence
<220> FEATURE:
<223> OTHER INFORMATION: Primer oSGly-1

<400> SEQUENCE: 40
ttcctgcagg ctagcctaag tacgtactc					29

<210> SEQ ID NO 41
<211> LENGTH: 21
<212> TYPE: DNA
<213> ORGANISM: Artificial Sequence
<220> FEATURE:
<223> OTHER INFORMATION: Primer oSGly-2

<400> SEQUENCE: 41
aagcggccgc ggtgatgact g					21

<210> SEQ ID NO 42
<211> LENGTH: 36
<212> TYPE: DNA
<213> ORGANISM: Artificial Sequence
<220> FEATURE:
<223> OTHER INFORMATION: Primer LegPro5'

<400> SEQUENCE: 42
tttctagacg tacgtccctt cttatctttg atctcc					36

<210> SEQ ID NO 43
<211> LENGTH: 34
<212> TYPE: DNA
<213> ORGANISM: Artificial Sequence
<220> FEATURE:
<223> OTHER INFORMATION: Primer LegPro3'

<400> SEQUENCE: 43
gcggccgcag ttggatagaa tatatgtttg tgac					34

<210> SEQ ID NO 44

```
<211> LENGTH: 41
<212> TYPE: DNA
<213> ORGANISM: Artificial Sequence
<220> FEATURE:
<223> OTHER INFORMATION: Primer LegTerm5'

<400> SEQUENCE: 44
ctatccaact gcggccgcat ttcgcaccaa atcaatgaaa g                          41

<210> SEQ ID NO 45
<211> LENGTH: 38
<212> TYPE: DNA
<213> ORGANISM: Artificial Sequence
<220> FEATURE:
<223> OTHER INFORMATION: Primer LegTerm3'

<400> SEQUENCE: 45
aatctagacg tacgtgaagg ttaaacatgg tgaatatg                              38

<210> SEQ ID NO 46
<211> LENGTH: 24
<212> TYPE: DNA
<213> ORGANISM: Artificial Sequence
<220> FEATURE:
<223> OTHER INFORMATION: Primer CGR4forward

<400> SEQUENCE: 46
gcggccgcat gggaacggac caag                                             24

<210> SEQ ID NO 47
<211> LENGTH: 24
<212> TYPE: DNA
<213> ORGANISM: Artificial Sequence
<220> FEATURE:
<223> OTHER INFORMATION: Primer CGR4reverse

<400> SEQUENCE: 47
gcggccgcct actcttcctt ggga                                             24

<210> SEQ ID NO 48
<211> LENGTH: 1270
<212> TYPE: DNA
<213> ORGANISM: Artificial Sequence
<220> FEATURE:
<223> OTHER INFORMATION: D8S-1: Synthetic gene codon-optimized for
      expression in Yarrowia lipolytica

<400> SEQUENCE: 48
ccatggagtc caagcgacag gctctgtctc ccctccagct gatggaacag acctacgacg      60
tcgtgaactt ccaccctggt ggagctgaaa tcattgagaa ctaccaggga cgagatgcta     120
ctgacgcctt catggttatg cactttcagg aagccttcga caagctcaag cgaatgccca     180
agatcaaccc ctcctttgag ctgcctcccc aggctgccgt caacgaagct caggaggatt     240
tccgaaagct ccgagaagag ctgatcgcca ctggcatgtt tgacgcctct cccctctggt     300
actcgtacaa gatctccacc accctgggtc ttggcgtgct tggatacttc ctgatggtcc     360
agtaccagat gtacttcatt ggtgctgtgc tgctcggtat gcactaccag caaatgggat     420
ggctgtctca tgacatctgc caccaccaga ccttcaagaa ccgaaactgg aataacctcg     480
tgggtctggt ctttggcaac ggactccagg gcttctccgt gacctgttgg aaggacagac     540
acaacgccca tcattctgct accaacgttc agggtcacga tccgacattg ataacctgc      600 ctcccctcgc ctggtccgag gacgatgtca ctcgagcttc tcccatctcc cgaaagctca     660
```

```
ttcagttcca acagtactat ttcctggtca tctgtattct cctgcgattc atctggtgtt      720
tccagtgcgt gctgaccgtt cgatccctca aggaccgaga caaccagttc taccgatctc      780
agtacaagaa agaggccatt ggactcgctc tgcactggac tctcaaggct ctgttccacc      840
tcttctttat gccctccatc ctgacctcgc tcctggtgtt ctttgtttcc gagctcgtcg      900
gtggcttcgg aattgccatc gtggtcttca tgaaccacta ccctctggag aagatcggtg      960
atcccgtctg ggacggacat ggcttctctg tgggtcagat ccatgagacc atgaacattc     1020
gacgaggcat cattactgac tggttctttg gaggcctgaa ctaccagatc gagcaccatc     1080
tctggcccac cctgcctcga cacaacctca ctgccgtttc ctaccaggtg aacagctgt      1140 gccagaagca caacctcccc taccgaaacc ctctgcccca tgaaggtctc gtcatcctgc     1200
tccgatacct ggccgtgttc gctcgaatgg ccgagaagca gcccgctggc aaggctctct     1260
aagcggccgc                                                            1270

<210> SEQ ID NO 49
<211> LENGTH: 104
<212> TYPE: DNA
<213> ORGANISM: Artificial Sequence
<220> FEATURE:
<223> OTHER INFORMATION: Primer D8-1A

<400> SEQUENCE: 49
atggagtcca agcgacaggc tctgtctccc ctccagctga tggaacagac ctacgacgtc       60
gtgaacttcc accctggtgg agctgaaatc attgagaact acca                      104

<210> SEQ ID NO 50
<211> LENGTH: 104
<212> TYPE: DNA
<213> ORGANISM: Artificial Sequence
<220> FEATURE:
<223> OTHER INFORMATION: Primer D8-1B

<400> SEQUENCE: 50
tccctggtag ttctcaatga tttcagctcc accagggtgg aagttcacga cgtcgtaggt       60
ctgttccatc agctggaggg gagacagagc ctgtcgcttg gact                      104

<210> SEQ ID NO 51
<211> LENGTH: 102
<212> TYPE: DNA
<213> ORGANISM: Artificial Sequence
<220> FEATURE:
<223> OTHER INFORMATION: Primer D8-2A

<400> SEQUENCE: 51
gggacgagat gctactgacg ccttcatggt tatgcacttt caggaagcct tcgacaagct       60
caagcgaatg cccaagatca ccccctcctt tgagctgcct cc                        102

<210> SEQ ID NO 52
<211> LENGTH: 102
<212> TYPE: DNA
<213> ORGANISM: Artificial Sequence
<220> FEATURE:
<223> OTHER INFORMATION: Primer D8-2B

<400> SEQUENCE: 52
ctggggaggc agctcaaagg aggggttgat cttgggcatt cgcttgagct tgtcgaaggc       60
ttcctgaaag tgcataacca tgaaggcgtc agtagcatct cg                        102
```

<210> SEQ ID NO 53
<211> LENGTH: 101
<212> TYPE: DNA
<213> ORGANISM: Artificial Sequence
<220> FEATURE:
<223> OTHER INFORMATION: Primer D8-3A

<400> SEQUENCE: 53
ccaggctgcc gtcaacgaag ctcaggagga tttccgaaag ctccgagaag agctgatcgc    60
cactggcatg tttgacgcct ctcccctctg gtactcgtac a                      101

<210> SEQ ID NO 54
<211> LENGTH: 101
<212> TYPE: DNA
<213> ORGANISM: Artificial Sequence
<220> FEATURE:
<223> OTHER INFORMATION: Primer D8-3B

<400> SEQUENCE: 54
atcttgtacg agtaccagag gggagaggcg tcaaacatgc cagtggcgat cagctcttct    60
cggagctttc ggaaatcctc ctgagcttcg ttgacggcag c                      101

<210> SEQ ID NO 55
<211> LENGTH: 101
<212> TYPE: DNA
<213> ORGANISM: Artificial Sequence
<220> FEATURE:
<223> OTHER INFORMATION: Primer D8-4A

<400> SEQUENCE: 55
ccaccaccct gggtcttggc gtgcttggat acttcctgat ggtccagtac cagatgtact    60
tcattggtgc tgtgctgctc ggtatgcact accagcaaat g                      101

<210> SEQ ID NO 56
<211> LENGTH: 101
<212> TYPE: DNA
<213> ORGANISM: Artificial Sequence
<220> FEATURE:
<223> OTHER INFORMATION: Primer D8-4B

<400> SEQUENCE: 56
atcccatttg ctggtagtgc ataccgagca gcacagcacc aatgaagtac atctggtact    60
ggaccatcag gaagtatcca agcacgccaa gacccagggt g                      101

<210> SEQ ID NO 57
<211> LENGTH: 104
<212> TYPE: DNA
<213> ORGANISM: Artificial Sequence
<220> FEATURE:
<223> OTHER INFORMATION: Primer D8-5A

<400> SEQUENCE: 57
ggatggctgt ctcatgacat ctgccaccac cagaccttca agaaccgaaa ctggaataac    60
ctcgtgggtc tggtctttgg caacggactc cagggcttct ccgt                   104

<210> SEQ ID NO 58
<211> LENGTH: 104
<212> TYPE: DNA
<213> ORGANISM: Artificial Sequence
<220> FEATURE:
<223> OTHER INFORMATION: Primer D8-5B

<400> SEQUENCE: 58

```
ggtcacggag aagccctgga gtccgttgcc aaagaccaga cccacgaggt tattccagtt    60
tcggttcttg aaggtctggt ggtggcagat gtcatgagac agcc                   104
```

<210> SEQ ID NO 59
<211> LENGTH: 101
<212> TYPE: DNA
<213> ORGANISM: Artificial Sequence
<220> FEATURE:
<223> OTHER INFORMATION: Primer D8-6A

<400> SEQUENCE: 59

```
gacctgttgg aaggacagac acaacgccca tcattctgct accaacgttc agggtcacga    60
tcccgacatt gataacctgc ctcccctcgc ctggtccgag g                      101
```

<210> SEQ ID NO 60
<211> LENGTH: 101
<212> TYPE: DNA
<213> ORGANISM: Artificial Sequence
<220> FEATURE:
<223> OTHER INFORMATION: Primer D8-6B

<400> SEQUENCE: 60

```
tcgtcctcgg accaggcgag gggaggcagg ttatcaatgt cgggatcgtg accctgaacg    60
ttggtagcag aatgatgggc gttgtgtctg tccttccaac a                      101
```

<210> SEQ ID NO 61
<211> LENGTH: 95
<212> TYPE: DNA
<213> ORGANISM: Artificial Sequence
<220> FEATURE:
<223> OTHER INFORMATION: Primer D8-7A

<400> SEQUENCE: 61

```
tcactcgagc ttctcccatc tcccgaaagc tcattcagtt ccaacagtac tatttcctgg    60
tcatctgtat tctcctgcga ttcatctggt gtttc                              95
```

<210> SEQ ID NO 62
<211> LENGTH: 95
<212> TYPE: DNA
<213> ORGANISM: Artificial Sequence
<220> FEATURE:
<223> OTHER INFORMATION: Primer D8-7B

<400> SEQUENCE: 62

```
actggaaaca ccagatgaat cgcaggagaa tacagatgac caggaaatag tactgttgga    60
actgaatgag ctttcgggag atgggagaag ctcga                              95
```

<210> SEQ ID NO 63
<211> LENGTH: 89
<212> TYPE: DNA
<213> ORGANISM: Artificial Sequence
<220> FEATURE:
<223> OTHER INFORMATION: Primer D8-8A

<400> SEQUENCE: 63

```
cagtgcgtgc tgaccgttcg atccctcaag gaccgagaca accagttcta ccgatctcag    60
tacaagaaag aggccattgg actcgctct                                     89
```

<210> SEQ ID NO 64
<211> LENGTH: 89
<212> TYPE: DNA
<213> ORGANISM: Artificial Sequence
<220> FEATURE:
<223> OTHER INFORMATION: Primer D8-8B

<400> SEQUENCE: 64
gtgcagagcg agtccaatgg cctctttctt gtactgagat cggtagaact ggttgtctcg    60
gtccttgagg gatcgaacgg tcagcacgc                                      89

<210> SEQ ID NO 65
<211> LENGTH: 85
<212> TYPE: DNA
<213> ORGANISM: Artificial Sequence
<220> FEATURE:
<223> OTHER INFORMATION: Primer D8-9A

<400> SEQUENCE: 65
gcactggact ctcaaggctc tgttccacct cttctttatg ccctccatcc tgacctcgct    60
cctggtgttc tttgtttccg agctc                                          85

<210> SEQ ID NO 66
<211> LENGTH: 85
<212> TYPE: DNA
<213> ORGANISM: Artificial Sequence
<220> FEATURE:
<223> OTHER INFORMATION: Primer D8-9B

<400> SEQUENCE: 66
cgacgagctc ggaaacaaag aacaccagga gcgaggtcag gatggagggc ataaagaaga    60
ggtggaacag agccttgaga gtcca                                          85

<210> SEQ ID NO 67
<211> LENGTH: 91
<212> TYPE: DNA
<213> ORGANISM: Artificial Sequence
<220> FEATURE:
<223> OTHER INFORMATION: Primer D8-10A

<400> SEQUENCE: 67
gtcggtggct tcggaattgc catcgtggtc ttcatgaacc actaccctct ggagaagatc    60
ggtgatcccg tctgggacgg acatggcttc t                                   91

<210> SEQ ID NO 68
<211> LENGTH: 91
<212> TYPE: DNA
<213> ORGANISM: Artificial Sequence
<220> FEATURE:
<223> OTHER INFORMATION: Primer D8-10B

<400> SEQUENCE: 68
acagagaagc catgtccgtc ccagacggga tcaccgatct tctccagagg gtagtggttc    60
atgaagacca cgatggcaat tccgaagcca c                                   91

<210> SEQ ID NO 69
<211> LENGTH: 92
<212> TYPE: DNA
<213> ORGANISM: Artificial Sequence
<220> FEATURE:
<223> OTHER INFORMATION: Primer D8-11A

<400> SEQUENCE: 69
ctgtgggtca gatccatgag accatgaaca ttcgacgagg catcattact gactggttct    60
ttggaggcct gaactaccag atcgagcacc at                                  92

<210> SEQ ID NO 70
<211> LENGTH: 92
<212> TYPE: DNA
<213> ORGANISM: Artificial Sequence
<220> FEATURE:
<223> OTHER INFORMATION: Primer D8-11B

<400> SEQUENCE: 70
agagatggtg ctcgatctgg tagttcaggc ctccaaagaa ccagtcagta atgatgcctc    60
gtcgaatgtt catggtctca tggatctgac cc    92

<210> SEQ ID NO 71
<211> LENGTH: 93
<212> TYPE: DNA
<213> ORGANISM: Artificial Sequence
<220> FEATURE:
<223> OTHER INFORMATION: Primer D8-12A

<400> SEQUENCE: 71
ctctggccca ctctgcctcg acacaacctc actgccgttt cctaccaggt ggaacagctg    60
tgccagaagc acaacctccc ctaccgaaac cct    93

<210> SEQ ID NO 72
<211> LENGTH: 93
<212> TYPE: DNA
<213> ORGANISM: Artificial Sequence
<220> FEATURE:
<223> OTHER INFORMATION: Primer D8-12B

<400> SEQUENCE: 72
gcagagggtt tcggtagggg aggttgtgct tctggcacag ctgttccacc tggtaggaaa    60
cggcagtgag gttgtgtcga ggcagagtgg gcc    93

<210> SEQ ID NO 73
<211> LENGTH: 90
<212> TYPE: DNA
<213> ORGANISM: Artificial Sequence
<220> FEATURE:
<223> OTHER INFORMATION: Primer D8-13A

<400> SEQUENCE: 73
ctgccccatg aaggtctcgt catcctgctc cgatacctgg ccgtgttcgc tcgaatggcc    60
gagaagcagc ccgctggcaa ggctctctaa    90

<210> SEQ ID NO 74
<211> LENGTH: 90
<212> TYPE: DNA
<213> ORGANISM: Artificial Sequence
<220> FEATURE:
<223> OTHER INFORMATION: Primer D8-13B

<400> SEQUENCE: 74
ccgcttagag agccttgcca gcgggctgct tctcggccat tcgagcgaac acggccaggt    60
atcggagcag gatgacgaga ccttcatggg    90

<210> SEQ ID NO 75
<211> LENGTH: 38
<212> TYPE: DNA
<213> ORGANISM: Artificial Sequence
<220> FEATURE:
<223> OTHER INFORMATION: Primer D8-1F

<400> SEQUENCE: 75
tttccatgga gtccaagcga caggctctgt ctcccctc                               38

<210> SEQ ID NO 76
<211> LENGTH: 37
<212> TYPE: DNA
<213> ORGANISM: Artificial Sequence
<220> FEATURE:
<223> OTHER INFORMATION: Primer D8-3R

<400> SEQUENCE: 76
tttagatctt gtacgagtac cagaggggag aggcgtc                                37

<210> SEQ ID NO 77
<211> LENGTH: 41
<212> TYPE: DNA
<213> ORGANISM: Artificial Sequence
<220> FEATURE:
<223> OTHER INFORMATION: Primer D8-4F

<400> SEQUENCE: 77
acaagatctc caccaccctg ggtcttggcg tgcttggata c                           41

<210> SEQ ID NO 78
<211> LENGTH: 43
<212> TYPE: DNA
<213> ORGANISM: Artificial Sequence
<220> FEATURE:
<223> OTHER INFORMATION: Primer D8-6R

<400> SEQUENCE: 78
tttctcgagt gacatcgtcc tcggaccagg cgaggggagg cag                         43

<210> SEQ ID NO 79
<211> LENGTH: 32
<212> TYPE: DNA
<213> ORGANISM: Artificial Sequence
<220> FEATURE:
<223> OTHER INFORMATION: Primer D8-7F

<400> SEQUENCE: 79
tcactcgagc ttctcccatc tcccgaaagc tc                                     32

<210> SEQ ID NO 80
<211> LENGTH: 29
<212> TYPE: DNA
<213> ORGANISM: Artificial Sequence
<220> FEATURE:
<223> OTHER INFORMATION: Primer D8-9R

<400> SEQUENCE: 80
cgacgagctc ggaaacaaag aacaccagg                                         29

<210> SEQ ID NO 81
<211> LENGTH: 39
<212> TYPE: DNA
<213> ORGANISM: Artificial Sequence
<220> FEATURE:
<223> OTHER INFORMATION: Primer D8-10F

<400> SEQUENCE: 81
tttgagctcg tcggtggctt cggaattgcc atcgtggtc                              39

<210> SEQ ID NO 82
<211> LENGTH: 36
<212> TYPE: DNA

<213> ORGANISM: Artificial Sequence
<220> FEATURE:
<223> OTHER INFORMATION: Primer D8-13R

<400> SEQUENCE: 82
tttgcggccg cttagagagc cttgccagcg ggctgc                              36

<210> SEQ ID NO 83
<211> LENGTH: 309
<212> TYPE: DNA
<213> ORGANISM: Artificial Sequence
<220> FEATURE:
<223> OTHER INFORMATION: 309 bp NcoI/BglII fragment of pT8(1-3)

<400> SEQUENCE: 83
catggagtcc aagcgacagg ctctgtctcc cctccagctg atggaacaga cctacgacgt     60
cgtgaacttc caccctggtg agctgaaat cattgagaac taccagggac gagatgctac    120
tgacgccttc atggttatgc actttcagga agccttcgac aagctcaagc gaatgcccaa    180
gatcaacccc tcctttgagc tgcctcccca ggctgccgtc aacgaagctc aggaggattt    240
ccgaaagctc cgagaagagc tgatcgccac tggcatgttt gacgcctctc ccctctggta    300
ctcgtacaa                                                           309

<210> SEQ ID NO 84
<211> LENGTH: 321
<212> TYPE: DNA
<213> ORGANISM: Artificial Sequence
<220> FEATURE:
<223> OTHER INFORMATION: 321 bp BglII/XhoI fragment of pT8(4-6)

<400> SEQUENCE: 84
gatctccacc accctgggtc ttggcgtgct tggatacttc ctgatggtcc agtaccagat     60
gtacttcatt ggtgctgtgc tgctcggtat gcactaccag caaatgggat ggctgtctca    120
tgacatctgc caccaccaga ccttcaagaa ccgaaactgg aataacctcg tgggtctggt    180 cttggcaac ggactccagg gcttctccgt gacctgttgg aaggacagac acaacgccca    240
tcattctgct accaacgttc agggtcacga tcccgacatt gataacctgc ctcccctcgc    300
ctggtccgag gacgatgtca c                                             321

<210> SEQ ID NO 85
<211> LENGTH: 264
<212> TYPE: DNA
<213> ORGANISM: Artificial Sequence
<220> FEATURE:
<223> OTHER INFORMATION: 264 bp XhoI/SacI fragment of pT8(7-9)

<400> SEQUENCE: 85
tcgagcttct cccatctccc gaaagctcat tcagttccaa cagtactatt tcctggtcat     60
ctgtattctc ctgcgattca tctggtgttt ccagtgcgtg ctgaccgttc gatccctcaa    120
ggaccgagac aaccagttct accgatctca gtacaagaaa gaggccattg gactcgctct    180
gcactggact ctcaaggctc tgttccacct cttctttatg ccctccatcc tgacctcgct    240
cctggtgttc tttgtttccg agct                                          264

<210> SEQ ID NO 86
<211> LENGTH: 369
<212> TYPE: DNA
<213> ORGANISM: Artificial Sequence
<220> FEATURE:
<223> OTHER INFORMATION: 369 bp Sac1/Not1 fragment of pT8(10-13)

```
<400> SEQUENCE: 86
cgtcggtggc ttcggaattg ccatcgtggt cttcatgaac cactaccctc tggagaagat    60
cggtgatccc gtctgggacg gacatggctt ctctgtgggt cagatccatg agaccatgaa   120
cattcgacga ggcatcatta ctgactggtt cttggaggc ctgaactacc agatcgagca    180
ccatctctgg cccacccctgc ctcgacacaa cctcactgcc gtttcctacc aggtggaaca   240
gctgtgccag aagcacaacc tcccctaccg aaaccctctg ccccatgaag gtctcgtcat   300
cctgctccga tacctggccg tgttcgctcg aatggccgag aagcagcccg ctggcaaggc   360
tctctaagc                                                           369

<210> SEQ ID NO 87
<211> LENGTH: 34
<212> TYPE: DNA
<213> ORGANISM: Artificial Sequence
<220> FEATURE:
<223> OTHER INFORMATION: Primer ODMW390

<400> SEQUENCE: 87
aagaatcatt caccatgaag tccaagcgac aggc                                34

<210> SEQ ID NO 88
<211> LENGTH: 34
<212> TYPE: DNA
<213> ORGANISM: Artificial Sequence
<220> FEATURE:
<223> OTHER INFORMATION: Primer ODMW391

<400> SEQUENCE: 88
gcctgtcgct tggacttcat ggtgaatgat tctt                                34

<210> SEQ ID NO 89
<211> LENGTH: 1852
<212> TYPE: DNA
<213> ORGANISM: Artificial Sequence
<220> FEATURE:
<223> OTHER INFORMATION: chimeric D8S-1::XPR terminator gene

<400> SEQUENCE: 89
cgatcaggag agaccgggtt ggcggcgtat ttgtgtccca aaaacagcc ccaattgccc      60 caattgaccc caaattgacc cagtagcggg cccaacccg gcgagagccc ccttcacccc     120
acatatcaaa cctcccccgg ttcccacact tgccgttaag ggcgtagggt actgcagtct    180
ggaatctacg cttgttcaga cttttgtacta gtttcttttgt ctggccatcc gggtaaccca   240
tgccggacgc aaaatagact actgaaaatt tttttgcttt gtggttggga ctttagccaa    300
gggtataaaa gaccaccgtc cccgaattac cttttcctctt cttttctctc tctccttgtc    360
aactcacacc cgaaatcgtt aagcatttcc ttctgagtat aagaatcatt caccatggag    420
tccaagcgac aggctctgtc tcccctccag ctgatggaac agacctacga cgtcgtgaac    480
ttccaccctg gtggagctga atcattgag aactaccagg gacgagatgc tactgacgcc     540
ttcatggtta tgcactttca ggaagccttc gacaagctca gcgaatgcc caagatcaac     600 ccctcctttg agctgcctcc ccaggctgcc gtcaacgaag ctcaggagga tttccgaaag    660
ctccgagaag agctgatcgc cactggcatg tttgacgcct ctcccctctg gtactcgtac    720
aagatctcca ccacccctggg tcttggcgtg cttggatact tcctgatggt ccagtaccag    780
atgtacttca ttggtgctgt gctgctcggt atgcactacc agcaaatggg atggctgtct    840
```

```
catgacatct gccaccacca gaccttcaag aaccgaaact ggaataaacct cgtgggtctg      900 gtctttggca acggactcca gggcttctcc gtgacctgtt ggaaggacag acacaacgcc      960
catcattctg ctaccaacgt tcagggtcac gatcccgaca ttgataacct gcctcccctc     1020
gcctggtccg aggacgatgt cactcgagct tctcccatct cccgaaagct cattcagttc     1080
caacagtact atttcctggt catctgtatt ctcctgcgat tcatctggtg tttccagtgc     1140
gtgctgaccg ttcgatccct caaggaccga gacaaccagt tctaccgatc tcagtacaag     1200
aaagaggcca ttggactcgc tctgcactgg actctcaagg ctctgttcca cctcttcttt     1260 atgcccctcca tcctgacctc gctcctggtg ttctttgttt ccgagctcgt cggtggcttc     1320
ggaattgcca tcgtggtctt catgaaccac taccctctgg agaagatcgg tgatcccgtc     1380
tgggacggac atggcttctc tgtgggtcag atccatgaga ccatgaacat cgacgaggc     1440 atcattactg actggttctt tggaggcctg aactaccaga tcgagcacca tctctggccc     1500
accctgcctc gacacaacct cactgccgtt cctaccagg tggaacagct gtgccagaag     1560
cacaacctcc cctaccgaaa ccctctgccc catgaaggtc tcgtcatcct gctccgatac     1620
ctggccgtgt tcgctcgaat ggccgagaag cagcccgctg gcaaggctct ctaagcggcc     1680
gccaccgccg agattccggc tcttcggcc gccaagcgac ccgggtggac gtctagaggt      1740
acctagcaat aacagatag tttgccggtg ataattctct taacctccca cactcctttg     1800
acataacgat ttatgtaacg aaactgaaat ttgaccagat attgtgtccg cg             1852

<210> SEQ ID NO 90
<211> LENGTH: 1898
<212> TYPE: DNA
<213> ORGANISM: Artificial Sequence
<220> FEATURE:
<223> OTHER INFORMATION: chimeric D8S-2::XPR terminator gene

<400> SEQUENCE: 90
cgatcaggag agaccgggtt ggcggcgtat ttgtgtccca aaaaacagcc ccaattgccc       60
caattgaccc caaattgacc cagtagcggg cccaaccccg gcgagagccc ccttcacccc      120
acatatcaaa cctcccccgg ttcccacact tgccgttaag ggcgtagggt actgcagtct      180
ggaatctacg cttgttcaga cttttgtacta gtttctttgt ctggccatcc gggtaaccca      240
tgccggacgc aaaatagact actgaaaatt ttttttgcttt gtggttggga ctttagccaa      300
gggtataaaa gaccaccgtc cccgaattac ctttcctctt cttttctctc tctccttgtc      360
aactcacacc cgaaatcgtt aagcatttcc ttctgagtat aagaatcatt caccatgaag      420
tccaagcgac aggctctgtc tcccctccag ctgatggaac agacctacga cgtcgtgaac      480
ttccaccctg gtggagctga atcattgag aactaccagg gacgagatgc tactgacgcc      540
ttcatggtta tgcactttca ggaagccttc gacaagctca gcgaatgcc caagatcaac      600 ccctcctttg agctgcctcc ccaggctgcc gtcaacgaag ctcaggagga tttccgaaag      660
ctccgagaag agctgatcgc cactggcatg tttgacgcct ctccccctctg gtactcgtac      720 aagatctcca ccaccctggg tcttggcgtg cttggatact tcctgatggt ccagtaccag      780
atgtacttca ttggtgctgt gctgctcggt atgcactacc agcaaatggg atggctgtct      840
catgacatct gccaccacca gaccttcaag aaccgaaact ggaataaacct cgtgggtctg      900 gtctttggca acggactcca gggcttctcc gtgacctgtt ggaaggacag acacaacgcc      960
catcattctg ctaccaacgt tcagggtcac gatcccgaca ttgataacct gcctcccctc     1020
gcctggtccg aggacgatgt cactcgagct tctcccatct cccgaaagct cattcagttc     1080
```

```
caacagtact atttcctggt catctgtatt ctcctgcgat tcatctggtg tttccagtgc   1140
gtgctgaccg ttcgatccct caaggaccga gacaaccagt tctaccgatc tcagtacaag   1200
aaagaggcca ttggactcgc tctgcactgg actctcaagg ctctgttcca cctcttcttt   1260
atgccctcca tcctgacctc gctcctggtg ttctttgttt ccgagctcgt cggtggcttc   1320
ggaattgcca tcgtggtctt catgaaccac taccctctgg agaagatcgg tgatcccgtc   1380
tgggacggac atggcttctc tgtgggtcag atccatgaga ccatgaacat cgacgaggc    1440 atcattactg actggttctt tggaggcctg aactaccaga tcgagcacca tctctggccc   1500
accctgcctc gacacaacct cactgccgtt tcctaccagg tggaacagct gtgccagaag   1560
cacaacctcc cctaccgaaa ccctctgccc catgaaggtc tcgtcatcct gctccgatac   1620
ctggccgtgt tcgctcgaat ggccgagaag cagcccgctg gcaaggctct ctaagcggcc   1680
gccaccgcgg cccgagattc cggcctcttc ggccgccaag cgacccgggt ggacgtctag   1740
aggtacctag caattaacag atagtttgcc ggtgataatt ctcttaacct cccacactcc   1800
tttgacataa cgatttatgt aacgaaactg aaatttgacc agatattgtg tccgcggtgg   1860
agctccagct tttgttccct ttagtgaggg ttaattaa                          1898

<210> SEQ ID NO 91
<211> LENGTH: 45
<212> TYPE: DNA
<213> ORGANISM: Artificial Sequence
<220> FEATURE:
<223> OTHER INFORMATION: Primer ODMW392

<400> SEQUENCE: 91
gaacagacct acgacgtctc cgcttgggtg aacttccacc ctggt                  45

<210> SEQ ID NO 92
<211> LENGTH: 45
<212> TYPE: DNA
<213> ORGANISM: Artificial Sequence
<220> FEATURE:
<223> OTHER INFORMATION: Primer ODMW393

<400> SEQUENCE: 92
accagggtgg aagttcaccc aagcggagac gtcgtaggtc tgttc                  45

<210> SEQ ID NO 93
<211> LENGTH: 1269
<212> TYPE: DNA
<213> ORGANISM: Artificial Sequence
<220> FEATURE:
<223> OTHER INFORMATION: D8S-3: synthetic delta 8-desaturase gene
      codon-optimized for Yarrowia lipolytica in pDMW261

<400> SEQUENCE: 93
atgaagtcca agcgacaggc tctgtctccc ctccagctga tggaacagac ctacgacgtc   60
tccgcttggg tgaacttcca ccctggtgga gctgaaatca ttgagaacta ccagggacga   120
gatgctactg acgccttcat ggttatgcac tttcaggaag ccttcgacaa gctcaagcga   180
atgcccaaga tcaacccctc ctttgagctg cctccccagg ctgccgtcaa cgaagctcag   240
gaggatttcc gaaagctccg agaagagctg atcgccactg gcatgtttga cgcctctccc   300
ctctggtact cgtacaagat ctccaccacc ctgggtcttg gcgtgcttgg atacttcctg   360
atggtccagt accagatgta cttcattggt gctgtgctgc tcggtatgca ctaccagcaa   420
atgggatggc tgtctcatga catctgccac caccagacct tcaagaaccg aaactggaat   480
```

```
aacctcgtgg gtctggtctt tggcaacgga ctccagggct tctccgtgac ctgttggaag      540
gacagacaca acgcccatca ttctgctacc aacgttcagg gtcacgatcc cgacattgat      600
aacctgcctc ccctcgcctg gtccgaggac gatgtcactc gagcttctcc catctcccga      660
aagctcattc agttccaaca gtactatttc ctggtcatct gtattctcct gcgattcatc      720
tggtgtttcc agtgcgtgct gaccgttcga tccctcaagg accgagacaa ccagttctac      780
cgatctcagt acaagaaaga ggccattgga ctcgctctgc actggactct caaggctctg      840
ttccacctct tctttatgcc ctccatcctg acctcgctcc tggtgttctt tgtttccgag      900
ctcgtcggtg gcttcggaat tgccatcgtg gtcttcatga accactaccc tctggagaag      960
atcggtgatc ccgtctggga cggacatggc ttctctgtgg gtcagatcca tgagaccatg     1020
aacattcgac gaggcatcat tactgactgg ttctttggag gcctgaacta ccagatcgag     1080
caccatctct ggcccaccct gcctcgacac aacctcactg ccgtttccta ccaggtggaa     1140
cagctgtgcc agaagcacaa cctcccctac cgaaaccctc tgccccatga aggtctcgtc     1200
atcctgctcc gatacctggc cgtgttcgct cgaatggccg agaagcagcc cgctggcaag     1260
gctctctaa                                                             1269

<210> SEQ ID NO 94
<211> LENGTH: 29
<212> TYPE: DNA
<213> ORGANISM: Artificial Sequence
<220> FEATURE:
<223> OTHER INFORMATION: Primer ODMW404

<400> SEQUENCE: 94
cctggtacca tgaagtccaa gcgacaggc                                        29

<210> SEQ ID NO 95
<211> LENGTH: 1272
<212> TYPE: DNA
<213> ORGANISM: Artificial Sequence
<220> FEATURE:
<223> OTHER INFORMATION: chimeric gene

<400> SEQUENCE: 95
catgaagtcc aagcgacagg ctctgtctcc cctccagctg atggaacaga cctacgacgt       60
ctccgcttgg gtgaacttcc accctggtgg agctgaaatc attgagaact accagggacg      120
agatgctact gacgccttca tggttatgca ctttcaggaa gccttcgaca agctcaagcg      180
aatgcccaag atcaacccct cctttgagct gcctccccag gctgccgtca acgaagctca      240
ggaggatttc cgaaagctcc gagaagagct gatcgccact ggcatgtttg acgcctctcc      300
cctctggtac tcgtacaaga tctccaccac cctgggtctt ggcgtgcttg atacttcct      360 gatggtccag taccagatgt acttcattgg tgctgtgctg ctcggtatgc actaccagca      420
aatgggatgg ctgtctcatg acatctgcca ccaccagacc ttcaagaacc gaaactggaa      480
taacctcgtg gtctggtctt tggcaacgg actccagggc ttctccgtga cctgttggaa      540
ggacagacac aacgcccatc attctgctac caacgttcag ggtcacgatc ccgacattga      600
taacctgcct cccctcgcct ggtccgagga cgatgtcact cgagcttctc ccatctcccg      660
aaagctcatt cagttccaac agtactattt cctggtcatc tgtattctcc tgcgattcat      720
ctggtgtttc agtgcgtgct gaccgttcg atccctcaag gaccgagaca accagttcta      780
ccgatctcag tacaagaaag aggccattgg actcgctctg cactggactc tcaaggctct      840
```

```
gttccacctc ttctttatgc cctccatcct gacctcgctc ctggtgttct ttgtttccga      900
gctcgtcggt ggcttcggaa ttgccatcgt ggtcttcatg aaccactacc ctctggagaa      960
gatcggtgat cccgtctggg acggacatgg cttctctgtg ggtcagatcc atgagaccat     1020
gaacattcga cgaggcatca ttactgactg gttctttgga ggcctgaact accagatcga     1080
gcaccatctc tggcccaccc tgcctcgaca caacctcact gccgtttcct accaggtgga     1140
acagctgtgc cagaagcaca acctccccta ccgaaaccct gccccatg aaggtctcgt      1200 catcctgctc cgatacctgg ccgtgttcgc tcgaatggcc gagaagcagc ccgctggcaa     1260
ggctctctaa gc                                                          1272
```

<210> SEQ ID NO 96
<211> LENGTH: 80
<212> TYPE: DNA
<213> ORGANISM: Artificial Sequence
<220> FEATURE:
<223> OTHER INFORMATION: Primer YL521

<400> SEQUENCE: 96

```
tttccatggt gaagtccaag cgacaggctc tgcccctcac catcgacgga actacctacg       60
acgtctccgc ttgggtgaac                                                   80
```

<210> SEQ ID NO 97
<211> LENGTH: 30
<212> TYPE: DNA
<213> ORGANISM: Artificial Sequence
<220> FEATURE:
<223> OTHER INFORMATION: Primer YL522

<400> SEQUENCE: 97

```
tggagatctt gtacgagtac cagaggggag                                        30
```

<210> SEQ ID NO 98
<211> LENGTH: 37
<212> TYPE: DNA
<213> ORGANISM: Artificial Sequence
<220> FEATURE:
<223> OTHER INFORMATION: Primer YL525

<400> SEQUENCE: 98

```
ccttcatggt tatgcactct caggaagcct tcgacaa                                37
```

<210> SEQ ID NO 99
<211> LENGTH: 37
<212> TYPE: DNA
<213> ORGANISM: Artificial Sequence
<220> FEATURE:
<223> OTHER INFORMATION: Primer YL526

<400> SEQUENCE: 99

```
ttgtcgaagg cttcctgaga gtgcataacc atgaagg                                37
```

<210> SEQ ID NO 100
<211> LENGTH: 38
<212> TYPE: DNA
<213> ORGANISM: Artificial Sequence
<220> FEATURE:
<223> OTHER INFORMATION: Primer YL527

<400> SEQUENCE: 100

```
ccaagatcaa cccctcctcc gagctgcctc cccaggct                               38
```

```
<210> SEQ ID NO 101
<211> LENGTH: 38
<212> TYPE: DNA
<213> ORGANISM: Artificial Sequence
<220> FEATURE:
<223> OTHER INFORMATION: Primer YL528

<400> SEQUENCE: 101
agcctgggga ggcagctcgg aggagggtt gatcttgg                              38

<210> SEQ ID NO 102
<211> LENGTH: 37
<212> TYPE: DNA
<213> ORGANISM: Artificial Sequence
<220> FEATURE:
<223> OTHER INFORMATION: Primer YL529

<400> SEQUENCE: 102
gggcttctcc gtgacctggt ggaaggacag acacaac                              37

<210> SEQ ID NO 103
<211> LENGTH: 37
<212> TYPE: DNA
<213> ORGANISM: Artificial Sequence
<220> FEATURE:
<223> OTHER INFORMATION: Primer YL530

<400> SEQUENCE: 103
gttgtgtctg tccttccacc aggtcacgga gaagccc                              37

<210> SEQ ID NO 104
<211> LENGTH: 38
<212> TYPE: DNA
<213> ORGANISM: Artificial Sequence
<220> FEATURE:
<223> OTHER INFORMATION: Primer YL531

<400> SEQUENCE: 104
acattgataa cctgcctctg ctcgcctggt ccgaggac                             38

<210> SEQ ID NO 105
<211> LENGTH: 38
<212> TYPE: DNA
<213> ORGANISM: Artificial Sequence
<220> FEATURE:
<223> OTHER INFORMATION: Primer YL532

<400> SEQUENCE: 105
gtcctcggac caggcgagca gaggcaggtt atcaatgt                             38

<210> SEQ ID NO 106
<211> LENGTH: 38
<212> TYPE: DNA
<213> ORGANISM: Artificial Sequence
<220> FEATURE:
<223> OTHER INFORMATION: Primer YL533

<400> SEQUENCE: 106
tcatctggtg tttccagtct gtgctgaccg ttcgatcc                             38

<210> SEQ ID NO 107
<211> LENGTH: 38
<212> TYPE: DNA
<213> ORGANISM: Artificial Sequence
<220> FEATURE:
<223> OTHER INFORMATION: Primer YL534
```

```
<400> SEQUENCE: 107
ggatcgaacg gtcagcacag actggaaaca ccagatga                                38

<210> SEQ ID NO 108
<211> LENGTH: 39
<212> TYPE: DNA
<213> ORGANISM: Artificial Sequence
<220> FEATURE:
<223> OTHER INFORMATION: Primer YL535

<400> SEQUENCE: 108
ctgcactgga ctctcaagac cctgttccac ctcttcttt                               39

<210> SEQ ID NO 109
<211> LENGTH: 39
<212> TYPE: DNA
<213> ORGANISM: Artificial Sequence
<220> FEATURE:
<223> OTHER INFORMATION: Primer YL536

<400> SEQUENCE: 109
aaagaagagg tggaacaggg tcttgagagt ccagtgcag                               39

<210> SEQ ID NO 110
<211> LENGTH: 37
<212> TYPE: DNA
<213> ORGANISM: Artificial Sequence
<220> FEATURE:
<223> OTHER INFORMATION: Primer YL537

<400> SEQUENCE: 110
ctggagaaga tcggtgattc cgtctgggac ggacatg                                 37

<210> SEQ ID NO 111
<211> LENGTH: 37
<212> TYPE: DNA
<213> ORGANISM: Artificial Sequence
<220> FEATURE:
<223> OTHER INFORMATION: Primer YL538

<400> SEQUENCE: 111
catgtccgtc ccagacggaa tcaccgatct tctccag                                 37

<210> SEQ ID NO 112
<211> LENGTH: 1272
<212> TYPE: DNA
<213> ORGANISM: Artificial Sequence
<220> FEATURE:
<223> OTHER INFORMATION: D8SF: synthetic delta-8 desaturase
      (codon-optimized for Yarrowia lipolytica)

<400> SEQUENCE: 112
catggtgaag tccaagcgac aggctctgcc cctcaccatc gacgaaacta cctacgacgt        60
ctccgcttgg gtgaacttcc accctggtgg agctgaaatc attgagaact accagggacg       120
agatgctact gacgccttca tggttatgca ctctcaggaa gccttcgaca agctcaagcg       180
aatgcccaag atcaaccctc ctccgagct gcctccccag gctgccgtca acgaagctca       240
ggaggatttc cgaaagctcc gagaagagct gatcgccact ggcatgtttg acgcctctcc       300
cctctggtac tcgtacaaga tctccaccac cctgggtctt ggcgtgcttg atacttcct       360 gatggtccag taccagatgt acttcattgg tgctgtgctg ctcggtatgc actaccagca       420
aatgggatgg ctgtctcatg acatctgcca ccaccagacc ttcaagaacc gaaactggaa       480
```

-continued

```
taacctcgtg ggtctggtct ttggcaacgg actccagggc ttctccgtga cctggtggaa    540
ggacagacac aacgcccatc attctgctac caacgttcag ggtcacgatc ccgacattga    600
taacctgcct ctgctcgcct ggtccgagga cgatgtcact cgagcttctc ccatctcccg    660
aaagctcatt cagttccaac agtactattt cctggtcatc tgtattctcc tgcgattcat    720
ctggtgtttc cagtctgtgc tgaccgttcg atccctcaag gaccgagaca accagttcta    780
ccgatctcag tacaagaaag aggccattgg actcgctctg cactggactc tcaagaccct    840
gttccacctc ttctttatgc cctccatcct gacctcgctc ctggtgttct ttgtttccga    900
gctcgtcggt ggcttcggaa ttgccatcgt ggtcttcatg aaccactacc ctctggagaa    960
gatcggtgat tccgtctggg acggacatgg cttctctgtg ggtcagatcc atgagaccat   1020
gaacattcga cgaggcatca ttactgactg gttctttgga ggcctgaact accagatcga   1080
gcaccatctc tggcccaccc tgcctcgaca caacctcact gccgtttcct accaggtgga   1140
acagctgtgc cagaagcaca acctccccta ccgaaaccct ctgccccatg aaggtctcgt   1200
catcctgctc cgatacctgg ccgtgttcgc tcgaatggcc gagaagcagc ccgctggcaa   1260
ggctctctaa gc                                                       1272
```

```

<210> SEQ ID NO 113
<211> LENGTH: 422
<212> TYPE: PRT
<213> ORGANISM: Artificial Sequence
<220> FEATURE:
<223> OTHER INFORMATION: D8SF: synthetic delta-8 desaturase
      (codon-optimized for Yarrowia lipolytica)

<400> SEQUENCE: 113

Met Val Lys Ser Lys Arg Gln Ala Leu Pro Leu Thr Ile Asp Gly Thr
1               5                   10                  15

Thr Tyr Asp Val Ser Ala Trp Val Asn Phe His Pro Gly Gly Ala Glu
            20                  25                  30

Ile Ile Glu Asn Tyr Gln Gly Arg Asp Ala Thr Asp Ala Phe Met Val
        35                  40                  45

Met His Ser Gln Glu Ala Phe Asp Lys Leu Lys Arg Met Pro Lys Ile
    50                  55                  60

Asn Pro Ser Ser Glu Leu Pro Pro Gln Ala Ala Val Asn Glu Ala Gln
65                  70                  75                  80

Glu Asp Phe Arg Lys Leu Arg Glu Glu Leu Ile Ala Thr Gly Met Phe
                85                  90                  95

Asp Ala Ser Pro Leu Trp Tyr Ser Tyr Lys Ile Ser Thr Thr Leu Gly
            100                 105                 110

Leu Gly Val Leu Gly Tyr Phe Leu Met Val Gln Tyr Gln Met Tyr Phe
        115                 120                 125

Ile Gly Ala Val Leu Leu Gly Met His Tyr Gln Gln Met Gly Trp Leu
    130                 135                 140

Ser His Asp Ile Cys His His Gln Thr Phe Lys Asn Arg Asn Trp Asn
145                 150                 155                 160

Asn Leu Val Gly Leu Val Phe Gly Asn Gly Leu Gln Gly Phe Ser Val
                165                 170                 175

Thr Trp Trp Lys Asp Arg His Asn Ala His His Ser Ala Thr Asn Val
            180                 185                 190

Gln Gly His Asp Pro Asp Ile Asp Asn Leu Pro Leu Leu Ala Trp Ser
        195                 200                 205

Glu Asp Asp Val Thr Arg Ala Ser Pro Ile Ser Arg Lys Leu Ile Gln
```

```
                   210                 215                 220
Phe Gln Gln Tyr Tyr Phe Leu Val Ile Cys Ile Leu Leu Arg Phe Ile
225                 230                 235                 240

Trp Cys Phe Gln Ser Val Leu Thr Val Arg Ser Leu Lys Asp Arg Asp
                245                 250                 255

Asn Gln Phe Tyr Arg Ser Gln Tyr Lys Lys Glu Ala Ile Gly Leu Ala
                260                 265                 270

Leu His Trp Thr Leu Lys Thr Leu Phe His Leu Phe Phe Met Pro Ser
            275                 280                 285

Ile Leu Thr Ser Leu Leu Val Phe Phe Val Ser Glu Leu Val Gly Gly
        290                 295                 300

Phe Gly Ile Ala Ile Val Val Phe Met Asn His Tyr Pro Leu Glu Lys
305                 310                 315                 320

Ile Gly Asp Ser Val Trp Asp Gly His Gly Phe Ser Val Gly Gln Ile
                325                 330                 335

His Glu Thr Met Asn Ile Arg Arg Gly Ile Ile Thr Asp Trp Phe Phe
            340                 345                 350

Gly Gly Leu Asn Tyr Gln Ile Glu His His Leu Trp Pro Thr Leu Pro
        355                 360                 365

Arg His Asn Leu Thr Ala Val Ser Tyr Gln Val Glu Gln Leu Cys Gln
    370                 375                 380

Lys His Asn Leu Pro Tyr Arg Asn Pro Leu Pro His Glu Gly Leu Val
385                 390                 395                 400

Ile Leu Leu Arg Tyr Leu Ala Val Phe Ala Arg Met Ala Glu Lys Gln
                405                 410                 415

Pro Ala Gly Lys Ala Leu
            420

<210> SEQ ID NO 114
<211> LENGTH: 995
<212> TYPE: DNA
<213> ORGANISM: Yarrowia lipolytica

<400> SEQUENCE: 114
agtgtacgca gtactataga ggaacaattg ccccggagaa gacggccagg ccgcctagat      60
gacaaattca acaactcaca gctgactttc tgccattgcc actagggggg ggccttttta     120
tatggccaag ccaagctctc cacgtcggtt gggctgcacc caacaataaa tgggtagggt     180
tgcaccaaca aagggatggg atgggggggta gaagatacga ggataacggg gctcaatggc     240
acaaataaga acgaatactg ccattaagac tcgtgatcca gcgactgaca ccattgcatc     300
atctaagggc ctcaaaacta cctcggaact gctgcgctga tctggacacc acagaggttc     360
cgagcacttt aggttgcacc aaatgtccca ccaggtgcag gcagaaaacg ctggaacagc     420
gtgtacagtt tgtcttaaca aaagtgagg gcgctgaggt cgagcagggt ggtgtgactt     480
gttatagcct ttagagctgc gaaagcgcgt atggatttgg ctcatcaggc cagattgagg     540
gtctgtggac acatgtcatg ttagtgtact tcaatcgccc cctggatata gccccgacaa     600
taggccgtgg cctcattttt ttgccttccg cacatttcca ttgctcggta cccacacctt     660
gcttctcctg cacttgccaa ccttaatact ggtttacatt gaccaacatc ttacaagcgg     720
ggggcttgtc tagggtatat ataaacagtg gctctcccaa tcggttgcca gtctcttttt     780 tccttcttt ccccacagat tcgaaatcta aactacacat cacacaatgc ctgttactga     840
cgtccttaag cgaaagtccg gtgtcatcgt cggcgacgat gtccgagccg tgagtatcca     900
```

```
cgacaagatc agtgtcgaga cgacgcgttt tgtgtaatga cacaatccga aagtcgctag    960
caacacacac tctctacaca aactaaccca gctct                              995

<210> SEQ ID NO 115
<211> LENGTH: 8502
<212> TYPE: DNA
<213> ORGANISM: Artificial Sequence
<220> FEATURE:
<223> OTHER INFORMATION: Plasmid pY54PC

<400> SEQUENCE: 115
ggccgccacc gcggcccgag attccggcct cttcggccgc caagcgaccc gggtggacgt     60
ctagaggtac ctagcaatta acagatagtt tgccggtgat aattctctta acctcccaca   120
ctcctttgac ataacgattt atgtaacgaa actgaaattt gaccagatat tgtgtccgcg   180
gtggagctcc agcttttgtt cccttttagtg agggttaatt aatcgagctt ggcgtaatca   240
tggtcatagc tgtttcctgt gtgaaattgt tatccgctca caattccaca caacatacga   300
gccggaagca taaagtgtaa agcctggggt gcctaatgag tgagctaact cacattaatt   360
gcgttgcgct cactgcccgc tttccagtcg ggaaacctgt cgtgccagct gcattaatga   420
atcggccaac gcgcgggggag aggcggtttg cgtattgggc gctcttccgc ttcctcgctc   480
actgactcgc tgcgctcggt cgttcggctg cggcgagcgg tatcagctca ctcaaaggcg   540
gtaatacggt tatccacaga atcaggggat aacgcaggaa agaacatgtg agcaaaaggc   600
cagcaaaagg ccaggaaccg taaaaaggcc gcgttgctgg cgttttttcca taggctccgc   660 ccccctgacg agcatcacaa aaatcgacgc tcaagtcaga ggtggcgaaa cccgacagga   720
ctataaagat accaggcgtt tcccctggaa gctccctcg tgcgctctcc tgttccgacc   780
ctgccgctta ccggatacct gtccgccttt ctcccttcgg gaagcgtggc gctttctcat   840
agctcacgct gtaggtatct cagttcggtg taggtcgttc gctccaagct gggctgtgtg   900
cacgaacccc ccgttcagcc cgaccgctgc gccttatccg gtaactatcg tcttgagtcc   960
aacccggtaa gacacgactt atcgccactg gcagcagcca ctggtaacag gattagcaga  1020
gcgaggtatg taggcggtgc tacagagttc ttgaagtggt ggcctaacta cggctacact  1080
agaaggacag tatttggtat ctgcgctctg ctgaagccag ttaccttcgg aaaaagagtt  1140
ggtagctctt gatccggcaa acaaaccacc gctggtagcg gtggtttttt tgtttgcaag  1200
cagcagatta cgcgcagaaa aaaggatct caagaagatc ctttgatctt ttctacgggg  1260
tctgacgctc agtggaacga aaactcacgt taagggattt tggtcatgag attatcaaaa  1320
aggatcttca cctagatcct tttaaattaa aaatgaagtt ttaaatcaat ctaaagtata  1380
tatgagtaaa cttggtctga cagttaccaa tgcttaatca gtgaggcacc tatctcagcg  1440
atctgtctat ttcgttcatc catagttgcc tgactccccg tcgtgtagat aactacgata  1500
cgggagggct taccatctgg ccccagtgct gcaatgatac gcgagaccc acgctcaccg  1560 gctccagatt tatcagcaat aaaccagcca gccggaaggg ccgagcgcag aagtggtcct  1620
gcaactttat ccgcctccat ccagtctatt aattgttgcc gggaagctag agtaagtagt  1680
tcgccagtta atagtttgcg caacgttgtt gccattgcta caggcatcgt ggtgtcacgc  1740
tcgtcgtttg gtatggcttc attcagctcc ggttcccaac gatcaaggcg agttacatga  1800
tcccccatgt tgtgcaaaaa agcggttagc tccttcggtc ctccgatcgt tgtcagaagt  1860
aagttggccg cagtgttatc actcatggtt atggcagcac tgcataattc tcttactgtc  1920
atgccatccg taagatgctt ttctgtgact ggtgagtact caaccaagtc attctgagaa  1980
```

```
tagtgtatgc ggcgaccgag ttgctcttgc ccggcgtcaa tacgggataa taccgcgcca    2040
catagcagaa ctttaaaagt gctcatcatt ggaaaacgtt cttcggggcg aaaactctca    2100
aggatcttac cgctgttgag atccagttcg atgtaaccca ctcgtgcacc caactgatct    2160
tcagcatctt ttactttcac cagcgtttct gggtgagcaa aaacaggaag gcaaaatgcc    2220
gcaaaaaagg gaataagggc gacacggaaa tgttgaatac tcatactctt ccttttcaa     2280
tattattgaa gcatttatca gggttattgt ctcatgagcg gatacatatt tgaatgtatt    2340
tagaaaaata aacaaatagg ggttccgcgc acatttcccc gaaaagtgcc acctgacgcg    2400
ccctgtagcg gcgcattaag cgcggcgggt gtggtggtta cgcgcagcgt gaccgctaca    2460
cttgccagcg ccctagcgcc cgctcctttc gctttcttcc cttcctttct cgccacgttc    2520
gccggctttc cccgtcaagc tctaaatcgg gggctcccct tagggttccg atttagtgct    2580
ttacggcacc tcgaccccaa aaaacttgat tagggtgatg gttcacgtag tgggccatcg    2640
ccctgataga cggttttcg ccctttgacg ttggagtcca cgttctttaa tagtggactc     2700
ttgttccaaa ctggaacaac actcaaccct atctcggtct attcttttga tttataaggg    2760
attttgccga tttcggccta ttggttaaaa aatgagctga tttaacaaaa atttaacgcg    2820
aattttaaca aaatattaac gcttacaatt tccattcgcc attcaggctg cgcaactgtt    2880
gggaagggcg atcggtgcgg gcctcttcgc tattacgcca gctggcgaaa ggggatgtg    2940
ctgcaaggcg attaagttgg gtaacgccag ggttttccca gtcacgacgt tgtaaaacga    3000
cggccagtga attgtaatac gactcactat agggcgaatt gggtaccggg ccccccctcg    3060
aggtcgacgg tatcgataag cttgatatcg aattcatgtc acacaaaccg atcttcgcct    3120
caaggaaacc taattctaca tccgagagac tgccagatc cagtctacac tgattaattt     3180
tcgggccaat aatttaaaaa aatcgtgtta tataatatta tatgtattat atatatacat    3240
catgatgata ctgacagtca tgtcccattg ctaaatagac agactccatc tgccgcctcc    3300
aactgatgtt ctcaatattt aaggggtcat ctcgcattgt ttaataataa acagactcca    3360
tctaccgcct ccaaatgatg ttctcaaaat atattgtatg aacttatttt tattacttag    3420
tattattaga caacttactt gctttatgaa aaacacttcc tatttaggaa acaatttata    3480
atggcagttc gttcatttaa caatttatgt agaataaatg ttataaatgc gtatgggaaa    3540
tcttaaatat ggatagcata aatgatatct gcattgccta attcgaaatc aacagcaacg    3600
aaaaaaatcc cttgtacaac ataaatagtc atcgagaaat atcaactatc aaagaacagc    3660
tattcacacg ttactattga gattattatt ggacgagaat cacacactca actgtctttc    3720
tctcttctag aaatacaggt acaagtatgt actattctca ttgttcatac ttctagtcat    3780
ttcatcccac atattccttg gatttctctc caatgaatga cattctatct tgcaaattca    3840
acaattataa taagatatac caaagtagcg gtatagtggc aatcaaaaag cttctctggt    3900
gtgcttctcg tatttatttt tattctaatg atccattaaa ggtatatatt tatttcttgt    3960
tatataatcc ttttgtttat tacatgggct ggatacataa aggtattttg atttaatttt    4020
ttgcttaaat tcaatccccc ctcgttcagt gtcaactgta atggtaggaa attaccatac    4080
ttttgaagaa gcaaaaaaaa tgaaagaaaa aaaaatcgt atttccaggt tagacgttcc     4140
gcagaatcta gaatgcggta tgcggtacat tgttcttcga acgtaaaagt tgcgctccct    4200
gagatattgt acatttttgc ttttacaagt acaagtacat cgtacaacta tgtactactg    4260
ttgatgcatc cacaacagtt tgtttgtttt tttttgttt ttttttttc taatgattca      4320
```

```
ttaccgctat gtatacctac ttgtacttgt agtaagccgg gttattggcg ttcaattaat    4380
catagactta tgaatctgca cggtgtgcgc tgcgagttac ttttagctta tgcatgctac    4440
ttgggtgtaa tattgggatc tgttcggaaa tcaacggatg ctcaaccgat ttcgacagta    4500
ataatttgaa tcgaatcgga gcctaaaatg aacccgagta tatctcataa aattctcggt    4560
gagaggtctg tgactgtcag tacaaggtgc cttcattatg ccctcaacct taccatacct    4620
cactgaatgt agtgtacctc taaaaatgaa atacagtgcc aaaagccaag gcactgagct    4680
cgtctaacgg acttgatata caaccaatta aaacaaatga aagaaatac agttctttgt     4740
atcatttgta acaattaccc tgtacaaact aaggtattga atcccacaa tattcccaaa     4800
gtccacccct ttccaaattg tcatgcctac aactcatata ccaagcacta acctaccaaa    4860
caccactaaa accccacaaa atatatctta ccgaatatac agtaacaagc taccaccaca    4920
ctcgttgggt gcagtcgcca gcttaaagat atctatccac atcagccaca actcccttcc    4980
tttaataaac cgactacacc cttggctatt gaggttatga gtgaatatac tgtagacaag    5040
acactttcaa gaagactgtt tccaaaacgt accactgtcc tccactacaa acacacccaa    5100
tctgcttctt ctagtcaagg ttgctacacc ggtaaattat aaatcatcat ttcattagca    5160
gggcagggcc cttttatag agtcttatac actagcggac cctgccggta gaccaacccg     5220
caggcgcgtc agtttgctcc ttccatcaat gcgtcgtaga aacgacttac tccttcttga    5280
gcagctcctt gaccttgttg caacaagtc tccgacctcg gaggtggagg aagagcctcc     5340
gatatcggcg gtagtgatac cagcctcgac ggactccttg acggcagcct caacagcgtc    5400
accggcgggc ttcatgttaa gagagaactt gagcatcatg gcggcagaca gaatggtggc    5460
aatggggttg accttctgct tgccgagatc gggggcagat ccgtgacagg gctcgtacag    5520
accgaacgcc tcgttggtgt cgggcagaga agccagagag gcggagggca gcagacccag    5580
agaaccgggg atgacggagg cctcgtcgga gatgatatcg ccaaacatgt tggtggtgat    5640
gatgatacca ttcatcttgg agggctgctt gatgaggatc atggcggccg agtcgatcag    5700
ctggtggttg agctcgagct gggggaattc gtccttgagg actcgagtga cagtcttttcg   5760
ccaaagtcga gaggaggcca gcacgttggc cttgtcaaga gaccacacgg gaagaggggg    5820
gttgtgctga agggccagga aggcggccat tcgggcaatt cgctcaacct caggaacgga    5880
gtaggtctcg gtgtcggaag cgacgccaga tccgtcatcc tcctttcgct ctccaaagta    5940
gatacctccg acgagctctc ggacaatgat gaagtcggtg ccctcaacgt ttcggatggg    6000
ggagagatcg gcgagcttgg gcgacagcag ctggcagggt cgcaggttgg cgtacaggtt    6060
caggtccttt cgcagcttga ggagaccctg ctcgggtcgc acgtcggttc gtccgtcggg    6120
agtggtccat acggtgttgg cagcgcctcc gacagcaccg agcataatag agtcagcctt    6180
tcggcagatg tcgagagtag cgtcggtgat gggctcgccc tccttctcaa tggcagctcc    6240
tccaatgagt cggtcctcaa acacaaactc ggtgccggag gcctcagcaa cagacttgag    6300
caccttgacg gcctcggcaa tcacctcggg gccacagaag tcgccgccga aagaacaat    6360
cttcttggag tcagtcttgg tcttcttagt ttcgggttcc attgtggatg tgtgtggttg    6420
tatgtgtgat gtggtgtgtg gagtgaaaat ctgtggctgg caaacgctct tgtatatata    6480
cgcacttttg cccgtgctat gtggaagact aaacctccga agattgtgac tcaggtagtg    6540
cggtatcggc tagggaccca aaccttgtcg atgccgatag cgctatcgaa cgtaccccag    6600
ccggccggga gtatgtcgga ggggacatac gagatcgtca agggtttgtg gccaactggt    6660
aaataaatga tgactcaggc gacgacggaa ttcctgcagc ccatcgatgc agaattcagg    6720
```

```
agagaccggg ttggcggcgt atttgtgtcc caaaaaacag ccccaattgc cccaattgac    6780
cccaaattga cccagtagcg ggcccaaccc cggcgagagc ccccttcacc ccacatatca    6840
aacctccccc ggttcccaca cttgccgtta agggcgtagg gtactgcagt ctggaatcta    6900
cgcttgttca gactttgtac tagtttcttt gtctggccat ccgggtaacc catgccggac    6960
gcaaaataga ctactgaaaa ttttttttgct ttgtggttgg gacttagcc aagggtataa    7020 aagaccaccg tccccgaatt acctttcctc ttcttttctc tctctccttg tcaactcaca    7080
cccgaaatcg ttaagcattt ccttctgagt ataagaatca ttcaccatgg ctgctgctcc    7140
cagtgtgagg acgtttactc gggccgaggt tttgaatgcc gaggctctga atgagggcaa    7200
gaaggatgcc gaggcaccct tcttgatgat catcgacaac aaggtgtacg atgtccgcga    7260
gttcgtccct gatcatcccg gtggaagtgt gattctcacg cacgttggca aggacggcac    7320
tgacgtcttt gacacttttc accccgaggc tgcttgggag actcttgcca acttttacgt    7380
tggtgatatt gacgagagcg accgcgatat caagaatgat gactttgcgg ccgaggtccg    7440
caagctgcgt accttgttcc agtctcttgg ttactacgat tcttccaagg catactacgc    7500
cttcaaggtc tcgttcaacc tctgcatctg gggtttgtcg acggtcattg tggccaagtg    7560
gggccagacc tcgaccctcg ccaacgtgct ctcggctgcg cttttgggtc tgttctggca    7620
gcagtgcgga tggttggctc acgactttt gcatcaccag gtcttccagg accgtttctg    7680
gggtgatctt ttcggcgcct tcttgggagg tgtctgccag ggcttctcgt cctcgtggtg    7740
gaaggacaag cacaacactc accacgccgc ccccaacgtc cacggcgagg atcccgacat    7800
tgacacccac cctctgttga cctggagtga gcatgcgttg gagatgttct cggatgtccc    7860
agatgaggag ctgacccgca tgtggtcgcg tttcatggtc ctgaaccaga cctggttta   7920 cttcccatt ctctcgtttg cccgtctctc ctggtgcctc cagtccattc tctttgtgct    7980
gcctaacggt caggcccaca agccctcggg cgcgcgtgtg cccatctcgt tggtcgagca    8040
gctgtcgctt gcgatgcact ggacctggta cctcgccacc atgttcctgt catcaagga    8100 tcccgtcaac atgctggtgt actttttggt gtcgcaggcg gtgtgcggaa acttgttggc    8160
gatcgtgttc tcgctcaacc acaacggtat gcctgtgatc tcgaaggagg aggcggtcga    8220
tatggatttc ttcacgaagc agatcatcac gggtcgtgat gtccaccggg tctatttgc    8280 caactggttc acgggtggat tgaactatca gatcgagcac cacttgttcc cttcgatgcc    8340
tcgccacaac ttttcaaaga tccagcctgc tgtcgagacc ctgtgcaaaa agtacaatgt    8400
ccgataccac accaccggta tgatcgaggg aactgcagag gtctttagcc gtctgaacga    8460
ggtctccaag gctacctcca agatgggtaa ggcgcagtaa gc                       8502
```

<210> SEQ ID NO 116
<211> LENGTH: 7145
<212> TYPE: DNA
<213> ORGANISM: Artificial Sequence
<220> FEATURE:
<223> OTHER INFORMATION: Plasmid pKUNFmkF2
<220> FEATURE:
<221> NAME/KEY: misc_feature
<222> LOCATION: (692)..(695)
<223> OTHER INFORMATION: n is a, c, g, or t
<220> FEATURE:
<221> NAME/KEY: misc_feature
<222> LOCATION: (700)..(700)
<223> OTHER INFORMATION: n is a, c, g, or t

<400> SEQUENCE: 116

```
catggcgtcc acttcggctc tgcccaagca gaaccctgcg cttagacgca ccgtcacctc    60
aactactgtg acggattctg agtctgccgc cgtctctcct tcagactctc cccgccactc   120
ggcctcttcc acatcgctct cgtccatgtc cgaggttgat atcgccaagc ccaagtccga   180
gtatggtgtc atgctcgaca cctacggcaa ccagttcgag gttcccgact ttaccatcaa   240
ggacatctac aatgccatcc ctaagcactg cttcaagcgc tccgctctca agggatacgg   300
ttatatcctc cgcgacattg tcctcctgac taccactttc agcatctggt acaactttgt   360 gaccccgaa tatatcccct ccaccccgc ccgcgctggt ctgtgggccg tgtacaccgt   420
tcttcagggt cttttcggta ctggtctctg ggttattgcc catgagtgcg gtcacggtgc   480
tttctccgat tctcgcatca tcaacgacat tactggctgg gttcttcact cttccctcct   540
tgtcccctac ttcagctggc aaatctccca ccgaaagcac cacaaggcca ctggcaacat   600
ggagcgtgac atggtcttcg ttccccgaac ccgcgagcag caggctactc gtctcggaaa   660
gatgacccac gagctcgctc atcttactga gnnnntcgtn ggctggccca actacctcat   720
caccaatgtt accggccaca actaccacga cgccagcgt gagggtcgcg gcaagggcaa   780
gcataacggc ctcggcggtg gtgttaacca cttcgatccc cgcagccctc tgtacgagaa   840
cagtgacgct aagctcatcg tcctcagcga tattggtatc ggtctgatgg ccactgctct   900
gtacttcctc gttcagaagt tcggtttcta caacatggcc atctggtact ttgttcccta   960
cctctgggtt aaccactggc tcgttgccat caccttcctc cagcacaccg accctaccct  1020
tccccactac accaacgacg agtggaactt cgtccgtggt gccgctgcta ccattgaccg  1080
tgagatgggc ttcatcggcc gccaccttct ccacggcatc atcgagactc atgtcctcca  1140
ccactacgtc agcagcatcc ccttctacaa cgcggacgag gccaccgagg ccattaagcc  1200
catcatgggc aagcactacc gggctgatgt ccaggatggt cctcgtggct tcatccgcgc  1260
catgtaccgc agtgcgcgta tgtgccagtg ggttgagccc agcgctggtg ccgagggtgc  1320
tggtaagggt gttctgttct ccgcaaccg caacaacgtg ggcaccccc ccgctgttat  1380 caagcccgtt gcttaagtag gcgcggccgc tatttatcac tctttacaac ttctacctca  1440
actatctact ttaataaatg aatatcgttt attctctatg attactgtat atgcgttcct  1500
ctaagacaaa tcgaaaccag catgtgatcg aatggcatac aaaagtttct tccgaagttg  1560
atcaatgtcc tgatagtcag gcagcttgag aagattgaca caggtggagg ccgtagggaa  1620
ccgatcaacc tgtctaccag cgttacgaat ggcaaatgac gggttcaaag ccttgaatcc  1680
ttgcaatggt gccttggata ctgatgtcac aaacttaaga agcagccgct tgtcctcttc  1740
ctcgatcgat ggtcatagct gtttcctgtg tgaaattgtt atccgctcac aattccacac  1800
aacgtacgaa gtcgtcaatg atgtcgatat gggttttgat catgcacaca taaggtccga  1860
ccttatcggc aagctcaatg agctccttgg tggtggtaac atccagagaa gcacacaggt  1920
tggttttctt ggctgccacg agcttgagca ctcgagcggc aaaggcggac ttgtggacgt  1980
tagctcgagc ttcgtaggag ggcattttgg tggtgaagag gagactgaaa taaatttagt  2040
ctgcagaact ttttatcgga accttatctg gggcagtgaa gtatatgtta tggtaatagt  2100
tacgagttag ttgaacttat agatagactg gactatacgg ctatcggtcc aaattagaaa  2160
gaacgtcaat ggctctctgg gcgtcgcctt tgccgacaaa aatgtgatca tgatgaaagc  2220
cagcaatgac gttgcagctg atattgttgt cggccaaccg cgccgaaaac gcagctgtca  2280
gacccacagc ctccaacgaa gaatgtatcg tcaaagtgat ccaagcacac tcatagttgg  2340
agtcgtactc caaaggcggc aatgacgagt cagacagata ctcgtcgacc ttttccttgg  2400
```

```
gaaccaccac cgtcagccct tctgactcac gtattgtagc caccgacaca ggcaacagtc    2460
cgtggatagc agaatatgtc ttgtcggtcc atttctcacc aactttaggc gtcaagtgaa    2520
tgttgcagaa gaagtatgtg ccttcattga gaatcggtgt tgctgatttc aataaagtct    2580
tgagatcagt ttggcgcgcc agctgcatta atgaatcggc caacgcgcgg ggagaggcgg    2640
tttgcgtatt gggcgctctt ccgcttcctc gctcactgac tcgctgcgct cggtcgttcg    2700
gctgcggcga gcggtatcag ctcactcaaa ggcggtaata cggttatcca cagaatcagg    2760
ggataacgca ggaaagaaca tgtgagcaaa aggccagcaa aaggccagga accgtaaaaa    2820
ggccgcgttg ctggcgtttt tccataggct ccgcccccct gacgagcatc acaaaaatcg    2880
acgctcaagt cagaggtggc gaaacccgac aggactataa agataccagg cgtttccccc    2940
tggaagctcc ctcgtgcgct ctcctgttcc gaccctgccg cttaccggat acctgtccgc    3000
ctttctccct tcgggaagcg tggcgctttc tcatagctca cgctgtaggt atctcagttc    3060
ggtgtaggtc gttcgctcca agctgggctg tgtgcacgaa ccccccgttc agcccgaccg    3120
ctgcgcctta tccggtaact atcgtcttga gtccaacccg gtaagacacg acttatcgcc    3180
actggcagca gccactggta acaggattag cagagcgagg tatgtaggcg gtgctacaga    3240
gttcttgaag tggtggccta actacggcta cactagaaga acagtatttg gtatctgcgc    3300
tctgctgaag ccagttacct tcggaaaaag agttggtagc tcttgatccg gcaaacaaac    3360
caccgctggt agcggtggtt ttttttgttg caagcagcag attacgcgca gaaaaaaagg    3420
atctcaagaa gatcctttga tcttttctac ggggtctgac gctcagtgga acgaaaactc    3480
acgttaaggg attttggtca tgagattatc aaaaaggatc ttcacctaga tccttttaaa    3540
ttaaaaatga agttttaaat caatctaaag tatatatgag taaacttggt ctgacagtta    3600
ccaatgctta atcagtgagg cacctatctc agcgatctgt ctatttcgtt catccatagt    3660
tgcctgactc cccgtcgtgt agataactac gatacgggag ggcttaccat ctggccccag    3720
tgctgcaatg ataccgcgag acccacgctc accggctcca gatttatcag caataaacca    3780
gccagccgga agggccgagc gcagaagtgg tcctgcaact ttatccgcct ccatccagtc    3840
tattaattgt tgccgggaag ctagagtaag tagttcgcca gttaatagtt tgcgcaacgt    3900
tgttgccatt gctacaggca tcgtggtgtc acgctcgtcg tttggtatgg cttcattcag    3960
ctccggttcc caacgatcaa ggcgagttac atgatccccc atgttgtgca aaaaagcggt    4020
tagctccttc ggtcctccga tcgttgtcag aagtaagttg gccgcagtgt tatcactcat    4080
ggttatggca gcactgcata attctcttac tgtcatgcca tccgtaagat gcttttctgt    4140
gactggtgag tactcaacca agtcattctg agaatagtgt atgcggcgac cgagttgctc    4200
ttgcccggcg tcaatacggg ataataccgc gccacatagc agaactttaa aagtgctcat    4260
cattggaaaa cgttcttcgg ggcgaaaact ctcaaggatc ttaccgctgt tgagatccag    4320
ttcgatgtaa cccactcgtg cacccaactg atcttcagca tcttttactt tcaccagcgt    4380
ttctgggtga gcaaaaacag gaaggcaaaa tgccgcaaaa aagggaataa gggcgacacg    4440
gaaatgttga atactcatac tcttcctttt tcaatattat tgaagcattt atcagggtta    4500
ttgtctcatg agcggataca tatttgaatg tatttagaaa aataaacaaa taggggttcc    4560
gcgcacattt ccccgaaaag tgccacctga tgcggtgtga ataccgcac agatgcgtaa    4620 ggagaaaata ccgcatcagg aaattgtaag cgttaatatt ttgttaaaat tcgcgttaaa    4680
tttttgttaa atcagctcat ttttttaacca ataggccgaa atcggcaaaa tcccttataa    4740
```

```
atcaaaagaa tagaccgaga tagggttgag tgttgttcca gtttggaaca agagtccact   4800
attaaagaac gtggactcca acgtcaaagg gcgaaaaacc gtctatcagg gcgatggccc   4860
actacgtgaa ccatcaccct aatcaagttt tttggggtcg aggtgccgta aagcactaaa   4920
tcggaaccct aaagggagcc cccgatttag agcttgacgg ggaaagccgg cgaacgtggc   4980
gagaaaggaa gggaagaaag cgaaaggagc gggcgctagg gcgctggcaa gtgtagcggt   5040
cacgctgcgc gtaaccacca cacccgccgc gcttaatgcg ccgctacagg gcgcgtccat   5100
tcgccattca ggctgcgcaa ctgttgggaa gggcgatcgg tgcgggcctc ttcgctatta   5160
cgccagctgg cgaaaggggg atgtgctgca aggcgattaa gttgggtaac gccagggttt   5220
tcccagtcac gacgttgtaa aacgacggcc agtgaattgt aatacgactc actatagggc   5280
gaattgggcc cgacgtcgca tgcagtggtg gtattgtgac tggggatgta gttgagaata   5340
agtcatacac aagtcagctt tcttcgagcc tcatataagt ataagtagtt caacgtatta   5400
gcactgtacc cagcatctcc gtatcgagaa acacaacaac atgccccatt ggacagatca   5460
tgcggataca caggttgtgc agtatcatac atactcgatc agacaggtcg tctgaccatc   5520
atacaagctg aacaagcgct ccatacttgc acgctctcta tatacacagt taaattacat   5580
atccatagtc taacctctaa cagttaatct tctggtaagc ctcccagcca gccttctggt   5640
atcgcttggc ctcctcaata ggatctcggt tctggccgta cagacctcgg ccgacaatta   5700
tgatatccgt tccggtagac atgacatcct caacagttcg gtactgctgt ccgagagcgt   5760
ctcccttgtc gtcaagaccc accccggggg tcagaataag ccagtcctca gagtcgccct   5820
taattaattt gaatcgaatc gatgagccta aaatgaaccc gagtatatct cataaaattc   5880
tcggtgagag gtctgtgact gtcagtacaa ggtgccttca ttatgccctc aaccttacca   5940
tacctcactg aatgtagtgt acctctaaaa atgaaataca gtgccaaaag ccaaggcact   6000
gagctcgtct aacggacttg atatacaacc aattaaaaca aatgaaaaga aatacagttc   6060
tttgtatcat ttgtaacaat taccctgtac aaactaaggt attgaaatcc cacaatattc   6120
ccaaagtcca ccccttttcca aattgtcatg cctacaactc atataccaag cactaaccta   6180
ccgtttaaac agtgtacgca gatctactat agaggaacat ttaaattgcc ccggagaaga   6240
cggccaggcc gcctagatga caaattcaac aactcacagc tgactttctg ccattgccac   6300
tagggggggg cctttttata tggccaagcc aagctctcca cgtcggttgg gctgcaccca   6360
acaataaatg ggtagggttg caccaacaaa gggatgggat gggggtagaa agatacgagg   6420
ataacggggc tcaatggcac aaataagaac gaatactgcc attaagactc gtgatccagc   6480
gactgacacc attgcatcat ctaagggcct caaaactacc tcggaactgc tgcgctgatc   6540
tggacaccac agaggttccg agcactttag gttgcaccaa atgtcccacc aggtgcaggc   6600
agaaaacgct ggaacagcgt gtacagtttg tcttaacaaa aagtgagggc gctgaggtcg   6660
agcagggtgg tgtgacttgt tatagccttt agagctgcga aagcgcgtat ggatttggct   6720
catcaggcca gattgagggt ctgtggacac atgtcatgtt agtgtacttc aatcgccccc   6780
tggatatagc cccgacaata ggccgtggcc tcattttttt gccttccgca catttccatt   6840
gctcgatacc cacaccttgc ttctcctgca cttgccaacc ttaatactgg tttacattga   6900
ccaacatctt acaagcgggg ggcttgtcta gggtatatat aaacagtggc tctcccaatc   6960
ggttgccagt ctcttttttc ctttctttcc ccacagattc gaaatctaaa ctacacatca   7020
cagaattccg agccgtgagt atccacgaca agatcagtgt cgagacgacg cgttttgtgt   7080
aatgacacaa tccgaaagtc gctagcaaca cacactctct acacaaacta acccagctct   7140
```

<210> SEQ ID NO 117
<211> LENGTH: 5553
<212> TYPE: DNA
<213> ORGANISM: Artificial Sequence
<220> FEATURE:
<223> OTHER INFORMATION: Plasmid pZF5T-PPC

<400> SEQUENCE: 117

```
ggccgcattg atgattggaa acacacacat gggttatatc taggtgagag ttagttggac      60
agttatatat taaatcagct atgccaacgg taacttcatt catgtcaacg aggaaccagt     120
gactgcaagt aatatagaat tgaccacct tgccattctc ttgcactcct ttactatatc     180
tcatttattt cttatataca aatcacttct tcttcccagc atcgagctcg gaaacctcat     240
gagcaataac atcgtggatc tcgtcaatag agggctttt ggactccttg ctgttggcca     300
ccttgtcctt gctgtctggc tcattctgtt tcaacgcctt ttaattaatc gagcttggcg     360
taatcatggt catagctgtt tcctgtgtga aattgttatc cgctcacaat tccacacaac     420
atacgagccg aagcataaa gtgtaaagcc tggggtgcct aatgagtgag ctaactcaca     480
ttaattgcgt tgcgctcact gcccgctttc cagtcgggaa acctgtcgtg ccagctgcat     540
taatgaatcg gccaacgcgc ggggagaggc ggtttgcgta ttgggcgctc ttccgcttcc     600
tcgctcactg actcgctgcg ctcggtcgtt cggctgcggc gagcggtatc agctcactca     660
aaggcggtaa tacggttatc cacagaatca ggggataacg caggaaagaa catgtgagca     720
aaaggccagc aaaaggccag gaaccgtaaa aaggccgcgt tgctggcgtt tttccatagg     780
ctccgccccc ctgacgagca tcacaaaaat cgacgctcaa gtcagaggtg gcgaaacccg     840
acaggactat aaagatacca ggcgtttccc cctggaagct ccctcgtgcg ctctcctgtt     900
ccgaccctgc cgcttaccgg atacctgtcc gcctttctcc cttcgggaag cgtggcgctt     960
tctcatagct cacgctgtag gtatctcagt tcggtgtagg tcgttcgctc caagctgggc    1020
tgtgtgcacg aaccccccgt tcagcccgac cgctgcgcct tatccggtaa ctatcgtctt    1080
gagtccaacc cggtaagaca cgacttatcg ccactggcag cagccactgg taacaggatt    1140
agcagagcga ggtatgtagg cggtgctaca gagttcttga agtggtggcc taactacggc    1200
tacactagaa ggacagtatt tggtatctgc gctctgctga agccagttac cttcggaaaa    1260
agagttggta gctcttgatc cggcaaacaa accaccgctg gtagcggtgg ttttttgtt    1320
tgcaagcagc agattacgcg cagaaaaaa ggatctcaag aagatccttt gatcttttct    1380
acggggtctg acgctcagtg aacgaaaac tcacgttaag ggattttggt catgagatta    1440
tcaaaaagga tcttcaccta gatccttta aattaaaaat gaagttttaa atcaatctaa    1500
agtatatatg agtaaacttg gtctgacagt taccaatgct taatcagtga ggcacctatc    1560
tcagcgatct gtctatttcg ttcatccata gttgcctgac tccccgtcgt gtagataact    1620
acgatacggg agggcttacc atctggcccc agtgctgcaa tgataccgcg agacccacgc    1680
tcaccggctc cagatttatc agcaataaac cagccagccg aagggccga gcgcagaagt    1740
ggtcctgcaa cttatccgc ctccatccag tctattaatt gttgccggga agctagagta    1800
agtagttcgc cagttaatag tttgcgcaac gttgttgcca ttgctacagg catcgtggtg    1860
tcacgctcgt cgtttggtat ggcttcattc agctccggtt cccaacgatc aaggcgagtt    1920
acatgatccc ccatgttgtg caaaaaagcg gttagctcct tcggtcctcc gatcgttgtc    1980
```

```
agaagtaagt tggccgcagt gttatcactc atggttatgg cagcactgca taattctctt    2040
actgtcatgc catccgtaag atgctttttct gtgactggtg agtactcaac caagtcattc    2100
tgagaatagt gtatgcggcg accgagttgc tcttgcccgg cgtcaatacg ggataatacc    2160
gcgccacata gcagaacttt aaaagtgctc atcattggaa aacgttcttc ggggcgaaaa    2220
ctctcaagga tcttaccgct gttgagatcc agttcgatgt aacccactcg tgcacccaac    2280
tgatcttcag catcttttac tttcaccagc gtttctgggt gagcaaaaac aggaaggcaa    2340
aatgccgcaa aaagggaat aagggcgaca cggaaatgtt gaatactcat actcttcctt    2400
tttcaatatt attgaagcat ttatcagggt tattgtctca tgagcggata catatttgaa    2460
tgtatttaga aaataaaca atagggggtt ccgcgcacat ttccccgaaa agtgccacct    2520
gacgcgccct gtagcggcgc attaagcgcg gcgggtgtgg tggttacgcg cagcgtgacc    2580
gctacacttg ccagcgccct agcgcccgct cctttcgctt tcttcccttc ctttctcgcc    2640
acgttcgccg gctttccccg tcaagctcta aatcgggggc tccctttagg gttccgattt    2700
agtgctttac ggcacctcga cccccaaaaaa cttgattagg gtgatggttc acgtagtggg    2760
ccatcgccct gatagacggt ttttcgccct ttgacgttgg agtccacgtt ctttaatagt    2820
ggactcttgt tccaaactgg aacaacactc aaccctatct cggtctattc ttttgattta    2880
taagggattt gccgatttc ggcctattgg ttaaaaaatg agctgattta acaaaaattt    2940
aacgcgaatt ttaacaaaat attaacgctt acaatttcca ttcgccattc aggctgcgca    3000
actgttggga agggcgatcg gtgcgggcct cttcgctatt acgccagctg gcgaaagggg    3060
gatgtgctgc aaggcgatta agttgggtaa cgccagggtt ttcccagtca cgacgttgta    3120
aaacgacggc cagtgaattg taatacgact cactataggg cgaattgggt accgggcccc    3180
ccctcgaggt cgacgtttaa acagtgtacg cagtactata gaggaacatc gattgccccg    3240
gagaagacgg ccaggccgcc tagatgacaa attcaacaac tcacagctga ctttctgcca    3300
ttgccactag ggggggggcct ttttatatgg ccaagccaag ctctccacgt cggttgggct    3360
gcacccaaca ataaatgggt agggttgcac caacaaaggg atgggatggg gggtagaaga    3420
tacgaggata acggggctca atggcacaaa taagaacgaa tactgccatt aagactcgtg    3480
atccagcgac tgacaccatt gcatcatcta agggcctcaa aactacctcg gaactgctgc    3540
gctgatctgg acaccacaga ggttccgagc actttaggtt gcaccaaatg tcccaccagg    3600
tgcaggcaga aaacgctgga acagcgtgta cagtttgtct taacaaaaag tgagggcgct    3660
gaggtcgagc agggtggtgt gacttgttat agcctttaga gctgcgaaag cgcgtatgga    3720
tttggctcat caggccagat tgagggtctg tggacacatg tcatgttagt gtacttcaat    3780
cgccccctgg atatagcccc gacaataggc cgtggcctca ttttttttgcc ttccgcacat    3840
ttccattgct cggtacccac accttgcttc tcctgcactt gccaacctta atactggttt    3900
acattgacca acatcttaca agcgggggc ttgtctaggg tatatataaa cagtggctct    3960
cccaatcggt tgccagtctc ttttttcctt tctttcccca cagattcgaa atctaaacta    4020
cacatcacac aatgcctgtt actgacgtcc ttaagcgaaa gtccggtgtc atcgtcggcg    4080
acgatgtccg agccgtgagt atccacgaca agatcagtgt cgagacgacg cgttttgtgt    4140
aatgacacaa tccgaaagtc gctagcaaca cacactctct acacaaacta acccagctct    4200
ccatgggaac ggaccaagga aaaaccttca cctgggaaga gctggcggcc cataacacca    4260
aggacgacct actcttggcc atccgcggca gggtgtacga tgtcacaaag ttcttgagcc    4320
gccatcctgg tggagtggac actctcctgc tcggagctgg ccgagatgtt actccggtct    4380
```

```
ttgagatgta tcacgcgttt ggggctgcag atgccattat gaagaagtac tatgtcggta    4440
cactggtctc gaatgagctg cccatcttcc cggagccaac ggtgttccac aaaaccatca    4500
agacgagagt cgagggctac tttacggatc ggaacattga tcccaagaat agaccagaga    4560
tctggggacg atacgctctt atctttggat ccttgatcgc ttcctactac gcgcagctct    4620
ttgtgccttt cgttgtcgaa cgcacatggc ttcaggtggt gtttgcaatc atcatgggat    4680 tgcgtgcgc acaagtcgga ctcaaccctc ttcatgatgc gtctcacttt tcagtgaccc    4740
acaaccccac tgtctggaag attctgggag ccacgcacga cttttttcaac ggagcatcgt    4800
```

<210> SEQ ID NO 119
<211> LENGTH: 792
<212> TYPE: DNA
<213> ORGANISM: Isochrysis galbana
<220> FEATURE:
<221> NAME/KEY: misc_feature
<223> OTHER INFORMATION: delta-9 elongase

<400> SEQUENCE: 119

```
atggccctcg caaacgacgc gggagagcgc atctgggcgg ctgtgaccga cccggaaatc      60
ctcattggca ccttctcgta cttgctactc aaaccgctgc tccgcaattc cgggctggtg     120
gatgagaaga agggcgcata caggacgtcc atgatctggt acaacgttct gctggcgctc     180
ttctctgcgc tgagcttcta cgtgacggcg accgccctcg gctgggacta tggtacgggc     240
gcgtggctgc gcaggcaaac cggcgacaca ccgcagccgc tcttccagtg cccgtccccg     300
gtttgggact cgaagctctt cacatgggac cgccaaggca tctattactc caagtacgtg     360
gagtacctcg acacggcctg gctggtgctc aagggcaaga gggtctcctt tctccaggcc     420
ttccaccact tggcgcgcc gtgggatgtg tacctcggca tccggctgca caacgagggc     480
gtatggatct tcatgttttt caactcgttc attcacacca tcatgtacac ctactacggc     540
ctcaccgccg ccgggtataa gttcaaggcc aagccgctca tcaccgcgat gcagatctgc     600
cagttcgtgg gcggcttcct gttggtctgg gactacatca acgtcccctg cttcaactcg     660
gacaaaggga agttgttcag ctgggctttc aactatgcat acgtcggctc ggtcttcttg     720
ctcttctgcc actttttcta ccaggacaac ttggcaacga gaaatcggc caaggcgggc     780
aagcagctct ag                                                         792
```

<210> SEQ ID NO 120
<211> LENGTH: 263
<212> TYPE: PRT
<213> ORGANISM: Isochrysis galbana

<400> SEQUENCE: 120

```
Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Leu Lys Pro
            20                  25                  30

Leu Leu Arg Asn Ser Gly Leu Val Asp Glu Lys Lys Gly Ala Tyr Arg
        35                  40                  45

Thr Ser Met Ile Trp Tyr Asn Val Leu Leu Ala Leu Phe Ser Ala Leu
    50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Trp Thr Ala Lys
            100                 105                 110

Ala Phe Tyr Tyr Ser Lys Tyr Val Glu Tyr Leu Asp Thr Ala Trp Leu
        115                 120                 125

Val Leu Lys Gly Lys Arg Val Ser Phe Leu Gln Ala Phe His His Phe
    130                 135                 140

Gly Ala Pro Trp Asp Val Tyr Leu Gly Ile Arg Leu His Asn Glu Gly
145                 150                 155                 160

Val Trp Ile Phe Met Phe Phe Asn Ser Phe Ile His Thr Ile Met Tyr
```

```
                    165                 170                 175
Thr Tyr Tyr Gly Leu Thr Ala Ala Gly Tyr Lys Phe Lys Ala Lys Pro
            180                 185                 190

Leu Ile Thr Ala Met Gln Ile Cys Gln Phe Val Gly Gly Phe Leu Leu
        195                 200                 205

Val Trp Asp Tyr Ile Asn Val Pro Cys Phe Asn Ser Asp Lys Gly Lys
    210                 215                 220

Leu Phe Ser Trp Ala Phe Asn Tyr Ala Tyr Val Gly Ser Val Phe Leu
225                 230                 235                 240

Leu Phe Cys His Phe Phe Tyr Gln Asp Asn Leu Ala Thr Lys Lys Ser
                245                 250                 255

Ala Lys Ala Gly Lys Gln Leu
            260

<210> SEQ ID NO 121
<211> LENGTH: 101
<212> TYPE: DNA
<213> ORGANISM: Artificial Sequence
<220> FEATURE:
<223> OTHER INFORMATION: Primer IL3-1A

<400> SEQUENCE: 121
gccaacgacg ctggcgagcg aatctgggct gccgtcaccg atcccgaaat cctcattggc    60
accttctcct acctgctcct gaagcctctc ctgcgaaact c                       101

<210> SEQ ID NO 122
<211> LENGTH: 101
<212> TYPE: DNA
<213> ORGANISM: Artificial Sequence
<220> FEATURE:
<223> OTHER INFORMATION: Primer IL3-1B

<400> SEQUENCE: 122
accagagttt cgcaggagag gcttcaggag caggtaggag aaggtgccaa tgaggatttc    60
gggatcggtg acggcagccc agattcgctc gccagcgtcg t                       101

<210> SEQ ID NO 123
<211> LENGTH: 100
<212> TYPE: DNA
<213> ORGANISM: Artificial Sequence
<220> FEATURE:
<223> OTHER INFORMATION: Primer IL3-2A

<400> SEQUENCE: 123
tggtctcgtg gacgagaaga aaggagccta ccgaacctcc atgatctggt acaacgtcct    60
cctggctctc ttctctgccc tgtccttcta cgtgactgcc                        100

<210> SEQ ID NO 124
<211> LENGTH: 100
<212> TYPE: DNA
<213> ORGANISM: Artificial Sequence
<220> FEATURE:
<223> OTHER INFORMATION: Primer IL3-2B

<400> SEQUENCE: 124
cggtggcagt cacgtagaag gacagggcag agaagagagc caggaggacg ttgtaccaga    60
tcatggaggt tcggtaggct cctttcttct cgtccacgag                        100

<210> SEQ ID NO 125
<211> LENGTH: 100
```

```
<212> TYPE: DNA
<213> ORGANISM: Artificial Sequence
<220> FEATURE:
<223> OTHER INFORMATION: Primer IL3-3A

<400> SEQUENCE: 125
accgctctcg gctgggacta cggtactgga gcctggctgc aagacagac cggtgatact       60 ccccagcctc tctttcagtg tccctctcct gtctgggact                           100

<210> SEQ ID NO 126
<211> LENGTH: 100
<212> TYPE: DNA
<213> ORGANISM: Artificial Sequence
<220> FEATURE:
<223> OTHER INFORMATION: Primer IL3-3B

<400> SEQUENCE: 126
ttggagtccc agacaggaga gggacactga aagagaggct ggggagtatc accggtctgt     60
cttcgcagcc aggctccagt accgtagtcc cagccgagag                          100

<210> SEQ ID NO 127
<211> LENGTH: 100
<212> TYPE: DNA
<213> ORGANISM: Artificial Sequence
<220> FEATURE:
<223> OTHER INFORMATION: Primer IL3-4A

<400> SEQUENCE: 127
ccaagctgtt cacctggact gccaaggcct tctactattc taagtacgtg gagtacctcg     60
acaccgcttg gctggtcctc aagggcaagc gagtgtcctt                          100

<210> SEQ ID NO 128
<211> LENGTH: 100
<212> TYPE: DNA
<213> ORGANISM: Artificial Sequence
<220> FEATURE:
<223> OTHER INFORMATION: Primer IL3-4B

<400> SEQUENCE: 128
cagaaaggac actcgcttgc ccttgaggac cagccaagcg gtgtcgaggt actccacgta     60
cttagaatag tagaaggcct tggcagtcca ggtgaacagc                          100

<210> SEQ ID NO 129
<211> LENGTH: 89
<212> TYPE: DNA
<213> ORGANISM: Artificial Sequence
<220> FEATURE:
<223> OTHER INFORMATION: Primer IL3-5A

<400> SEQUENCE: 129
ttccatcact ttggagctcc ctgggacgtc tacctcggca ttcgactgca caacgagggt     60
gtgtggatct tcatgttctt taactcgtt                                       89

<210> SEQ ID NO 130
<211> LENGTH: 89
<212> TYPE: DNA
<213> ORGANISM: Artificial Sequence
<220> FEATURE:
<223> OTHER INFORMATION: Primer IL3-5B

<400> SEQUENCE: 130
aatgaacgag ttaagaaaca tgaagatcca cacccctcg ttgtgcagtc gaatgccgag      60
```

-continued gtagacgtcc cagggagctc caaagtgat    89

<210> SEQ ID NO 131
<211> LENGTH: 91
<212> TYPE: DNA
<213> ORGANISM: Artificial Sequence
<220> FEATURE:
<223> OTHER INFORMATION: Primer IL3-6A

<400> SEQUENCE: 131
cattcacacc atcatgtaca cctactatgg actgactgcc gctggctaca agttcaaggc    60
caagcctctg atcactgcca tgcagatttg c    91

<210> SEQ ID NO 132
<211> LENGTH: 91
<212> TYPE: DNA
<213> ORGANISM: Artificial Sequence
<220> FEATURE:
<223> OTHER INFORMATION: Primer IL3-6B

<400> SEQUENCE: 132
actggcaaat ctgcatggca gtgatcagag gcttggcctt gaacttgtag ccagcggcag    60
tcagtccata gtaggtgtac atgatggtgt g    91

<210> SEQ ID NO 133
<211> LENGTH: 94
<212> TYPE: DNA
<213> ORGANISM: Artificial Sequence
<220> FEATURE:
<223> OTHER INFORMATION: Primer IL3-7A

<400> SEQUENCE: 133
cagttcgtcg gtggctttct cctggtctgg gactacatca acgttccctg cttcaactct    60
gacaagggca agctgttctc ctgggctttc aact    94

<210> SEQ ID NO 134
<211> LENGTH: 94
<212> TYPE: DNA
<213> ORGANISM: Artificial Sequence
<220> FEATURE:
<223> OTHER INFORMATION: Primer IL3-7B

<400> SEQUENCE: 134
gcgtagttga agcccagga gaacagcttg cccttgtcag agttgaagca gggaacgttg    60
atgtagtccc agaccaggag aaagccaccg acga    94

<210> SEQ ID NO 135
<211> LENGTH: 91
<212> TYPE: DNA
<213> ORGANISM: Artificial Sequence
<220> FEATURE:
<223> OTHER INFORMATION: Primer IL3-8A

<400> SEQUENCE: 135
acgcctacgt cggatctgtc tttctcctgt tctgtcactt cttttaccag gacaacctgg    60
ccaccaagaa atccgctaag gctggtaagc a    91

<210> SEQ ID NO 136
<211> LENGTH: 91
<212> TYPE: DNA
<213> ORGANISM: Artificial Sequence
<220> FEATURE:
<223> OTHER INFORMATION: Primer IL3-8B

<400> SEQUENCE: 136
aagctgctta ccagccttag cggatttctt ggtggccagg ttgtcctggt aaaagaagtg    60
acagaacagg agaaagacag atccgacgta g    91

<210> SEQ ID NO 137
<211> LENGTH: 41
<212> TYPE: DNA
<213> ORGANISM: Artificial Sequence
<220> FEATURE:
<223> OTHER INFORMATION: Primer IL3-1F

<400> SEQUENCE: 137
tttccatggc tctggccaac gacgctggcg agcgaatctg g    41

<210> SEQ ID NO 138
<211> LENGTH: 36
<212> TYPE: DNA
<213> ORGANISM: Artificial Sequence
<220> FEATURE:
<223> OTHER INFORMATION: Primer IL3-4R

<400> SEQUENCE: 138
tttctgcaga aaggacactc gcttgccctt gaggac    36

<210> SEQ ID NO 139
<211> LENGTH: 41
<212> TYPE: DNA
<213> ORGANISM: Artificial Sequence
<220> FEATURE:
<223> OTHER INFORMATION: Primer IL3-5F

<400> SEQUENCE: 139
tttctgcagg ccttccatca ctttggagct ccctgggacg t    41

<210> SEQ ID NO 140
<211> LENGTH: 42
<212> TYPE: DNA
<213> ORGANISM: Artificial Sequence
<220> FEATURE:
<223> OTHER INFORMATION: Primer IL3-8R

<400> SEQUENCE: 140
tttgcggccg ctaaagctgc ttaccagcct tagcggattt ct    42

<210> SEQ ID NO 141
<211> LENGTH: 417
<212> TYPE: DNA
<213> ORGANISM: Artificial Sequence
<220> FEATURE:
<223> OTHER INFORMATION: 417 bp NcoI/PstI fragment pT9(1-4)

<400> SEQUENCE: 141
catggctctg gccaacgacg ctggcgagcg aatctgggct gccgtcaccg atcccgaaat    60
cctcattggc accttctcct acctgctcct gaagcctctc ctgcgaaact ctggtctcgt   120
ggacgagaag aaaggagcct accgaacctc catgatctgg tacaacgtcc tcctggctct   180
cttctctgcc ctgtccttct acgtgactgc caccgctctc ggctgggact acggtactgg   240
agcctggctg cgaagacaga ccggtgatac tccccagcct ctctttcagt gtccctctcc   300
tgtctgggac tccaagctgt tcacctggac tgccaaggcc ttctactatt ctaagtacgt   360
ggagtacctc gacaccgctt ggctggtcct caagggcaag cgagtgtcct ttctgca     417

<210> SEQ ID NO 142
<211> LENGTH: 377
<212> TYPE: DNA
<213> ORGANISM: Artificial Sequence
<220> FEATURE:
<223> OTHER INFORMATION: 377 bp PstI/Not1 fragment pT9(5-8)

<400> SEQUENCE: 142

```
ggccttccat cactttggag ctccctggga cgtctacctc ggcattcgac tgcacaacga      60
gggtgtgtgg atcttcatgt tctttaactc gttcattcac accatcatgt acacctacta     120
tggactgact gccgctggct acaagttcaa ggccaagcct ctgatcactg ccatgcagat     180
ttgccagttc gtcggtggct ttctcctggt ctgggactac atcaacgttc cctgcttcaa     240
ctctgacaag ggcaagctgt tctcctgggc tttcaactac gcctacgtcg gatctgtctt     300
tctcctgttc tgtcacttct tttaccagga caacctggcc accaagaaat ccgctaaggc     360
tggtaagcag ctttagc                                                    377
```

<210> SEQ ID NO 143
<211> LENGTH: 8165
<212> TYPE: DNA
<213> ORGANISM: Artificial Sequence
<220> FEATURE:
<223> OTHER INFORMATION: Plasmid pZUF17

<400> SEQUENCE: 143

```
gtacgagccg gaagcataaa gtgtaaagcc tggggtgcct aatgagtgag ctaactcaca      60
ttaattgcgt tgcgctcact gcccgctttc cagtcgggaa acctgtcgtg ccagctgcat     120
taatgaatcg gccaacgcgc ggggagaggc ggtttgcgta ttgggcgctc ttccgcttcc     180
tcgctcactg actcgctgcg ctcggtcgtt cggctgcggc gagcggtatc agctcactca     240
aaggcggtaa tacggttatc cacagaatca ggggataacg caggaaagaa catgtgagca     300
aaaggccagc aaaaggccag gaaccgtaaa aaggccgcgt tgctggcgtt tttccatagg     360
ctccgccccc ctgacgagca tcacaaaaat cgacgctcaa gtcagaggtg gcgaaacccg     420
acaggactat aaagatacca ggcgtttccc cctggaagct ccctcgtgcg ctctcctgtt     480
ccgaccctgc cgcttaccgg atacctgtcc gcctttctcc cttcgggaag cgtggcgctt     540
tctcatagct cacgctgtag gtatctcagt tcggtgtagg tcgttcgctc caagctgggc     600
tgtgtgcacg aacccccgt tcagcccgac cgctgcgcct tatccggtaa ctatcgtctt     660
gagtccaacc cggtaagaca cgacttatcg ccactggcag cagccactgg taacaggatt     720
agcagagcga ggtatgtagg cggtgctaca gagttcttga agtggtggcc taactacggc     780
tacactagaa ggacagtatt tggtatctgc gctctgctga gccagttac cttcggaaaa     840
agagttggta gctcttgatc cggcaaacaa accaccgctg gtagcggtgg ttttttgtt     900
tgcaagcagc agattacgcg cagaaaaaaa ggatctcaag aagatccttt gatcttttct     960
acggggtctg acgctcagtg gaacgaaaac tcacgttaag ggattttggt catgagatta    1020
tcaaaaagga tcttcaccta gatccttta aattaaaaat gaagttttaa atcaatctaa    1080
agtatatatg agtaaacttg gtctgacagt taccaatgct taatcagtga ggcacctatc    1140
tcagcgatct gtctatttcg ttcatccata gttgcctgac tccccgtcgt gtagataact    1200
acgatacggg agggcttacc atctggcccc agtgctgcaa tgataccgcg agacccacgc    1260
tcaccggctc cagatttatc agcaataaac cagccagccg aagggccga gcgcagaagt    1320
ggtcctgcaa ctttatccgc ctccatccag tctattaatt gttgccggga agctagagta    1380
```

```
agtagttcgc cagttaatag tttgcgcaac gttgttgcca ttgctacagg catcgtggtg   1440
tcacgctcgt cgtttggtat ggcttcattc agctccggtt cccaacgatc aaggcgagtt   1500
acatgatccc ccatgttgtg caaaaaagcg gttagctcct tcggtcctcc gatcgttgtc   1560
agaagtaagt tggccgcagt gttatcactc atggttatgg cagcactgca taattctctt   1620
actgtcatgc catccgtaag atgctttcct gtgactggtg agtactcaac caagtcattc   1680
tgagaatagt gtatgcggcg accgagttgc tcttgcccgg cgtcaatacg ggataatacc   1740
gcgccacata gcagaacttt aaaagtgctc atcattggaa aacgttcttc ggggcgaaaa   1800
ctctcaagga tcttaccgct gttgagatcc agttcgatgt aacccactcg tgcacccaac   1860
tgatcttcag catcttttac tttcaccagc gtttctgggt gagcaaaaac aggaaggcaa   1920
aatgccgcaa aaaagggaat aagggcgaca cggaaatgtt gaatactcat actcttcctt   1980
tttcaatatt attgaagcat ttatcagggt tattgtctca tgagcggata catatttgaa   2040
tgtatttaga aaaataaaca aatagggGtt ccgcgcacat ttccccgaaa agtgccacct   2100
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcggggGc tccctttagg gttccgattt   2280
agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt tcccagtca cgacgttgta   2700 aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880 taatttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tatttttatt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tattttttatt ctaatgatcc attaaaggta tatatttatt   3660
tcttgttata taatcctttt gtttattaca tgggctggat acataaaggt attttgattt   3720
```

```
aattttttgc ttaaattcaa tcccccctcg ttcagtgtca actgtaatgg taggaaatta   3780 ccatacttt  gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgtttttt  ttgtttttt  tttttctaat   4020 gattcattac cgctatgtat acctacttgt acttgtagta agccgggtta ttggcgttca   4080
attaatcata gacttatgaa tctgcacggt gtgcgctgcg agttacttt  agcttatgca   4140 tgctacttgg gtgtaatatt gggatctgtt cggaaatcaa cggatgctca atcgatttcg   4200
acagtaatta attaagtcat acacaagtca gctttcttcg agcctcatat aagtataagt   4260
agttcaacgt attagcactg tacccagcat ctccgtatcg agaaacacaa caacatgccc   4320
cattggacag atcatgcgga tacacaggtt gtgcagtatc atacatactc gatcagacag   4380
gtcgtctgac catcatacaa gctgaacaag cgctccatac ttgcacgctc tctatataca   4440
cagttaaatt acatatccat agtctaacct ctaacagtta atcttctggt aagcctccca   4500
gccagccttc tggtatcgct tggcctcctc aataggatct cggttctggc cgtacagacc   4560
tcggccgaca attatgatat ccgttccggt agacatgaca tcctcaacag ttcggtactg   4620
ctgtccgaga gcgtctccct tgtcgtcaag acccacccg  ggggtcagaa taagccagtc   4680
ctcagagtcg cccttaggtc ggttctgggc aatgaagcca accacaaact cggggtcgga   4740
tcgggcaagc tcaatggtct gcttggagta ctcgccagtg gccagagagc ccttgcaaga   4800
cagctcggcc agcatgagca gacctctggc cagcttctcg ttgggagagg ggactaggaa   4860
ctccttgtac tgggagttct cgtagtcaga gacgtcctcc ttcttctgtt cagagacagt   4920
ttcctcggca ccagctcgca ggccagcaat gattccggtt ccgggtacac cgtgggcgtt   4980
ggtgatatcg gaccactcgg cgattcggtg acaccggtac tggtgcttga cagtgttgcc   5040
aatatctgcg aactttctgt cctcgaacag gaagaaaccg tgcttaagag caagttcctt   5100 gaggggggagc acagtgccgg cgtaggtgaa gtcgtcaatg atgtcgatat gggttttgat   5160
catgcacaca taaggtccga ccttatcggc aagctcaatg agctccttgg tggtggtaac   5220
atccagagaa gcacacaggt tggttttctt ggctgccacg agcttgagca ctcgagcggc   5280
aaaggcggac ttgtggacgt tagctcgagc ttcgtaggag ggcattttgg tggtgaagag   5340
gagactgaaa taaatttagt ctgcagaact ttttatcgga accttatctg gggcagtgaa   5400
gtatatgtta tggtaatagt tacgagttag ttgaacttat agatagactg gactatacgg   5460
ctatcggtcc aaattagaaa gaacgtcaat ggctctctgg gcgtcgcctt gccgacaaa    5520 aatgtgatca tgatgaaagc cagcaatgac gttgcagctg atattgttgt cggccaaccg   5580
cgccgaaaac gcagctgtca gacccacagc ctccaacgaa gaatgtatcg tcaaagtgat   5640
ccaagcacac tcatagttgg agtcgtactc caaaggcggc aatgacgagt cagacagata   5700
ctcgtcgact caggcgacga cggaattcct gcagcccatc tgcagaattc aggagagacc   5760
gggttggcgg cgtatttgtg tcccaaaaaa cagccccaat tgccccggag aagacggcca   5820
ggccgcctag atgacaaatt caacaactca cagctgactt tctgccattg ccactagggg   5880 ggggccttt  tatatggcca agccaagctc tccacgtcgg ttgggctgca cccaacaata   5940
aatgggtagg gttgcaccaa caaagggatg ggatggggg  tagaagatac gaggataacg   6000
gggctcaatg gcacaaataa gaacgaatac tgccattaag actcgtgatc cagcgactga   6060
caccattgca tcatctaagg gcctcaaaac tacctcggaa ctgctgcgct gatctggaca   6120
```

```
ccacagaggt tccgagcact ttaggttgca ccaaatgtcc caccaggtgc aggcagaaaa    6180
cgctggaaca gcgtgtacag tttgtcttaa caaaaagtga gggcgctgag gtcgagcagg    6240
gtggtgtgac ttgttatagc ctttagagct gcgaaagcgc gtatggattt ggctcatcag    6300
gccagattga gggtctgtgg acacatgtca tgttagtgta cttcaatcgc ccctggata    6360
tagccccgac aataggccgt ggcctcattt ttttgcctc cgcacatttc cattgctcgg    6420
tacccacacc ttgcttctcc tgcacttgcc aaccttaata ctggtttaca ttgaccaaca    6480
tcttacaagc gggggcttg tctagggtat atataaacag tggctctccc aatcggttgc    6540
cagtctcttt tttcctttct ttccccacag attcgaaatc taaactacac atcacacaat    6600
gcctgttact gacgtcctta agcgaaagtc cggtgtcatc gtcggcgacg atgtccgagc    6660
cgtgagtatc cacgacaaga tcagtgtcga cgacgcgt tttgtgtaat gacacaatcc      6720
gaaagtcgct agcaacacac actctctaca caaactaacc cagctctcca tggctgagga    6780
taagaccaag gtcgagttcc ctaccctgac tgagctgaag cactctatcc ctaacgcttg    6840
ctttgagtcc aacctcggac tctcgctcta ctacactgcc cgagcgatct tcaacgcatc    6900
tgcctctgct gctctgctct acgctgcccg atctactccc ttcattgccg ataacgttct    6960
gctccacgct ctggtttgcg ccacctacat ctacgtgcag ggtgtcatct tctgggtttt    7020
ctttaccgtc ggtcacgact gtggtcactc tgccttctcc cgataccact ccgtcaactt    7080
catcattggc tgcatcatgc actctgccat tctgactccc ttcgagtcct ggcgagtgac    7140
ccaccgacac catcacaaga acactggcaa cattgataag gacgagatct ctaccctca    7200
tcggtccgtc aaggacctcc aggacgtgcg acaatgggtc tacaccctcg gaggtgcttg    7260
gtttgtctac ctgaaggtcg gatatgctcc tcgaaccatg tcccactttg accccgggga    7320
ccctctcctg cttcgacgag cctccgctgt catcgtgtcc ctcggagtct gggctgcctt    7380
cttcgctgcc tacgcctacc tcacatactc gctcggcttt gccgtcatgg gcctctacta    7440
ctatgctcct ctctttgtct ttgcttcgtt cctcgtcatt actaccttct tgcatcacaa    7500
cgacgaagct actccctggt acggtgactc ggagtggac tacgtcaagg gcaacctgag    7560
ctccgtcgac cgatcgtacg gagctttcgt ggacaacctg tctcaccaca ttggcaccca    7620
ccaggtccat cacttgttcc ctatcattcc ccactacaag ctcaacgaag ccaccaagca    7680
ctttgctgcc gcttaccctc acctcgtgag acgtaacgac gagcccatca ttactgcctt    7740
cttcaagacc gctcacctct ttgtcaacta cggagctgtg cccgagactg ctcagatttt    7800
caccctcaaa gagtctgccg ctgcagccaa ggccaagagc gactaagcgg ccgcaagtgt    7860
ggatggggaa gtgagtgccc ggttctgtgt gcacaattgg caatccaaga tggatggatt    7920
caacacaggg atatagcgag ctacgtggtg gtgcgaggat atagcaacgg atatttatgt    7980
ttgacacttg agaatgtacg atacaagcac tgtccaagta caatactaaa catactgtac    8040
atactcatac tcgtacccgg gcaacggttt cacttgagtg cagtggctag tgctcttact    8100
cgtacagtgt gcaatactgc gtatcatagt ctttgatgta tatcgtattc attcatgtta    8160
gttgc                                                                8165
```

<210> SEQ ID NO 144
<211> LENGTH: 7879
<212> TYPE: DNA
<213> ORGANISM: Artificial Sequence
<220> FEATURE:
<223> OTHER INFORMATION: Plasmid pDMW237

<400> SEQUENCE: 144

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgagccggaa gcataaagtg taaagcctgg ggtgcctaat     360
gagtgagcta actcacatta attgcgttgc gctcactgcc cgctttccag tcgggaaacc     420
tgtcgtgcca gctgcattaa tgaatcggcc aacgcgcggg gagaggcggt ttgcgtattg     480
ggcgctcttc cgcttcctcg ctcactgact cgctgcgctc ggtcgttcgg ctgcggcgag     540
cggtatcagc tcactcaaag gcggtaatac ggttatccac agaatcaggg gataacgcag     600
gaaagaacat gtgagcaaaa ggccagcaaa aggccaggaa ccgtaaaaag ccgcgttgc      660
tggcgttttt ccataggctc cgcccccctg acgagcatca caaaaatcga cgctcaagtc     720
agaggtggcg aaacccgaca ggactataaa gataccaggc gtttccccct ggaagctccc     780
tcgtgcgctc tcctgttccg accctgccgc ttaccggata cctgtccgcc tttctccctt     840
cgggaagcgt ggcgctttct catagctcac gctgtaggta tctcagttcg gtgtaggtcg     900
ttcgctccaa gctgggctgt gtgcacgaac cccccgttca gcccgaccgc tgcgccttat     960
ccggtaacta tcgtcttgag tccaacccgg taagacacga cttatcgcca ctggcagcag    1020
ccactggtaa caggattagc agagcgaggt atgtaggcgg tgctacagag ttcttgaagt    1080
ggtggcctaa ctacggctac actagaagga cagtatttgg tatctgcgct ctgctgaagc    1140
cagttacctt cggaaaaaga gttggtagct cttgatccgg caaacaaacc accgctggta    1200
gcggtggttt ttttgtttgc aagcagcaga ttacgcgcag aaaaaaagga tctcaagaag    1260
atcctttgat cttttctacg gggtctgacg ctcagtggaa cgaaaactca cgttaaggga    1320
ttttggtcat gagattatca aaaaggatct caccctagat cctttttaaat taaaaatgaa    1380
gttttaaatc aatctaaagt atatatgagt aaacttggtc tgacagttac caatgcttaa    1440
tcagtgaggc acctatctca gcgatctgtc tatttcgttc atccatagtt gcctgactcc    1500
ccgtcgtgta gataactacg atacgggagg gcttaccatc tggccccagt gctgcaatga    1560
taccgcgaga cccacgctca ccggctccag atttatcagc aataaaccag ccagccggaa    1620
gggccgagcg cagaagtggt cctgcaactt tatccgcctc catccagtct attaattgtt    1680
gccgggaagc tagagtaagt agttcgccag ttaatagttt gcgcaacgtt gttgccattg    1740
ctacaggcat cgtggtgtca cgctcgtcgt ttggtatggc ttcattcagc tccgttccc     1800
aacgatcaag gcgagttaca tgatccccca tgttgtgcaa aaaagcggtt agctccttcg    1860
gtcctccgat cgttgtcaga agtaagttgg ccgcagtgtt atcactcatg gttatggcag    1920
cactgcataa ttctcttact gtcatgccat ccgtaagatg cttttctgtg actggtgagt    1980
actcaaccaa gtcattctga gaatagtgta tgcggcgacc gagttgctct tgcccggcgt    2040
caatacggga taataccgcg ccacatagca gaactttaaa agtgctcatc attggaaaac    2100
gttcttcggg gcgaaaactc tcaaggatct taccgctgtt gagatccagt tcgatgtaac    2160
ccactcgtgc acccaactga tcttcagcat cttttacttt caccagcgtt tctgggtgag    2220
caaaaacagg aaggcaaaat gccgcaaaaa agggaataag ggcgacacgg aaatgttgaa    2280
tactcatact cttccttttt caatattatt gaagcattta tcagggttat tgtctcatga    2340
```

```
gcggatacat atttgaatgt atttagaaaa ataaacaaat aggggttccg cgcacatttc    2400
cccgaaaagt gccacctgac gcgccctgta gcggcgcatt aagcgcggcg ggtgtggtgg    2460
ttacgcgcag cgtgaccgct acacttgcca gcgccctagc gcccgctcct ttcgctttct    2520
tcccttcctt tctcgccacg ttcgccggct ttccccgtca agctctaaat cgggggctcc    2580
ctttagggtt ccgatttagt gctttacggc acctcgaccc caaaaaactt gattagggtg    2640
atggttcacg tagtgggcca tcgccctgat agacggtttt tcgcccttg acgttggagt    2700 ccacgttctt taatagtgga ctcttgttcc aaactggaac aacactcaac cctatctcgg    2760
tctattcttt tgatttataa gggattttgc cgatttcggc ctattggtta aaaaatgagc    2820
tgatttaaca aaaatttaac gcgaatttta acaaaatatt aacgcttaca atttccattc    2880
gccattcagg ctgcgcaact gttgggaagg gcgatcggtg cgggcctctt cgctattacg    2940
ccagctggcg aaaggggggat gtgctgcaag gcgattaagt tgggtaacgc cagggttttc    3000
ccagtcacga cgttgtaaaa cgacggccag tgaattgtaa tacgactcac tatagggcga    3060
attgggtacc gggccccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaaggggt catctcgcat    3360
tgtttaataa taaacagact ccatctaccg cctccaaatg atgttctcaa atatatattgt   3420 atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tccttttgtt tattacatgg gctggataca    4020
taaaggtatt ttgatttaat tttttgctta aattcaatcc cccctcgttc agtgtcaact    4080
gtaatggtag gaaattacca tacttttgaa gaagcaaaaa aaatgaaaga aaaaaaaat    4140 cgtatttcca ggttagacgt tccgcagaat ctagaatgcg gtatgcggta cattgttctt    4200
cgaacgtaaa agttgcgctc cctgagatat tgtacatttt tgcttttaca agtacaagta    4260
catcgtacaa ctatgtacta ctgttgatgc atccacaaca gtttgttttg tttttttttg    4320
tttttttttt ttctaatgat tcattaccgc tatgtatacc tacttgtact tgtagtaagc    4380
cgggttattg gcgttcaatt aatcatagac ttatgaatct gcacggtgtg cgctgcgagt    4440
tacttttagc ttatgcatgc tacttgggtg taatattggg atctgttcgg aaatcaacgg    4500
atgctcaatc gatttcgaca gtaattaatt aagtcataca caagtcagct ttcttcgagc    4560
ctcatataag tataagtagt tcaacgtatt agcactgtac ccagcatctc cgtatcgaga    4620
aacacaacaa catgccccat tggacagatc atgcggatac acaggttgtg cagtatcata    4680
```

```
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
acaaactcgg ggtcggatcg ggcaagctca atggtctgct ggagtactc gccagtggcc    5100 agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag ggggagcaca gtgccggcgt aggtgaagtc gtcaatgatg   5460
tcgatatggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
attttggtgg tgaagaggag actgaaataa atttagtctg cagaacttttt tatcggaacc   5700 ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgactcag gcgacgacgg aattcctgca gcccatctgc   6060
agaattcagg agagaccggg ttggcggcgt atttgtgtcc caaaaaacag ccccaattgc   6120
cccggagaag acggccaggc cgcctagatg acaaattcaa caactcacag ctgactttct   6180
gccattgcca ctagggggg gcctttttat atggccaagc caagctctcc acgtcggttg    6240
ggctgcaccc aacaataaat gggtagggtt gcaccaacaa agggatggga tgggggtag    6300 aagatacgag gataacgggg ctcaatggca caaataagaa cgaatactgc cattaagact   6360
cgtgatccag cgactgacac cattgcatca tctaagggcc tcaaaactac ctcggaactg   6420
ctgcgctgat ctggacacca cagaggttcc gagcacttta ggttgcacca aatgtcccac   6480
caggtgcagg cagaaaacgc tggaacagcg tgtacagttt gtcttaacaa aaagtgaggg   6540
cgctgaggtc gagcagggtg gtgtgacttg ttatagcctt tagagctgcg aaagcgcgta   6600
tggatttggc tcatcaggcc agattgaggg tctgtggaca catgtcatgt tagtgtactt   6660
caatcgcccc ctggatatag ccccgacaat aggccgtggc ctcattttttt tgccttccgc   6720 acatttccat tgctcggtac ccacaccttg cttctcctgc acttgccaac cttaatactg   6780
gtttacattg accaacatct tacaagcggg gggcttgtct agggtatata taaacagtgg   6840
ctctcccaat cggttgccag tctctttttt cctttctttc cccacagatt cgaaatctaa   6900
actacacatc acacaatgcc tgttactgac gtccttaagc gaaagtccgg tgtcatcgtc   6960
ggcgacgatg tccgagccgt gagtatccac gacaagatca gtgtcgagac gacgcgtttt   7020
gtgtaatgac acaatccgaa agtcgctagc aacacacact ctctacacaa actaacccag   7080
```

```
ctctccatgg ctctggccaa cgacgctggc gagcgaatct gggctgccgt caccgatccc    7140
gaaatcctca ttggcacctt ctcctacctg ctcctgaagc ctctcctgcg aaactctggt    7200
ctcgtggacg agaagaaagg agcctaccga acctccatga tctggtacaa cgtcctcctg    7260
gctctcttct ctgccctgtc cttctacgtg actgccaccg ctctcggctg ggactacggt    7320
actggagcct ggctgcgaag acagaccggt gatactcccc agcctctctt tcagtgtccc    7380
tctcctgtct gggactccaa gctgttcacc tggactgcca aggccttcta ctattctaag    7440
tacgtggagt acctcgacac cgcttggctg gtcctcaagg gcaagcgagt gtcctttctg    7500
caggccttcc atcactttgg agctccctgg gacgtctacc tcggcattcg actgcacaac    7560
gagggtgtgt ggatcttcat gttctttaac tcgttcattc acaccatcat gtacacctac    7620
tatggactga ctgccgctgg ctacaagttc aaggccaagc ctctgatcac tgccatgcag    7680
atttgccagt tcgtcggtgg cttttctcct gtctgggact acatcaacgt tccctgcttc    7740
aactctgaca agggcaagct gttctcctgg gctttcaact acgcctacgt cggatctgtc    7800
tttctcctgt tctgtcactt cttttaccag gacaacctgg ccaccaagaa atccgctaag    7860
gctggtaagc agctttagc                                                 7879

<210> SEQ ID NO 145
<211> LENGTH: 6457
<212> TYPE: DNA
<213> ORGANISM: Artificial Sequence
<220> FEATURE:
<223> OTHER INFORMATION: Plasmid pKUNT2

<400> SEQUENCE: 145
tttgaatcga atcgatgagc taaaatgaa cccgagtata tctcataaaa ttctcggtga      60
gaggtctgtg actgtcagta caaggtgcct tcattatgcc ctcaacctta ccatacctca    120
ctgaatgtag tgtacctcta aaaatgaaat acagtgccaa aagccaaggc actgagctcg    180
tctaacggac ttgatataca accaattaaa acaaatgaaa agaaatacag ttctttgtat    240
catttgtaac aattaccctg tacaaactaa ggtattgaaa tcccacaata ttcccaaagt    300
ccaccccttt ccaaattgtc atgcctacaa ctcatatacc aagcactaac ctaccgttta    360
aacaccacta aaaccccaca aaatatatct taccgaatat acagatctgc gacgacggaa    420
ttcctgcagc ccatctgcag aattcaggag agaccgggtt ggcggcgtat ttgtgtccca    480
aaaaacagcc ccaattgccc caattgaccc caaattgacc cagtagcggg cccaaccccg    540
gcgagagccc ccttcacccc acatatcaaa cctcccccgg ttcccacact tgccgttaag    600
ggcgtagggt actgcagtct ggaatctacg cttgttcaga cttgtacta gtttctttgt    660 ctggccatcc gggtaaccca tgccggacgc aaaatagact actgaaaatt tttttgcttt    720
gtggttggga cttagccaa gggtataaaa gaccaccgtc cccgaattac cttccctctt    780
cttttctctc tctccttgtc aactcacacc cgaaatcgtt aagcatttcc ttctgagtat    840
aagaatcatt caccatggat tcgaccacgc agaccaacac cggcaccggc aaggtggccg    900
tgcagccccc cacggccttc attaagccca ttgagaaggt gtccgagccc gtctacgaca    960 cctttgcaa cgagttcact cctccagact actctatcaa ggatattctg gatgccattc   1020 ccaggagtg ctacaagcgg tcctacgtta agtcctactc gtacgtggcc cgagactgct   1080
tctttatcgc cgttttttgcc tacatggcct acgcgtacct gctcttatt ccctcggctt   1140 ccggccgagc tgtggcctgg gccatgtact ccattgtcca gggtctgttt ggcaccggtc   1200
```

-continued

```
tgtgggttct tgcccacgag tgtggccact ctgctttctc cgactctaac accgtcaaca    1260
acgtcaccgg atgggttctg cactcctcca tgctggtccc ttactacgcc tggaagctga    1320
cccactccat gcaccacaag tccactggtc acctcacccg tgatatggtg tttgtgccca    1380
aggaccgaaa ggagtttatg gagaaccgag gcgcccatga ctggtctgag cttgctgagg    1440
acgctcccct catgaccctc tacgcctca tcacccagca ggtgtttgga tggcctctgt     1500
atctgctgtc ttacgttacc ggacagaagt accccaagct caacaaatgg gctgtcaacc    1560
acttcaaccc caacgccccg ctgtttgaga agaaggactg gttcaacatc tggatctcta    1620
acgtcggtat tggtatcacc atgtccgtca tcgcatactc catcaaccga tggggcctgg    1680
cttccgtcac cctctactac ctgatcccct acctgtgggt caaccactgg ctcgtggcca    1740
tcacctacct gcagcacacc gaccccactc tgccccacta ccacgccgac cagtggaact    1800
tcacccgagg agccgccgcc accatcgacc gagagtttgg cttcatcggc tccttctgct    1860
tccatgacat catcgagacc cacgttctgc caccactacg gtctcgaatt cccttctaca    1920
acgcccgaat cgccactgag aagatcaaga aggtcatggg caagcactac cgacacgacg    1980
acaccaactt catcaagtct ctttacactg tcgcccgaac ctgccagttt gttgaaggta    2040
aggaaggcat tcagatgttt agaaacgtca atggagtcgg agttgctcct gacggcctgc    2100
cttctaaaaa gtaggcggcc gcaagtgtgg atggggaagt gagtgcccgg ttctgtgtgc    2160
acaattggca atccaagatg gatggattca acacagggat atagcgagct acgtggtggt    2220
gcgaggatat agcaacggat atttatgttt gacacttgag aatgtacgat acaagcactg    2280
tccaagtaca atactaaaca tactgtacat actcatactc gtacccgggc aacggtttca    2340
cttgagtgca gtggctagtg ctcttactcg tacagtgtgc aatactgcgt atcatagtct    2400
ttgatgtata tcgtattcat tcatgttagt tgcgtacgaa gtcgtcaatg atgtcgatat    2460
gggttttgat catgcacaca taaggtccga ccttatcggc aagctcaatg agctccttgg    2520
tggtggtaac atccagagaa gcacacaggt tggttttctt ggctgccacg agcttgagca    2580
ctcgagcggc aaaggcggac ttgtggacgt tagctcgagc ttcgtaggag gcattttgg     2640 tggtgaagag gagactgaaa taaatttagt ctgcagaact ttttatcgga accttatctg    2700
gggcagtgaa gtatatgtta tggtaatagt tacgagttag ttgaacttat agatagactg    2760
gactatacgg ctatcggtcc aaattagaaa gaacgtcaat ggctctctgg gcgtcgcctt    2820
tgccgacaaa aatgtgatca tgatgaaagc cagcaatgac gttgcagctg atattgttgt    2880
cggccaaccg cgccgaaaac gcagctgtca gacccacagc ctccaacgaa gaatgtatcg    2940
tcaaagtgat ccaagcacac tcatagttgg agtcgtactc caaaggcggc aatgacgagt    3000
cagacagata ctcgtcgacc ttttccttgg gaaccaccac cgtcagccct tctgactcac    3060
gtattgtagc caccgacaca ggcaacagtc cgtggatagc agaatatgtc ttgtcggtcc    3120
atttctcacc aactttaggc gtcaagtgaa tgttgcagaa gaagtatgtg ccttcattga    3180
gaatcggtgt tgctgatttc aataaagtct tgagatcagt ttggcgcgcc agctgcatta    3240
atgaatcggc caacgcgcgg ggagaggcgg tttgcgtatt gggcgctctt ccgcttcctc    3300
gctcactgac tcgctgcgct cggtcgttcg gctgcggcga gcggtatcag ctcactcaaa    3360
ggcggtaata cggttatcca cagaatcagg ggataacgca ggaaagaaca tgtgagcaaa    3420
aggccagcaa aaggccagga accgtaaaaa ggccgcgttg ctggcgtttt tccataggct    3480
ccgcccccct gacgagcatc acaaaaatcg acgctcaagt cagaggtggc gaaacccgac    3540
aggactataa agataccagg cgtttccccc tggaagctcc ctcgtgcgct ctcctgttcc    3600
```

```
gaccctgccg cttaccggat acctgtccgc ctttctccct tcgggaagcg tggcgctttc   3660
tcatagctca cgctgtaggt atctcagttc ggtgtaggtc gttcgctcca agctgggctg   3720
tgtgcacgaa ccccccgttc agcccgaccg ctgcgcctta tccggtaact atcgtcttga   3780
gtccaacccg gtaagacacg acttatcgcc actggcagca gccactggta acaggattag   3840
cagagcgagg tatgtaggcg gtgctacaga gttcttgaag tggtggccta actacggcta   3900
cactagaaga acagtatttg gtatctgcgc tctgctgaag ccagttacct tcggaaaaag   3960
agttggtagc tcttgatccg gcaaacaaac caccgctggt agcggtggtt ttttttgtttg   4020
caagcagcag attacgcgca gaaaaaaagg atctcaagaa gatcctttga tcttttctac   4080
ggggtctgac gctcagtgga acgaaaactc acgttaaggg attttggtca tgagattatc   4140
aaaaaggatc ttcacctaga tccttttaaa ttaaaaatga agttttaaat caatctaaag   4200
tatatatgag taaacttggt ctgacagtta ccaatgctta atcagtgagg cacctatctc   4260
agcgatctgt ctatttcgtt catccatagt tgcctgactc cccgtcgtgt agataactac   4320
gatacgggag ggcttaccat ctggccccag tgctgcaatg ataccgcgag acccacgctc   4380
accggctcca gatttatcag caataaacca gccagccgga agggccgagc gcagaagtgg   4440
tcctgcaact ttatccgcct ccatccagtc tattaattgt tgccgggaag ctagagtaag   4500
tagttcgcca gttaatagtt tgcgcaacgt tgttgccatt gctacaggca tcgtggtgtc   4560
acgctcgtcg tttggtatgg cttcattcag ctccggttcc caacgatcaa ggcgagttac   4620
atgatccccc atgttgtgca aaaaagcggt tagctccttc ggtcctccga tcgttgtcag   4680
aagtaagttg gccgcagtgt tatcactcat ggttatggca gcactgcata attctcttac   4740
tgtcatgcca tccgtaagat gcttttctgt gactggtgag tactcaacca agtcattctg   4800
agaatagtgt atgcggcgac cgagttgctc ttgcccggcg tcaatacggg ataataccgc   4860
gccacatagc agaactttaa aagtgctcat cattggaaaa cgttcttcgg ggcgaaaact   4920
ctcaaggatc ttaccgctgt tgagatccag ttcgatgtaa cccactcgtg cacccaactg   4980
atcttcagca tcttttactt tcaccagcgt ttctgggtga gcaaaaacag gaaggcaaaa   5040
tgccgcaaaa aagggaataa gggcgacacg gaaatgttga atactcatac tcttcctttt   5100
tcaatattat tgaagcattt atcagggtta ttgtctcatg agcggataca tatttgaatg   5160
tatttagaaa aataaacaaa tagggggttcc gcgcacattt ccccgaaaag tgccacctga   5220
tgcggtgtga ataccgcac agatgcgtaa ggagaaaata ccgcatcagg aaattgtaag   5280
cgttaatatt ttgttaaaat tcgcgttaaa ttttttgttaa atcagctcat tttttaacca   5340
ataggccgaa atcggcaaaa tcccttataa atcaaaagaa tagaccgaga tagggttgag   5400
tgttgttcca gtttggaaca agagtccact attaaagaac gtggactcca acgtcaaagg   5460
gcgaaaaacc gtctatcagg gcgatggccc actacgtgaa ccatcaccct aatcaagttt   5520
tttggggtcg aggtgccgta agcactaaa tcggaaccct aaagggagcc cccgatttag   5580
agcttgacgg ggaaagccgg cgaacgtggc gagaaaggaa gggaagaaag cgaaaggagc   5640
gggcgctagg gcgctggcaa gtgtagcggt cacgctgcgc gtaaccacca cacccgccgc   5700
gcttaatgcg ccgctacagg gcgcgtccat tcgccattca ggctgcgcaa ctgttgggaa   5760
gggcgatcgg tgcgggcctc ttcgctatta cgccagctgg cgaaagggg atgtgctgca   5820
aggcgattaa gttgggtaac gccagggttt cccagtcac gacgttgtaa aacgacggcc   5880
agtgaattgt aatacgactc actataggc gaattgggcc cgacgtcgca tgcagtggtg   5940
```

-continued

```
gtattgtgac tggggatgta gttgagaata agtcatacac aagtcagctt tcttcgagcc      6000
tcatataagt ataagtagtt caacgtatta gcactgtacc cagcatctcc gtatcgagaa      6060
acacaacaac atgccccatt ggacagatca tgcggataca caggttgtgc agtatcatac      6120
atactcgatc agacaggtcg tctgaccatc atacaagctg aacaagcgct ccatacttgc      6180
acgctctcta tatacacagt taaattacat atccatagtc taacctctaa cagttaatct      6240
tctggtaagc ctcccagcca gccttctggt atcgcttggc ctcctcaata ggatctcggt      6300
tctggccgta cagacctcgg ccgacaatta tgatatccgt tccggtagac atgacatcct      6360
caacagttcg gtactgctgt ccgagagcgt ctcccttgtc gtcaagaccc accccggggg      6420
tcagaataag ccagtcctca gagtcgccct taattaa                              6457
```

<210> SEQ ID NO 146
<211> LENGTH: 1936
<212> TYPE: DNA
<213> ORGANISM: Yarrowia lipolytica
<220> FEATURE:
<221> NAME/KEY: CDS
<222> LOCATION: (283)..(1539)
<223> OTHER INFORMATION: delta-12 desaturase

<400> SEQUENCE: 146

```
cgtagttata tacaagaggt agatgcgtgc tggtgttaga ggggctctca ggattaggag        60
gaaaatttga cattggccct caacatataa cctcgggtgt gcctctgttt accctcagct       120
tttgcttgtc cccaagtcag tcacgccagg ccaaaaaggt tggtggattg acagggagaa       180
aaaaaaaagc ctagtgggtt taaactcgag gtaagacatt gaaatatata ccggtcggca       240
tcctgagtcc ctttctcgta ttccaacaga ccgaccatag aa atg gat tcg acc          294
                                              Met Asp Ser Thr
                                                1
```

```
acg cag acc aac acc ggc acc ggc aag gtg gcc gtg cag ccc ccc acg        342
Thr Gln Thr Asn Thr Gly Thr Gly Lys Val Ala Val Gln Pro Pro Thr
  5                  10                  15                  20 gcc ttc att aag ccc att gag aag gtg tcc gag ccc gtc tac gac acc        390
Ala Phe Ile Lys Pro Ile Glu Lys Val Ser Glu Pro Val Tyr Asp Thr
             25                  30                  35 ttt ggc aac gag ttc act cct cca gac tac tct atc aag gat att ctg        438
Phe Gly Asn Glu Phe Thr Pro Pro Asp Tyr Ser Ile Lys Asp Ile Leu
         40                  45                  50 gat gcc att ccc cag gag tgc tac aag cgg tcc tac gtt aag tcc tac        486
Asp Ala Ile Pro Gln Glu Cys Tyr Lys Arg Ser Tyr Val Lys Ser Tyr
     55                  60                  65 tcg tac gtg gcc cga gac tgc ttc ttt atc gcc gtt ttt gcc tac atg        534
Ser Tyr Val Ala Arg Asp Cys Phe Phe Ile Ala Val Phe Ala Tyr Met
 70                  75                  80 gcc tac gcg tac ctg cct ctt att ccc tcg gct tcc ggc cga gct gtg        582
Ala Tyr Ala Tyr Leu Pro Leu Ile Pro Ser Ala Ser Gly Arg Ala Val
85                  90                  95                 100 gcc tgg gcc atg tac tcc att gtc cag ggt ctg ttt ggc acc ggt ctg        630
Ala Trp Ala Met Tyr Ser Ile Val Gln Gly Leu Phe Gly Thr Gly Leu
                105                 110                 115 tgg gtt ctt gcc cac gag tgt ggc cac tct gct ttc tcc gac tct aac        678
Trp Val Leu Ala His Glu Cys Gly His Ser Ala Phe Ser Asp Ser Asn
            120                 125                 130 acc gtc aac aac gtc acc gga tgg gtt ctg cac tcc tcc atg ctg gtc        726
Thr Val Asn Asn Val Thr Gly Trp Val Leu His Ser Ser Met Leu Val
        135                 140                 145 cct tac tac gcc tgg aag ctg acc cac tcc atg cac cac aag tcc act        774
```

```
                Pro Tyr Tyr Ala Trp Lys Leu Thr His Ser Met His His Lys Ser Thr
                    150                 155                 160 ggt cac ctc acc cgt gat atg gtg ttt gtg ccc aag gac cga aag gag        822
Gly His Leu Thr Arg Asp Met Val Phe Val Pro Lys Asp Arg Lys Glu
165                 170                 175                 180 ttt atg gag aac cga ggc gcc cat gac tgg tct gag ctt gct gag gac        870
Phe Met Glu Asn Arg Gly Ala His Asp Trp Ser Glu Leu Ala Glu Asp
                    185                 190                 195 gct ccc ctc atg acc ctc tac ggc ctc atc acc cag cag gtg ttt gga        918
Ala Pro Leu Met Thr Leu Tyr Gly Leu Ile Thr Gln Gln Val Phe Gly
                200                 205                 210 tgg cct ctg tat ctg ctg tct tac gtt acc gga cag aag tac ccc aag        966
Trp Pro Leu Tyr Leu Leu Ser Tyr Val Thr Gly Gln Lys Tyr Pro Lys
            215                 220                 225 ctc aac aaa tgg gct gtc aac cac ttc aac ccc aac gcc ccg ctg ttt       1014
Leu Asn Lys Trp Ala Val Asn His Phe Asn Pro Asn Ala Pro Leu Phe
        230                 235                 240 gag aag aag gac tgg ttc aac atc tgg atc tct aac gtc ggt att ggt       1062
Glu Lys Lys Asp Trp Phe Asn Ile Trp Ile Ser Asn Val Gly Ile Gly
245                 250                 255                 260 atc acc atg tcc gtc atc gca tac tcc atc aac cga tgg ggc ctg gct       1110
Ile Thr Met Ser Val Ile Ala Tyr Ser Ile Asn Arg Trp Gly Leu Ala
                265                 270                 275 tcc gtc acc ctc tac tac ctg atc ccc tac ctg tgg gtc aac cac tgg       1158
Ser Val Thr Leu Tyr Tyr Leu Ile Pro Tyr Leu Trp Val Asn His Trp
                280                 285                 290 ctc gtg gcc atc acc tac ctg cag cac acc gac ccc act ctg ccc cac       1206
Leu Val Ala Ile Thr Tyr Leu Gln His Thr Asp Pro Thr Leu Pro His
            295                 300                 305 tac cac gcc gac cag tgg aac ttc acc cga gga gcc gcc gcc acc atc       1254
Tyr His Ala Asp Gln Trp Asn Phe Thr Arg Gly Ala Ala Ala Thr Ile
        310                 315                 320 gac cga gag ttt ggc ttc atc ggc tcc ttc tgc ttc cat gac atc atc       1302
Asp Arg Glu Phe Gly Phe Ile Gly Ser Phe Cys Phe His Asp Ile Ile
325                 330                 335                 340 gag acc cac gtt ctg cac cac tac gtg tct cga att ccc ttc tac aac       1350
Glu Thr His Val Leu His His Tyr Val Ser Arg Ile Pro Phe Tyr Asn
                345                 350                 355 gcc cga atc gcc act gag aag atc aag aag gtc atg ggc aag cac tac       1398
Ala Arg Ile Ala Thr Glu Lys Ile Lys Lys Val Met Gly Lys His Tyr
                360                 365                 370 cga cac gac gac acc aac ttc atc aag tct ctt tac act gtc gcc cga       1446
Arg His Asp Asp Thr Asn Phe Ile Lys Ser Leu Tyr Thr Val Ala Arg
            375                 380                 385 acc tgc cag ttt gtt gaa ggt aag gaa ggc att cag atg ttt aga aac       1494
Thr Cys Gln Phe Val Glu Gly Lys Glu Gly Ile Gln Met Phe Arg Asn
        390                 395                 400 gtc aat gga gtc gga gtt gct cct gac ggc ctg cct tct aaa aag           1539
Val Asn Gly Val Gly Val Ala Pro Asp Gly Leu Pro Ser Lys Lys
405                 410                 415 tagagctaga aatgttattt gattgtgttt taactgaaca gcaccgagcc cgaggctaag     1599
ccaagcgaag ccgaggggtt gtgtagtcca tggacgtaac gagtaggcga tatcaccgca     1659
ctcggcactg cgtgtctgcg ttcatgggcg aagtcacatt acgctgacaa ccgttgtagt     1719
ttccctttag tatcaatact gttacaagta ccggtctcgt actcgtactg atacgaatct    1779
gtgggaagaa gtcacccctta tcagacccttc atactgatgt ttcggatatc aatagaactg  1839
gcatagagcc gttaaagaag tttcacttaa tcactccaac cctcctactt gtagattcaa    1899
```
gcagatcgat aagatggatt tgatggtcag tgctagc 1936

<210> SEQ ID NO 147
<211> LENGTH: 419
<212> TYPE: PRT
<213> ORGANISM: Yarrowia lipolytica

<400> SEQUENCE: 147

```
Met Asp Ser Thr Thr Gln Thr Asn Thr Gly Thr Gly Lys Val Ala Val
1               5                   10                  15

Gln Pro Pro Thr Ala Phe Ile Lys Pro Ile Glu Lys Val Ser Glu Pro
            20                  25                  30

Val Tyr Asp Thr Phe Gly Asn Glu Phe Thr Pro Pro Asp Tyr Ser Ile
        35                  40                  45

Lys Asp Ile Leu Asp Ala Ile Pro Gln Glu Cys Tyr Lys Arg Ser Tyr
50                  55                  60

Val Lys Ser Tyr Ser Tyr Val Ala Arg Asp Cys Phe Phe Ile Ala Val
65                  70                  75                  80

Phe Ala Tyr Met Ala Tyr Ala Tyr Leu Pro Leu Ile Pro Ser Ala Ser
                85                  90                  95

Gly Arg Ala Val Ala Trp Ala Met Tyr Ser Ile Val Gln Gly Leu Phe
            100                 105                 110

Gly Thr Gly Leu Trp Val Leu Ala His Glu Cys Gly His Ser Ala Phe
        115                 120                 125

Ser Asp Ser Asn Thr Val Asn Asn Val Thr Gly Trp Val Leu His Ser
130                 135                 140

Ser Met Leu Val Pro Tyr Tyr Ala Trp Lys Leu Thr His Ser Met His
145                 150                 155                 160

His Lys Ser Thr Gly His Leu Thr Arg Asp Met Val Phe Val Pro Lys
                165                 170                 175

Asp Arg Lys Glu Phe Met Glu Asn Arg Gly Ala His Asp Trp Ser Glu
            180                 185                 190

Leu Ala Glu Asp Ala Pro Leu Met Thr Leu Tyr Gly Leu Ile Thr Gln
        195                 200                 205

Gln Val Phe Gly Trp Pro Leu Tyr Leu Leu Ser Tyr Val Thr Gly Gln
210                 215                 220

Lys Tyr Pro Lys Leu Asn Lys Trp Ala Val His Phe Asn Pro Asn
225                 230                 235                 240

Ala Pro Leu Phe Glu Lys Lys Asp Trp Phe Asn Ile Trp Ile Ser Asn
                245                 250                 255

Val Gly Ile Gly Ile Thr Met Ser Val Ile Ala Tyr Ser Ile Asn Arg
            260                 265                 270

Trp Gly Leu Ala Ser Val Thr Leu Tyr Tyr Leu Ile Pro Tyr Leu Trp
        275                 280                 285

Val Asn His Trp Leu Val Ala Ile Thr Tyr Leu Gln His Thr Asp Pro
        290                 295                 300

Thr Leu Pro His Tyr His Ala Asp Gln Trp Asn Phe Thr Arg Gly Ala
305                 310                 315                 320

Ala Ala Thr Ile Asp Arg Glu Phe Gly Phe Ile Gly Ser Phe Cys Phe
                325                 330                 335

His Asp Ile Ile Glu Thr His Val Leu His His Tyr Val Ser Arg Ile
            340                 345                 350

Pro Phe Tyr Asn Ala Arg Ile Ala Thr Glu Lys Ile Lys Lys Val Met
        355                 360                 365
```

```
Gly Lys His Tyr Arg His Asp Asp Thr Asn Phe Ile Lys Ser Leu Tyr
            370                 375                 380

Thr Val Ala Arg Thr Cys Gln Phe Val Glu Gly Lys Glu Gly Ile Gln
385                 390                 395                 400

Met Phe Arg Asn Val Asn Gly Val Gly Val Ala Pro Asp Gly Leu Pro
                405                 410                 415

Ser Lys Lys

<210> SEQ ID NO 148
<211> LENGTH: 10448
<212> TYPE: DNA
<213> ORGANISM: Artificial Sequence
<220> FEATURE:
<223> OTHER INFORMATION: Plasmid pDMW297

<400> SEQUENCE: 148
```

| | | | | | |
|---|---|---|---|---|---|
| cgattgcccc | ggagaagacg | gccaggccgc | ctagatgaca | aattcaacaa | ctcacagctg | 60 |
| actttctgcc | attgccacta | gggggggggcc | tttttatatg | gccaagccaa | gctctccacg | 120 |
| tcggttgggc | tgcacccaac | aataaatggg | tagggttgca | ccaacaaagg | gatgggatgg | 180 |
| ggggtagaag | atacgaggat | aacggggctc | aatggcacaa | ataagaacga | atactgccat | 240 |
| taagactcgt | gatccagcga | ctgacaccat | tgcatcatct | aagggcctca | aaactacctc | 300 |
| ggaactgctg | cgctgatctg | gacaccacag | aggttccgag | cactttaggt | tgcaccaaat | 360 |
| gtcccaccag | gtgcaggcag | aaaacgctgg | aacagcgtgt | acagtttgtc | ttaacaaaaa | 420 |
| gtgagggcgc | tgaggtcgag | cagggtggtg | tgacttgtta | tagcctttag | agctgcgaaa | 480 |
| gcgcgtatgg | atttggctca | tcaggccaga | ttgagggtct | gtggacacat | gtcatgttag | 540 |
| tgtacttcaa | tcgcccctg | gatatagccc | cgacaatagg | ccgtggcctc | atttttttgc | 600 |
| cttccgcaca | tttccattgc | tcggtaccca | caccttgctt | ctcctgcact | tgccaacctt | 660 |
| aatactggtt | tacattgacc | aacatcttac | aagcgggggg | cttgtctagg | gtatatataa | 720 |
| acagtggctc | tcccaatcgg | ttgccagtct | cttttttcct | ttctttcccc | acagattcga | 780 |
| aatctaaact | acacatcaca | caatgcctgt | tactgacgtc | cttaagcgaa | agtccggtgt | 840 |
| catcgtcggc | gacgatgtcc | gagccgtgag | tatccacgac | aagatcagtg | tcgagacgac | 900 |
| gcgttttgtg | taatgacaca | atccgaaagt | cgctagcaac | acacactctc | tacacaaact | 960 |
| aacccagctc | tccatggtga | agtccaagcg | acaggctctg | cccctcacca | tcgacggaac | 1020 |
| tacctacgac | gtctccgctt | gggtgaactt | ccacctggt | ggagctgaaa | tcattgagaa | 1080 |
| ctaccaggga | cgagatgcta | ctgacgcctt | catggttatg | cactctcagg | aagccttcga | 1140 |
| caagctcaag | cgaatgccca | agatcaaccc | tcctccgag | ctgcctcccc | aggctgccgt | 1200 |
| caacgaagct | caggaggatt | tccgaaagct | ccgagaagag | ctgatcgcca | ctggcatgtt | 1260 |
| tgacgcctct | cccctctggt | actcgtacaa | gatctccacc | accctgggtc | ttggcgtgct | 1320 |
| tggatacttc | ctgatggtcc | agtaccagat | gtacttcatt | ggtgctgtgc | tgctcggtat | 1380 |
| gcactaccag | caaatgggat | ggctgtctca | tgacatctgc | caccaccaga | ccttcaagaa | 1440 |
| ccgaaactgg | aataacctcg | tgggtctggt | ctttggcaac | ggactccagg | gcttctccgt | 1500 |
| gacctggtgg | aaggacagac | acaacgccca | tcattctgct | accaacgttc | agggtcacga | 1560 |
| tcccgacatt | gataacctgc | ctctgctcgc | ctggtccgag | gacgatgtca | ctcgagcttc | 1620 |
| tcccatctcc | cgaaagctca | ttcagttcca | acagtactat | ttcctggtca | tctgtattct | 1680 |
| cctgcgattc | atctggtgtt | tccagtctgt | gctgaccgtt | cgatccctca | aggaccgaga | 1740 |

```
caaccagttc taccgatctc agtacaagaa agaggccatt ggactcgctc tgcactggac    1800
tctcaagacc ctgttccacc tcttctttat gccctccatc ctgacctcgc tcctggtgtt    1860
ctttgtttcc gagctcgtcg gtggcttcgg aattgccatc gtggtcttca tgaaccacta    1920
ccctctggag aagatcggtg attccgtctg ggacggacat ggcttctctg tgggtcagat    1980
ccatgagacc atgaacattc gacgaggcat cattactgac tggttctttg gaggcctgaa    2040
ctaccagatc gagcaccatc tctggcccac cctgcctcga cacaacctca ctgccgtttc    2100
ctaccaggtg aacagctgt gccagaagca aacctcccc taccgaaacc ctctgcccca     2160
tgaaggtctc gtcatcctgc tccgatacct ggccgtgttc gctcgaatgg ccgagaagca    2220
gcccgctggc aaggctctct aagcggccgc attgatgatt ggaaacacac acatgggtta    2280
tatctaggtg agagttagtt ggacagttat atattaaatc agctatgcca acggtaactt    2340
cattcatgtc aacgaggaac cagtgactgc aagtaatata gaatttgacc accttgccat    2400
tctcttgcac tcctttacta tatctcattt atttcttata tacaaatcac ttcttcttcc    2460
cagcatcgag ctcggaaacc tcatgagcaa taacatcgtg gatctcgtca atagagggct    2520
ttttggactc cttgctgttg gccaccttgt ccttgctgtc tggctcattc tgtttcaacg    2580
cctttaatt aagtcataca caagtcagct ttcttcgagc ctcatataag tataagtagt     2640
tcaacgtatt agcactgtac ccagcatctc cgtatcgaga aacacaacaa catgccccat    2700
tggacagatc atgcggatac acaggttgtg cagtatcata catactcgat cagacaggtc    2760
gtctgaccat catacaagct gaacaagcgc tccatacttg cacgctctct atatacacag    2820
ttaaattaca tatccatagt ctaacctcta acagttaatc ttctggtaag cctcccagcc    2880
agccttctgg tatcgcttgg cctcctcaat aggatctcgg ttctggccgt acagacctcg    2940
gccgacaatt atgatatccg ttccggtaga catgacatcc tcaacagttc ggtactgctg    3000
tccgagagcg tctcccttgt cgtcaagacc cacccccgggg gtcagaataa gccagtcctc   3060
agagtcgccc ttaggtcggt tctgggcaat gaagccaacc acaaactcgg ggtcggatcg    3120
ggcaagctca atggtctgct tggagtactc gccagtggcc agagagccct tgcaagacag    3180
ctcggccagc atgagcagac ctctggccag cttctcgttg ggagagggga ctaggaactc    3240
cttgtactgg gagttctcgt agtcagagac gtcctccttc ttctgttcag agacagtttc    3300
ctcggcacca gctcgcaggc cagcaatgat tccggttccg ggtacaccgt gggcgttggt    3360
gatatcggac cactcggcga ttcggtgaca ccggtactgg tgcttgacag tgttgccaat    3420
atctgcgaac tttctgtcct cgaacaggaa gaaaccgtgc ttaagagcaa gttccttgag    3480
ggggagcaca gtgccggcgt aggtgaagtc gtcaatgatg tcgatatggg ttttgatcat    3540
gcacacataa ggtccgacct tatcggcaag ctcaatgagc tccttggtgg tggtaacatc    3600
cagagaagca cacaggttgg ttttcttggc tgccacgagc ttgagcactc gagcggcaaa    3660
ggcggacttg tggacgttag ctcgagcttc gtaggagggc attttggtgg tgaagaggag    3720
actgaaataa atttagtctg cagaacttt tatcggaacc ttatctgggg cagtgaagta    3780
tatgttatgg taatagttac gagttagttg aacttataga tagactggac tatacggcta    3840
tcggtccaaa ttagaaagaa cgtcaatggc tctctgggcg tcgcctttgc cgacaaaaat    3900
gtgatcatga tgaaagccag caatgacgtt gcagctgata ttgttgtcgg ccaaccgcgc    3960
cgaaaacgca gctgtcagac ccacagcctc caacgaagaa tgtatcgtca aagtgatcca    4020
agcacactca tagttggagt cgtactccaa aggcggcaat gacgagtcag acagatactc    4080
gtcgactcag gcgacgacgg aattcctgca gcccatctgc agaattcagg agagaccggg    4140
```

```
ttggcggcgt atttgtgtcc caaaaaacag ccccaattgc cccggagaag acggccaggc    4200
cgcctagatg acaaattcaa caactcacag ctgactttct gccattgcca ctaggggggg    4260 gccttttat atggccaagc caagctctcc acgtcggttg ggctgcaccc aacaataaat     4320
gggtagggtt gcaccaacaa agggatggga tgggggtag aagatacgag gataacgggg    4380
ctcaatggca caaataagaa cgaatactgc cattaagact cgtgatccag cgactgacac    4440
cattgcatca tctaagggcc tcaaaactac ctcggaactg ctgcgctgat ctggacacca    4500
cagaggttcc gagcacttta ggttgcacca aatgtcccac caggtgcagg cagaaaacgc    4560
tggaacagcg tgtacagttt gtcttaacaa aaagtgaggg cgctgaggtc gagcagggtg    4620
gtgtgacttg ttatagcctt tagagctgcg aaagcgcgta tggatttggc tcatcaggcc    4680
agattgaggg tctgtggaca catgtcatgt tagtgtactt caatcgcccc ctggatatag    4740
ccccgacaat aggccgtggc ctcattttt tgccttccgc acatttccat tgctcggtac     4800
ccacaccttg cttctcctgc acttgccaac cttaatactg gtttacattg accaacatct    4860
tacaagcggg gggcttgtct agggtatata taaacagtgg ctctcccaat cggttgccag    4920 tctcttttt cctttctttc cccacagatt cgaaatctaa actacacatc acacaatgcc     4980
tgttactgac gtccttaagc gaaagtccgg tgtcatcgtc ggcgacgatg tccgagccgt    5040
gagtatccac gacaagatca gtgtcgagac gacgcgtttt gtgtaatgac acaatccgaa    5100
agtcgctagc aacacacact ctctacacaa actaacccag ctctccatgg ctctggccaa    5160
cgacgctggc gagcgaatct gggctgccgt caccgatccc gaaatcctca ttggcaccct    5220
ctcctacctg ctcctgaagc ctctcctgcg aaactctggt ctcgtggacg agaagaaagg    5280
agcctaccga acctccatga tctggtacaa cgtcctcctg gctctcttct ctgccctgtc    5340
cttctacgtg actgccaccg ctctcggctg ggactacggt actggagcct ggctgcgaag    5400
acagaccggt gatactcccc agcctctctt tcagtgtccc tctcctgtct gggactccaa    5460
gctgttcacc tggactgcca aggccttcta ctattctaag tacgtggagt acctcgacac    5520
cgcttggctg gtcctcaagg gcaagcgagt gtcctttctg caggccttcc atcactttgg    5580
agctccctgg gacgtctacc tcggcattcg actgcacaac gagggtgtgt ggatcttcat    5640
gttctttaac tcgttcattc acaccatcat gtacacctac tatggactga ctgccgctgg    5700
ctacaagttc aaggccaagc ctctgatcac tgccatgcag atttgccagt cgtcggtgg     5760 cttttctcctg gtctgggact acatcaacgt tccctgcttc aactctgaca agggcaagct    5820
gttctcctgg gctttcaact acgcctacgt cggatctgtc tttctcctgt tctgtcactt    5880
cttttaccag gacaacctgg ccaccaagaa atccgctaag gctggtaagc agctttagcg    5940
gccgcaagtg tggatgggga agtgagtgcc cggttctgtg tgcacaattg gcaatccaag    6000
atggatggat tcaacacagg gatatagcga gctacgtggt ggtgcgagga tatagcaacg    6060
gatatttatg tttgacactt gagaatgtac gatacaagca ctgtccaagt acaatactaa    6120
acatactgta catactcata ctcgtacccg ggcaacggtt tcacttgagt gcagtggcta    6180
gtgctcttac tcgtacagtg tgcaatactg cgtatcatag tctttgatgt atatcgtatt    6240
cattcatgtt agttgcgtac gagccggaag cataaagtgt aaagcctggg gtgcctaatg    6300
agtgagctaa ctcacattaa ttgcgttgcg ctcactgccc gctttccagt cgggaaacct    6360
gtcgtgccag ctgcattaat gaatcggcca acgcgcgggg agaggcggtt tgcgtattgg    6420
gcgctcttcc gcttcctcgc tcactgactc gctgcgctcg gtcgttcggc tgcggcgagc    6480
```

```
ggtatcagct cactcaaagg cggtaatacg gttatccaca gaatcagggg ataacgcagg    6540
aaagaacatg tgagcaaaag gccagcaaaa ggccaggaac cgtaaaaagg ccgcgttgct    6600 ggcgttttc  cataggctcc gcccccctga cgagcatcac aaaaatcgac gctcaagtca    6660
gaggtggcga aacccgacag gactataaag ataccaggcg tttccccctg gaagctccct    6720
cgtgcgctct cctgttccga ccctgccgct taccggatac ctgtccgcct ttctcccttc    6780
gggaagcgtg gcgctttctc atagctcacg ctgtaggtat ctcagttcgg tgtaggtcgt    6840
tcgctccaag ctgggctgtg tgcacgaacc ccccgttcag cccgaccgct gcgccttatc    6900
cggtaactat cgtcttgagt ccaacccggt aagacacgac ttatcgccac tggcagcagc    6960
cactggtaac aggattagca gagcgaggta tgtaggcggt gctacagagt tcttgaagtg    7020
gtggcctaac tacggctaca ctagaaggac agtatttggt atctgcgctc tgctgaagcc    7080
agttaccttc ggaaaaagag ttggtagctc ttgatccggc aaacaaacca ccgctggtag    7140
cggtggtttt tttgtttgca agcagcagat tacgcgcaga aaaaaggat  ctcaagaaga    7200 tcctttgatc ttttctacgg ggtctgacgc tcagtggaac gaaaactcac gttaagggat    7260
tttggtcatg agattatcaa aaaggatctt cacctagatc cttttaaatt aaaaatgaag    7320
ttttaaatca atctaaagta tatatgagta aacttggtct gacagttacc aatgcttaat    7380
cagtgaggca cctatctcag cgatctgtct atttcgttca tccatagttg cctgactccc    7440
cgtcgtgtag ataactacga tacgggaggg cttaccatct ggccccagtg ctgcaatgat    7500
accgcgagac ccacgctcac cggctccaga tttatcagca ataaaccagc cagccggaag    7560
ggccgagcgc agaagtggtc ctgcaacttt atccgcctcc atccagtcta ttaattgttg    7620
ccgggaagct agagtaagta gttcgccagt taatagtttg cgcaacgttg ttgccattgc    7680
tacaggcatc gtggtgtcac gctcgtcgtt tggtatggct tcattcagct ccggttccca    7740
acgatcaagg cgagttacat gatcccccat gttgtgcaaa aaagcggtta gctccttcgg    7800
tcctccgatc gttgtcagaa gtaagttggc cgcagtgtta tcactcatgg ttatggcagc    7860
actgcataat tctcttactg tcatgccatc cgtaagatgc ttttctgtga ctggtgagta    7920
ctcaaccaag tcattctgag aatagtgtat gcggcgaccg agttgctctt gcccggcgtc    7980
aatacgggat aataccgcgc cacatagcag aactttaaaa gtgctcatca ttggaaaacg    8040
ttcttcgggg cgaaaactct caaggatctt accgctgttg agatccagtt cgatgtaacc    8100
cactcgtgca cccaactgat cttcagcatc ttttactttc accagcgttt ctgggtgagc    8160
aaaaacagga aggcaaaatg ccgcaaaaaa gggaataagg gcgacacgga aatgttgaat    8220
actcatactc ttcctttttc aatattattg aagcatttat cagggttatt gtctcatgag    8280
cggatacata tttgaatgta tttagaaaaa taaacaaata ggggttccgc gcacatttcc    8340
ccgaaaagtg ccacctgacg cgccctgtag cggcgcatta agcgcggcgg gtgtggtggt    8400
tacgcgcagc gtgaccgcta cacttgccag cgccctagcg cccgctcctt tcgctttctt    8460
cccttccttt ctcgccacgt tcgccggctt tccccgtcaa gctctaaatc ggggctccc   8520 tttagggttc cgatttagtg ctttacggca cctcgacccc aaaaaacttg attagggtga    8580
tggttcacgt agtgggccat cgccctgata cggttttt  cgccctttga cgttggagtc    8640
cacgttcttt aatagtggac tcttgttcca actggaaca  acactcaacc ctatctcggt    8700
ctattctttt gatttataag ggattttgcc gatttcggcc tattggttaa aaaatgagct    8760
gatttaacaa aaatttaacg cgaattttaa caaaatatta acgcttacaa tttccattcg    8820
ccattcaggc tgcgcaactg ttgggaaggg cgatcggtgc gggcctcttc gctattacgc    8880
```

```
cagctggcga aaggggatg tgctgcaagg cgattaagtt gggtaacgcc agggttttcc    8940
cagtcacgac gttgtaaaac gacggccagt gaattgtaat acgactcact atagggcgaa    9000
ttgggtaccg ggccccccct cgaggtcgat ggtgtcgata agcttgatat cgaattcatg    9060
tcacacaaac cgatcttcgc ctcaaggaaa cctaattcta catccgagag actgccgaga    9120
tccagtctac actgattaat tttcgggcca ataatttaaa aaaatcgtgt tatataatat    9180
tatatgtatt atatatatac atcatgatga tactgacagt catgtcccat tgctaaatag    9240
acagactcca tctgccgcct ccaactgatg ttctcaatat ttaaggggtc atctcgcatt    9300
gtttaataat aaacagactc catctaccgc ctccaaatga tgttctcaaa atatattgta    9360
tgaacttatt tttattactt agtattatta gacaacttac ttgctttatg aaaaacactt    9420
cctatttagg aaacaattta taatggcagt tcgttcattt aacaatttat gtagaataaa    9480
tgttataaat gcgtatggga aatcttaaat atggatagca taaatgatat ctgcattgcc    9540
taattcgaaa tcaacagcaa cgaaaaaaat cccttgtaca acataaatag tcatcgagaa    9600
atatcaacta tcaaagaaca gctattcaca cgttactatt gagattatta ttggacgaga    9660
atcacacact caactgtctt tctctcttct agaaatacag gtacaagtat gtactattct    9720
cattgttcat acttctagtc atttcatccc acatattcct tggatttctc tccaatgaat    9780
gacattctat cttgcaaatt caacaattat aataagatat accaaagtag cggtatagtg    9840
gcaatcaaaa agcttctctg gtgtgcttct cgtatttatt tttattctaa tgatccatta    9900
aaggtatata tttatttctt gttatataat ccttttgttt attacatggg ctggatacat    9960
aaaggtattt tgatttaatt ttttgcttaa attcaatccc ccctcgttca gtgtcaactg   10020
taatggtagg aaaattaccat actttgaag agcaaaaaaa aatgaaagaa aaaaaaaatc   10080
gtatttccag gttagacgtt ccgcagaatc tagaatgcgg tatgcggtac attgttcttc   10140
gaacgtaaaa gttgcgctcc ctgagatatt gtacattttt gcttttacaa gtacaagtac   10200
atcgtacaac tatgtactac tgttgatgca tccacaacag tttgttttgt ttttttttgt   10260
ttttttttt tctaatgatt cattaccgct atgtatacct acttgtactt gtagtaagcc   10320
gggttattgg cgttcaatta atcatagact tatgaatctg cacggtgtgc gctgcgagtt   10380
acttttagct tatgcatgct acttgggtgt aatattggga tctgttcgga aatcaacgga   10440
tgctcaat                                                           10448

<210> SEQ ID NO 149
<211> LENGTH: 28
<212> TYPE: DNA
<213> ORGANISM: Artificial Sequence
<220> FEATURE:
<223> OTHER INFORMATION: Primer oIGsel1-1

<400> SEQUENCE: 149
agcggccgca ccatggctct ggccaacg                                        28

<210> SEQ ID NO 150
<211> LENGTH: 25
<212> TYPE: DNA
<213> ORGANISM: Artificial Sequence
<220> FEATURE:
<223> OTHER INFORMATION: Primer oIGsel1-2

<400> SEQUENCE: 150
tgcggccgct aaagctgctt accag                                           25
```

```
<210> SEQ ID NO 151
<211> LENGTH: 69
<212> TYPE: DNA
<213> ORGANISM: Artificial Sequence
<220> FEATURE:
<223> OTHER INFORMATION: Primer

<400> SEQUENCE: 151
catggtcaat caatgagacg ccaacttctt aatctattga gacctgcagg tctagaaggg    60
cggatcccc                                                            69
```